US012004495B2

(12) United States Patent
Shen et al.

(10) Patent No.: US 12,004,495 B2
(45) Date of Patent: Jun. 11, 2024

(54) GENETICALLY MODIFIED NON-HUMAN ANIMALS WITH HUMANIZED IMMUNOGLOBULIN LOCUS

(71) Applicant: Biocytogen Pharmaceuticals (Beijing) Co., Ltd., Beijing (CN)

(72) Inventors: Yuelei Shen, Beijing (CN); Jiawei Yao, Beijing (CN); Huizhen Zhao, Beijing (CN); Yabo Zhang, Beijing (CN); Lili Liu, Beijing (CN); Hui Lu, Beijing (CN); Shuwen Huang, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 17/010,587

(22) Filed: Sep. 2, 2020

(65) Prior Publication Data

US 2020/0390073 A1 Dec. 17, 2020

Related U.S. Application Data

(63) Continuation of application No. PCT/CN2020/075698, filed on Feb. 18, 2020.

(30) Foreign Application Priority Data

Feb. 18, 2019 (WO) ............... PCT/CN2019/075406
Sep. 18, 2019 (WO) ............... PCT/CN2019/106320

(51) Int. Cl.
*A01K 67/0278* (2024.01)
*C07K 16/00* (2006.01)

(52) U.S. Cl.
CPC .......... *A01K 67/0278* (2013.01); *C07K 16/00* (2013.01); *A01K 2207/15* (2013.01); *A01K 2227/105* (2013.01); *A01K 2267/01* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. |
| 4,603,112 A | 7/1986 | Paoletti et al. |
| 4,769,330 A | 9/1988 | Paoletti et al. |
| 4,777,127 A | 10/1988 | Suni et al. |
| 5,017,487 A | 5/1991 | Stunnenberg et al. |
| 6,586,251 B2 | 7/2003 | Economides et al. |
| 6,596,541 B2 † | 7/2003 | Murphy |
| 7,105,348 B2 | 9/2006 | Murphy et al. |
| 7,129,084 B2 | 10/2006 | Buelow et al. |
| 7,262,028 B2 | 8/2007 | Van Berkel et al. |
| 7,541,513 B2 | 6/2009 | Bruggeman et al. |
| 7,816,578 B2 | 10/2010 | Tomizuka et al. |
| 8,367,888 B2 | 2/2013 | Bruggemann et al. |
| 8,502,018 B2 | 8/2013 | Murphy et al. |
| 8,759,105 B2 | 6/2014 | Economides et al. |
| 8,791,323 B2 | 7/2014 | Murphy et al. |
| 8,846,402 B2 | 9/2014 | Economides et al. |
| 8,877,688 B2 | 11/2014 | Vasquez et al. |
| 8,907,157 B2 | 12/2014 | Buelow |
| 9,253,965 B2 | 2/2016 | Bradley et al. |
| 9,353,394 B2 | 5/2016 | Murphy et al. |
| 9,371,553 B2 | 6/2016 | Murphy et al. |
| 9,376,699 B2 | 6/2016 | Murphy et al. |
| 9,382,567 B2 | 7/2016 | Murphy et al. |
| 9,388,446 B2 | 7/2016 | Murphy et al. |
| 9,434,782 B2 | 9/2016 | Bradley et al. |
| 9,439,405 B2 | 9/2016 | Bruggemann et al. |
| 9,445,581 B2 | 9/2016 | Bradley et al. |
| 9,447,177 B2 | 9/2016 | Bradley et al. |
| 9,504,236 B2 | 11/2016 | Bradley et al. |
| 9,505,827 B2 | 11/2016 | Bradley et al. |
| 9,528,136 B2 | 12/2016 | Murphy et al. |
| 9,677,129 B2 | 6/2017 | Economides et al. |
| 9,708,635 B2 | 7/2017 | Murphy et al. |
| 9,783,593 B2 | 10/2017 | Bradley et al. |
| 9,788,534 B2 | 10/2017 | Bradley et al. |
| 9,896,516 B2 | 2/2018 | Bradley et al. |
| 9,924,705 B2 | 3/2018 | Liang et al. |
| 9,938,357 B2 | 4/2018 | Bradley et al. |
| 9,938,358 B2 | 4/2018 | Bradley et al. |
| 9,963,501 B2 | 5/2018 | Haynes et al. |
| 10,064,398 B2 | 9/2018 | Bradley et al. |

(Continued)

FOREIGN PATENT DOCUMENTS

| | | |
|---|---|---|
| AU | 2001284703 | 2/2002 |
| AU | 2002220048 | 5/2002 |

(Continued)

OTHER PUBLICATIONS

IMGT Repertoire (IG and TR) Gene Positions: Human (*Homo sapiens*) IGH. [online database], downloaded on Feb. 23, 2021 from http://imgt.org/IMGTrepertoire/index.php?section=LocusGenes&repertoire=GenePositions&species=human&group=IGH, last updated Mar. 29, 2016; 8 pages.*

IMGT Repertoire (IG and TR) Gene Table: Human (*Homo sapiens*) IGKV. [online database] downloaded on Feb. 23, 2021 from http://imgt.org/IMGTrepertoire/index.php?section=LocusGenes&repertoire=genetable&species=human&group=IGKV; last updated Mar. 4, 2015; 9 pages.*

IMGT Repertoire (IG and TR) Gene Table: Human (Homo sapiens) IGKJ. [online database] downloaded on Feb. 23, 2021 from http://imgt.org/IMGTrepertoire/index.php?section=LocusGenes&repertoire=genetable&species=human&group=IGKJ; last updated Dec. 3, 2015; 3 pages.*

(Continued)

*Primary Examiner* — Allison M Fox
*Assistant Examiner* — Kimberly A Aron
(74) *Attorney, Agent, or Firm* — Fish & Richardson P.C.

(57) ABSTRACT

The present disclosure relates to genetically modified animals and cells with humanized heavy chain immunoglobulin locus and/or humanized light chain immunoglobulin locus.

22 Claims, 105 Drawing Sheets

Specification includes a Sequence Listing.

(56) References Cited

U.S. PATENT DOCUMENTS

| | | | |
|---|---|---|---|
| 10,149,462 | B2 | 12/2018 | Lee et al. |
| 10,165,763 | B2 | 1/2019 | Bradley et al. |
| 10,194,645 | B2 | 2/2019 | Bruggemann et al. |
| 10,226,033 | B2 | 3/2019 | Bradley et al. |
| 10,227,625 | B2 | 3/2019 | Murphy et al. |
| 10,251,377 | B2 | 4/2019 | Clube |
| 10,344,299 | B2 | 7/2019 | Economides et al. |
| 10,378,037 | B2 | 8/2019 | Murphy et al. |
| 10,378,038 | B2 | 8/2019 | Murphy et al. |
| 10,378,039 | B2 | 8/2019 | Murphy et al. |
| 10,378,040 | B2 | 8/2019 | Murphy et al. |
| 10,526,630 | B2 | 1/2020 | Murphy et al. |
| 2009/0253902 | A1 | 10/2009 | Tomizuka et al. |
| 2010/0122361 | A1 | 5/2010 | Smith et al. |
| 2012/0093785 | A1 | 4/2012 | Oshimura et al. |
| 2014/0033336 | A1 | 1/2014 | Murphy et al. |
| 2014/0041067 | A1 | 2/2014 | Bradley et al. |
| 2014/0331343 | A1 | 11/2014 | Bradley et al. |
| 2016/0219847 | A1 | 8/2016 | Mcwhirter et al. |
| 2016/0316731 | A1 | 11/2016 | Murphy et al. |
| 2017/0320936 | A1 | 11/2017 | Bradley et al. |
| 2019/0174729 | A1 | 6/2019 | Lee et al. |
| 2023/0064196 | A1 | 3/2023 | Shen et al. |
| 2023/0128645 | A1 | 4/2023 | Zhang et al. |

FOREIGN PATENT DOCUMENTS

| | | |
|---|---|---|
| AU | 2002239422 | 6/2002 |
| AU | 2002244023 | 9/2002 |
| AU | 2008259939 | 12/2008 |
| AU | 2010269978 | 1/2011 |
| AU | 2011266843 | 12/2011 |
| AU | 2011286185 | 2/2012 |
| AU | 2012311286 | 3/2013 |
| AU | 2012311288 | 3/2013 |
| AU | 2012343587 | 6/2013 |
| AU | 2013239501 | 10/2013 |
| AU | 2014214863 | 8/2014 |
| AU | 2016101604 | 10/2016 |
| CA | 2362098 | 8/2000 |
| CA | 2430013 | 6/2002 |
| CA | 2438390 | 8/2002 |
| CA | 2688834 | 12/2008 |
| CN | 1200014 | 11/1998 |
| CN | 1717483 | 1/2006 |
| CN | 101688228 | 3/2010 |
| CN | 102791866 | 11/2012 |
| CN | 103228130 | 7/2013 |
| CN | 103571872 | 2/2014 |
| CN | 104244709 | 12/2014 |
| CN | 104334732 | 2/2015 |
| CN | 104540383 | 4/2015 |
| CN | 104994729 | 10/2015 |
| CN | 104994730 | 10/2015 |
| CN | 105308184 | 2/2016 |
| CN | 107602696 | 1/2018 |
| CN | 109837307 | 6/2019 |
| EP | 0345242 | 12/1989 |
| EP | 1151010 | 11/2001 |
| EP | 1354034 | 10/2003 |
| EP | 1360287 | 11/2003 |
| EP | 1399559 | 3/2004 |
| EP | 2003960 | 12/2008 |
| EP | 2152880 | 2/2010 |
| EP | 2264163 | 12/2010 |
| EP | 2421357 | 2/2012 |
| EP | 2501817 | 9/2012 |
| EP | 2505654 | 10/2012 |
| EP | 2517556 | 10/2012 |
| EP | 2517557 | 10/2012 |
| EP | 2564695 | 3/2013 |
| EP | 2602323 | 6/2013 |
| EP | 2604110 | 6/2013 |
| EP | 2649184 | 10/2013 |
| EP | 2757875 | 7/2014 |
| EP | 2758535 | 7/2014 |
| EP | 2786657 | 10/2014 |
| EP | 2787075 | 10/2014 |
| EP | 2792236 | 10/2014 |
| EP | 2798950 | 11/2014 |
| EP | 2831244 | 2/2015 |
| EP | 2877571 | 6/2015 |
| EP | 2967013 | 1/2016 |
| EP | 3028564 | 6/2016 |
| EP | 3028565 | 6/2016 |
| EP | 3051942 | 8/2016 |
| EP | 3085779 | 10/2016 |
| EP | 3085780 | 10/2016 |
| EP | 2792236 B1 † | 11/2017 |
| GB | 2200651 | 8/1988 |
| JP | 2001-505059 | 4/2001 |
| WO | WO 1989/001973 | 3/1989 |
| WO | WO 1991/002805 | 3/1991 |
| WO | WO 9627011 | 9/1996 |
| WO | WO 1998/24893 | 6/1998 |
| WO | WO 0046251 | 8/2000 |
| WO | WO 0212437 | 2/2002 |
| WO | WO 0236789 | 5/2002 |
| WO | WO 0243478 | 6/2002 |
| WO | WO 02066630 | 8/2002 |
| WO | WO 03000737 | 1/2003 |
| WO | WO 2005/097185 | 10/2005 |
| WO | WO 2007117410 | 10/2007 |
| WO | WO 2008/077546 | 7/2008 |
| WO | WO 2008151081 | 12/2008 |
| WO | WO 2009/157771 | 12/2009 |
| WO | WO 2011004192 | 1/2011 |
| WO | WO 2011/097603 | 8/2011 |
| WO | WO 2011158009 | 12/2011 |
| WO | WO 2012018610 | 2/2012 |
| WO | 2012141798 A1 † | 10/2012 |
| WO | WO 2012/141798 | 10/2012 |
| WO | WO 2013041844 | 3/2013 |
| WO | WO 2013041845 | 3/2013 |
| WO | WO 2013041846 | 3/2013 |
| WO | WO 2013061098 | 5/2013 |
| WO | WO 2013079953 | 6/2013 |
| WO | WO 2013144566 | 10/2013 |
| WO | WO 2013144567 | 10/2013 |
| WO | WO 2013171505 | 11/2013 |
| WO | WO 2014124156 | 8/2014 |
| WO | WO 2015040402 | 3/2015 |
| WO | WO 2015049517 | 4/2015 |
| WO | WO 2017201476 | 11/2017 |
| WO | WO 2018001241 | 1/2018 |
| WO | WO 2018041118 | 3/2018 |
| WO | WO 2018041119 | 3/2018 |
| WO | WO 2018041120 | 3/2018 |
| WO | WO 2018041121 | 3/2018 |
| WO | WO 2018068756 | 4/2018 |
| WO | WO 2018086583 | 5/2018 |
| WO | WO 2018086594 | 5/2018 |
| WO | WO 2018121787 | 7/2018 |
| WO | WO 2018136823 | 7/2018 |
| WO | WO 2018177440 | 10/2018 |
| WO | WO 2018177441 | 10/2018 |
| WO | WO 2019/008123 | 1/2019 |
| WO | WO 2020169022 | 8/2020 |
| WO | WO 2023/284850 | 1/2023 |

OTHER PUBLICATIONS

Lee et al. Complete Humanization of the Mouse Immunoglobulin Loci Enables Efficient Therapeutic Antibody Discovery. Nature Biotechnology, 32(4): 356-567.*

IMGT Repertoire (IG and TR) Gene Positions: IGH Mouse (*Mus musculus*) C57BL/6J in GRCm38.93 assembly, [online database] downloaded on Feb. 23, 2021 from http://imgt.org/IMGTrepertoire/index.php?section=LocusGenes&repertoire=GenePositions&species=mouse&group=IGH, updated May 27, 2016, 7 pages.*

Genbank Accession No. AB019437. Earliest priority 1998. 82 pages.*

IMGT Repertoire (IG and TR) Gene Table: Human (*Homo sapiens*) IGHV. [online database], downloaded on Jun. 18, 2021 from http://

(56) References Cited

OTHER PUBLICATIONS www.imgt.org/IMGTrepertoire/index.php?section=LocusGenes&repertoire=genetable&species=human&group=IGHV, last updated Apr. 10, 2018; 16 pages.*
Green et al. Regulation of B Cell Development by Variable Gene Complexity in Mice Reconstituted with Human Immunoglobulin Yeast Artificial Chromosomes. Journal of Experimental Medicine, 1998. 188(3):483-495.*
Takehara et al. A Novel Transchromosomic System: Stable Maintenance of an Engineered Mb-sized Human Genomic Fragment Translocated to a Mouse Chromosome Terminal Region. Transgenic Research, 2014. 23:441-453.*
Joyce et al. Comparisons of the Antibody Repertoires of a Humanized Rodent and Humans by High throughput Sequencing. Scientific Reports, 2020. 10:1120, 9 pages, plus Supplement.*
Abhinandan, et al. "Analysis and improvements to Kabat and structurally correct numbering of antibody variable domains," Molecular Immunology, 2008, 45(14):3832-3839.
Auerbach et al., "Establishment and Chimera Analysis of 129/SvEv- and C57BL/6-Derived Mouse Embryonic Stem Cell Lines," BioTechniques, 2000, 29(5):1-6.
Chothia et al., "Conformations of immunoglobulin hypervariable regions," Nature, 1989, 342(6252):877-883.
Festing et al., "Revised nomenclature for strain 129 mice," Mammalian Genome, 1999, 10:836.
GenBank Accession No. NC_000002.12, "Homo sapiens chromosome 2, GRCh38.p7 Primary Assembly," Jun. 6, 2016, 3 pages.
GenBank Accession No. NC_000078.6, "Mus musculus strain C57BL/6J chromosome 12, GRCm38.p4 C57BL/6J," Jun. 22, 2016, 2 pages.
Irani, et al. "Molecular properties of human IgG subclasses and their implications for designing therapeutic monoclonal antibodies against infectious diseases." Molecular Immunology, 2015, 67(2):171-182.
Janssens et al., "Generation of heavy-chain-only antibodies in mice," Proceedings of the National Academy of Sciences, Oct. 2006, 103(41):15130-15135.
Kohler et al., "Continuous cultures of fused cells secreting antibody of predefined specificity," Nature, Aug. 1975, 256:495-497.
Kozbor et al., "The production of monoclonal antibodies from human lymphocytes," Immunol. Today, 1983, 4:72-79.
Kuroiwa et al., "Manipulation of human minichromosomes to carry greater than megabase-sized chromosome inserts," Nature Biotechnology, 2000, 18(10):1086-1090.
Lee et al., "Complete humanization of the mouse immunoglobulin loci enables efficient therapeutic antibody discovery," Nature Biotechnology, Apr. 2014, 4(32):356-366.
Martin et al., "Molecular modeling of antibody combining sites," Methods Enzymol., 1991, 203:121-153.
Martin, "Protein sequence and structure analysis of antibody variable domains," Antibody engineering, Springer Berlin Heidelberg, 2001, 422-439.
Morea et al., "Antibody structure, prediction and redesign ," Biophys Chem., 1997, 68(1-3):9-16.
Morea et al., "Conformations of the third hypervariable region in the VH domain of immunoglobulins," J Mol Biol., 1998, 275(2):269-294.
Paulis, "Chromosome Transfer Via Cell Fusion," Methods in Molecular Biology, 2011, 738:57-67.
PCT International Search Report and Written Opinion in International Appln. No. PCT/CN2020/075698, mailed May 20, 2020, 11 pages.
Ponomarenko et al., "Antibody-protein interactions: benchmark datasets and prediction tools evaluation ," BMC Structural Biology, 2007, 7:64, 19 pages.
Sanford et al., "General protocol for microcell-mediated chromosome transfer," Somatic Cell and Molecular Genetics, May 1987, 13(3):279-284.
Shinohara et al., "Stability of transferred human chromosome fragments in cultured cells and in mice," Chromosome Research, Nov. 2000, 8:713-725.
Tomizuka et al., "Functional expression and germline atransmission of a human chromosome fragment in chimaeric mice," Nature Genetics, 1997, 16(2):133-143.
Vidarsson, et al., "IgG subclasses and allotypes: from structure to effector functions," Frontiers in Immunology, Oct. 2014, 5(520):1-17.
Williams et al., "Co-FISH, COD-FISH, ReD-FISH, SKY-FISH," Genes, Chromosomes & Cancer, 1995, 14:126127, 113-124.
Wolff et al., "Monoclonal antibody homodimers: enhanced antitumor activity in nude mice," Cancer Res., 1993, 53:2560-2565.
Wu et al., "An analysis of the sequences of the variable regions of Bence Jones proteins and myeloma light chains and their implications for antibody complementarity," J. Exp. Med., 1970, 132:211-250.
Xu et al., "Production of bispecific antibodies in 'knobs-into-holes' using a cell-free expression system," mAbs, Jan. 2015, 7(1):231-242.
Yin et al., "Delivery technologies for genome editing," Nature Reviews Drug Discovery, 2017, 16(6):387-399.
Lee et al. Supplementary Material, "Massive genome engineering: Complete Humanization of the Mouse Immunoglobulin Loci for Therapeutic Antibody Discovery," Nature Biotechnology, Apr. 2014, 32(4): 356-567, 16 pages.
Lefranc, "Nomenclature of the Human Immunoglobulin Genes," Current Protocols Immunol., 2000, 40(1): 37 Pages.
Lefranc et al., "Chromosomal localization, organization of the loci and potential repertoire," in The Immunoglobulin Facts Book, 1st Ed., pp. 45-68, London: Academic Press, 2001.
Macdonald et al., "Precise and in situ genetic humanization of 6 Mb of mouse immunoglobulin genes," PNAS, 2014, 111(14): 5147-5152.
Macdonald, et al., "Velocigene Technology Extended to Humanization of Several Megabases of Complex Loci," presented at the 1st International MUGEN Conference on Animal Models for Human Immunological Disease, Athens, Greece, Sep. 2006, 1 page Abstract.
Mendez et al., "Functional transplant of megabase human immunoglobulin loci recapitulates human antibody response in mice," Nature genetics, Feb. 1997, 15(2):146-156.
Murphy et al., "Mice with megabase humanization of their immunoglobulin genes generate antibodies as efficiently as normal mice," Proceedings of the National Academy of Sciences, Apr. 8, 2014, 111(14):5153-5158.
Murphy et al., Supporting Information for "Mice with megabase humanization of their immunoglobulin genes generate antibodies as efficiently as normal mice," Proceedings of the National Academy of Sciences, Apr. 8, 2014, 111(14):5153-5158, 6 pages.
Murphy, "VelocImmune: immunoglobulin variable region humanized mice," Recombinant antibodies for immunotherapy, Jul. 27, 2009, 100-107.
Pink et al., "Pseudogenes: pseudo-functional or key regulators in health and disease?" RNA, May 1, 2011, 17(5):792-798.
Stevens, S, et al., "Velocimmune: Humanization of Immunoglobulin Loci Using Velocigene Technology, presented at the 1st International MUGEN Conference on Animal Models for Human Immunoglobulin Disease," Athens, Greece, Sep. 2006, 1 page Abstract.
Vihinen, "Contribution of pseudogenes to sequence diversity," Pseudogenes, 2014:15-24.
Voronina et al., "Deletion of Adam6 in Mus musculus leads to male subfertility and deficits in sperm ascent into the oviduct," Biology of reproduction, Mar. 1, 2019, 100(3):686-696.
International Preliminary Report on Patentability in International Appln. No. PCT/CN2020/075698, dated Aug. 26, 2021, 6 pages.
Zhu et al., "Humanising the mouse genome piece by piece," Nature communications, Apr. 23, 2019, 10(1):1-13.
*Regeneron Pharmaceuticals, Inc.*, v. *Merus B.V.*, Case No. 14 Civ. 1650(KBF), dated Nov. 21, 2014, 21 pages.
Extended European Search Report in European Appln. No. 20760285.5, mailed on Oct. 27, 2022, 14 pages.
International Search Report and Written Opinion in International Appln. No. PCT/CN2021/097652, mailed Aug. 31, 2021, 13 pages.
Karlsson et al., "Kinetic and concentration analysis using BIA technology," Methods, Jun. 1, 1994, (2):99-110.

(56) References Cited

OTHER PUBLICATIONS

Shiraiwa et al., "Engineering a bispecific antibody with a common light chain: Identification and optimization of an anti-CD3 epsilon and anti-GPC3 bispecific antibody, ERY974," Methods, Feb. 1, 2019, 154:10-20, Abstract only.
Brevini et al., "No. shortcuts to pig embryonic stem cells," Theriogenology, Sep. 1, 2010, 74(4):544-550.
Buta et al., "Reconsidering pluripotency tests: do we still need teratoma assays?" Stem cell research, Jul. 1, 2013, 11(1):552-562.
Gómez et al., "Derivation of cat embryonic stem-like cells from in vitro-produced blastocysts on homologous and heterologous feeder cells," Theriogenology, Sep. 1, 2010, 74(4):498-515.
Heiman-Patterson et al., "Effect of genetic background on phenotype variability in transgenic mouse models of amyotrophic lateral sclerosis: a window of opportunity in the search for genetic modifiers," Amyotrophic Lateral Sclerosis, Mar. 1, 2011, 12(2): 9 pages.
Hong et al., "Derivation and characterization of embryonic stem cells lines derived from transgenic Fischer 344 and Dark Agouti rats," Stem cells and development, Jun. 10, 2012, 21(9):1571-1586.
Jax.org [online], "Same mutation, different phenotype?", Nov. 11, 2014, retrieved on May 5, 2023, retrieved from URL<https://www.jax.org/news-and-insights/jax-blog/2014/november/same-mutation-different-phenotype>, 6 pages.
Kakoki et al., "Altering the expression in mice of genes by modifying their 3' regions," Developmental cell, Apr. 1, 2004, 6(4):597-606.
Munoz et al., "Conventional pluripotency markers are unspecific for bovine embryonic-derived cell-lines," Theriogenology, Jun. 1, 2008, 69(9):1159-1164.
Paris et al., "Equine embryos and embryonic stem cells: defining reliable markers of pluripotency," Theriogenology, Sep. 1, 2010, 74(4): 26 pages.
Tong et al., "Production of p53 gene knockout rats by homologous recombination in embryonic stem cells," Nature, Sep. 9, 2010, 467(7312): 13 pages.
Boyd et al., "Individual variation in the germline Ig gene repertoire inferred from variable region gene rearrangements," The Journal of Immunology, Jun. 15, 2010, 184(12):6986-6992.
Brensing-Küppers et al., "The human immunoglobulin κ locus on yeast artificial chromosomes (YACs)," Gene, Jun. 3, 1997, 191(2):173-181.
Call et al., "A cre-lox recombination system for the targeted integration of circular yeast artificial chromosomes into embryonic stem cells," Human molecular genetics, Jul. 22, 2000, 9(12):1745-1751.
Davies et al., "Creation of mice expressing human antibody light chains by introduction of a yeast artificial chromosome containing the core region of the human immunoglobulin κ locus," Bio/Technology, Aug. 1, 1993, 11(8): Abstract 1 page.
Jackson et al., "Divergent human populations show extensive shared IGK rearrangements in peripheral blood B cells," Immunogenetics, Jan. 2012, 64:3-14.
Li et al., "Generation of transgenic mice with megabase-sized human yeast artificial chromosomes by yeast spheroplast-embryonic stem cell fusion," Nature protocols, Aug. 2013, 8(8): Abstract 1 page.
Matsuda et al., "The complete nucleotide sequence of the human immunoglobulin heavy chain variable region locus," The Journal of experimental medicine, Dec. 7, 1998, 188(11):2151-2162.
Blanco et al., "Age-associated distribution of normal B-cell and plasma cell subsets in peripheral blood," Journal of Allergy and Clinical Immunology, 2018, 141(6):2208-2219e16.
Candelaria et al., "Antibodies Targeting the Transferrin Receptor 1 (TfR1) as Direct Anti-cancer Agents," Frontiers in Immunology, 2021, 12(607692):1-21.
De Wildt et al., "Analysis of heavy and light chain pairings indicates that receptor editing shapes the human antibody repertoire," J. Mol. Biol., 1999, 285:895-901.
Estep et al., "High throughput solution-based measurement of antibody-antigen affinity and epitope binning," mAbs, 2013, 5(2):270-278.
Fisher-Hoch et al., "Protection of rhesus monkeys from fatal Lassa fever by vaccination with a recombinant vaccinia virus containing the Lassa virus glycoprotein gene," Proc. Natl. Acad. Sci. USA, 1989, 86:317-321.
GenBank Accession No. NC_000078.7, "Mus musculus strain C57BL/6J chromosome 12, GRCm39," Sep. 22, 2020, 2 pages.
Guzman et al., "Efficient and selective adenovirus-mediated gene transfer into vascular neointima," Circulation, 1993, 88(6):2838-2848.
Guzman et al., "Efficient gene transfer into myocardium by direct injection of adenovirus vectors," Circulation Research, 1993, 73(6):1202-1207.
Haldi et al., "Large human YACs constructed in a rad52 strain show a reduced rate of chimerism," Genomics, Dec. 1, 1994, 24(3):478-484.
Kass-Eisler et al., "Quantitative determination of adenovirus-mediated gene delivery to rat cardiac myocytes in vitro and in vivo," 1993, Proc. Natl. Acad. Sci. USA, 90(24):11498-11502.
Kolls et al., "Prolonged and effective blockade of tumor necrosis factor activity through adenovirus-mediated gene transfer," 1994, Proc. Natl. Acad. Sci. USA, 91(1):215-219.
Ma et al., "Genome-wide analysis of pseudogenes reveals HBBP1's human-specific essentiality in erythropoiesis and implication in ß-thalassemia," Developmental Cell, 2021, 56:478-493.
Moore et al., "Antibody cross-competition analysis of the human immunodeficiency virus type 1 gp120 exterior envelope glycoprotein," Journal of Virology, 1996, 70(3):1863-1872.
Shen et al., "Transferrin receptor 1 in cancer: a new sight for cancer therapy," American Journal of Cancer Research, 2018, 8(6):916-931.
Takeda et al., "Deletion of the immunoglobulin κ chain intron enhancer abolishes κ chain gene rearrangement in cis hut not γ chain gene rearrangement in trans," The EMBO Journal, 1993, 12(6):2329-2336.
Zou et al., "Block in development at the pre-B-II to immature B cell stage in mice without Igκ and Igλ Light Chain," The Journal of Immunology, 2003, 170(3):1354-1361.
Zou et al., "Gene targeting in the Ig kappa locus: efficient generation of lambda chain-expressing B cells, independent of gene rearrangements in Ig kappa," The EMBO Journal, 1993, 12(3):811-820.
Zou et al., "Subtle differences in antibody responses and hypermutation of lambda light chains in mice with a disrupted chi constant region," Eur J Immunol., 1995, 25(8):2154-2162.
Dennis, "Welfare issues of genetically modified animals," ILAR Journal, 2002, 43(2):100-109.
Devoy et al., "Genomically humanised mice: technologies and promise," Nature Reviews Genetics, 2011, 13(1):14-20 (Author Manuscript; available in PMC on Mar. 8, 2016).
Feng et al., "Site-specific chromosomal integration in mammalian cells: highly efficient CRE recombinase-mediated cassette exchange," Journal of Molecular Biology, Oct. 1, 1999, 292(4):779-785.
Zhou et al., "Developing tTA transgenic rats for inducible and reversible gene expression," International Journal of Biological Sciences, 2009, 5(2):171-181.
Macdonald et al, Precise and in situ genetic humanization of 6 Mb of mouse immunoglobulin genes, PNAS 111(14): 5147-5152 2014.†
Murphy et al, Mice with Megabase Humanization of Their Immunoglobulin Genes Generate Antibodies as Efficiently as Normal Mice, PNAS USA 111(14): 5153-5158, 2014.†
Lefranc, M, P, Nomenclature of the Human Immunoglobulin Genes, Current Protocols Immunol., 40(1): A.1P.1-A.1P.37, 2000.†
Murphy, A, VelocImmune: Immunoglobulin Variable Region Humanized Mice, in M. Little (ed.), Recombinant Antibodies for Immunotherapy, pp. 100-107, New York, NY: Cambridge University Press, Jul. 27, 2009.†
Stevens, S, et al, Velocimmune: Humanization of Immunoglobulin Loci Using Velocigene Technology, presented at the 1st International MUGEN Conference on Animal Models for Human Immunoglobulin Disease, Athens, Greece, Sep. 10-13, 2006.†

(56) References Cited

OTHER PUBLICATIONS

Lefranc, Marie, P and Lefranc, Gerard, Chromosomal localization, organization of the loci and potential repertoire, in The Immunoglobulin Facts Book, 1st Ed., pp. 45-68, London: Academic Press, 2001.†

Macdonald, et al, Velocigene Technology Extended to Humanization of Several Megabases of Complex Loci, presented at the 1st International MUGEN Conference on Animal Models for Human Immunological Disease, Athens, Greece, Sep. 10-13, 2006.†

Lee, et al, Complete Humanization of the mouse immunoglobulin loci enables efficient therapeutic antibody discovery, Nature Biotechnology, (32): 356-363 and Suppl. Figures 1-8 and Suppl. Tables 1-7, 2014.†

Mendez, et al, Functional transplant of megabase human immunoglobulin loci recapitulates human antibody response in mice, Nature Genetics, 15(2): 146-156, 1997.†

Voronina, et al, Deletion of Adam6 in Mus musculus leads to male subfertility and deficits in sperm ascent into the oviduct, Biology of Reproduction, 100(3), 686-696, 2018.†

\* cited by examiner
† cited by third party

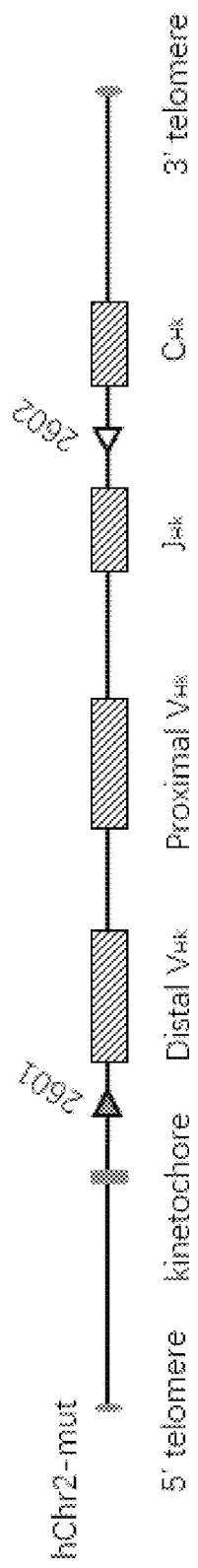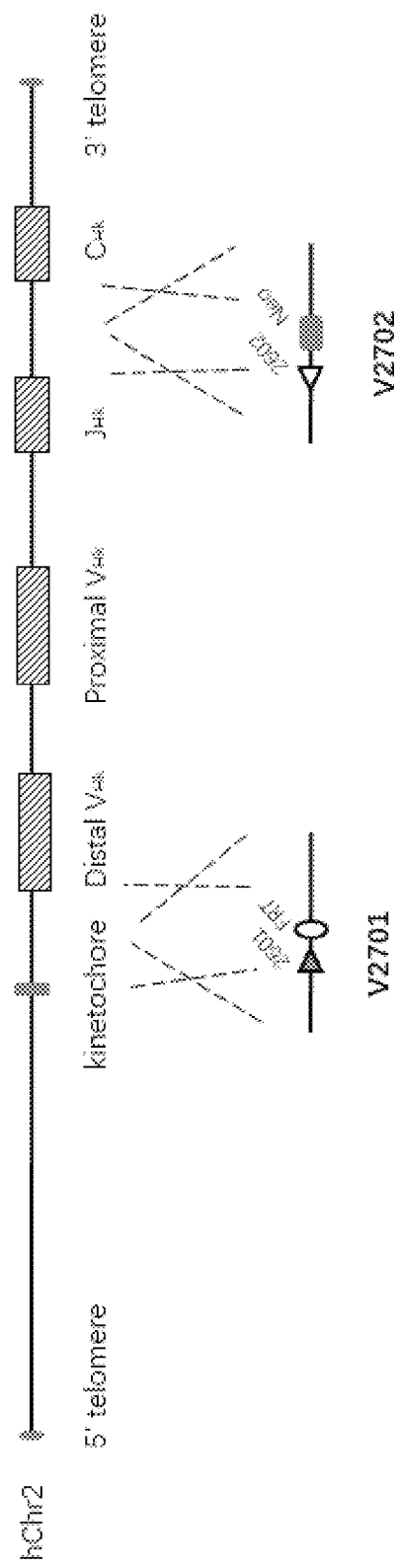
FIG. 29
FIG. 30

FIG. 41

| Gene | IMGT | | | | | | NCBI | |
|------|------|------|------|------|------|------|------|------|
| | Location | Orientation | Locus | Position | Accession number | Positions | Gene positions on chromosome | Accession number | Gene positions in sequences |
| IGHA2 | 14q32.33 | REV | IGH | | J00221 | 1227..1618 | 105124322..105124713 | NT_026437.11 | 87054322..87054713 |
| IGHA2 | 14q32.33 | REV | IGH | | J00221 | 684..1004 | 105124936..105125256 | NT_026437.11 | 87054936..87055256 |
| IGHA2 | 14q32.33 | REV | IGH | | J00221 | 164..469 | 105125474..105125776 | NT_026437.11 | 87055474..87055776 |
| IGHE | 14q32.33 | REV | IGH | | J00222 | 2540..2868 | 105137451..105137779 | NT_026437.11 | 87067451..87067779 |
| IGHE | 14q32.33 | REV | IGH | | J00222 | 2133..2456 | 105137863..105138186 | NT_026437.11 | 87067863..87068186 |
| IGHE | 14q32.33 | REV | IGH | | J00222 | 1726..2046 | 105138273..105138593 | NT_026437.11 | 87068273..87068593 |
| IGHE | 14q32.33 | REV | IGH | | J00222 | 1210..1518 | 105138801..105139109 | NT_026437.11 | 87068801..87069109 |
| IGHG4 | 14q32.33 | REV | IGH | | K01316 | 1481..1800 | 105161861..105162180 | NT_026437.11 | 87091861..87092180 |
| IGHG4 | 14q32.33 | REV | IGH | | K01316 | 1054..1383 | 105162278..105162607 | NT_026437.11 | 87092278..87092607 |
| IGHG4 | 14q32.33 | REV | IGH | | K01316 | 900..935 | 105162726..105162761 | NT_026437.11 | 87092726..87092761 |
| IGHG4 | 14q32.33 | REV | IGH | | K01316 | 216..509 | 105163154..105163447 | NT_026437.11 | 87093154..87093447 |
| IGHG2 | 14q32.33 | REV | IGH | | J00230 | 1480..1799 | 105180588..105180907 | NT_026437.11 | 87110588..87110907 |
| IGHG2 | 14q32.33 | REV | IGH | | J00230 | 1056..1382 | 105181005..105181331 | NT_026437.11 | 87111005..87111331 |
| IGHG2 | 14q32.33 | REV | IGH | | J00230 | 902..937 | 105181450..105181485 | NT_026437.11 | 87111450..87111485 |
| IGHG2 | 14q32.33 | REV | IGH | | J00230 | 216..509 | 105181878..105182171 | NT_026437.11 | 87111878..87112171 |
| IGHGP | 14q32.33 | REV | IGH | | X06766 | 1474..1790 | 105205635..105205947 | NT_026437.11 | 87135635..87135947 |
| IGHGP | 14q32.33 | REV | IGH | | X06766 | 1047..1376 | 105206045..105206374 | NT_026437.11 | 87136045..87136374 |
| IGHGP | 14q32.33 | REV | IGH | | X06766 | 878..928 | 105206493..105206543 | NT_026437.11 | 87136493..87136543 |
| IGHGP | 14q32.33 | REV | IGH | | X06766 | 195..488 | 105206933..105207226 | NT_026437.11 | 87136933..87137226 |
| IGHA1 | 14q32.33 | REV | IGH | | J00220 | 1244..1635 | 105244553..105244944 | NT_026437.11 | 87174553..87174944 |
| IGHA1 | 14q32.33 | REV | IGH | | J00220 | 662..1021 | 105245167..105245526 | NT_026437.11 | 87175167..87175526 |
| IGHA1 | 14q32.33 | REV | IGH | | J00223 | 142..447 | 105245741..105246046 | NT_026437.11 | 87175741..87176046 |
| IGHEP1 | 14q32.33 | REV | IGH | | J00223 | 849..1177 | 105259179..105259507 | NT_026437.11 | 87189179..87189507 |
| IGHEP1 | 14q32.33 | REV | IGH | | J00223 | 447..765 | 105259591..105259909 | NT_026437.11 | 87189591..87189909 |
| IGHG1 | 14q32.33 | REV | IGH | | J00228 | 1481..1800 | 105278858..105279177 | NT_026437.11 | 87208858..87209177 |
| IGHG1 | 14q32.33 | REV | IGH | | J00228 | 1055..1384 | 105279275..105279604 | NT_026437.11 | 87209275..87209604 |
| IGHG1 | 14q32.33 | REV | IGH | | J00228 | 892..936 | 105279723..105279767 | NT_026437.11 | 87209723..87209767 |
| IGHG1 | 14q32.33 | REV | IGH | | J00228 | 210..503 | 105280159..105280452 | NT_026437.11 | 87210159..87210452 |
| IGHG3 | 14q32.33 | REV | IGH | | X03604 | 2061..2380 | 105306622..105306941 | NT_026437.11 | 87236622..87236941 |
| IGHG3 | 14q32.33 | REV | IGH | | X03604 | 1634..1963 | 105307039..105307368 | NT_026437.11 | 87237039..87237368 |
| IGHG3 | 14q32.33 | REV | IGH | | X03604 | 1471..1515 | 105307487..105307531 | NT_026437.11 | 87237487..87237531 |
| IGHG3 | 14q32.33 | REV | IGH | | X03604 | 1283..1327 | 105307675..105307719 | NT_026437.11 | 87237675..87237719 |
| IGHG3 | 14q32.33 | REV | IGH | | X03604 | 1095..1139 | 105307863..105307907 | NT_026437.11 | 87237863..87237907 |
| IGHG3 | 14q32.33 | REV | IGH | | X03604 | 901..951 | 105308051..105308101 | NT_026437.11 | 87238051..87238101 |
| IGHG3 | 14q32.33 | REV | IGH | | X03604 | 216..509 | 105308494..105308787 | NT_026437.11 | 87238494..87238787 |
| IGHD | 14q32.33 | REV | IGH | | K02880 | 25..50 | 105375785..105375810 | NT_026437.11 | 87305785..87305810 |

FIG. 41 (Continued)

| | | | | | | | |
|---|---|---|---|---|---|---|---|
| IGHD | 14q32.33 | REV | IGH | | K02879 | 101.424 | 105377748..105378071 | NT_026437.11 | 87307748..87308071 |
| IGHD | 14q32.33 | REV | IGH | | K02878 | 101.424 | 105378282..105378605 | NT_026437.11 | 87308282..87308605 |
| IGHD | 14q32.33 | REV | IGH | | K02877 | 101.172 | 105379342..105379413 | NT_026437.11 | 87309342..87309413 |
| IGHD | 14q32.33 | REV | IGH | | K02876 | 101.202 | 105382203..105382304 | NT_026437.11 | 87312203..87312304 |
| IGHM | 14q32.33 | REV | IGH | | K02875 | 101.403 | 105382753..105383055 | NT_026437.11 | 87312753..87313055 |
| IGHM | 14q32.33 | REV | IGH | | X14940 | 1708.2096 | 105391496..105391887 | NT_026437.11 | 87321496..87321887 |
| IGHM | 14q32.33 | REV | IGH | | X14940 | 1212.1529 | 105392067..105392384 | NT_026437.11 | 87322067..87322384 |
| IGHM | 14q32.33 | REV | IGH | | X14940 | 631.966 | 105392630..105392965 | NT_026437.11 | 87322630..87322965 |
| IGHM | 14q32.33 | REV | IGH | | X14940 | 233.544 | 105393056..105393367 | NT_026437.11 | 87323056..87323367 |
| IGHJ6 | 14q32.33 | REV | IGH | 960175..960275 | J00256 | 2909.3009 | 105400453..105400553 | NT_026437.11 | 87330453..87330553 |
| IGHJ3P | 14q32.33 | REV | IGH | 959970..960057 | J00256 | 2709.2797 | 105400671..105400758 | NT_026437.11 | 87330671..87330758 |
| IGHJ5 | 14q32.33 | REV | IGH | 959571..959659 | J00256 | 2317.2404 | 105401084..105401156 | NT_026437.11 | 87331069..87331141 |
| IGHJ4 | 14q32.33 | REV | IGH | 959172..959258 | J00256 | 1873.1959 | 105401470..105401556 | NT_026437.11 | 87331470..87331556 |
| IGHJ3 | 14q32.33 | REV | IGH | 958789..958886 | J00256 | 1498.1586 | 105401865..105401930 | NT_026437.11 | 87331842..87331907 |
| IGHJ2P | 14q32.33 | REV | IGH | 958583..958682 | J00256 | 1284.1380 | 105402046..105402145 | NT_026437.11 | 87332046..87332145 |
| IGHJ2 | 14q32.33 | REV | IGH | 958184..958274 | J00256 | 893.984 | 105402454..105402544 | NT_026437.11 | 87332454..87332544 |
| IGHJ1 | 14q32.33 | REV | IGH | 957977..958066 | J00256 | 686.774 | 105402662..105402751 | NT_026437.11 | 87332662..87332751 |
| IGHD7-27 | 14q32.33 | REV | IGH | 957884..957950 | J00256 | 592.659 | 105402781..105402845 | NT_026437.11 | 87332778..87332842 |
| IGHJ1P | 14q32.33 | REV | IGH | 957759..957849 | J00256 | 467.557 | 105402879..105402969 | NT_026437.11 | 87332879..87332969 |
| IGHD1-26 | 14q32.33 | REV | IGH | 942598..942673 | X97051 | 72141.72216 | 105417909..105417984 | NT_026437.11 | 87347909..87347984 |
| IGHD6-25 | 14q32.33 | REV | IGH | 942095..942168 | X97051 | 71638.71711 | 105418414..105418487 | NT_026437.11 | 87348414..87348487 |
| IGHD5-24 | 14q32.33 | REV | IGH | 939730..939805 | X97051 | 69272..69347 | 105420778..105420853 | NT_026437.11 | 87350778..87350853 |
| IGHD4-23 | 14q32.33 | REV | IGH | 938765..938839 | X97051 | 68306..68380 | 105421745..105421819 | NT_026437.11 | 87351745..87351819 |
| IGHD3-22 | 14q32.33 | REV | IGH | 937592..937678 | X93616 | 2.88 | 105422906..105422992 | NT_026437.11 | 87352906..87352992 |
| IGHD2-21 | 14q32.33 | REV | IGH | 935075..935158 | J00235 | 1.63 | 105425447..105425509 | NT_026437.11 | 87355447..87355509 |
| IGHD1-20 | 14q32.33 | REV | IGH | 932446..932518 | X97051 | 61987..62059 | 105428066..105428138 | NT_026437.11 | 87358066..87358138 |
| IGHD6-19 | 14q32.33 | REV | IGH | 931934..932010 | X97051 | 61475..61551 | 105428574..105428650 | NT_026437.11 | 87358574..87358650 |
| IGHD5-18 | 14q32.33 | REV | IGH | 930093..930168 | X13972 | 2885..2960 | 105430417..105430492 | NT_026437.11 | 87360417..87360492 |
| IGHD4-17 | 14q32.33 | REV | IGH | 929131..929202 | X97051 | 58671..58742 | 105431383..105431454 | NT_026437.11 | 87361383..87361454 |
| IGHD3-16 | 14q32.33 | REV | IGH | 927984..928076 | J00234 | 2..94 | 105432511..105432601 | NT_026437.11 | 87362511..87362601 |
| IGHD2-15 | 14q32.33 | REV | IGH | 925668..925753 | X13972 | 14490..14562 | 105434853..105434918 | NT_026437.11 | 87364853..87364918 |
| IGHD1-14 | 14q32.33 | REV | IGH | 923001..923073 | X13972 | 13983..14059 | 105437513..105437585 | NT_026437.11 | 87367513..87367585 |
| IGHD6-13 | 14q32.33 | REV | IGH | 922493..922569 | X13972 | 12478..12556 | 105438017..105438093 | NT_026437.11 | 87368017..87368093 |
| IGHD5-12 | 14q32.33 | REV | IGH | 920984..921062 | X13972 | 11522..11593 | 105439524..105439602 | NT_026437.11 | 87369524..87369602 |
| IGHD4-11 | 14q32.33 | REV | IGH | 920024..920095 | X13972 | 10631..10717 | 105440491..105440562 | NT_026437.11 | 87370491..87370562 |
| IGHD3-10 | 14q32.33 | REV | IGH | 919128..919214 | X13972 | 10447..10533 | 105441372..105441458 | NT_026437.11 | 87371372..87371458 |
| IGHD3-9 | 14q32.33 | REV | IGH | 918944..919030 | X13972 | 7921.8007 | 105441556..105441642 | NT_026437.11 | 87371556..87371642 |
| IGHD2-8 | 14q32.33 | REV | IGH | 916414..916500 | X13972 | 5238.5310 | 105444086..105444172 | NT_026437.11 | 87374086..87374172 |
| IGHD1-7 | 14q32.33 | REV | IGH | 913731..913803 | X13972 | 4734.4807 | 105446783..105446855 | NT_026437.11 | 87376783..87376855 |
| IGHD6-6 | 14q32.33 | REV | IGH | 913227..913300 | X13972 | 59633.59708 | 105447287..105447359 | NT_026437.11 | 87377286..87377358 |
| IGHD5-5 | 14q32.33 | REV | IGH | 911378..911453 | X97051 | | 105449133..105449208 | NT_026437.11 | 87379133..87379208 |

| | | | | | | | |
|---|---|---|---|---|---|---|---|
| IGHD4-4 | 14q32.33 | REV | IGH | 910417..910488 | X13972 | 1924..1995 | 105450098..105450169 | NT_026437.11 | 87380098..87380169 |
| IGHD3-3 | 14q32.33 | REV | IGH | 909265..909351 | X13972 | 776..862 | 105451235..105451321 | NT_026437.11 | 87381235..87381321 |
| IGHD2-2 | 14q32.33 | REV | IGH | 906798..906884 | J00232 | 1..66 | 105453723..105453788 | NT_026437.11 | 87383723..87383788 |
| IGHD1-1 | 14q32.33 | REV | IGH | 904136..904208 | X97051 | 33686..33758 | 105456378..105456450 | NT_026437.11 | 87386378..87386450 |
| IGHV4-30-2 | 14q32.33 | REV | IGH | | L10089 | 1..297 | 105476885..105476952 | NT_026437.11 | 87406660..87406727 |
| IGHV4-4 | 14q32.33 | REV | IGH | 811002..811472 | L10098 | 1..325 | 105476906..105476984 | NT_026437.11 | 87406894..87406972 |
| IGHV(II)-1-1 | 14q32.33 | REV | IGH | 878294..878475 | AB019441 | 78294..78475 | 105482211..105482292 | NT_026437.11 | 87412111..87412292 |
| IGHV3-21 | 14q32.33 | REV | IGH | 597417..597909 | AB019439 | 197417..197909 | 106282330..106282428 | NT_026437.11 | 88211936..88212034 |
| IGHV1-2 | 14q32.33 | REV | IGH | 836435..836911 | X07448 | 126..603 | 105523675..105524151 | NT_026437.11 | 87453675..87454151 |
| IGHV3-41 | 14q32.33 | REV | IGH | 390047..390538 | M99670 | 189..680 | 106119868..106120165 | NT_026437.11 | 88049868..88050165 |
| IGHV1-3 | 14q32.33 | REV | IGH | 817860..818336 | X62109 | 21..497 | 105542250..105542726 | NT_026437.11 | 87472250..87472726 |
| IGHV4-59 | 14q32.33 | REV | IGH | 205856..206326 | AB019438 | 1..291 | 106154301..106154591 | NT_026437.11 | 88084301..88084591 |
| IGHV2-5 | 14q32.33 | REV | IGH | 794964..795446 | X62111 | 71..553 | 105565140..105565622 | NT_026437.11 | 87495140..87495622 |
| IGHV(III)-5-1 | 14q32.33 | REV | IGH | 793545..793643 | AB019440 | 193545..193643 | 105566943..105567041 | NT_026437.11 | 87496943..87497041 |
| IGHV(III)-5-2 | 14q32.33 | REV | IGH | 787450..787749 | AB019440 | 187450..187749 | 105572837..105573136 | NT_026437.11 | 87502837..87503136 |
| IGHV3-6 | 14q32.33 | REV | IGH | 777310..777803 | M99650 | 13..506 | 105582783..105583276 | NT_026437.11 | 87512783..87513276 |
| IGHV3-7 | 14q32.33 | REV | IGH | 770688..771182 | M99649 | 184..678 | 105589404..105589898 | NT_026437.11 | 87519404..87519898 |
| IGHV6-1 | 14q32.33 | REV | IGH | 883485..883971 | J04097 | 337..823 | 105763091..105763163 | NT_026437.11 | 87692677..87692749 |
| IGHV3-9 | 14q32.33 | REV | IGH | 736812..737296 | M99651 | 132..616 | 105623290..105623774 | NT_026437.11 | 87553290..87553774 |
| IGHV2-10 | 14q32.33 | REV | IGH | 729561..730040 | M99647 | 71..550 | 105630549..105631025 | NT_026437.11 | 87560549..87561025 |
| IGHV3-11 | 14q32.33 | REV | IGH | 715861..716349 | M99652 | 48..536 | 105644237..105644725 | NT_026437.11 | 87574237..87574725 |
| IGHV(III)-11-1 | 14q32.33 | REV | IGH | 712240..712656 | AB019440 | 112240..112656 | 105647930..105648346 | NT_026437.11 | 87577930..87578346 |
| IGHV1-12 | 14q32.33 | REV | IGH | 710238..710527 | X92210 | 191..628 | 105649911..105650348 | NT_026437.11 | 87579911..87580348 |
| IGHV1-13 | 14q32.33 | REV | IGH | 702954..703445 | X92217 | 2..493 | 105657141..105657632 | NT_026437.11 | 87587141..87587632 |
| IGHV(III)-13-1 | 14q32.33 | REV | IGH | 690249..690586 | AB019440 | 90249..90586 | 105670000..105670337 | NT_026437.11 | 87600000..87600337 |
| IGHV1-14 | 14q32.33 | REV | IGH | 686675..687009 | AB019440 | 86675..87009 | 105673577..105673911 | NT_026437.11 | 87603577..87603911 |
| IGHV1-15 | 14q32.33 | REV | IGH | 678769..679269 | X92216 | 2..502 | 105681317..105681817 | NT_026437.11 | 87611317..87611817 |
| IGHV(II)-15-1 | 14q32.33 | REV | IGH | 669050..669320 | AB019440 | 69050..69320 | 105691266..105691536 | NT_026437.11 | 87621266..87621536 |
| IGHV3-16 | 14q32.33 | REV | IGH | 667196..667688 | M99655 | 30..522 | 105692898..105693390 | NT_026437.11 | 87622898..87623390 |
| IGHV(II)-16-1 | 14q32.33 | REV | IGH | 661801..662105 | AB019440 | 61801..62105 | 105698481..105698785 | NT_026437.11 | 87628481..87628785 |
| IGHV1-17 | 14q32.33 | REV | IGH | 658074..658549 | M99640 | 45..521 | 105702037..105702512 | NT_026437.11 | 87632037..87632512 |
| IGHV1-18 | 14q32.33 | REV | IGH | 647544..648019 | M99641 | 47..522 | 105712567..105713042 | NT_026437.11 | 87642567..87643042 |
| IGHV3-19 | 14q32.33 | REV | IGH | 635792..636211 | M99656 | 211..630 | 105724375..105724794 | NT_026437.11 | 87654375..87654794 |
| IGHV3-20 | 14q32.33 | REV | IGH | 621508..622001 | M99657 | 10..504 | 105738585..105739078 | NT_026437.11 | 87668585..87669078 |
| IGHV(II)-20-1 | 14q32.33 | REV | IGH | 619576..620076 | AB019440 | 19576..20076 | 105740510..105741010 | NT_026437.11 | 87670510..87671010 |
| IGHV1-58 | 14q32.33 | REV | IGH | 210733..211209 | M29809 | 151..627 | 106149377..106149853 | NT_026437.11 | 88079377..88079853 |
| IGHV3-22 | 14q32.33 | REV | IGH | 574720..575220 | M99659 | 85..585 | 105785366..105785866 | NT_026437.11 | 87715366..87715866 |
| IGHV(II)-22-1 | 14q32.33 | REV | IGH | 569320..569588 | AB019439 | 169320..169588 | 105790998..105791266 | NT_026437.11 | 87720998..87721266 |

FIG. 41 (Continued)

| | | | | | | | |
|---|---|---|---|---|---|---|---|
| IGHV(III)-22-2 | 14q32.33 | REV | IGH | 568065..568262 | AB019439 | 168065..168262 | 105792324..105792521 | NT_026437.11 | 87722324..87722521 |
| IGHV1-23 | 14q32.33 | REV | IGH | 563887..564381 | M99660 | 10..504 | 105796205..105796699 | NT_026437.11 | 87726205..87726699 |
| IGHV1-24 | 14q32.33 | REV | IGH | 559962..556438 | M99642 | 68..544 | 105804148..105804624 | NT_026437.11 | 87734148..87734624 |
| IGHV1-25 | 14q32.33 | REV | IGH | 543468..543960 | M99661 | 78..570 | 105816626..105817118 | NT_026437.11 | 87746626..87747118 |
| IGHV(III)-25-1 | 14q32.33 | REV | IGH | 539140..539381 | AB019439 | 139140..139381 | 105821205..105821446 | NT_026437.11 | 87751205..87751446 |
| IGHV2-26 | 14q32.33 | REV | IGH | 531449..531931 | M99648 | 21..503 | 105828655..105829137 | NT_026437.11 | 87758655..87759137 |
| IGHV(III)-26-1 | 14q32.33 | REV | IGH | 523568..523874 | AB019439 | 123568..123874 | 105836712..105837018 | NT_026437.11 | 87766712..87767018 |
| IGHV(II)-26-2 | 14q32.33 | REV | IGH | 518318..518630 | AB019439 | 118318..118630 | 105841956..105842268 | NT_026437.11 | 87771956..87772268 |
| IGHV7-27 | 14q32.33 | REV | IGH | 515042..515455 | M99643 | 65..526 | 105845083..105845544 | NT_026437.11 | 87775083..87775544 |
| IGHV4-31 | 14q32.33 | REV | IGH | 483897..484373 | X05713 | 153..626 | 105851517..105851990 | NT_026437.11 | 87781517..87781990 |
| IGHV(II)-31-1 | 14q32.33 | REV | IGH | 503603..503855 | AB019439 | 103603..103855 | 105856731..105856983 | NT_026437.11 | 87786731..87786983 |
| IGHV3-29 | 14q32.33 | REV | IGH | 501726..502222 | AB019439 | 101726..102222 | 105858364..105858860 | NT_026437.11 | 87788364..87788860 |
| IGHV3-30 | 14q32.33 | REV | IGH | 498085..498577 | M83134 | 1782..2274 | 105862009..105862501 | NT_026437.11 | 87792009..87792501 |
| IGHV3-30-1 | 14q32.33 | REV | IGH | 490666..490939 | AB019439 | 90666..90939 | 105869647..105869920 | NT_026437.11 | 87799647..87799920 |
| IGHV3-30-2 | 14q32.33 | REV | IGH | 488784..489232 | AB019439 | 88784..89232 | 105871354..105871802 | NT_026437.11 | 87801354..87801802 |
| IGHV4-28 | 14q32.33 | REV | IGH | 508596..509069 | X05714 | 151..624 | 105549114..105549584 | NT_026437.11 | 87479114..87479584 |
| IGHV(II)-31-1 | 14q32.33 | REV | IGH | 478924..479232 | AB019439 | 78924..79232 | 105881354..105881662 | NT_026437.11 | 87811354..87811662 |
| IGHV3-32 | 14q32.33 | REV | IGH | 477013..477509 | AB019439 | 77013..77509 | 105883077..105883573 | NT_026437.11 | 87813077..87813573 |
| IGHV3-33 | 14q32.33 | REV | IGH | 473368..473860 | AB019439 | 73368..73860 | 105886726..105887218 | NT_026437.11 | 87816726..87817218 |
| IGHV(II)-33-1 | 14q32.33 | REV | IGH | 465947..466220 | AB019439 | 65947..66220 | 105894366..105894639 | NT_026437.11 | 87824366..87824639 |
| IGHV3-33-2 | 14q32.33 | REV | IGH | 464064..464512 | AB019439 | 64064..64512 | 105896074..105896522 | NT_026437.11 | 87826074..87826522 |
| IGHV4-34 | 14q32.33 | REV | IGH | 459517..459988 | AB019439 | 1..343 | 105900598..105900940 | NT_026437.11 | 87830598..87830940 |
| IGHV7-34-1 | 14q32.33 | REV | IGH | 455877..456349 | AB019439 | 55877..56349 | 105904237..105904709 | NT_026437.11 | 87834237..87834709 |
| IGHV3-35 | 14q32.33 | REV | IGH | 443767..444259 | M99666 | 140..632 | 105916327..105916819 | NT_026437.11 | 87846327..87846819 |
| IGHV3-36 | 14q32.33 | REV | IGH | 440399..440861 | M99667 | 218..681 | 105919724..105920187 | NT_026437.11 | 87849724..87850187 |
| IGHV3-37 | 14q32.33 | REV | IGH | 436515..437003 | M99668 | 10..489 | 105923586..105924071 | NT_026437.11 | 87853586..87854071 |
| IGHV(III)-38-1 | 14q32.33 | REV | IGH | 422685..423175 | M99669 | 10..497 | 105937413..105937901 | NT_026437.11 | 87867413..87867901 |
| IGHV(III)-38-1 | 14q32.33 | REV | IGH | 415315..415645 | AB019439 | 15315..15645 | 105944941..105945271 | NT_026437.11 | 87874941..87875271 |
| IGHV4-30-4 | 14q32.33 | REV | IGH | 408075..408316 | Z14238 | 1..438 | 105876252..105876689 | NT_026437.11 | 87806252..87806689 |
| IGHV7-40 | 14q32.33 | REV | IGH | | M99644 | 164..497 | 105952270..105952592 | NT_026437.11 | 87882270..87882592 |
| IGHV(III)-40-1 | 14q32.33 | REV | IGH | 392620..392696 | AB019438 | 192620..192696 | 105967890..105967966 | NT_026437.11 | 87897890..87897966 |
| IGHV3-30-3 | 14q32.33 | REV | IGH | | X92283 | 1..294 | 105970093..105970379 | NT_026437.11 | 87900093..87900378 |
| IGHV3-42 | 14q32.33 | REV | IGH | 369925..370362 | M99671 | 1..461 | 105762906..105763129 | NT_026437.11 | 87692869..87693089 |
| IGHV3-43 | 14q32.33 | REV | IGH | 362897..363393 | M99672 | 170..666 | 105997193..105997689 | NT_026437.11 | 87927193..87927689 |
| IGHV(II)-43-1 | 14q32.33 | REV | IGH | 360618..360826 | AB019438 | 160618..160826 | 105999760..105999968 | NT_026437.11 | 87929760..87929968 |
| IGHV(III)-44 | 14q32.33 | REV | IGH | 355142..355318 | M99673 | 62..511 | 106005056..106005444 | NT_026437.11 | 87935056..87935444 |

FIG. 41 (Continued)

| | | | | | | | |
|---|---|---|---|---|---|---|---|
| IGHV(IV)-44-1 | 14q32.33 | REV | IGH | 343764..344231 | AB019438 | 143764..144231 | 106016355..106016822 | NT_026437.11 | 87946355..87946822 |
| IGHV(II)-44-2 | 14q32.33 | REV | IGH | 339146..339382 | AB019438 | 136146..139382 | 106021204..106024440 | NT_026437.11 | 87951204..87954440 |
| IGHV1-45 | 14q32.33 | REV | IGH | 326175..326651 | X92209 | 2..478 | 106033935..106034411 | NT_026437.11 | 87963935..87964411 |
| IGHV1-46 | 14q32.33 | REV | IGH | 322057..322533 | X92343 | 153..629 | 106038053..106038529 | NT_026437.11 | 87968053..87968529 |
| IGHV(II)-46-1 | 14q32.33 | REV | IGH | 317614..317771 | AB019438 | 117614..117771 | 106042815..106042972 | NT_026437.11 | 87972815..87972972 |
| IGHV3-47 | 14q32.33 | REV | IGH | 314580..315074 | Z18900 | 1..291 | 106045553..106045843 | NT_026437.11 | 87975553..87975843 |
| IGHV(II)-47-1 | 14q32.33 | REV | IGH | 302103..302406 | AB019438 | 102103..102406 | 106058180..106058483 | NT_026437.11 | 87988180..87988483 |
| IGHV3-48 | 14q32.33 | REV | IGH | 295274..295768 | M99675 | 174..668 | 106064818..106065312 | NT_026437.11 | 87994818..87995312 |
| IGHV3-49 | 14q32.33 | REV | IGH | 276144..276644 | M99676 | 224..724 | 106083946..106084442 | NT_026437.11 | 88013946..88014442 |
| IGHV(II)-49-1 | 14q32.33 | REV | IGH | 268955..269225 | AB019438 | 68955..69225 | 106091361..106091631 | NT_026437.11 | 88021361..88021631 |
| IGHV3-50 | 14q32.33 | REV | IGH | 266998..267453 | M99677 | 10..283 | 106093318..106093588 | NT_026437.11 | 88023316..88023585 |
| IGHV5-51 | 14q32.33 | REV | IGH | 254379..254853 | M99686 | 168..641 | 106105734..106106207 | NT_026437.11 | 88035734..88036207 |
| IGHV(II)-51-1 | 14q32.33 | REV | IGH | 249747..250053 | AB019438 | 49747..50053 | 106110533..106110839 | NT_026437.11 | 88040533..88040839 |
| IGHV(II)-51-2 | 14q32.33 | REV | IGH | 248581..248843 | AB019438 | 48581..48843 | 106111743..106112005 | NT_026437.11 | 88041743..88042005 |
| IGHV3-52 | 14q32.33 | REV | IGH | 246731..247220 | M99678 | 212..701 | 106113366..106113855 | NT_026437.11 | 88043366..88043855 |
| IGHV3-53 | 14q32.33 | REV | IGH | 240421..240910 | M99679 | 38..527 | 106282134..106282436 | NT_026437.11 | 88212134..88212436 |
| IGHV(II)-53-1 | 14q32.33 | REV | IGH | 233605..233874 | AB019438 | 33605..33874 | 106126712..106126981 | NT_026437.11 | 88056712..88056981 |
| IGHV3-54 | 14q32.33 | REV | IGH | 231746..232232 | M99680 | 147..631 | 106128356..106128840 | NT_026437.11 | 88058356..88058840 |
| IGHV4-55 | 14q32.33 | REV | IGH | 226980..227454 | M99685 | 230..704 | 106133132..106133606 | NT_026437.11 | 88063132..88063606 |
| IGHV7-56 | 14q32.33 | REV | IGH | 223335..223808 | M29810 | 136..429 | 106136958..106137251 | NT_026437.11 | 88066958..88067251 |
| IGHV3-57 | 14q32.33 | REV | IGH | 214314..214658 | M29815 | 7..568 | 106146106..106146421 | NT_026437.11 | 88076106..88076381 |
| IGHV1-8 | 14q32.33 | REV | IGH | 750026..750503 | M99637 | 58..535 | 105540083..105610560 | NT_026437.11 | 87540083..87540560 |
| IGHV4-39 | 14q32.33 | REV | IGH | 411486..411963 | AB019439 | 1..328 | 105948662..105948989 | NT_026437.11 | 87878662..87878989 |
| IGHV(II)-60 | 14q32.33 | REV | IGH | 201883..202375 | AB019438 | 1883..2375 | 106158211..106158703 | NT_026437.11 | 88088211..88088703 |
| IGHV3-60-1 | 14q32.33 | REV | IGH | 195563..195869 | AB019437 | 195563..195831 | 106164755..106165023 | NT_026437.11 | 88094755..88095023 |
| IGHV4-61 | 14q32.33 | REV | IGH | 193980..194456 | M29811 | 151..628 | 106166130..106166606 | NT_026437.11 | 88096130..88096606 |
| IGHV3-62 | 14q32.33 | REV | IGH | 189953..190447 | AB019437 | 189953..190447 | 106170139..106170633 | NT_026437.11 | 88100139..88100633 |
| IGHV(II)-62-1 | 14q32.33 | REV | IGH | 182749..183060 | AB019437 | 182749..183060 | 106177526..106177837 | NT_026437.11 | 88107526..88107837 |
| IGHV3-63 | 14q32.33 | REV | IGH | 180846..181313 | M99681 | 10..506 | 106179251..106179740 | NT_026437.11 | 88109251..88109740 |
| IGHV3-64 | 14q32.33 | REV | IGH | 175347..175841 | M99682 | 78..575 | 106184745..106185242 | NT_026437.11 | 88114745..88115242 |
| IGHV3-65 | 14q32.33 | REV | IGH | 166993..167487 | Z27503 | 1..301 | 106193140..106193440 | NT_026437.11 | 88123140..88123440 |
| IGHV(II)-65-1 | 14q32.33 | REV | IGH | 821563..821903 | AB019441 | 21563..21903 | 105538683..105539023 | NT_026437.11 | 87468683..87469023 |
| IGHV4-61 | 14q32.33 | REV | IGH | 161481..161753 | AB019437 | 161481..161753 | 106198833..106199105 | NT_026437.11 | 88128833..88129105 |
| IGHV3-66 | 14q32.33 | REV | IGH | 158060..158549 | X92218 | 2..491 | 106202037..106202526 | NT_026437.11 | 88132037..88132526 |
| IGHV1-67 | 14q32.33 | REV | IGH | 152482..152960 | AB019437 | 1..434 | 106207626..106208059 | NT_026437.11 | 88137626..88138059 |
| IGHV(II)-67-1 | 14q32.33 | REV | IGH | 146982..147131 | AB019437 | 146982..147131 | 106213455..106213604 | NT_026437.11 | 88143455..88143604 |
| IGHV(III)-67-2 | 14q32.33 | REV | IGH | 146324..146422 | AB019437 | 146324..146422 | 106214164..106214262 | NT_026437.11 | 88144164..88144262 |

| | | | | | | | |
|---|---|---|---|---|---|---|---|
| IGHV(III)-67-3 | 14q32.33 | REV | IGH | 140636..140910 | AB019437 | 140636..140910 | 106219676..106219950 | NT_026437.11 | 88149676..88149950 |
| IGHV(III)-67-4 | 14q32.33 | REV | IGH | 138127..138432 | AB019437 | 138127..138432 | 106222154..106222459 | NT_026437.11 | 88152154..88152459 |
| IGHV1-68 | 14q32.33 | REV | IGH | 129238..129717 | AB019437 | 129238..129717 | 106230869..106231348 | NT_026437.11 | 88160869..88161348 |
| IGHV1-69 | 14q32.33 | REV | IGH | 119174..119651 | L22582 | 233..710 | 106240935..106241412 | NT_026437.11 | 88170935..88171412 |
| IGHV2-70 | 14q32.33 | REV | IGH | 110279..110761 | L21969 | 1..444 | 106249864..106250307 | NT_026437.11 | 88179864..88180307 |
| IGHV3-71 | 14q32.33 | REV | IGH | 105684..106184 | AB019437 | 105684..106184 | 106254402..106254902 | NT_026437.11 | 88184402..88184902 |
| IGHV3-72 | 14q32.33 | REV | IGH | 90150..90650 | X92206 | 87..587 | 106269936..106270436 | NT_026437.11 | 88199936..88200436 |
| IGHV3-73 | 14q32.33 | REV | IGH | 78150..78650 | X70197 | 1..300 | 105990226..105990526 | NT_026437.11 | 87920226..87920526 |
| IGHV3-74 | 14q32.33 | REV | IGH | 70412..70906 | L33851 | 23..476 | 106289721..106290174 | NT_026437.11 | 88219721..88220174 |
| IGHV(II)-74-1 | 14q32.33 | REV | IGH | 59900..60068 | AB019437 | 59900..60068 | 106300518..106300686 | NT_026437.11 | 88230518..88230686 |
| IGHV3-75 | 14q32.33 | REV | IGH | 57164..57672 | Z27510 | 4..308 | 106302955..106303259 | NT_026437.11 | 88232955..88233259 |
| IGHV3-76 | 14q32.33 | REV | IGH | 53003..53492 | AB019437 | 53003..53492 | 106307134..106307425 | NT_026437.11 | 88237134..88237425 |
| IGHV(III)-76-1 | 14q32.33 | REV | IGH | 49245..49551 | AB019437 | 49245..49551 | 106311035..106311341 | NT_026437.11 | 88241035..88241341 |
| IGHV5-78 | 14q32.33 | REV | IGH | 29780..30228 | X92213 | 592..1027 | 106330373..106330806 | NT_026437.11 | 88260373..88260806 |
| IGHV(II)-78-1 | 14q32.33 | REV | IGH | 15431..15744 | AB019437 | 15431..15744 | 106344842..106345155 | NT_026437.11 | 88274842..88275155 |
| IGHV3-79 | 14q32.33 | REV | IGH | 13237..13688 | AB019437 | 13237..13688 | 106346898..106347349 | NT_026437.11 | 88276898..88277349 |
| IGHV4-80 | 14q32.33 | REV | IGH | 8147..8547 | AB019437 | 8147..8547 | 106352039..106352439 | NT_026437.11 | 88282039..88282439 |
| IGHV7-81 | 14q32.33 | REV | IGH | 6315..6790 | AB019437 | 6315..6790 | 106353796..106354271 | NT_026437.11 | 88283796..88284271 |
| IGHV(II)-82 | 14q32.33 | REV | IGH | 1490..1781 | AB019437 | 1490..1781 | 106358805..106359096 | NT_026437.11 | 88288805..88289096 |

FIG. 42

| IMGT Gene | Chromosomal localization | Orientation | NCBI Gene ID | Reference GRCm38.p3 C57BL/6J | NCBI Gene positions in sequence | Orientation sequence | MGI ID | MGI symbol |
|---|---|---|---|---|---|---|---|---|
| IGHV1-86 | 12F2 (62.59 cM) | REV | 668599 | NC_000078.6 | 116009659..116009954 | -1 | MGI:3645729 | Ighv1-86 |
| IGHV1-85 | 12F2 (62.59 cM) | REV | 668597 | NC_000078.6 | 116000028..116000321 | -1 | MGI:3645723 | Ighv1-85 |
| IGHV1-84 | 12F2 (62.59 cM) | REV | 434609 | NC_000078.6 | 115980702..115981134 | -1 | MGI:3644235 | Ighv1-84 |
| IGHV1-83 | 12F2 (62.59 cM) | REV | 620140 | NC_000078.6 | 115963817..115964109 | -1 | MGI:3648939 | Ighv1-83 |
| IGHV1-82 | 12F2 (62.59 cM) | REV | 1.01E+08 | NC_000078.6 | 115952538..115952831 | -1 | MGI:4439671 | Ighv1-82 |
| IGHV1-81 | 12F2 (62.59 cM) | REV | 668591 | NC_000078.6 | 115920279..115920572 | -1 | MGI:4439635 | Ighv1-81 |
| IGHV1-80 | 12F2 (62.59 cM) | REV | 668589 | NC_000078.6 | 115912344..115912637 | -1 | MGI:4439738 | Ighv1-80 |

| | | | | | | |
|---|---|---|---|---|---|---|
| IGHV1-79 | 12F2 (62.59 cM) | REV | 435331 | NC_000078.6 | 115888096..115888389 | -1 | MGI:3648258 | Ighv1-79 |
| IGHV1-78 | 12F2 (62.59 cM) | REV | 213570 | NC_000078.6 | 115868773..115869066 | -1 | MGI:4439736 | Ighv1-78 |
| IGHV1-77 | 12F2 (62.59 cM) | REV | 619994 | NC_000078.6 | 115861867..115862160 | -1 | MGI:4439670 | Ighv1-77 |
| IGHV8-16 | 12F2 (62.59 cM) | REV | 1.01E+08 | NC_000078.6 | 115858008..115858301 | -1 | MGI:5434409 | Ighv8-16 |
| IGHV1-76 | 12F2 (62.59 cM) | REV | 1.01E+08 | NC_000078.6 | 115847881..115848174 | -1 | MGI:4439737 | Ighv1-76 |
| IGHV8-15 | 12F2 (62.59 cM) | REV | 1.01E+08 | NC_000078.6 | 115844016..115844309 | -1 | MGI:5434408 | Ighv8-15 |
| IGHV1-75 | 12F2 (62.59 cM) | REV | 622728 | NC_000078.6 | 115833950..115834243 | -1 | MGI:4439735 | Ighv1-75 |
| IGHV8-14 | 12F2 (62.59 cM) | REV | 668582 | NC_000078.6 | 115808427..115808727 | -1 | MGI:3648977 | Ighv8-14 |
| IGHV1-74 | 12F2 (62.59 cM) | REV | 1.01E+08 | NC_000078.6 | 115802690..115803080 | -1 | MGI:4439634 | Ighv1-74 |
| IGHV1-73 | 12F2 (62.59 cM) | REV | 668577 | NC_000078.6 | 115790593..115790887 | -1 | MGI:3645131 | Ighv1-73 |
| IGHV8-13 | 12F2 (62.59 cM) | REV | 1.01E+08 | NC_000078.6 | 115765335..115765635 | -1 | MGI:4439734 | Ighv8-13 |
| IGHV1-72 | 12F2 (62.59 cM) | REV | 619916 | NC_000078.6 | 115757984..115758277 | -1 | MGI:4439633 | Ighv1-72 |
| IGHV1-71 | 12F2 (62.59 cM) | REV | 619886 | NC_000078.6 | 115742205..115742506 | -1 | MGI:3643033 | Ighv1-71 |
| IGHV1-70 | 12F2 (62.59 cM) | REV | 638634 | NC_000078.6 | 115691889..115692182 | -1 | MGI:3644620 | Ighv1-70 |
| IGHV8-12 | 12F2 (62.59 cM) | REV | 780960 | NC_000078.6 | 115647945..115648245 | -1 | MGI:3642873 | Ighv8-12 |
| IGHV1-69 | 12F2 (62.59 cM) | REV | 619833 | NC_000078.6 | 115623203..115623595 | -1 | MGI:4439632 | Ighv1-69 |
| IGHV1-68 | 12F2 (62.59 cM) | REV | 780959 | NC_000078.6 | 115611340..115611633 | -1 | MGI:5009923 | Ighv1-68 |
| IGHV1-67 | 12F2 (62.59 cM) | REV | 435328 | NC_000078.6 | 115603940..115604233 | -1 | MGI:3645228 | Ighv1-67 |
| IGHV1-66 | 12F2 (62.59 cM) | REV | 380824 | NC_000078.6 | 115593110..115593403 | -1 | MGI:4439825 | Ighv1-66 |
| IGHV8-11 | 12F2 (62.59 cM) | REV | 636462 | NC_000078.6 | 115567149..115567449 | -1 | MGI:3644925 | Ighv8-11 |
| IGHV1-65 | 12F2 (62.58 cM) | REV | 780958 | NC_000078.6 | 115532055..115532347 | -1 | MGI:5009922 | Ighv1-65 |
| IGHV8-10 | 12F2 (62.58 cM) | REV | 780957 | NC_000078.6 | 115519340..115519640 | -1 | MGI:5009921 | Ighv8-10 |
| IGHV1-64 | 12F2 (62.58 cM) | REV | 619833 | NC_000078.6 | 115507587..115507977 | -1 | MGI:4439789 | Ighv1-64 |
| IGHV1-63 | 12F2 (62.58 cM) | REV | 380823 | NC_000078.6 | 115495625..115496058 | -1 | MGI:3642755 | Ighv1-63 |
| IGHV8-9 | 12F2 (62.57 cM) | REV | 432709 | NC_000078.6 | 115468331..115468632 | -1 | MGI:3644475 | Ighv8-9 |
| IGHV1-62-3 | 12F2 (62.57 cM) | REV | 668549 | NC_000078.6 | 115460999..115461431 | -1 | MGI:3648544 | Ighv1-62-3 |
| IGHV1-62-2 | 12F2 (62.57 cM) | REV | 238448 | NC_000078.6 | 115446417..115446710 | -1 | MGI:3644968 | Ighv1-62-2 |
| IGHV1-62-1 | 12F2 (62.55 cM) | REV | 668544 | NC_000078.6 | 115386707..115386988 | -1 | MGI:3704125 | Ighv1-62-1 |
| IGHV1-62 | 12F2 (62.55 cM) | REV | 668542 | NC_000078.6 | 115371986..115372278 | -1 | MGI:5009844 | Ighv1-62 |

FIG. 42 (Continued)

| | | | | | | | |
|---|---|---|---|---|---|---|---|
| IGHV1-61 | 12F2 (62.55 cM) | REV | 674018 | NC_000078.6 | 115359140..115359433 | -1 | MGI:4439824 | ighv1-61 |
| IGHV1-60 | 12F2 (62.55 cM) | REV | 780940 | NC_000078.6 | 115344537..115344830 | -1 | MGI:5009920 | ighv1-60 |
| IGHV1-59 | 12F2 (62.54 cM) | REV | 432708 | NC_000078.6 | 115335057..115335513 | -1 | MGI:3644474 | ighv1-59 |
| IGHV1-58 | 12F2 (62.54 cM) | REV | 780939 | NC_000078.6 | 115312166..115312597 | -1 | MGI:4439557 | ighv1-58 |
| IGHV8-8 | 12F2 (62.54 cM) | REV | 780938 | NC_000078.6 | 115294066..115294362 | -1 | MGI:3815333 | ighv8-8 |
| IGHV1-57 | 12F2 (62.53 cM) | REV | 780937 | NC_000078.6 | 115268424..115268715 | -1 | MGI:5009919 | ighv1-57 |
| IGHV8-7 | 12F2 (62.53 cM) | REV | 780936 | NC_000078.6 | 115258139..115258432 | -1 | MGI:5009918 | ighv8-7 |
| IGHV1-56 | 12F2 (62.53 cM) | REV | 382695 | NC_000078.6 | 115242802..115243095 | -1 | MGI:4439715 | ighv1-56 |
| IGHV1-55 | 12F2 (62.52 cM) | REV | 780932 | NC_000078.6 | 115208137..115208527 | -1 | MGI:4439716 | ighv1-55 |
| IGHV1-54 | 12F2 (62.52 cM) | REV | 211331 | NC_000078.6 | 115193675..115193968 | -1 | MGI:3647133 | ighv1-54 |
| IGHV8-6 | 12F2 (62.51 cM) | REV | 629930 | NC_000078.6 | 115165777..115166077 | -1 | MGI:3645823 | ighv8-6 |
| IGHV1-53 | 12F2 (62.51 cM) | REV | 780931 | NC_000078.6 | 115158445..115158835 | -1 | MGI:3576502 | ighv1-53 |
| IGHV1-52 | 12F2 (62.51 cM) | REV | 382696 | NC_000078.6 | 115145487..115145780 | -1 | MGI:4439752 | ighv1-52 |
| IGHV1-51 | 12F2 (62.51 cM) | REV | 780930 | NC_000078.6 | 115131375..115131668 | -1 | MGI:5009917 | ighv1-51 |
| IGHV1-50 | 12F2 (62.5 cM) | REV | 780929 | NC_000078.6 | 115119748..115120041 | -1 | MGI:4439753 | ighv1-50 |
| IGHV8-5 | 12F2 (62.49 cM) | REV | 640506 | NC_000078.6 | 115067560..115067860 | -1 | MGI:3645478 | ighv8-5 |
| IGHV1-49 | 12F2 (62.49 cM) | REV | 629925 | NC_000078.6 | 115055223..115055516 | -1 | MGI:4439754 | ighv1-49 |
| IGHV1-48 | 12F2 (62.49 cM) | REV | 780928 | NC_000078.6 | 115038227..115038520 | -1 | MGI:5009916 | ighv1-48 |
| IGHV8-4 | 12F2 (62.48 cM) | REV | 629919 | NC_000078.6 | 115024026..115024318 | -1 | MGI:3646040 | ighv8-4 |
| IGHV8-3 | 12F2 (62.48 cM) | REV | 780927 | NC_000078.6 | 115003418..115003712 | -1 | MGI:5009915 | ighv8-3 |
| IGHV1-47 | 12F2 (62.48 cM) | REV | 629915 | NC_000078.6 | 114991108..114991401 | -1 | MGI:4439890 | ighv1-47 |
| IGHV1-46 | 12F2 (62.48 cM) | REV | 668522 | NC_000078.6 | 114977693..114977986 | -1 | MGI:5009843 | ighv1-46 |
| IGHV1-45 | 12F2 (62.47 cM) | REV | 780894 | NC_000078.6 | 114970055..114970348 | -1 | MGI:5009913 | ighv1-45 |
| IGHV1-44 | 12F2 (62.47 cM) | REV | 668521 | NC_000078.6 | 114963380..114963674 | -1 | MGI:5009842 | ighv1-44 |
| IGHV1-43 | 12F2 (62.47 cM) | REV | 629908 | NC_000078.6 | 114945950..114946243 | -1 | MGI:3704124 | ighv1-43 |
| IGHV1-42 | 12F2 (62.47 cM) | REV | 629906 | NC_000078.6 | 114937154..114937544 | -1 | MGI:3704123 | ighv1-42 |
| IGHV1-41 | 12F2 (62.47 cM) | REV | 629904 | NC_000078.6 | 114932371..114932664 | -1 | MGI:3649084 | ighv1-41 |
| IGHV1-40 | 12F2 (62.47 cM) | REV | 780892 | NC_000078.6 | 114924941..114925233 | -1 | MGI:5009912 | ighv1-40 |
| IGHV1-39 | 12F2 (62.46 cM) | REV | 780891 | NC_000078.6 | 114914599..114914892 | -1 | MGI:4439888 | ighv1-39 |

FIG. 42 (Continued)

| | | | | | | | |
|---|---|---|---|---|---|---|---|
| IGHV1-38 | 12F2 (62.46 cM) | REV | 780890 | NC_000078.6 | 114910011..114910303 | -1 | MGI:5009911 | ighv1-38 |
| IGHV1-37 | 12F2 (62.46 cM) | REV | 668517 | NC_000078.6 | 114896238..114896531 | -1 | MGI:4439640 | ighv1-37 |
| IGHV1-36 | 12F2 (62.46 cM) | REV | 629897 | NC_000078.6 | 114879888..114880181 | -1 | MGI:4439639 | ighv1-36 |
| IGHV1-35 | 12F2 (62.46 cM) | REV | 668515 | NC_000078.6 | 114875302..114875597 | -1 | MGI:3644935 | ighv1-35 |
| IGHV1-34 | 12F2 (62.45 cM) | REV | 628614 | NC_000078.6 | 114851190..114851483 | -1 | MGI:4439659 | ighv1-34 |
| IGHV1-33 | 12F2 (62.45 cM) | REV | 641247 | NC_000078.6 | 114843693..114844083 | -1 | MGI:4439617 | ighv1-33 |
| IGHV1-32 | 12F2 (62.45 cM) | REV | 780888 | NC_000078.6 | 114835223..114835516 | -1 | MGI:5009910 | ighv1-32 |
| IGHV1-31 | 12F2 (62.45 cM) | REV | 629893 | NC_000078.6 | 114829264..114829557 | -1 | MGI:4439889 | ighv1-31 |
| IGHV1-30 | 12F2 (62.44 cM) | REV | 668511 | NC_000078.6 | 114817099..114817390 | -1 | MGI:4937173 | ighv1-30 |
| IGHV1-29 | 12F2 (62.44 cM) | REV | 780887 | NC_000078.6 | 114812321..114812605 | -1 | MGI:5009909 | ighv1-29 |
| IGHV1-28 | 12F2 (62.44 cM) | REV | 668510 | NC_000078.6 | 114809421..114809714 | -1 | MGI:3644938 | ighv1-28 |
| IGHV1-27 | 12F2 (62.44 cM) | REV | 780886 | NC_000078.6 | 114804616..114804909 | -1 | MGI:5009908 | ighv1-27 |
| IGHV1-26 | 12F2 (62.44 cM) | REV | 629884 | NC_000078.6 | 114788372..114788665 | -1 | MGI:4439641 | ighv1-26 |
| IGHV1-25 | 12F2 (62.44 cM) | REV | 640497 | NC_000078.6 | 114781409..114781702 | -1 | MGI:3648295 | ighv1-25 |
| IGHV1-24 | 12F2 (62.44 cM) | REV | 780885 | NC_000078.6 | 114772928..114773221 | -1 | MGI:3815052 | ighv1-24 |
| IGHV1-23 | 12F2 (62.43 cM) | REV | 780884 | NC_000078.6 | 114764450..114764743 | -1 | MGI:3815050 | ighv1-23 |
| IGHV1-22 | 12F2 (62.43 cM) | REV | 780883 | NC_000078.6 | 114746273..114746566 | -1 | MGI:4439784 | ighv1-22 |
| IGHV1-21 | 12F2 (62.43 cM) | REV | 668499 | NC_000078.6 | 114740383..114740840 | -1 | MGI:5009841 | ighv1-21 |
| IGHV1-21-1 | 12F2 (62.43 cM) | REV | 631595 | NC_000078.6 | 114736245..114736538 | -1 | MGI:3645737 | ighv1-21-1 |
| IGHV1-20 | 12F2 (62.42 cM) | REV | 668497 | NC_000078.6 | 114723772..114724065 | -1 | MGI:3644607 | ighv1-20 |
| IGHV1-19 | 12F2 (62.42 cM) | REV | 382692 | NC_000078.6 | 114708648..114708941 | -1 | MGI:4439779 | ighv1-19 |
| IGHV1-19-1 | 12F2 (62.42 cM) | REV | 668493 | NC_000078.6 | 114704147..114704440 | -1 | MGI:3644603 | ighv1-19-1 |
| IGHV1-18 | 12F2 (62.42 cM) | REV | 629871 | NC_000078.6 | 114682632..114682925 | -1 | MGI:4439780 | ighv1-18 |
| IGHV1-17 | 12F2 (62.42 cM) | REV | 629869 | NC_000078.6 | 114676749..114677042 | -1 | MGI:3647700 | ighv1-17 |
| IGHV1-17-1 | 12F2 (62.42 cM) | REV | 780926 | NC_000078.6 | 114671968..114672262 | -1 | MGI:5009914 | ighv1-17-1 |
| IGHV1-16 | 12F2 (62.42 cM) | REV | 629866 | NC_000078.6 | 114665872..114666165 | -1 | MGI:3647704 | ighv1-16 |
| IGHV1-15 | 12F2 (62.41 cM) | REV | 629865 | NC_000078.6 | 114657353..114657646 | -1 | MGI:4439782 | ighv1-15 |
| IGHV1-14 | 12F2 (62.41 cM) | REV | 629863 | NC_000078.6 | 114646572..114646865 | -1 | MGI:4439781 | ighv1-14 |
| IGHV1-13 | 12F2 (62.41 cM) | REV | 780865 | NC_000078.6 | 114630680..114630973 | -1 | MGI:5009907 | ighv1-13 |

FIG. 42 (Continued)

| | | | | | | | | |
|---|---|---|---|---|---|---|---|---|
| IGHV1-12 | 12F2 (62.41 cM) | REV | 629860 | NC_000078.6 | 114615850..114616143 | -1 | MGI:3646284 | ighv1-12 |
| IGHV1-11 | 12F2 (62.41 cM) | REV | 629859 | NC_000078.6 | 114612244..114612536 | -1 | MGI:5009835 | ighv1-11 |
| IGHV1-10 | 12F2 (62.40 cM) | REV | 637050 | NC_000078.6 | 114597878..114598175 | -1 | MGI:5009837 | ighv1-10 |
| IGHV1-9 | 12F2 (62.40 cM) | REV | 668478 | NC_000078.6 | 114583569..114583862 | -1 | MGI:4439621 | ighv1-9 |
| IGHV15-2 | 12F2 (62.40 cM) | REV | 780864 | NC_000078.6 | 114564578..114564874 | -1 | MGI:4947963 | ighv15-2 |
| IGHV1-8 | 12F2 (62.39 cM) | REV | 780863 | NC_000078.6 | 114555610..114555902 | -1 | MGI:5009906 | ighv1-8 |
| IGHV10-4 | 12F2 (62.39 cM) | REV | 780862 | NC_000078.6 | 114547258..114547556 | -1 | MGI:5009905 | ighv10-4 |
| IGHV1-7 | 12F2 (62.39 cM) | REV | 668474 | NC_000078.6 | 114538495..114538788 | -1 | MGI:3704122 | ighv1-7 |
| IGHV1-6 | 12F2 (62.39 cM) | REV | 780861 | NC_000078.6 | 114532972..114533264 | -1 | MGI:5009904 | ighv1-6 |
| IGHV10-3 | 12F2 (62.39 cM) | REV | 380809 | NC_000078.6 | 114523441..114523887 | -1 | MGI:3648785 | ighv10-3 |
| IGHV1-5 | 12F2 (62.39 cM) | REV | 668469 | NC_000078.6 | 114513330..114513623 | -1 | MGI:3704121 | ighv1-5 |
| IGHV10-2 | 12F2 (62.38 cM) | REV | 780860 | NC_000078.6 | 114496003..114496300 | -1 | MGI:5009903 | ighv10-2 |
| IGHV1-4 | 12F2 (62.38 cM) | REV | 432702 | NC_000078.6 | 114487136..114487429 | -1 | MGI:4439618 | ighv1-4 |
| IGHV1-3 | 12F2 (62.38 cM) | REV | 780859 | NC_000078.6 | 114481615..114481916 | -1 | MGI:5009902 | ighv1-3 |
| IGHV10-1 | 12F2 (62.38 cM) | REV | 380808 | NC_000078.6 | 114479007..114479451 | -1 | MGI:4439620 | ighv10-1 |
| IGHV1-2 | 12F2 (62.38 cM) | REV | 238428 | NC_000078.6 | 114469075..114469371 | -1 | MGI:4439924 | ighv1-2 |
| IGHV8-2 | 12F2 (62.38 cM) | REV | 629849 | NC_000078.6 | 114462290..114462589 | -1 | MGI:3647474 | ighv8-2 |
| IGHV6-7 | 12F2 (62.38 cM) | REV | 432701 | NC_000078.6 | 114455626..114455925 | -1 | MGI:3644477 | ighv6-7 |
| IGHV6-6 | 12F2 (62.37 cM) | REV | 238427 | NC_000078.6 | 114434788..114435087 | -1 | MGI:4439619 | ighv6-6 |
| IGHV6-5 | 12F2 (62.37 cM) | REV | 639510 | NC_000078.6 | 114416596..114416895 | -1 | MGI:3647134 | ighv6-5 |
| IGHV6-4 | 12F2 (62.37 cM) | REV | 628398 | NC_000078.6 | 114406474..114406773 | -1 | MGI:3704120 | ighv6-4 |
| IGHV6-3 | 12F2 (62.36 cM) | REV | 629845 | NC_000078.6 | 114391712..114392010 | -1 | MGI:4439854 | ighv6-3 |
| IGHV12-3 | 12F2 (62.36 cM) | REV | 435321 | NC_000078.6 | 114366526..114366819 | -1 | MGI:3646760 | ighv12-3 |
| IGHV13-2 | 12F2 (62.36 cM) | REV | 629842 | NC_000078.6 | 114357761..114358060 | -1 | MGI:3705861 | ighv13-2 |
| IGHV1-1 | 12F2 (62.36 cM) | REV | 780834 | NC_000078.6 | 114351705..114351995 | -1 | MGI:5009901 | ighv1-1 |
| IGHV8-1 | 12F2 (62.35 cM) | REV | 780833 | NC_000078.6 | 114332796..114333086 | -1 | MGI:5009900 | ighv8-1 |
| IGHV3-8 | 12F2 (62.35 cM) | REV | 780831 | NC_000078.6 | 114322376..114322666 | -1 | MGI:3645298 | ighv3-8 |
| IGHV5-21 | 12F2 (62.35 cM) | REV | 780832 | NC_000078.6 | 114320030..114320324 | -1 | MGI:5009899 | ighv5-21 |
| IGHV3-7 | 12F2 (62.35 cM) | REV | 780830 | NC_000078.6 | 114314186..114314479 | -1 | MGI:5009898 | ighv3-7 |

FIG. 42 (Continued)

| | | | | | | |
|---|---|---|---|---|---|---|
| IGHV9-4 | 12F2 (62.34 cM) | REV | 636260 | NC_000078.6 | 114299961..114300254 | -1 | MGI:3646379 | ighv9-4 |
| IGHV3-6 | 12F2 (62.34 cM) | REV | 780829 | NC_000078.6 | 114288152..114288447 | -1 | MGI:4439856 | ighv3-6 |
| IGHV13-1 | 12F2 (62.33 cM) | REV | 780828 | NC_000078.6 | 114267607..114267906 | -1 | MGI:4439855 | ighv13-1 |
| IGHV3-5 | 12F2 (62.33 cM) | REV | 633457 | NC_000078.6 | 114262652..114262950 | -1 | MGI:3648045 | ighv3-5 |
| IGHV3-4 | 12F2 (62.33 cM) | REV | 629833 | NC_000078.6 | 114253617..114253915 | -1 | MGI:3644034 | ighv3-4 |
| IGHV7-4 | 12F2 (62.32 cM) | REV | 632654 | NC_000078.6 | 114222788..114223254 | -1 | MGI:4439763 | ighv7-4 |
| IGHV3-3 | 12F2 (62.31 cM) | REV | 668438 | NC_000078.6 | 114196439..114196875 | -1 | MGI:3643949 | ighv3-3 |
| IGHV14-4 | 12F2 (62.30 cM) | REV | 629826 | NC_000078.6 | 114176438..114176867 | -1 | MGI:4439765 | ighv14-4 |
| IGHV15-1 | 12F2 (62.30 cM) | REV | 780827 | NC_000078.6 | 114158025..114158315 | -1 | MGI:5009897 | ighv15-1 |
| IGHV7-3 | 12F2 (62.30 cM) | REV | 629822 | NC_000078.6 | 114153180..114153644 | -1 | MGI:4439766 | ighv7-3 |
| IGHV9-3 | 12F2 (62.29 cM) | REV | 780825 | NC_000078.6 | 114140692..114141122 | -1 | MGI:3642720 | ighv9-3 |
| IGHV12-2 | 12F2 (62.29 cM) | REV | 780824 | NC_000078.6 | 114127533..114127984 | -1 | MGI:5009896 | ighv12-2 |
| IGHV9-2 | 12F2 (62.28 cM) | REV | 629818 | NC_000078.6 | 114109001..114109430 | -1 | MGI:3643816 | ighv9-2 |
| IGHV12-1 | 12F2 (62.28 cM) | REV | 780823 | NC_000078.6 | 114107259..114107563 | -1 | MGI:5295669 | ighv12-1 |
| IGHV9-1 | 12F2 (62.28 cM) | REV | 195180 | NC_000078.6 | 114093928..114094221 | -1 | MGI:4439911 | ighv9-1 |
| IGHV6-2 | 12F2 (62.28 cM) | REV | 780822 | NC_000078.6 | 114089387..114089681 | -1 | MGI:5009895 | ighv6-2 |
| IGHV16-1 | 12F2 (62.27 cM) | REV | 629812 | NC_000078.6 | 114068828..114069126 | -1 | MGI:3643819 | ighv16-1 |
| IGHV14-3 | 12F2 (62.27 cM) | REV | 238418 | NC_000078.6 | 114059845..114060273 | -1 | MGI:4439764 | ighv14-3 |
| IGHV11-2 | 12F2 (62.27 cM) | REV | 780818 | NC_000078.6 | 114048241..114048704 | -1 | MGI:4947968 | ighv11-2 |
| IGHV3-2 | 12F2 (62.26 cM) | REV | 780817 | NC_000078.6 | 114033803..114034097 | -1 | MGI:4439923 | ighv3-2 |
| IGHV4-2 | 12F2 (62.26 cM) | REV | 668423 | NC_000078.6 | 114013144..114013439 | -1 | MGI:5009840 | ighv4-2 |
| IGHV14-2 | 12F2 (62.25 cM) | REV | 668421 | NC_000078.6 | 113994469..113994898 | -1 | MGI:4439607 | ighv14-2 |
| IGHV11-1 | 12F2 (62.25 cM) | REV | 780804 | NC_000078.6 | 113981879..113982174 | -1 | MGI:4439535 | ighv11-1 |
| IGHV3-1 | 12F2 (62.24 cM) | REV | 780803 | NC_000078.6 | 113964390..113964683 | -1 | MGI:4439534 | ighv3-1 |
| IGHV4-1 | 12F2 (62.24 cM) | REV | 780802 | NC_000078.6 | 113948284..113948577 | -1 | MGI:4439536 | ighv4-1 |
| IGHV14-1 | 12F2 (62.23 cM) | REV | 780801 | NC_000078.6 | 113931953..113932246 | -1 | MGI:4439920 | ighv14-1 |
| IGHV7-2 | 12F2 (62.23 cM) | REV | 780800 | NC_000078.6 | 113912025..113912483 | -1 | MGI:4439623 | ighv7-2 |
| IGHV7-1 | 12F2 (62.22 cM) | REV | 780799 | NC_000078.6 | 113896408..113896946 | -1 | MGI:4439622 | ighv7-1 |
| IGHV5-19 | 12F2 (62.22 cM) | REV | 780798 | NC_000078.6 | 113884761..113885342 | -1 | MGI:5009894 | ighv5-19 |

FIG. 42 (Continued)

| | | | | | | | |
|---|---|---|---|---|---|---|---|
| IGHV2-9 | 12F2 (62.22 cM) | REV | 640046 | NC_000078.6 | 113879097..113879388 | | MGI:4439624 | Ighv2-9 |
| IGHV2-8 | 12F2 (62.22 cM) | REV | 780797 | NC_000078.6 | 113877361..113877659 | -1 | MGI:5009893 | Ighv2-8 |
| IGHV5-18 | 12F2 (62.22 cM) | REV | 780796 | NC_000078.6 | 113875772..113876239 | -1 | MGI:5009892 | Ighv5-18 |
| IGHV5-17 | 12F2 (62.21 cM) | REV | 780794 | NC_000078.6 | 113859149..113859442 | -1 | MGI:4439533 | Ighv5-17 |
| IGHV5-16 | 12F2 (62.21 cM) | REV | 633568 | NC_000078.6 | 113838528..113838821 | -1 | MGI:4439556 | Ighv5-16 |
| IGHV5-15 | 12F2 (62.20 cM) | REV | 780792 | NC_000078.6 | 113826648..113826941 | -1 | MGI:4439812 | Ighv5-15 |
| IGHV2-7 | 12F2 (62.20 cM) | REV | 780793 | NC_000078.6 | 113807314..113807747 | -1 | MGI:4439521 | Ighv2-7 |
| IGHV2-6-8 | 12F2 (62.19 cM) | REV | 791090 | NC_000078.6 | 113796138..113796430 | -1 | MGI:4439811 | Ighv2-6-8 |
| IGHV2-9-1 | 12F2 (62.18 cM) | REV | 791089 | NC_000078.6 | 113769857..113770142 | -1 | MGI:4439519 | Ighv2-9-1 |
| IGHV5-12-4 | 12F2 (62.18 cM) | REV | 628098 | NC_000078.6 | 113762251..113762544 | -1 | MGI:3645977 | Ighv5-12-4 |
| IGHV5-9-1 | 12F2 (62.17 cM) | REV | 641178 | NC_000078.6 | 113736113..113736406 | -1 | MGI:4439810 | Ighv5-9-1 |
| IGHV2-6 | 12F2 (62.17 cM) | REV | 630486 | NC_000078.6 | 113716672..113716962 | -1 | MGI:4439518 | Ighv2-6 |
| IGHV5-12 | 12F2 (62.16 cM) | REV | 668395 | NC_000078.6 | 113702126..113702419 | -1 | MGI:4439516 | Ighv5-12 |
| IGHV5-11 | 12F2 (62.16 cM) | REV | 777784 | NC_000078.6 | 113687229..113687505 | -1 | MGI:5009891 | Ighv5-11 |
| IGHV2-5 | 12F2 (62.16 cM) | REV | 638605 | NC_000078.6 | 113685482..113685774 | -1 | MGI:4439517 | Ighv2-5 |
| IGHV5-10 | 12F2 (62.16 cM) | REV | 777783 | NC_000078.6 | 113669673..113669968 | -1 | MGI:3642589 | Ighv5-10 |
| IGHV5-9 | 12F2 (62.15 cM) | REV | 544896 | NC_000078.6 | 113661771..113662228 | -1 | MGI:4439873 | Ighv5-9 |
| IGHV5-8 | 12F2 (62.15 cM) | REV | 777782 | NC_000078.6 | 113654967..113655245 | -1 | MGI:5009890 | Ighv5-8 |
| IGHV2-4 | 12F2 (62.15 cM) | REV | 668389 | NC_000078.6 | 113653291..113653583 | -1 | MGI:3643263 | Ighv2-4 |
| IGHV5-7 | 12F2 (62.15 cM) | REV | 777781 | NC_000078.6 | 113634686..113634981 | -1 | MGI:3642590 | Ighv5-7 |
| IGHV5-6 | 12F2 (62.14 cM) | REV | 777780 | NC_000078.6 | 113625508..113625801 | -1 | MGI:4439815 | Ighv5-6 |
| IGHV5-5 | 12F2 (62.14 cM) | REV | 777779 | NC_000078.6 | 113612965..113613442 | -1 | MGI:5009889 | Ighv5-5 |
| IGHV2-3 | 12F2 (62.14 cM) | REV | 238412 | NC_000078.6 | 113611184..113611476 | -1 | MGI:4439872 | Ighv2-3 |
| IGHV6-1 | 12F2 (62.14 cM) | REV | 777689 | NC_000078.6 | 113603460..113603928 | -1 | MGI:5009888 | Ighv6-1 |
| IGHV5-4 | 12F2 (62.13 cM) | REV | 777688 | NC_000078.6 | 113597448..113597741 | -1 | MGI:4439895 | Ighv5-4 |
| IGHV5-3 | 12F2 (62.13 cM) | REV | 777687 | NC_000078.6 | 113589967..113590243 | -1 | MGI:5009887 | Ighv5-3 |
| IGHV2-2 | 12F2 (62.13 cM) | REV | 777686 | NC_000078.6 | 113588267..113588700 | -1 | MGI:4439894 | Ighv2-2 |
| IGHV5-2 | 12F2 (62.13 cM) | REV | 777685 | NC_000078.6 | 113578504..113578990 | -1 | MGI:4439893 | Ighv5-2 |
| IGHV2-1 | 12F2 (62.13 cM) | REV | 777684 | NC_000078.6 | 113574247..113574540 | -1 | MGI:4936981 | Ighv2-1 |

FIG. 42 (Continued)

| | | | | | | |
|---|---|---|---|---|---|---|
| IGHV5-1 | 12F2 (62.13 cM) | REV | 777683 | NC_000078.6 | 113572929..113573222 | -1 | MGI:5009886 | Ighv5-1 |
| IGHD5-1 | 12F2 (62.11 cM) | REV | 777682 | NC_000078.6 | 113526800..113526809 | -1 | MGI:4937117 | Ighd5-1 |
| IGHD3-1 | 12F2 (62.11 cM) | REV | 777681 | NC_000078.6 | 113525313..113525329 | -1 | MGI:4439891 | Ighd3-1 |
| IGHD1-1 | 12F2 (62.10 cM) | REV | 777657 | NC_000078.6 | 113482170..113482192 | -1 | MGI:4439871 | Ighd1-1 |
| IGHD6-1 | 12F2 (62.10 cM) | REV | 777680 | NC_000078.6 | 113480143..113480171 | -1 | MGI:4937254 | Ighd6-1 |
| IGHD2-3 | 12F2 (62.10 cM) | REV | 777679 | NC_000078.6 | 113475400..113475416 | -1 | MGI:4439708 | Ighd2-3 |
| IGHD6-2 | 12F2 (62.10 cM) | REV | 777678 | NC_000078.6 | 113474875..113474903 | -1 | MGI:4937120 | Ighd6-2 |
| IGHD2-4 | 12F2 (62.10 cM) | REV | 777677 | NC_000078.6 | 113470694..113470710 | -1 | MGI:4439709 | Ighd2-4 |
| IGHD5-2 | 12F2 (62.10 cM) | REV | 777676 | NC_000078.6 | 113469426..113469435 | -1 | MGI:4936898 | Ighd5-2 |
| IGHD2-5 | 12F2 (62.10 cM) | REV | 777675 | NC_000078.6 | 113466027..113466043 | -1 | MGI:4439705 | Ighd2-5 |
| IGHD5-3 | 12F2 (62.10 cM) | REV | 777674 | NC_000078.6 | 113464761..113464770 | -1 | MGI:4937297 | Ighd5-3 |
| IGHD5-7 | 12F2 (62.10 cM) | REV | 777673 | NC_000078.6 | 113464524..113464552 | -1 | MGI:4936973 | Ighd5-7 |
| IGHD2-6 | 12F2 (62.10 cM) | REV | 777672 | NC_000078.6 | 113461369..113461385 | -1 | MGI:4439865 | Ighd2-6 |
| IGHD5-4 | 12F2 (62.10 cM) | REV | 777670 | NC_000078.6 | 113460101..113460110 | -1 | MGI:4937058 | Ighd5-4 |
| IGHD5-8 | 12F2 (62.10 cM) | REV | 777669 | NC_000078.6 | 113459864..113459892 | -1 | MGI:4937171 | Ighd5-8 |
| IGHD2-7 | 12F2 (62.10 cM) | REV | 777667 | NC_000078.6 | 113456720..113456736 | -1 | MGI:4439866 | Ighd2-7 |
| IGHD5-5 | 12F2 (62.10 cM) | REV | 777665 | NC_000078.6 | 113454942..113454951 | -1 | MGI:4937334 | Ighd5-5 |
| IGHD2-8 | 12F2 (62.10 cM) | REV | 777664 | NC_000078.6 | 113450851..113450867 | -1 | MGI:4439706 | Ighd2-8 |
| IGHD5-6 | 12F2 (62.10 cM) | REV | 777663 | NC_000078.6 | 113449588..113449597 | -1 | MGI:4937234 | Ighd5-6 |
| IGHD3-2 | 12F2 (62.10 cM) | REV | 777662 | NC_000078.6 | 113448214..113448229 | -1 | MGI:4439707 | Ighd3-2 |
| IGHD4-1 | 12F2 (62.10 cM) | REV | 777661 | NC_000078.6 | 113430528..113430538 | -1 | MGI:4439801 | Ighd4-1 |
| IGHJ1 | 12F2 (62.10 cM) | REV | 777648 | NC_000078.6 | 113429781..113429833 | -1 | MGI:4439802 | Ighj1 |
| IGHJ2 | 12F2 (62.10 cM) | REV | 777654 | NC_000078.6 | 113429468..113429515 | -1 | MGI:4439803 | Ighj2 |
| IGHJ3 | 12F2 (62.10 cM) | REV | 777655 | NC_000078.6 | 113429085..113429132 | -1 | MGI:4439767 | Ighj3 |
| IGHJ4 | 12F2 (62.10 cM) | REV | 777656 | NC_000078.6 | 113428514..113428567 | -1 | MGI:4439658 | Ighj4 |
| IGHM | 12F2 (62.10 cM) | REV | 16019 | NC_000078.6 | 113418826..113422730 | -1 | MGI:96448 | Ighm |
| IGHD | 12F2 (62.10 cM) | REV | 380797 | NC_000078.6 | 113407535..113416324 | -1 | MGI:96447 | Ighd |
| IGHG3 | 12F2 (62.10 cM) | REV | 380795 | NC_000078.6 | 113357442..113361232 | -1 | MGI:2144790 | Ighg3 |
| IGHG1 | 12F2 (62.10 cM) | REV | 16017 | NC_000078.6 | 113326544..113330523 | -1 | MGI:96446 | Ighg1 |

| IGHG2B | 12F2 (62.10 cM) | REV | 16016 | NC_000078.6 | 113304314..113307933 | -1 | MGI:96445 | Ighg2b |
| IGHG2C | 12F2 (62.10 cM) | REV | 404711 | NC_000078.6 | 113287389..113288932 | -1 | MGI:2686979 | Ighg2c |
| IGHE | 12F2 (62.10 cM) | REV | 380792 | NC_000078.6 | 113269263..113273248 | -1 | MGI:2685746 | Ighe |
| IGHA | 12F2 (62.09 cM) | REV | 238447 | NC_000078.6 | 113256204..113260236 | -1 | MGI:96444 | Igha |

FIG. 43

| IMGT | | | | | | NCBI | | |
|---|---|---|---|---|---|---|---|---|
| Gene | Loc. | Orient. | Locus | Position | Accession number | Positions | Gene positions on chromosome | Accession number | Gene positions in sequences |
| IGKC | 2q11.2 | REV | IGK | 1714339..1714417 | J00241 | 334..653 | 88937992..88938311 | NT_022184.14 | 67900421..67900740 |
| IGKJ5 | 2q11.2 | REV | IGK | 1714024..1714102 | J00242 | 1536..1612 | 88941195..88941271 | NT_022184.14 | 67903624..67903700 |
| IGKJ4 | 2q11.2 | REV | IGK | 1713683..1713760 | J00242 | 1221..1297 | 88941513..88941589 | NT_022184.14 | 67903942..67904018 |
| IGKJ3 | 2q11.2 | REV | IGK | 1713376..1713455 | J00242 | 880..955 | 88941848..88941923 | NT_022184.14 | 67904277..67904352 |
| IGKJ2 | 2q11.2 | REV | IGK | 1713015..1713093 | J00242 | 573..650 | 88942152..88942229 | NT_022184.14 | 67904581..67904658 |
| IGKJ1 | 2q11.2 | REV | IGK | 1688795..1689406 | J00242 | 212..288 | 88942513..88942589 | NT_022184.14 | 67904942..67905018 |
| IGKV4-1 | 2q11.2 | FWD | IGK | 1677164..1677682 | Z00023 | 98..709 | 88966203..88966814 | NT_022184.14 | 67928632..67929243 |
| IGKV5-2 | 2q11.2 | FWD | IGK | 1659301..1659929 | X02485 | 304..822 | 88977926..88978445 | NT_022184.14 | 67940355..67940874 |
| IGKV7-3 | 2q11.2 | REV | IGK | 1642592..1643349 | X12682 | 683..1281 | 88995711..88996309 | NT_022184.14 | 67958140..67958738 |
| IGKV2-4 | 2q11.2 | REV | IGK | 1627192..1627697 | X72814 | 569..1296 | 89012284..89013011 | NT_022184.14 | 67974713..67975440 |
| IGKV1-5 | 2q11.2 | REV | IGK | 1608228..1608734 | Z00001 | 297..802 | 89027904..89028409 | NT_022184.14 | 67990333..67990838 |
| IGKV1-6 | 2q11.2 | REV | IGK | 1595082..1596528 | M64858 | 131..637 | 89046866..89047372 | NT_022184.14 | 68009295..68009801 |
| IGKV3-7 | 2q11.2 | REV | IGK | 1582087..1582586 | X02725 | 134..680 | 89059072..89059618 | NT_022184.14 | 68021501..68022047 |
| IGKV1-8 | 2q11.2 | REV | IGK | 1564529..1565034 | K02097 | 950..1427 | 89073041..89073518 | NT_022184.14 | 68035470..68035947 |
| IGKV1-9 | 2q11.2 | REV | IGK | 1554301..1555022 | K02096 | 691..1168 | 89090592..89091069 | NT_022184.14 | 68053021..68053498 |
| IGKV2-10 | 2q11.2 | REV | IGK | 1547302..1547845 | Z00012 | 121..814 | 89100604..89101297 | NT_022184.14 | 68063033..68063726 |
| IGKV3-11 | 2q11.2 | REV | IGK | 1534288..1534792 | X01668 | 134..677 | 89107753..89108296 | NT_022184.14 | 68070182..68070725 |
| IGKV1-12 | 2q11.2 | REV | IGK | 1534288..1534792 | V01577 | 1170..1674 | 89120806..89121310 | NT_022184.14 | 68083235..68083739 |

FIG. 43 (Continued)

| | | | | | | | |
|---|---|---|---|---|---|---|---|
| IGKV1-13 | 2q11.2 | REV | IGK | 1528520..1529026 | K02093 | 427..903 | 89126602..89127078 | NT_022184.14 | 68089031..68089507 |
| IGKV2-14 | 2q11.2 | REV | IGK | 1496203..1496996 | X72810 | 191..956 | 89158630..89159395 | NT_022184.14 | 68121059..68121824 |
| IGKV3-15 | 2q11.2 | REV | IGK | 1489297..1489840 | M23090 | 676..1219 | 89165758..89166301 | NT_022184.14 | 68128187..68128730 |
| IGKV1-16 | 2q11.2 | REV | IGK | 1474657..1475162 | J00248 | 131..636 | 89180437..89180942 | NT_022184.14 | 68142866..68143371 |
| IGKV1-17 | 2q11.2 | REV | IGK | 1457171..1457676 | X72808 | 397..902 | 89197918..89198423 | NT_022184.14 | 68160347..68160852 |
| IGKV2-18 | 2q11.2 | REV | IGK | 1445516..1446322 | X63400 | 341..1117 | 89209304..89210080 | NT_022184.14 | 68171733..68172509 |
| IGKV2-19 | 2q11.2 | REV | IGK | 1439747..1440043 | X12692 | 814..1080 | 89215579..89215845 | NT_022184.14 | 68178008..68178274 |
| IGKV3-20 | 2q11.2 | REV | IGK | 1431886..1432450 | X12686 | 108..672 | 89223142..89223706 | NT_022184.14 | 68185571..68186135 |
| IGKV6-21 | 2q11.2 | REV | IGK | 1414698..1415279 | X63399 | 507..1088 | 89240320..89240901 | NT_022184.14 | 68202749..68203330 |
| IGKV1-22 | 2q11.2 | REV | IGK | 1403796..1404293 | X71885 | 2665..3132 | 89251344..89251811 | NT_022184.14 | 68213773..68214240 |
| IGKV1-23 | 2q11.2 | REV | IGK | 1401965..1403001 | X71885 | 834..1549 | 89252927..89253642 | NT_022184.14 | 68215356..68216071 |
| IGKV2-24 | 2q11.2 | REV | IGK | 1397878..1398710 | X12684 | 154..986 | 89256897..89257729 | NT_022184.14 | 68219326..68220158 |
| IGKV3-25 | 2q11.2 | REV | IGK | 1380742..1382545 | X06583 | 636..2411 | 89273094..89274871 | NT_022184.14 | 68235523..68237300 |
| IGKV2-26 | 2q11.2 | REV | IGK | 1378180..1378960 | X71884 | 505..1257 | 89276679..89277432 | NT_022184.14 | 68239108..68239861 |
| IGKV1-27 | 2q11.2 | REV | IGK | 1361116..1361620 | X63398 | 323..827 | 89293993..89294497 | NT_022184.14 | 68256422..68256926 |
| IGKV2-28 | 2q11.2 | REV | IGK | 1352578..1353341 | X63397 | 305..1068 | 89302264..89303027 | NT_022184.14 | 68264693..68265456 |
| IGKV1-29 | 2q11.2 | REV | IGK | 1340097..1340853 | X63396 | 322..1078 | 89314751..89315507 | NT_022184.14 | 68277180..68277936 |
| IGKV2-30 | 2q11.2 | REV | IGK | 1329442..1330257 | X63403 | 898..1713 | 89325349..89326164 | NT_022184.14 | 68287778..68288593 |
| IGKV2-31 | 2q11.2 | REV | IGK | 1322273..1322839 | X71883 | 1839..2376 | 89332799..89333336 | NT_022184.14 | 68295228..68295765 |
| IGKV1-32 | 2q11.2 | REV | IGK | 1320994..1321488 | X71883 | 560..1034 | 89334142..89334616 | NT_022184.14 | 68296571..68297045 |
| IGKV1-33 | 2q11.2 | REV | IGK | 1306433..1306937 | M64856 | 131..635 | 89348843..89349347 | NT_022184.14 | 68311272..68311776 |
| IGKV3-34 | 2q11.2 | REV | IGK | 1299120..1299680 | X71891 | 588..1120 | 89356128..89356660 | NT_022184.14 | 68318557..68319089 |
| IGKV1-35 | 2q11.2 | REV | IGK | 1287738..1288241 | X71890 | 456..930 | 89367568..89368042 | NT_022184.14 | 68329997..68330471 |
| IGKV2-36 | 2q11.2 | REV | IGK | 1279452..1279685 | X71889 | 144..377 | 89376096..89376329 | NT_022184.14 | 68338525..68338758 |
| IGKV1-37 | 2q11.2 | REV | IGK | 1277171..1277675 | X59316 | 356..860 | 89378106..89378610 | NT_022184.14 | 68340535..68341039 |
| IGKV2-38 | 2q11.2 | REV | IGK | 1264765..1265034 | X71888 | 580..819 | 89390775..89391014 | NT_022184.14 | 68353204..68353443 |
| IGKV1-39 | 2q11.2 | REV | IGK | 1254806..1255310 | X59315 | 134..638 | 89400468..89400972 | NT_022184.14 | 68362897..68363401 |
| IGKV2-40 | 2q11.2 | REV | IGK | 1244063..1244826 | X59314 | 889..1652 | 89411128..89411721 | NT_022184.14 | 68373387..68373980 |
| IGKV2D-36 | 2q11.2 | FWD | IGK | 387386..387619 | X71893 | 2718..2951 | 89562873..89563106 | NT_032994.5 | 1322..1555 |

FIG. 43 (Continued)

| | | | | | | | |
|---|---|---|---|---|---|---|---|
| IGKV1D-35 | 2q11.2 | FWD | IGK | 378827..379330 | X71894 | 121.595 | 89571166..89571640 | NT_032994.5 | 9615..10089 |
| IGKV3D-34 | 2q11.2 | FWD | IGK | 367325..367885 | X71895 | 588..1120 | 89582610..89583142 | NT_032994.5 | 21059..21591 |
| IGKV1D-33 | 2q11.2 | FWD | IGK | 360069..360573 | M64855 | 131..635 | 89589921..89590425 | NT_032994.5 | 28370..28874 |
| IGKV1D-32 | 2q11.2 | FWD | IGK | 345540..346034 | X71896 | 578..1052 | 89604539..89605013 | NT_032994.5 | 42988..43462 |
| IGKV3D-31 | 2q11.2 | FWD | IGK | 344188..344755 | X71896 | 1857..2394 | 89605819..89606356 | NT_032994.5 | 44268..44805 |
| IGKV2D-30 | 2q11.2 | FWD | IGK | 336744..337959 | X63402 | 507..1322 | 89613009..89613824 | NT_032994.5 | 51458..52273 |
| IGKV2D-29 | 2q11.2 | FWD | IGK | 326154..326911 | M31952 | 324..1081 | 89623657..89624414 | NT_032994.5 | 62106..62863 |
| IGKV2D-28 | 2q11.2 | FWD | IGK | 313676..314439 | X12691 | 304..1067 | 89636130..89636893 | NT_032994.5 | 74579..75342 |
| IGKV1D-27 | 2q11.2 | FWD | IGK | 305082..305587 | Z00004 | 525..1030 | 89644980..89645485 | NT_032994.5 | 83429..83934 |
| IGKV2D-26 | 2q11.2 | FWD | IGK | 287726..288491 | AP001216 | 30326..31106 | 89662063..89662843 | NT_032994.5 | 100512..101292 |
| IGKV3D-25 | 2q11.2 | FWD | IGK | 284165..285949 | X71886 | 628..2412 | 89664611..89666397 | NT_032994.5 | 103060..104846 |
| IGKV2D-24 | 2q11.2 | FWD | IGK | 268793..269625 | X63401 | 185..1017 | 89680942..89681774 | NT_032994.5 | 119391..120223 |
| IGKV2D-23 | 2q11.2 | FWD | IGK | 264526..265540 | X71887 | 834..1839 | 89685026..89686031 | NT_032994.5 | 123475..124480 |
| IGKV1D-22 | 2q11.2 | FWD | IGK | 263213..263710 | X71887 | 2664.3131 | 89686856..89687323 | NT_032994.5 | 125305..125772 |
| IGKV6D-21 | 2q11.2 | FWD | IGK | 252235..252816 | X12683 | 378..959 | 89697749..89698330 | NT_032994.5 | 136198..136779 |
| IGKV3D-20 | 2q11.2 | FWD | IGK | 234918..235482 | X12687 | 108..672 | 89715082..89715646 | NT_032994.5 | 153531..154095 |
| IGKV2D-19 | 2q11.2 | FWD | IGK | 227325..227621 | X71882 | 433..699 | 89722943..89723209 | NT_032994.5 | 161392..161658 |
| IGKV2D-18 | 2q11.2 | FWD | IGK | 221028..221834 | X63395 | 308..1084 | 89728733..89729509 | NT_032994.5 | 167182..167958 |
| IGKV6D-41 | 2q11.2 | FWD | IGK | 204147..204727 | M27751 | 220..772 | 89745835..89746387 | NT_032994.5 | 184284..184836 |
| IGKV1D-17 | 2q11.2 | FWD | IGK | 191094..191599 | X63392 | 986..1491 | 89758963..89759468 | NT_032994.5 | 197412..197917 |
| IGKV1D-16 | 2q11.2 | FWD | IGK | 173645..174150 | K01323 | 131..636 | 89776410..89776915 | NT_032994.5 | 214859..215364 |
| IGKV3D-15 | 2q11.2 | FWD | IGK | 158967..159510 | X72815 | 71..614 | 89791050..89791593 | NT_032994.5 | 229499..230042 |
| IGKV2D-14 | 2q11.2 | FWD | IGK | 151823..152616 | X72811 | 221..986 | 89797944..89798709 | NT_032994.5 | 236393..237158 |
| IGKV1D-13 | 2q11.2 | FWD | IGK | 119800..120306 | X17262 | 130..636 | 89830253..89830759 | NT_032994.5 | 268702..269208 |
| IGKV1D-12 | 2q11.2 | FWD | IGK | 114055..114538 | X17263 | 131..607 | 89836021..89836497 | NT_032994.5 | 274470..274946 |
| IGKV3D-11 | 2q11.2 | FWD | IGK | 100971..101514 | X17264 | 83..626 | 89849045..89849588 | NT_032994.5 | 287494..288037 |
| IGKV2D-10 | 2q11.2 | FWD | IGK | 93730..94523 | X17265 | 122..887 | 89856036..89856801 | NT_032994.5 | 294485..295250 |
| IGKV1D-42 | 2q11.2 | FWD | IGK | 83687..84183 | X72816 | 209..705 | 89866370..89866866 | NT_032994.5 | 304819..305315 |
| IGKV1D-43 | 2q11.2 | FWD | IGK | 63823..64328 | X72817 | 150..655 | 89886225..89886730 | NT_032994.5 | 324674..325179 |

FIG. 43 (Continued)

| IGKV1D-8 | 2q11.2 | FWD | IGK | 52970.53474 | Z00008 | 305..781 | 89897079..89897555 | NT_032994.5 | 335528..336004 |
| IGKV3D-7 | 2q11.2 | FWD | IGK | 39007..39568 | X72820 | 441..1002 | 89911009..89911570 | NT_032994.5 | 349458..350019 |

FIG. 44

| IMGT Gene | Chromosomal localization | Orientation | NCBI Gene ID | Reference GRCm38.p3 C57BL/6J | NCBI Gene positions in sequence | Orientation sequence | MGI ID | MGI symbol |
|---|---|---|---|---|---|---|---|---|
| IGKV2-137 | 6C1 (30.89 cM) | FWD | 692187 | NC_000072.6 | 67555636..67556216 | 1 | MGI:4439879 | Igkv2-137 |
| IGKV1-136 | 6C1 (30.90 cM) | FWD | 692186 | NC_000072.6 | 67593876..67594308 | 1 | MGI:4947614 | Igkv1-136 |
| IGKV1-135 | 6C1 (30.91 cM) | FWD | 243420 | NC_000072.6 | 67609745..67610508 | 1 | MGI:3819952 | Igkv1-135 |
| IGKV14-134-1 | 6C1 (30.94 cM) | REV | 692185 | NC_000072.6 | 67711174..67711628 | -1 | MGI:5009883 | Igkv14-134-1 |
| IGKV17-134 | 6C1 (30.94 cM) | REV | 692184 | NC_000072.6 | 67720729..67721225 | -1 | MGI:4936953 | Igkv17-134 |
| IGKV1-133 | 6C1 (30.94 cM) | FWD | 628027 | NC_000072.6 | 67724914..67725661 | 1 | MGI:3648380 | Igkv1-133 |
| IGKV1-132 | 6C1 (30.96 cM) | FWD | 243423 | NC_000072.6 | 67759700..67760413 | 1 | MGI:3648800 | Igkv1-132 |
| IGKV1-131 | 6C1 (30.96 cM) | REV | 628056 | NC_000072.6 | 67766036..67766772 | -1 | MGI:3645551 | Igkv1-131 |
| IGKV14-130 | 6C1 (30.97 cM) | FWD | 628072 | NC_000072.6 | 67791046..67791511 | 1 | MGI:3645770 | Igkv14-130 |
| IGKV9-129 | 6C1 (30.98 cM) | FWD | 692182 | NC_000072.6 | 67839793..67840266 | 1 | MGI:3525017 | Igkv9-129 |
| IGKV9-128 | 6C1 (30.99 cM) | FWD | 692181 | NC_000072.6 | 67847409..67847874 | 1 | MGI:3809196 | Igkv9-128 |
| IGKV17-127 | 6C1 (30.99 cM) | FWD | 243433 | NC_000072.6 | 67861159..67861659 | 1 | MGI:3646891 | Igkv17-127 |
| IGKV14-126-1 | 6C1 (30.99 cM) | FWD | 692180 | NC_000072.6 | 67876011..67876477 | 1 | MGI:5009882 | Igkv14-126-1 |
| IGKV14-126 | 6C1 (31.00 cM) | FWD | 628127 | NC_000072.6 | 67896177..67896642 | 1 | MGI:3643131 | Igkv14-126 |
| IGKV11-125 | 6C1 (31.01 cM) | FWD | 243428 | NC_000072.6 | 67913573..67914052 | 1 | MGI:3642338 | Igkv11-125 |
| IGKV9-124 | 6C1 (31.02 cM) | REV | 243431 | NC_000072.6 | 67942076..67942540 | -1 | MGI:3646892 | Igkv9-124 |
| IGKV9-123 | 6C1 (31.02 cM) | REV | 628144 | NC_000072.6 | 67954230..67954690 | -1 | MGI:3643848 | Igkv9-123 |
| IGKV1-122 | 6C1 (31.04 cM) | FWD | 434024 | NC_000072.6 | 68016742..68017488 | 1 | MGI:4439722 | Igkv1-122 |
| IGKV17-121 | 6C1 (31.05 cM) | FWD | 667435 | NC_000072.6 | 68036818..68037318 | 1 | MGI:3647671 | Igkv17-121 |
| IGKV9-120 | 6C1 (31.05 cM) | FWD | 434025 | NC_000072.6 | 68049983..68050454 | 1 | MGI:3647784 | Igkv9-120 |
| IGKV9-119 | 6C1 (31.05 cM) | FWD | 692177 | NC_000072.6 | 68056345..68056810 | 1 | MGI:5009881 | Igkv9-119 |

FIG. 44 (Continued)

| | | | | | | | |
|---|---|---|---|---|---|---|---|
| IGKV14-118-2 | 6C1 (31.06 cM) | FWD | 692176 | NC_000072.6 | 68066369..68066828 | 1 | MGI:5009880 | Igkv14-118-2 |
| IGKV14-118-1 | 6C1 (31.06 cM) | FWD | 692175 | NC_000072.6 | 68082547..68083145 | 1 | MGI:5009879 | Igkv14-118-1 |
| IGKV11-118 | 6C1 (31.07 cM) | FWD | 692174 | NC_000072.6 | 68105414..68105880 | 1 | MGI:5009878 | Igkv11-118 |
| IGKV1-117 | 6C1 (31.06 cM) | FWD | 16098 | NC_000072.6 | 68121091..68121825 | 1 | MGI:4439721 | Igkv1-117 |
| IGKV1-115 | 6C1 (31.09 cM) | FWD | 628206 | NC_000072.6 | 68160797..68161716 | 1 | MGI:3644873 | Igkv1-115 |
| IGKV11-114 | 6C1 (31.09 cM) | FWD | 692173 | NC_000072.6 | 68164459..68164923 | 1 | MGI:5009877 | Igkv11-114 |
| IGKV2-113 | 6C1 (31.09 cM) | FWD | 692172 | NC_000072.6 | 68178801..68179564 | 1 | MGI:5009876 | Igkv2-113 |
| IGKV2-112 | 6C1 (31.11 cM) | FWD | 381776 | NC_000072.6 | 68219981..68220705 | 1 | MGI:3644894 | Igkv2-112 |
| IGKV14-111 | 6C1 (31.12 cM) | FWD | 545847 | NC_000072.6 | 68256404..68256869 | 1 | MGI:4439863 | Igkv14-111 |
| IGKV1-110 | 6C1 (31.12 cM) | FWD | 381777 | NC_000072.6 | 68270527..68271265 | 1 | MGI:4439558 | Igkv1-110 |
| IGKV2-109 | 6C1 (31.13 cM) | FWD | 628268 | NC_000072.6 | 68302439..68303158 | 1 | MGI:3642626 | Igkv2-109 |
| IGKV1-108 | 6C1 (31.13 cM) | FWD | 628272 | NC_000072.6 | 68312054..68312359 | 1 | MGI:3644576 | Igkv1-108 |
| IGKV2-107 | 6C1 (31.14 cM) | FWD | 628283 | NC_000072.6 | 68326098..68326752 | 1 | MGI:3645630 | Igkv2-107 |
| IGKV11-106 | 6C1 (31.14 cM) | FWD | 628293 | NC_000072.6 | 68339527..68339995 | 1 | MGI:3648899 | Igkv11-106 |
| IGKV2-105 | 6C1 (31.15 cM) | FWD | 692170 | NC_000072.6 | 68348661..68349441 | 1 | MGI:5009874 | Igkv2-105 |
| IGKV16-104 | 6C1 (31.17 cM) | FWD | 381778 | NC_000072.6 | 68425605..68426072 | 1 | MGI:2685913 | Igkv16-104 |
| IGKV15-103 | 6C1 (31.18 cM) | FWD | 692169 | NC_000072.6 | 68437468..68437925 | 1 | MGI:96513 | Igkv15-103 |
| IGKV15-102 | 6C1 (31.18 cM) | REV | 692171 | NC_000072.6 | 68466126..68466590 | -1 | MGI:5009875 | Igkv15-102 |
| IGKV20-101-2 | 6C1 (31.19 cM) | FWD | 724035 | NC_000072.6 | 68474888..68475098 | 1 | MGI:5009884 | Igkv20-101-2 |
| IGKV15-101-1 | 6C1 (31.19 cM) | FWD | 692167 | NC_000072.6 | 68479082..68479573 | 1 | MGI:5009872 | Igkv15-101-1 |
| IGKV15-101 | 6C1 (31.19 cM) | REV | 692168 | NC_000072.6 | 68481421..68481718 | -1 | MGI:5009873 | Igkv15-101 |
| IGKV14-100 | 6C1 (31.20 cM) | FWD | 243439 | NC_000072.6 | 68519012..68519477 | 1 | MGI:4439559 | Igkv14-100 |
| IGKV1-99 | 6C1 (31.21 cM) | FWD | 434028 | NC_000072.6 | 68541658..68542422 | 1 | MGI:4439724 | Igkv1-99 |
| IGKV12-98 | 6C1 (31.22 cM) | FWD | 435900 | NC_000072.6 | 68570763..68571235 | 1 | MGI:4439560 | Igkv12-98 |
| IGKV15-97 | 6C1 (31.22 cM) | FWD | 692166 | NC_000072.6 | 68591380..68591832 | 1 | MGI:5009871 | Igkv15-97 |
| IGKV10-96 | 6C1 (31.24 cM) | REV | 692165 | NC_000072.6 | 68631965..68632430 | -1 | MGI:4439561 | Igkv10-96 |
| IGKV2-95-2 | 6C1 (31.24 cM) | REV | 692164 | NC_000072.6 | 68647999..68648531 | -1 | MGI:4937167 | Igkv2-95-2 |
| IGKV2-95-1 | 6C1 (31.25 cM) | FWD | 692163 | NC_000072.6 | 68670752..68671335 | 1 | MGI:5009870 | Igkv2-95-1 |
| IGKV10-95 | 6C1 (31.25 cM) | FWD | 434031 | NC_000072.6 | 68680379..68680848 | 1 | MGI:3644598 | Igkv10-95 |

FIG. 44 (Continued)

| | | | | | | |
|---|---|---|---|---|---|---|
| IGKV10-94 | 6C1 (31.26 cM) | REV | 667550 | NC_000072.6 | 68704508..68704978 | -1 | MGI:3646140 | Igkv10-94 |
| IGKV2-93-1 | 6C1 (31.26 cM) | REV | 692162 | NC_000072.6 | 68712925..68713508 | -1 | MGI:5009869 | Igkv2-93-1 |
| IGKV19-93 | 6C1 (31.27 cM) | REV | 692161 | NC_000072.6 | 68736297..68736764 | -1 | MGI:107617 | Igkv19-93 |
| IGKV4-92 | 6C1 (31.28 cM) | REV | 384410 | NC_000072.6 | 68755038..68755593 | -1 | MGI:2686254 | Igkv4-92 |
| IGKV4-91 | 6C1 (31.28 cM) | REV | 434033 | NC_000072.6 | 68768555..68769103 | -1 | MGI:3642277 | Igkv4-91 |
| IGKV4-90 | 6C1 (31.29 cM) | REV | 434034 | NC_000072.6 | 68807180..68807708 | -1 | MGI:4439830 | Igkv4-90 |
| IGKV13-89-1 | 6C1 (31.29 cM) | FWD | 692155 | NC_000072.6 | 68810495..68810543 | 1 | MGI:5009868 | Igkv13-89-1 |
| IGKV12-89 | 6C1 (31.29 cM) | REV | 384411 | NC_000072.6 | 68834846..68835307 | -1 | MGI:4439829 | Igkv12-89 |
| IGKV1-88 | 6C1 (31.31 cM) | REV | 692154 | NC_000072.6 | 68862265..68863031 | -1 | MGI:4439828 | Igkv1-88 |
| IGKV13-87 | 6C1 (31.32 cM) | FWD | 692153 | NC_000072.6 | 68902801..68903266 | 1 | MGI:3779399 | Igkv13-87 |
| IGKV4-86 | 6C1 (31.33 cM) | REV | 243451 | NC_000072.6 | 68910411..68910938 | -1 | MGI:2685305 | Igkv4-86 |
| IGKV13-85 | 6C1 (31.33 cM) | REV | 434036 | NC_000072.6 | 68930269..68930734 | -1 | MGI:4439827 | Igkv13-85 |
| IGKV13-84 | 6C1 (31.34 cM) | FWD | 692152 | NC_000072.6 | 68939602..68940067 | 1 | MGI:96514 | Igkv13-84 |
| IGKV13-83 | 6C1 (31.34 cM) | REV | 692145 | NC_000072.6 | 68961378..68962019 | -1 | MGI:5009867 | Igkv13-83 |
| IGKV13-82 | 6C1 (31.35 cM) | FWD | 692144 | NC_000072.6 | 68979198..68979663 | 1 | MGI:5009866 | Igkv13-82 |
| IGKV4-81 | 6C1 (31.35 cM) | REV | 243453 | NC_000072.6 | 68990758..68991294 | -1 | MGI:2685306 | Igkv4-81 |
| IGKV13-80-1 | 6C1 (31.36 cM) | FWD | 692143 | NC_000072.6 | 69009143..69009513 | 1 | MGI:5009865 | Igkv13-80-1 |
| IGKV4-80 | 6C1 (31.36 cM) | REV | 545848 | NC_000072.6 | 69016558..69017080 | -1 | MGI:4439653 | Igkv4-80 |
| IGKV4-79 | 6C1 (31.37 cM) | REV | 213684 | NC_000072.6 | 69042972..69043505 | -1 | MGI:2685040 | Igkv4-79 |
| IGKV13-78-1 | 6C1 (31.37 cM) | FWD | 628498 | NC_000072.6 | 69051444..69051794 | 1 | MGI:3647961 | Igkv13-78-1 |
| IGKV4-78 | 6C1 (31.38 cM) | REV | 545849 | NC_000072.6 | 69059690..69060224 | -1 | MGI:3819775 | Igkv4-78 |
| IGKV4-77 | 6C1 (31.39 cM) | FWD | 667621 | NC_000072.6 | 69110904..69111432 | 1 | MGI:3647937 | Igkv4-77 |
| IGKV13-76 | 6C1 (31.40 cM) | FWD | 692142 | NC_000072.6 | 69137866..69138332 | 1 | MGI:5009864 | Igkv13-76 |
| IGKV4-75 | 6C1 (31.41 cM) | REV | 692141 | NC_000072.6 | 69156118..69156659 | -1 | MGI:5009863 | Igkv4-75 |
| IGKV13-74-1 | 6C1 (31.41 cM) | FWD | 692140 | NC_000072.6 | 69177416..69177787 | 1 | MGI:5009862 | Igkv13-74-1 |
| IGKV4-74 | 6C1 (31.42 cM) | REV | 236047 | NC_000072.6 | 69184826..69185361 | -1 | MGI:3819447 | Igkv4-74 |
| IGKV13-73-1 | 6C1 (31.42 cM) | FWD | 692139 | NC_000072.6 | 69190073..69190282 | 1 | MGI:5009861 | Igkv13-73-1 |
| IGKV4-73 | 6C1 (31.42 cM) | REV | 628516 | NC_000072.6 | 69197583..69198116 | -1 | MGI:3645825 | Igkv4-73 |
| IGKV4-72 | 6C1 (31.43 cM) | REV | 385109 | NC_000072.6 | 69226854..69227383 | -1 | MGI:2686345 | Igkv4-72 |

FIG. 44 (Continued)

| | | | | | | | |
|---|---|---|---|---|---|---|---|
| IGKV13-71-1 | 6C1 (31.43 cM) | FWD | 692138 | NC_000072.6 | 69235927..69236158 | 1 | MGI:5009860 | Igkv13-71-1 |
| IGKV4-71 | 6C1 (31.43 cM) | REV | 434586 | NC_000072.6 | 69243160..69243688 | -1 | MGI:4439654 | Igkv4-71 |
| IGKV4-70 | 6C1 (31.44 cM) | REV | 385120 | NC_000072.6 | 69267888..69268412 | -1 | MGI:2686348 | Igkv4-70 |
| IGKV4-69 | 6C1 (31.45 cM) | REV | 628541 | NC_000072.6 | 69283794..69284319 | -1 | MGI:3648668 | Igkv4-69 |
| IGKV4-68 | 6C1 (31.45 cM) | REV | 384515 | NC_000072.6 | 69304834..69305363 | -1 | MGI:2686265 | Igkv4-68 |
| IGKV12-67 | 6C1 (31.46 cM) | REV | 628551 | NC_000072.6 | 69324177..69324646 | -1 | MGI:3645399 | Igkv12-67 |
| IGKV12-66 | 6C1 (31.46 cM) | REV | 692133 | NC_000072.6 | 69334604..69335076 | -1 | MGI:5009859 | Igkv12-66 |
| IGKV4-65 | 6C1 (31.47 cM) | REV | 667670 | NC_000072.6 | 69342472..69343004 | -1 | MGI:3644339 | Igkv4-65 |
| IGKV13-64 | 6C1 (31.47 cM) | FWD | 628564 | NC_000072.6 | 69362722..69363187 | 1 | MGI:5009834 | Igkv13-64 |
| IGKV4-63 | 6C1 (31.48 cM) | REV | 628571 | NC_000072.6 | 69377944..69378472 | -1 | MGI:3645235 | Igkv4-63 |
| IGKV13-62-1 | 6C1 (31.48 cM) | FWD | 692119 | NC_000072.6 | 69392439..69392815 | 1 | MGI:5009858 | Igkv13-62-1 |
| IGKV4-62 | 6C1 (31.48 cM) | REV | 636752 | NC_000072.6 | 69399812..69400344 | -1 | MGI:3643587 | Igkv4-62 |
| IGKV13-61-1 | 6C1 (31.49 cM) | FWD | 692118 | NC_000072.6 | 69409499..69409875 | 1 | MGI:5009857 | Igkv13-61-1 |
| IGKV4-61 | 6C1 (31.49 cM) | REV | 546244 | NC_000072.6 | 69416893..69417425 | -1 | MGI:4439819 | Igkv4-61 |
| IGKV4-59 | 6C1 (31.50 cM) | REV | 667683 | NC_000072.6 | 69438218..69438741 | -1 | MGI:3646808 | Igkv4-59 |
| IGKV4-60 | 6C1 (31.51 cM) | REV | 385277 | NC_000072.6 | 69463288..69463725 | -1 | MGI:3708737 | Igkv4-60 |
| IGKV4-58 | 6C1 (31.52 cM) | REV | 381831 | NC_000072.6 | 69500254..69500758 | -1 | MGI:2685923 | Igkv4-58 |
| IGKV13-57-2 | 6C1 (31.52 cM) | FWD | 724106 | NC_000072.6 | 69523739..69524016 | 1 | MGI:5009885 | Igkv13-57-2 |
| IGKV4-57-1 | 6C1 (31.53 cM) | REV | 384514 | NC_000072.6 | 69544368..69544892 | -1 | MGI:2686264 | Igkv4-57-1 |
| IGKV13-57-1 | 6C1 (31.54 cM) | FWD | 692114 | NC_000072.6 | 69569737..69570109 | 1 | MGI:5009856 | Igkv13-57-1 |
| IGKV4-57 | 6C1 (31.54 cM) | REV | 235952 | NC_000072.6 | 69575975..69576500 | -1 | MGI:2685035 | Igkv4-57 |
| IGKV13-56-1 | 6C1 (31.54 cM) | FWD | 692113 | NC_000072.6 | 69581244..69581452 | 1 | MGI:5009855 | Igkv13-56-1 |
| IGKV4-56 | 6C1 (31.54 cM) | REV | 619743 | NC_000072.6 | 69587295..69587810 | -1 | MGI:4439916 | Igkv4-56 |
| IGKV13-55-1 | 6C1 (31.55 cM) | FWD | 692112 | NC_000072.6 | 69599886..69600262 | 1 | MGI:5009854 | Igkv13-55-1 |
| IGKV4-55 | 6C1 (31.55 cM) | REV | 385253 | NC_000072.6 | 69607275..69607801 | -1 | MGI:2686370 | Igkv4-55 |
| IGKV13-54-1 | 6C1 (31.55 cM) | FWD | 692105 | NC_000072.6 | 69617048..69617423 | 1 | MGI:5009853 | Igkv13-54-1 |
| IGKV4-54 | 6C1 (31.56 cM) | REV | 385291 | NC_000072.6 | 69631648..69632178 | -1 | MGI:5009821 | Igkv4-54 |
| IGKV4-53 | 6C1 (31.56 cM) | REV | 546213 | NC_000072.6 | 69648824..69649354 | -1 | MGI:2686266 | Igkv4-53 |
| IGKV4-51 | 6C1 (31.58 cM) | REV | 619806 | NC_000072.6 | 69681406..69681939 | -1 | MGI:5009829 | Igkv4-51 |

FIG. 44 (Continued)

| | | | | | | | |
|---|---|---|---|---|---|---|---|
| IGKV4-50 | 6C1 (31.58 cM) | REV | 381782 | NC_000072.6 | 69700767..69701287 | -1 | MGI:2685915 | Igkv4-50 |
| IGKV12-49 | 6C1 (31.59 cM) | REV | 619824 | NC_000072.6 | 69716498..69716956 | -1 | MGI:5009830 | Igkv12-49 |
| IGKV5-48 | 6C1 (31.59 cM) | REV | 619846 | NC_000072.6 | 69726573..69727125 | -1 | MGI:3642817 | Igkv5-48 |
| IGKV12-47 | 6C1 (31.60 cM) | REV | 434037 | NC_000072.6 | 69750854..69751310 | -1 | MGI:3644595 | Igkv12-47 |
| IGKV12-46 | 6C1 (31.61 cM) | REV | 692245 | NC_000072.6 | 69764523..69764992 | -1 | MGI:4439773 | Igkv12-46 |
| IGKV5-45 | 6C1 (31.61 cM) | REV | 545850 | NC_000072.6 | 69775750..69776306 | -1 | MGI:4439774 | Igkv5-45 |
| IGKV12-44 | 6C1 (31.63 cM) | REV | 545851 | NC_000072.6 | 69814631..69815100 | -1 | MGI:4439775 | Igkv12-44 |
| IGKV5-43 | 6C1 (31.63 cM) | REV | 381783 | NC_000072.6 | 69823355..69823911 | -1 | MGI:4943320 | Igkv5-43 |
| IGKV12-42 | 6C1 (31.64 cM) | REV | 677861 | NC_000072.6 | 69834792..69835245 | -1 | MGI:5009852 | Igkv12-42 |
| IGKV12-41 | 6C1 (31.65 cM) | REV | 619960 | NC_000072.6 | 69858420..69858884 | -1 | MGI:4439772 | Igkv12-41 |
| IGKV5-40-1 | 6C1 (31.65 cM) | REV | 619974 | NC_000072.6 | 69868595..69869193 | -1 | MGI:5009831 | Igkv5-40-1 |
| IGKV12-40 | 6C1 (31.66 cM) | REV | 435904 | NC_000072.6 | 69879350..69879819 | -1 | MGI:3643951 | Igkv12-40 |
| IGKV5-39 | 6C1 (31.67 cM) | REV | 620017 | NC_000072.6 | 69900424..69900977 | -1 | MGI:2686255 | Igkv5-39 |
| IGKV12-38 | 6C1 (31.69 cM) | REV | 620050 | NC_000072.6 | 69943186..69943648 | -1 | MGI:4439614 | Igkv12-38 |
| IGKV5-37 | 6C1 (31.69 cM) | REV | 384417 | NC_000072.6 | 69963312..69963861 | -1 | MGI:2686256 | Igkv5-37 |
| IGKV18-36 | 6C1 (31.71 cM) | REV | 620088 | NC_000072.6 | 69992465..69992977 | -1 | MGI:4439613 | Igkv18-36 |
| IGKV1-35 | 6C1 (31.72 cM) | REV | 620105 | NC_000072.6 | 70010949..70011673 | -1 | MGI:4439612 | Igkv1-35 |
| IGKV8-34 | 6C1 (31.73 cM) | REV | 620126 | NC_000072.6 | 70044112..70044678 | -1 | MGI:4949914 | Igkv8-34 |
| IGKV7-33 | 6C1 (31.74 cM) | REV | 243461 | NC_000072.6 | 70058632..70059199 | -1 | MGI:3577282 | Igkv7-33 |
| IGKV6-32 | 6C1 (31.74 cM) | REV | 434039 | NC_000072.6 | 70074024..70074584 | -1 | MGI:3641634 | Igkv6-32 |
| IGKV8-31 | 6C1 (31.76 cM) | REV | 546905 | NC_000072.6 | 70105860..70106179 | -1 | MGI:3644798 | Igkv8-31 |
| IGKV8-30 | 6C1 (31.76 cM) | REV | 384419 | NC_000072.6 | 70117061..70117617 | -1 | MGI:3642250 | Igkv8-30 |
| IGKV6-29 | 6C1 (31.77 cM) | REV | 620191 | NC_000072.6 | 70138462..70139082 | -1 | MGI:4439616 | Igkv6-29 |
| IGKV8-28 | 6C1 (31.78 cM) | REV | 434040 | NC_000072.6 | 70143593..70144161 | -1 | MGI:3642251 | Igkv8-28 |
| IGKV8-27 | 6C1 (31.79 cM) | REV | 434041 | NC_000072.6 | 70171809..70172270 | -1 | MGI:4439868 | Igkv8-27 |
| IGKV8-26 | 6C1 (31.80 cM) | FWD | 620240 | NC_000072.6 | 70193228..70193797 | 1 | MGI:4439869 | Igkv8-26 |
| IGKV6-25 | 6C1 (31.81 cM) | FWD | 381784 | NC_000072.6 | 70215433..70215957 | 1 | MGI:4439867 | Igkv6-25 |
| IGKV8-24 | 6C1 (31.81 cM) | REV | 677858 | NC_000072.6 | 70216858..70217421 | -1 | MGI:4947958 | Igkv8-24 |
| IGKV8-23-1 | 6C1 (31.82 cM) | FWD | 434685 | NC_000072.6 | 70240427..70240710 | 1 | MGI:4947960 | Igkv8-23-1 |

FIG. 44 (Continued)

| | | | | | | |
|---|---|---|---|---|---|---|
| IGKV6-23 | 6C1 (31.83 cM) | REV | 637227 | NC_000072.6 | 70260409..70260933 | -1 | MGI:3711980 | Igkv6-23 |
| IGKV8-22 | 6C1 (31.85 cM) | REV | 620387 | NC_000072.6 | 70297554..70298119 | -1 | MGI:5009833 | Igkv8-22 |
| IGKV8-21 | 6C1 (31.85 cM) | REV | 620400 | NC_000072.6 | 70314895..70315452 | -1 | MGI:1330840 | Igkv8-21 |
| IGKV6-20 | 6C1 (31.86 cM) | REV | 108024 | NC_000072.6 | 70335841..70336479 | -1 | MGI:1330836 | Igkv6-20 |
| IGKV8-19 | 6C1 (31.87 cM) | REV | 232065 | NC_000072.6 | 70340876..70341448 | -1 | MGI:1330844 | Igkv8-19 |
| IGKV8-18 | 6C1 (31.87 cM) | FWD | 667859 | NC_000072.6 | 70355877..70356445 | 1 | MGI:1330845 | Igkv8-18 |
| IGKV6-17 | 6C1 (31.88 cM) | FWD | 667865 | NC_000072.6 | 70371469..70371993 | 1 | MGI:1330833 | Igkv6-17 |
| IGKV8-16 | 6C1 (31.89 cM) | REV | 640340 | NC_000072.6 | 70386672..70387238 | -1 | MGI:1330843 | Igkv8-16 |
| IGKV6-15 | 6C1 (31.89 cM) | REV | 108022 | NC_000072.6 | 70406469..70406992 | -1 | MGI:1330831 | Igkv6-15 |
| IGKV6-14 | 6C1 (31.91 cM) | REV | 667881 | NC_000072.6 | 70434952..70435476 | -1 | MGI:1330830 | Igkv6-14 |
| IGKV6-13 | 6C1 (31.92 cM) | REV | 667899 | NC_000072.6 | 70457503..70458036 | -1 | MGI:1330829 | Igkv6-13 |
| IGKV3-12-1 | 6C1 (31.94 cM) | REV | 667908 | NC_000072.6 | 70497662..70498342 | -1 | MGI:3645632 | Igkv3-12-1 |
| IGKV3-12 | 6C1 (31.95 cM) | FWD | 667914 | NC_000072.6 | 70518250..70518849 | 1 | MGI:1330815 | Igkv3-12 |
| IGKV3-11 | 6C1 (31.96 cM) | FWD | 667917 | NC_000072.6 | 70553274..70554440 | 1 | MGI:1330820 | Igkv3-11 |
| IGKV3-10 | 6C1 (31.97 cM) | FWD | 667924 | NC_000072.6 | 70572633..70573230 | 1 | MGI:1330821 | Igkv3-10 |
| IGKV3-9 | 6C1 (31.98 cM) | FWD | 667928 | NC_000072.6 | 70588189..70588777 | 1 | MGI:1330856 | Igkv3-9 |
| IGKV3-8 | 6C1 (31.98 cM) | FWD | 108010 | NC_000072.6 | 70588871..70589452 | 1 | MGI:1330857 | Igkv3-8 |
| IGKV3-7 | 6C1 (31.99 cM) | FWD | 108005 | NC_000072.6 | 70607437..70608036 | 1 | MGI:1330852 | Igkv3-7 |
| IGKV3-6 | 6C1 (31.99 cM) | FWD | 667936 | NC_000072.6 | 70642405..70643565 | 1 | MGI:1330853 | Igkv3-6 |
| IGKV3-5 | 6C1 (32.00 cM) | FWD | 667940 | NC_000072.6 | 70663298..70663895 | 1 | MGI:1330854 | Igkv3-5 |
| IGKV3-4 | 6C1 (32.01 cM) | FWD | 626347 | NC_000072.6 | 70671789..70672377 | 1 | MGI:1330855 | Igkv3-4 |
| IGKV3-3 | 6C1 (32.02 cM) | FWD | 667946 | NC_000072.6 | 70686946..70687534 | 1 | MGI:1330849 | Igkv3-3 |
| IGKV3-2 | 6C1 (32.03 cM) | FWD | 626583 | NC_000072.6 | 70698468..70699067 | 1 | MGI:1330850 | Igkv3-2 |
| IGKV3-1 | 6C1 (32.03 cM) | FWD | 108004 | NC_000072.6 | 70703578..70704177 | 1 | MGI:1330851 | Igkv3-1 |
| IGKJ1 | 6C1 (32.04 cM) | FWD | 110759 | NC_000072.6 | 70722562..70722599 | 1 | MGI:1316689 | Igkj1 |
| IGKJ2 | 6C1 (32.04 cM) | FWD | 110760 | NC_000072.6 | 70722916..70722954 | 1 | MGI:1316690 | Igkj2 |
| IGKJ3 | 6C1 (32.04 cM) | FWD | 110761 | NC_000072.6 | 70723223..70723260 | 1 | MGI:1316691 | Igkj3 |
| IGKJ4 | 6C1 (32.04 cM) | FWD | 110762 | NC_000072.6 | 70723548..70723585 | 1 | MGI:1316692 | Igkj4 |
| IGKJ5 | 6C1 (32.04 cM) | FWD | 110763 | NC_000072.6 | 70723886..70723923 | 1 | MGI:1316738 | Igkj5 |

FIG. 44 (Continued)

| IGKC | 6C1 (32.04 cM) | FWD | 16071 | NC_000072.6 | 70726435..70726754 | 1 | MGI:96495 | Igkc |
|---|---|---|---|---|---|---|---|---|

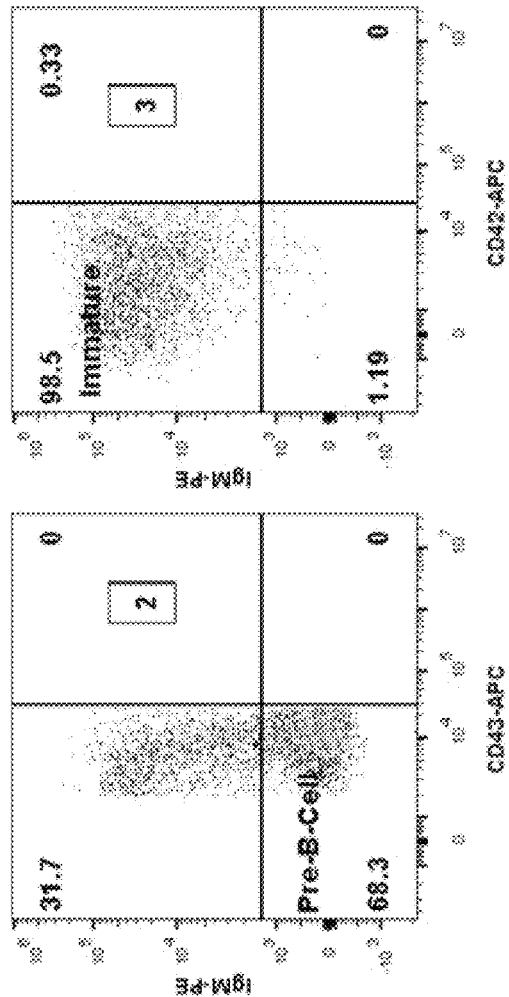
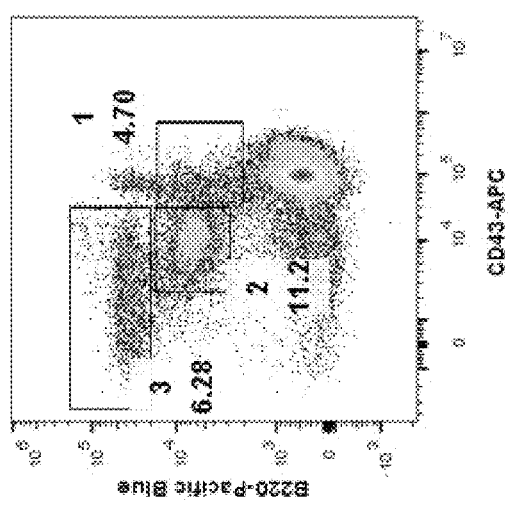
FIG. 51C

| Proximal V-CLUSTER from 3' (top of column) to 5' (bottom of column) | Distal V-CLUSTER from 3' (bottom of column) to 5' (top of column) |
|---|---|
| IGKV4-1 | |
| IGKV5-2 | |
| IGKV7-3 | |
| IGKV2-4 | |
| IGKV1-5 | |
| IGKV1-6 | |
| IGKV3-7 | IGKV3D-7 |
| IGKV1-8 | IGKV1D-8 |
| | IGKV1D-43 |
| | IGKV1D-42 |
| IGKV1-9 | |
| IGKV2-10 | IGKV2D-10 |
| IGKV3-11 | IGKV3D-11 |
| IGKV1-12 | IGKV1D-12 |
| IGKV1-13 | IGKV1D-13 |
| IGKV2-14 | IGKV2D-14 |
| IGKV3-15 | IGKV3D-15 |
| IGKV1-16 | IGKV1D-16 |
| IGKV1-17 | IGKV1D-17 |
| | IGKV6D-41 |
| IGKV2-18 | IGKV2D-18 |
| IGKV2-19 | IGKV2D-19 |
| IGKV3-20 | IGKV3D-20 |
| IGKV6-21 | IGKV6D-21 |
| IGKV1-22 | IGKV1D-22 |
| IGKV2-23 | IGKV2D-23 |
| IGKV2-24 | IGKV2D-24 |
| IGKV3-25 | IGKV3D-25 |
| IGKV2-26 | IGKV2D-26 |
| IGKV1-27 | IGKV1D-27 |
| IGKV2-28 | IGKV2D-28 |
| IGKV2-29 | IGKV2D-29 |
| IGKV2-30 | IGKV2D-30 |
| IGKV3-31 | IGKV3D-31 |
| IGKV1-32 | IGKV1D-32 |
| IGKV1-33 | IGKV1D-33 |
| IGKV3-34 | IGKV3D-34 |
| IGKV1-35 | IGKV1D-35 |
| IGKV2-36 | IGKV2D-36 |
| IGKV1-37 | IGKV1D-37 |
| IGKV2-38 | IGKV2D-38 |
| IGKV1-39 | IGKV1D-39 |
| IGKV2-40 | IGKV2D-40 |

FIG. 64

GENETICALLY MODIFIED NON-HUMAN ANIMALS WITH HUMANIZED IMMUNOGLOBULIN LOCUS

CLAIM OF PRIORITY

This application is a continuation of International Application PCT/CN2020/075698, with an international filing date of Feb. 18, 2020, which then claims priority to PCT/CN2019/075406, filed on Feb. 18, 2019 and PCT/CN2019/106320, filed on Sep. 18, 2019 under 35 U.S.C. § 365(b). The entire contents of the foregoing are incorporated herein by reference.

TECHNICAL FIELD

This disclosure relates to genetically modified animals and cells with humanized heavy chain immunoglobulin locus and/or humanized light chain immunoglobulin locus.

BACKGROUND

Therapeutic antibodies are one of the fastest growing classes of therapeutic compounds, rapidly outpacing the growth of small-molecule drugs. These therapeutic antibodies are usually human or humanized antibodies. The human or humanized antibodies can be generated by humanization of a rodent antibody (e.g., a mouse antibody) or by using phage libraries. The antibodies that are generated by these methods often have suboptimal binding affinities and biophysical attributes, leading to difficulties in manufacture and poor pharmacokinetics. Particularly, the humanization process may adversely affect the binding affinity and introduce immunogenic epitopes to the antibodies, and antibodies discovered using phage libraries show limited diversity and non-native pairing of immunoglobulin heavy and light chains. Iterative and time-consuming experiments are often required to improve the properties. And in some cases, these antibodies can also be immunogenic in patients, leading to attenuation of their efficacy over time.

One possible approach for generating fully human antibodies is to use transgenic animals engineered to express a human antibody repertoire. The generation of transgenic animals, such as mice having varied immunoglobulin loci, has allowed the use of such transgenic animals in various research and development applications, e.g., in drug discovery and basic research into various biological systems. Many of the early generation transgenic animals had incomplete human antibody repertoires, had antibody production below the normal rates due to less efficient V(D)J recombination, had endogenous antibody repertoires which may introduce immunogenic epitopes, and various other issues. There is a need for efficient and cost-effective methods of producing human antibodies, and a need for non-human animals comprising humanized immunoglobulin locus, which have the ability to respond to an antigen to generate humanized antibodies.

SUMMARY

The present disclosure relates to genetically modified animals and cells with humanized heavy chain and light chain immunoglobulin locus.

In some aspects, the disclosure relates to a genetically-modified, non-human animal comprising at an endogenous heavy chain immunoglobulin gene locus, one or more human IGHV genes, one or more human IGHD genes, and one or more human IGHJ genes. In some embodiments, the human IGHV genes, the human IGHD genes, and the human IGHJ genes are operably linked and can undergo VDJ rearrangement.

In some embodiments, the animal comprises about or at least 150, 151, 152, 153, 154, 155, 156, 157, 158, 159, 160 or 161 human IGHV genes selected from Table 1, about or at least 20, 21, 22, 23, 24, 25, 26, or 27 human IGHD genes selected from Table 2, and about or at least 5, 6, 7, 8, or 9 human IGHJ genes selected from Table 3. In some embodiments, the animal comprises all human IGHV genes in Table 1 except IGHV2-10, IGHV3-9, and IGHV1-8, all human IGHD genes in Table 2, and all human IGHJ genes in Table 3. In some embodiments, the animal comprises all human IGHV genes in Table 1 except IGHV5-10-1 and IGHV3-64D, all human IGHD genes in Table 2, and all human IGHJ genes in Table 3. In some embodiments, the animal comprises all human IGHV genes, all human IGHD genes, and all human IGHJ genes at the endogenous heavy chain immunoglobulin gene locus of human chromosome 14 of a human subject. In some embodiments, the animal comprises all human IGHV genes, all human IGHD genes, and all human IGHJ genes at the endogenous heavy chain immunoglobulin gene locus of human chromosome 14 of a human cell (e.g., a somatic cell, a cultured cell, a non-immune cell, a cell without any V(D)J rearrangement).

In some embodiments, the animal comprises a disruption in the animal's endogenous heavy chain immunoglobulin gene locus.

In some embodiments, the animal is a mouse and the disruption in the animal's endogenous heavy chain immunoglobulin gene locus comprises a deletion of one or more mouse IGHV genes in Table 4, one or more mouse IGHD genes in Table 5, and/or one or more mouse IGHJ genes in Table 6.

In some embodiments, the animal is a mouse and the disruption in the animal's endogenous heavy chain immunoglobulin gene locus comprises a deletion of a contiguous sequence starting from mouse IGHV1-85 gene to mouse IGHJ4 gene.

In some embodiments, the animal comprises one or more endogenous IGHM, IGHδ, IGHG3, IGHG1, IGHG2b, IGHG2a, IGHE, and IGHA genes.

In some embodiments, the animal comprises an unmodified human sequence derived from a human heavy chain immunoglobulin gene locus.

In some embodiments, the unmodified human sequence is about or at least 10, 20, 30, 40, 50, 60, 70, 80, 90, 100, 200, 300, 400, 500, 600, 700, 800, 900, or 1000 kb.

In some embodiments, the animal comprises an unmodified human sequence derived from a human heavy chain immunoglobulin gene locus starting from human IGHV (III)-82 to human IGHV1-2. In some embodiments, the animal comprises an unmodified human sequence derived from a human heavy chain immunoglobulin gene locus starting from human IGHV(III)-82 to human IGHV6-1. In some embodiments, the animal comprises an unmodified human sequence derived from a human heavy chain immunoglobulin gene locus starting from human IGHD1-1 to human IGHJ6.

In some embodiments, the animal comprises an unmodified human sequence derived from a human heavy chain immunoglobulin gene locus starting from human IGHV (III)-82 to human IGHJ6.

In some embodiments, the animal is homozygous with respect to the heavy chain immunoglobulin gene locus. In some embodiments, the animal is heterozygous with respect to the heavy chain immunoglobulin gene locus.

In some embodiments, the animal further comprises at an endogenous light chain immunoglobulin gene locus, one or more human IGKV genes, and one or more human IGKJ genes.

In some embodiments, the animal comprises a disruption in the animal's endogenous lambda light chain immunoglobulin gene locus.

In some embodiments, the animal is a rodent (e.g., a mouse).

In some aspects, the disclosure relates to a genetically-modified animal comprising at an endogenous heavy chain immunoglobulin gene locus, a first sequence comprising one or more human IGHV genes; a second sequence comprising an endogenous sequence; and a third sequence comprising one or more human IGHD genes, and one or more human IGHJ genes, wherein the first sequence, the second sequence, and the third sequence are operably linked.

In some embodiments, the first sequence comprises about or at least 150, 151, 152, 153, 154, 155, 156, 157, 158, 159, 160 or 161 human IGHV genes selected from Table 1. In some embodiments, the first sequence comprises about or at least 20, 21, 22, 23, 24, 25, 26, or 27 human IGHD genes selected from Table 2.

In some embodiments, the first sequence is an unmodified sequence derived from a human heavy chain immunoglobulin gene locus. In some embodiments, the first sequence is about or at least 10, 20, 30, 40, 50, 60, 70, 80, 90, 100, 200, 300, 400, 500, 600, 700, 800, 900, or 1000 kb.

In some embodiments, the second sequence comprises an endogenous sequence that is about or at least 1, 2, 3, 4, 5, 6, 7, 8, 9, 10, 11, 12, 13, 14, 15, 16, 17, 18, 19, or 20 kb.

In some embodiments, the third sequence comprises about or at least 20, 21, 22, 23, 24, 25, 26, or 27 human IGHD genes selected from Table 2. In some embodiments, the third sequence comprises about or at least 5, 6, 7, 8, or 9 human IGHJ genes selected from Table 3. In some embodiments, the third sequence comprises all human IGHD genes in Table 2, and all human IGHJ genes in Table 3.

In some embodiments, the third sequence is an unmodified sequence derived from a human heavy chain immunoglobulin gene locus. In some embodiments, the third sequence is about or at least 10, 20, 30, 40, 50, 60, 70, 80, 90 or 100 kb.

In some embodiments, the animal comprises a disruption in the animal's endogenous heavy chain immunoglobulin gene locus.

In some embodiments, the animal is a mouse and the disruption in the animal's endogenous heavy chain immunoglobulin gene locus comprises a deletion of one or more mouse IGHV genes in Table 4, one or more mouse IGHD genes in Table 5, and one or more mouse IGHJ genes in Table 6.

In some embodiments, the animal is a mouse and the disruption in the animal's endogenous heavy chain immunoglobulin gene locus comprises a deletion of a sequence starting from mouse IGHV1-85 to mouse IGHJ4.

In some embodiments, the animal comprises one or more endogenous genes selected from the group consisting of IGHM, IGHδ, IGHG3, IGHG1, IGHG2b, IGHG2a, IGHE, and IGHA genes.

In some embodiments, the animal is homozygous with respect to the heavy chain immunoglobulin gene locus. In some embodiments, the animal is heterozygous with respect to the heavy chain immunoglobulin gene locus.

In some embodiments, the animal further comprises at an endogenous light chain immunoglobulin gene locus, one or more human IGKV genes, and one or more human IGKJ genes.

In some embodiments, the animal comprises a disruption in the animal's endogenous lambda light chain immunoglobulin gene locus.

In some embodiments, the animal is a rodent (e.g., a mouse).

In some aspects, the disclosure relates to a genetically-modified, non-human animal comprising at an endogenous light chain immunoglobulin gene locus, one or more human IGKV genes and one or more human IGKJ genes.

In some embodiments, the animal comprises about or at least 65, 66, 67, 68, 69, 70, 71, 72, 73, 74, 75, or 76 human IGKV genes in Table 7, and/or comprises about or at least 1, 2, 3, 4, or 5 human IGKJ genes in Table 8.

In some embodiments, the animal comprises an unmodified sequence derived from a human light chain immunoglobulin gene locus starting from human IGKV3D-7 to human IGKJ5.

In some embodiments, the animal comprises a disruption in the animal's endogenous light chain immunoglobulin gene locus.

In some embodiments, the animal is a mouse and the disruption in the animal's endogenous light chain immunoglobulin gene locus comprises a deletion of one or more mouse IGKV genes in Table 9 and one or more mouse IGKJ genes in Table 10. In some embodiments, the animal comprises all human IGKV genes, and all human IGKJ genes at the endogenous kappa chain immunoglobulin gene locus of human chromosome 2 of a human subject. In some embodiments, the animal comprises all human IGKV genes, and all human IGKJ genes at the endogenous heavy chain immunoglobulin gene locus of human chromosome 2 of a human cell (e.g., a somatic cell, a cultured cell, a non-immune cell, a cell without any V(D)J rearrangement).

In some embodiments, the animal is a mouse and the disruption in the animal's endogenous light chain immunoglobulin gene locus comprises a deletion of a sequence starting from mouse IGKV2-137 to mouse IGKJ5.

In some embodiments, the animal comprises an endogenous IGKC.

In some embodiments, the animal is homozygous with respect to the light chain immunoglobulin gene locus. In some embodiments, the animal is heterozygous with respect to the light chain immunoglobulin gene locus.

In some embodiments, the animal further comprises at an endogenous heavy chain immunoglobulin gene locus, one or more human IGHV genes, one or more human IGHD genes, and one or more human IGHJ genes.

In some embodiments, the animal comprises a disruption in the animal's endogenous lambda light chain immunoglobulin gene locus.

In some embodiments, the animal is a rodent (e.g., a mouse).

In some aspects, the disclosure relates to a genetically-modified, non-human animal whose genome comprises an endogenous heavy chain immunoglobulin locus comprising: a replacement of one or more endogenous IGHV, endogenous IGHD, and endogenous IGHJ genes with one or more human IGHV, human IGHD, and human IGHJ genes. In some embodiments, human IGHV, human IGHD, and human IGHJ genes are operably linked to one or more of endogenous genes selected from the group consisting of IGHM, IGHδ, IGHG, IGHE, and IGHA genes.

In some embodiments, one or more endogenous IGHV, endogenous IGHD, and endogenous IGHJ genes are replaced by about or at least 150, 151, 152, 153, 154, 155, 156, 157, 158, 159, 160 or 161 human IGHV genes in Table 1, about or at least 20, 21, 22, 23, 24, 25, 26, or 27 human IGHD genes in Table 2, and about or at least 5, 6, 7, 8, or 9 human IGHJ genes in Table 3.

In some embodiments, the animal is a mouse, and about or at least 180 mouse IGHV genes in Table 4, all mouse IGHD genes in Table 5, and all mouse IGHJ genes in Table 6 are replaced.

In some aspects, the disclosure relates to a genetically-modified, non-human animal whose genome comprises an endogenous light chain immunoglobulin locus comprising: a replacement of one or more endogenous IGKV and endogenous IGKJ genes with one or more human IGKV and human IGKJ genes. In some embodiments, the human IGKV and human IGKJ genes are operably linked to an endogenous IGKC gene.

In some embodiments, one or more endogenous IGKV and endogenous IGKJ genes are replaced by about or at least 65, 66, 67, 68, 69, 70, 71, 72, 73, 74, 75, or 76 human IGKV genes in Table 7, and about or at least 1, 2, 3, 4, or 5 human IGKJ genes in Table 8.

In some embodiments, the animal is a mouse, and all mouse IGKV genes in Table 9 and all mouse IGKJ genes in Table 10 are replaced.

In some embodiments, the animal lacks an endogenous immunoglobulin heavy chain variable region locus that is capable of rearranging and forming a nucleic acid sequence that encodes an endogenous heavy chain variable domain (e.g., a mouse heavy chain variable domain).

In some embodiments, the animal lacks an endogenous immunoglobulin light chain variable region locus that is capable of rearranging and forming a nucleic acid sequence that encodes an endogenous light chain variable domain (e.g., a mouse light chain variable domain).

In some embodiments, the animal can produce a humanized antibody.

In some aspects, the disclosure relates to a cell obtained from the animal as described herein.

In some embodiments, the cell is a B cell that expresses a chimeric immunoglobulin heavy chain comprising an immunoglobulin heavy chain variable domain that is derived from a rearrangement of one or more human IGHV genes, one or more human IGHD genes, and one or more human IGHJ genes. In some embodiments, the immunoglobulin heavy chain variable domain is operably linked to a non-human heavy chain constant region.

In some embodiments, the cell is a B cell that expresses a chimeric immunoglobulin light chain comprising an immunoglobulin light chain variable domain that is derived from a rearrangement of one or more human IGKV genes and one or more human IGKJ genes, and wherein the immunoglobulin light chain variable domain is operably linked to a non-human light chain constant region.

In some embodiments, the cell is an embryonic stem (ES) cell.

In some aspects, the disclosure relates to a method of making a chimeric antibody that specifically binds to an antigen, the method comprising exposing the animal as described herein to the antigen; producing a hybridoma from a cell collected from the animal; and collecting the chimeric antibody produced by the hybridoma. In some embodiments, the cell of interest is isolated and sequencing is performed to determine the sequences of rearranged heavy chain variable region and light chain variable region.

In some embodiments, the method further comprises sequencing the genome of the hybridoma.

In some aspects, the disclosure relates to a method of modifying genome of a cell, the method comprising modifying a human chromosome; introducing the modified human chromosome into a cell of the animal; and inducing recombination between the modified human chromosome and an endogenous chromosome, thereby replacing one or more endogenous genes with one or more human genes.

In some embodiments, the modified human chromosome comprises two or more exogenous recombination sites.

In some embodiments, the endogenous chromosome comprises two or more exogenous recombination sites.

In some embodiments, about or at least 150, 151, 152, 153, 154, 155, 156, 157, 158, 159, 160 or 161 human IGHV genes selected from Table 1, about or at least 20, 21, 22, 23, 24, 25, 26, or 27 human IGHD genes selected from Table 2, and about or at least 5, 6, 7, 8, or 9 human IGHJ genes selected from Table 3 are integrated into the endogenous chromosome by recombination.

In some embodiments, about or at least 65, 66, 67, 68, 69, 70, 71, 72, 73, 74, 75, or 76 human IGKV genes in Table 7, and about or at least 1, 2, 3, 4, or 5 human IGKJ genes in Table 8 are integrated into the endogenous chromosome by recombination.

In some embodiments, a human sequence is integrated into the endogenous chromosome by recombination, and the human sequence is about or at least 10, 20, 30, 40, 50, 60, 70, 80, 90, 100, 200, 300, 400, 500, 600, 700, 800, 900, or 1000 kb.

In one aspect, the disclosure provides a method of making an antibody that specifically binds to an antigen. The method involves obtaining a nucleic acid sequence encoding human heavy and light chain immunoglobulin variable regions in a cell that expresses a hybrid antibody that specifically binds to the antigen, wherein the cell is obtained by exposing the animal as described herein to the antigen; operably linking the nucleic acid encoding the human heavy chain immunoglobulin variable region with a nucleic acid encoding a human heavy chain immunoglobulin constant region and the nucleic acid encoding the human light chain immunoglobulin variable region with a nucleic acid encoding a human light chain immunoglobulin constant region; and expressing the nucleic acid in a cell, thereby obtaining the antibody.

In one aspect, the disclosure provides a method of obtaining a nucleic acid that encodes an antibody binding domain that specifically binds to an antigen. The method involves exposing the animal as described herein to the antigen; and sequencing nucleic acids encoding human heavy and light chain immunoglobulin variable regions in a cell that expresses a hybrid antibody that specifically binds to the antigen.

In one aspect, the disclosure provides a method of obtaining a sample, the method comprising exposing the animal as described herein to the antigen; and collecting the sample from the animal. In some embodiments, the sample is a spleen tissue, a spleen cell, or a B cell.

In one aspect, the disclosure provides a method of making an antibody that specifically binds to an antigen. The method involves exposing the animal as described herein to the antigen; obtaining the sequence of (e.g. by sequencing) nucleic acids encoding human heavy and light chain immunoglobulin variable regions in a cell that expresses a hybrid antibody that specifically binds to the antigen; and operably linking in a cell the nucleic acid encoding the human heavy chain immunoglobulin variable region with a nucleic acid encoding a human heavy chain immunoglobulin constant region and the nucleic acid encoding the human light chain immunoglobulin variable region with a nucleic acid encoding a human light chain immunoglobulin constant region.

The disclosure also relates to an offspring of the non-human mammal.

In some embodiments, the non-human mammal is a rodent. In some embodiments, the non-human mammal is a mouse.

The disclosure also provides to a cell including the targeting vector as described herein.

The disclosure also relates to a cell (e.g., a stem cell, an embryonic stem cell, an immune cell, a B cell, a T cell, or a hybridoma) or a cell line, or a primary cell culture thereof derived from the non-human mammal or an offspring thereof. The disclosure further relates to the tissue, organ or a culture thereof derived from the non-human mammal or an offspring thereof.

The disclosure further relates to the use of the non-human mammal or an offspring thereof, the animal model generated through the method as described herein in the development of a product related to an immunization processes, the manufacture of a human antibody, or the model system for a research in pharmacology, immunology, microbiology and medicine.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 29 is a schematic diagram showing the modified human chromosome 2.

FIG. 30 is a schematic diagram showing a gene targeting strategy for human chromosome 2.

FIG. 41 lists IMGT repertoire for human heavy chain immunoglobulin locus (IGH).

FIG. 42 lists IMGT repertoire for mouse IGH.

FIG. 43 lists IMGT repertoire for human kappa chain immunoglobulin locus (IGK).

FIG. 44 lists IMGT repertoire for mouse IGK.

FIG. 51C shows flow cytometry analysis results for B cells at different development stages in the bone marrow obtained from humanized heavy chain homozygous mice. Area 1 represents pro-B-cells, Area 2 represents pre-B-cells, and Area 3 represents immature B-cells.

FIG. 64 shows a list of human distal Vκ cluster IGKV genes and a list of human proximal Vκ cluster IGKV genes.

DETAILED DESCRIPTION

The present disclosure relates to genetically modified animals and cells with humanized heavy chain immunoglobulin locus and/or humanized light chain immunoglobulin locus (e.g., kappa chain locus).

Figure 1A:
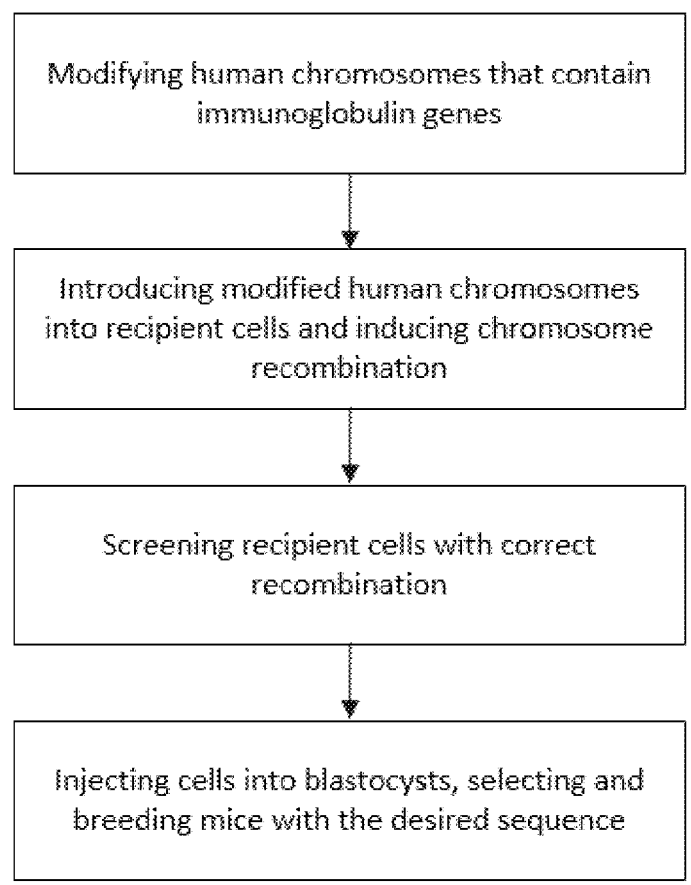
FIG. 1A is a flow chart of a method of introducing human immunoglobulin genes into the mouse genome.

The genetically modified animals can be made by introducing human immunoglobulin genes into the genome of non-human animals to produce animals that can express humanized antibodies or chimeric antibodies. FIG. 1A shows the methods of making the humanized mice. In some embodiments, the methods first involve modifying the human immunoglobulin region on the human chromosome. The modified human chromosomes are then introduced into the mouse recipient cell. The human immunoglobulin variable region is then introduced into the corresponding region of the mouse genome by direct replacement (e.g., in one step replacement). The recipient cells are then screened, preferably for the cells that do not contain the human chromosomes. The cells are then injected to blastocysts to prepare chimeric animals (e.g., mice). Subsequent breeding can be performed to obtain animals containing intact humanized immunoglobulin locus.

The genetically modified animals described herein can have various advantages. For examples, in some cases, the genetically modified animals described herein have complete human antibody repertoires. Thus, the variable domains generated by these animals can have a diversity that is very similar to the diversity of the variable domains in human. Furthermore, because the entire sequence at the human immunoglobulin locus are introduced into the animal genome (with no modifications or limited modifications), these genes can undergo the V(D)J recombination in a way that is very similar to what happens in human. In addition, the antibody production can be very efficient and has a rate that is similar to the normal rates due to the efficient V(D)J recombination. In addition, because V(D)J recombination may occur between endogenous IGHV, IGHD, IGHJ, IGKV and IGKJ genes and human genes, if the endogenous IGHV, IGHD, IGHJ, IGKV and IGKJ genes are incorporated in the rearranged heavy chain VDJ segment or the rearranged light chain VJ segment, it is likely that the antibodies generated by the antibody repertoires have immunogenic epitopes in human. The immunogenicity can lead to production of anti-drug-antibodies and may comprise efficacy. Here, the endogenous IGHV, IGHD, IGHJ, IGKV and IGKJ genes have been effectively deleted. It is less likely that the antibodies generated by the antibody repertoires are immunogenic in humans. Thus, the antibodies are more suitable for being used as therapeutics in humans. Therefore, the genetically modified animals provide an advantageous platform to produce humanized antibodies.

As used herein, the term "antibody" refers to an immunoglobulin molecule comprising four polypeptide chains, two heavy (H) chains and two light (L) chains inter-connected by disulfide bonds. Each heavy chain comprises a heavy chain variable (VH) domain and a heavy chain constant region (CH). Each light chain comprises a light chain variable (VL) domain and a light chain constant region (CL). The VH and VL domains can be further subdivided into regions of hypervariability, termed complementarity determining regions (CDR), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a $K_D$ with respect to its target epitope about of $10^{-9}$ M or lower (e.g., about or lower than $1\times10^{-9}$ M, $1\times10^{-10}$ M, $1\times10^{-11}$ M, or $1\times10^{-12}$ M). In some embodiments, $K_D$ can be measured by surface plasmon resonance, e.g., BIACORE™ or ELISA.

As used herein, the term "antigen-binding fragment" refers to a portion of a full-length antibody, wherein the portion of the antibody is capable of specifically binding to an antigen. In some embodiments, the antigen-binding fragment contains at least one variable domain (e.g., a variable domain of a heavy chain or a variable domain of light chain). Non-limiting examples of antibody fragments include, e.g., Fab, Fab', F(ab')2, and Fv fragments.

As used herein, the term "human antibody" refers to an antibody that is encoded by a nucleic acid (e.g., rearranged human immunoglobulin heavy or light chain locus) present in a human. In some embodiments, a human antibody is collected from a human or produced in a human cell culture (e.g., human hybridoma cells). In some embodiments, a human antibody is produced in a non-human cell (e.g., a mouse or hamster cell line). In some embodiments, a human antibody is produced in a bacterial or yeast cell. In some embodiments, a human antibody is produced in a transgenic non-human animal (e.g., a mouse) containing an unrearranged or rearranged human immunoglobulin locus (e.g., heavy or light chain human immunoglobulin locus).

As used herein, the term "chimeric antibody" refers to an antibody that contains a sequence present in at least two different antibodies (e.g., antibodies from two different mammalian species such as a human and a mouse antibody). A non-limiting example of a chimeric antibody is an antibody containing the variable domain sequences (e.g., all or part of a light chain and/or heavy chain variable domain sequence) of a human antibody and the constant domains of a non-human antibody. Additional examples of chimeric antibodies are described herein and are known in the art.

As used herein, the term "humanized antibody" refers to a non-human antibody which contains sequence derived from a non-human (e.g., mouse) immunoglobulin and contains sequences derived from a human immunoglobulin.

As used herein, the term "single-chain antibody" refers to a single polypeptide that contains at least two immunoglobulin variable domains (e.g., a variable domain of a mammalian immunoglobulin heavy chain or light chain) that is capable of specifically binding to an antigen.

As used herein, the terms "subject" and "patient" are used interchangeably throughout the specification and describe an animal, human or non-human. Veterinary and non-veterinary applications are contemplated by the present disclosure. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, when referring to an antibody, the phrases "specifically binding" and "specifically binds" mean that the antibody interacts with its target molecule preferably to other molecules, because the interaction is dependent upon the presence of a particular structure (i.e., the antigenic determinant or epitope) on the target molecule; in other words, the reagent is recognizing and binding to molecules that include a specific structure rather than to all molecules in general. An antibody that specifically binds to the target molecule may be referred to as a target-specific antibody.

As used herein, the terms "polypeptide," "peptide," and "protein" are used interchangeably to refer to polymers of amino acids of any length of at least two amino acids.

As used herein, the terms "polynucleotide," "nucleic acid molecule," and "nucleic acid sequence" are used interchangeably herein to refer to polymers of nucleotides of any length of at least two nucleotides, and include, without limitation, DNA, RNA, DNA/RNA hybrids, and modifications thereof.

As used herein, the term "an unmodified human sequence" refers to a sequence that is derived from a human subject, a human cell, a cultured human cell or a human cell line, wherein the sequence is identical to the genetic sequence of a human subject, a human cell, a cultured human cell or a human cell line.

Genetically Modified Heavy Chain Immunoglobulin Locus

Heavy chain immunoglobulin locus (also known as IGH or immunoglobulin heavy locus) is a region on the chromosome (e.g., human chromosome 14) that contains genes for the heavy chains of human antibodies (or immunoglobulins).

This region represents the germline organization of the heavy chain locus. The locus includes V (variable), D (diversity), J (joining), and C (constant) segments. The genes in the V region form a V gene cluster (also known as IGHV gene cluster). The genes in the D region form a D gene cluster (also known as IGHD gene cluster). The genes in the J region form a J gene cluster (also known as IGHJ gene cluster).

During B cell development, a recombination event at the DNA level joins a single D segment (also known as an IGHD gene) with a J segment (also known as an IGHJ gene); the fused D-J exon of this partially rearranged D-J region is then joined to a V segment (also known as an IGHV gene). The rearranged V-D-J region containing a fused V-D-J exon is then transcribed and fused at the RNA level to the IGHM constant region; this transcript encodes a mu heavy chain. Later in development B cells generate V-D-J-Cmu-Cdelta pre-messenger RNA, which is alternatively spliced to encode either a mu or a delta heavy chain. Mature B cells in the lymph nodes undergo switch recombination, so that the fused V-D-J gene segment is brought in proximity to one of the IGHG, IGHA, or IGHE gene segments and each cell expresses either the gamma, alpha, or epsilon heavy chain. Potential recombination of many different IGHV genes with several IGHJ genes provides a wide range of antigen recognition. Additional diversity is attained by junctional diversity, resulting from the random addition of nucleotides by terminal deoxynucleotidyl transferase, and by somatic hypermutation, which occurs during B cell maturation in the spleen and lymph nodes. Several V, D, J, and C segments are known to be incapable of encoding a protein and are considered pseudogenous gene segments (often simply referred to as pseudogenes).

The human heavy chain immunoglobulin locus is located on human chromosome 14. Table 1 lists IGHV genes and its relative orders in this locus.

TABLE 1

List of IGHV genes on human chromosome 14

| Gene names | Order |
|---|---|
| IGHV(III)-82 | 1 |
| IGHV7-81 | 2 |
| IGHV4-80 | 3 |
| IGHV3-79 | 4 |
| IGHV(II)-78-1 | 5 |
| IGHV5-78 | 6 |
| IGHV7-77 | 7 |
| IGHV(III)-76-1 | 8 |
| IGHV3-76 | 9 |
| IGHV3-75 | 10 |
| IGHV(II)-74-1 | 11 |
| IGHV3-74 | 12 |
| IGHV3-73 | 13 |
| IGHV3-72 | 14 |
| IGHV3-71 | 15 |
| IGHV2-70 | 16 |
| IGHV1-69D | 17 |
| IGHV1-69-2 | 18 |
| IGHV3-69-1 | 19 |
| IGHV2-70D | 20 |
| IGHV1-69 | 21 |
| IGHV1-68 | 22 |
| IGHV(III)-67-4 | 23 |
| IGHV(III)-67-3 | 24 |
| IGHV(III)-67-2 | 25 |
| IGHV(II)-67-1 | 26 |
| SLC20A1P1 (GLVR1) | 27 |
| IGHV1-67 | 28 |
| IGHV3-66 | 29 |
| IGHV(II)-65-1 | 30 |
| IGHV3-65 | 31 |
| IGHV3-64 | 32 |
| GOLGA4P3 (Golgin) | 33 |
| IGHV3-63 | 34 |
| IGHV(II)-62-1 | 35 |
| IGHV3-62 | 36 |
| IGHV4-61 | 37 |
| IGHV(II)-60-1 | 38 |
| IGHV3-60 | 39 |
| IGHV4-59 | 40 |
| IGHV1-58 | 41 |
| IGHV3-57 | 42 |
| IGHV7-56 | 43 |
| IGHV4-55 | 44 |
| IGHV3-54 | 45 |
| IGHV(II)-53-1 | 46 |
| IGHV3-53 | 47 |
| IGHV3-52 | 48 |
| IGHV(II)-51-2 | 49 |
| IGHV(III)-51-1 | 50 |
| IGHV5-51 | 51 |
| IGHV3-50 | 52 |
| IGHV(II)-49-1 | 53 |
| IGHV3-49 | 54 |
| IGHV3-48 | 55 |
| IGHV(III)-47-1 | 56 |
| IGHV3-47 | 57 |
| IGHV(II)-46-1 | 58 |
| IGHV1-46 | 59 |
| IGHV1-45 | 60 |
| IGHV(II)-44-2 | 61 |
| IGHV(IV)-44-1 | 62 |
| IGHV(III)-44 | 63 |
| IGHV(II)-43-1 | 64 |
| IGHV3-43 | 65 |
| IGHV3-42 | 66 |
| IGHV3-41 | 67 |
| IGHV(II)-40-1 | 68 |
| IGHV7-40 | 69 |
| IGHV4-39 | 70 |
| IGHV1-38-4 | 71 |
| IGHV(III)-38-1D | 72 |
| IGHV3-38-3 | 73 |
| IGHV(III)-44D | 74 |
| IGHV(II)-43-1D | 75 |
| IGHV3-43D | 76 |
| IGHV3-42D | 77 |
| IGHV7-40D | 78 |
| IGHV4-38-2 | 79 |
| IGHV(III)-38-1 | 80 |
| IGHV3-38 | 81 |
| IGHV3-37 | 82 |
| IGHV3-36 | 83 |
| IGHV3-35 | 84 |
| IGHV7-34-1 | 85 |
| IGHV4-34 | 86 |
| IGHV3-33-2 | 87 |
| IGHV(II)-33-1 | 88 |
| IGHV3-33 | 89 |
| GOLGA4P1 (Golgin) | 90 |
| IGHV3-32 | 91 |
| IGHV(II)-31-1 | 92 |
| IGHV4-31 | 93 |
| IGHV3-30-52 | 94 |
| IGHV(II)-30-51 | 95 |
| IGHV3-30-5 | 96 |
| IGHV3-30-42 | 97 |
| IGHV(II)-30-41 | 98 |
| IGHV4-30-4 | 99 |
| IGHV3-30-33 | 100 |
| IGHV(II)-30-32 | 101 |
| IGHV3-30-3 | 102 |
| IGHV3-30-22 | 103 |
| IGHV(II)-30-21 | 104 |
| IGHV4-30-2 | 105 |
| IGHV4-30-1 | 106 |
| IGHV3-30-2 | 107 |
| IGHV(II)-30-1 | 108 |
| IGHV3-30 | 109 |
| GOLGA4P2 (Golgin) | 110 |
| IGHV3-29 | 111 |
| IGHV(II)-28-1 | 112 |
| IGHV4-28 | 113 |
| IGHV7-27 | 114 |
| IGHV(II)-26-2 | 115 |
| IGHV(III)-26-1 | 116 |
| IGHV2-26 | 117 |
| IGHV(III)-25-1 | 118 |
| IGHV3-25 | 119 |
| IGHV1-24 | 120 |
| IGHV3-23D | 121 |
| IGHV(III)-22-2D | 122 |
| IGHV(II)-22-1D | 123 |
| IGHV3-23 | 124 |
| IGHV(III)-22-2 | 125 |
| IGHV(II)-22-1 | 126 |
| IGHV3-22 | 127 |
| IGHV3-21 | 128 |
| IGHV(II)-20-1 | 129 |
| IGHV3-20 | 130 |
| IGHV3-19 | 131 |
| IGHV1-18 | 132 |
| SLC20A1P2 | 133 |
| IGHV1-17 | 134 |
| IGHV(III)-16-1 | 135 |
| IGHV3-16 | 136 |
| IGHV(II)-15-1 | 137 |
| IGHV3-15 | 138 |
| IGHV1-14 | 139 |
| IGHV(III)-13-1 | 140 |
| IGHV3-13 | 141 |

TABLE 1-continued

List of IGHV genes on human chromosome 14

| Gene names | Order |
|---|---|
| IGHV1-12 | 142 |
| IGHV(III)-11-1 | 143 |
| IGHV3-11 | 144 |
| IGHV2-10 | 145 |
| IGHV3-9 | 146 |
| IGHV1-8 | 147 |
| IGHV5-10-1 | 148 |
| IGHV3-64D | 149 |
| IGHV3-7 | 150 |
| IGHV3-6 | 151 |
| IGHV(III)-5-2 | 152 |
| IGHV(III)-5-1 | 153 |
| IGHV2-5 | 154 |
| IGHV7-4-1 | 155 |
| IGHV4-4 | 156 |
| IGHV1-3 | 157 |
| IGHV(III)-2-1 | 158 |
| IGHV1-2 | 159 |
| * | |
| * | |
| IGHV(II)-1-1 | 162 |
| IGHV6-1 | 163 |
| * | |

Figure 37:
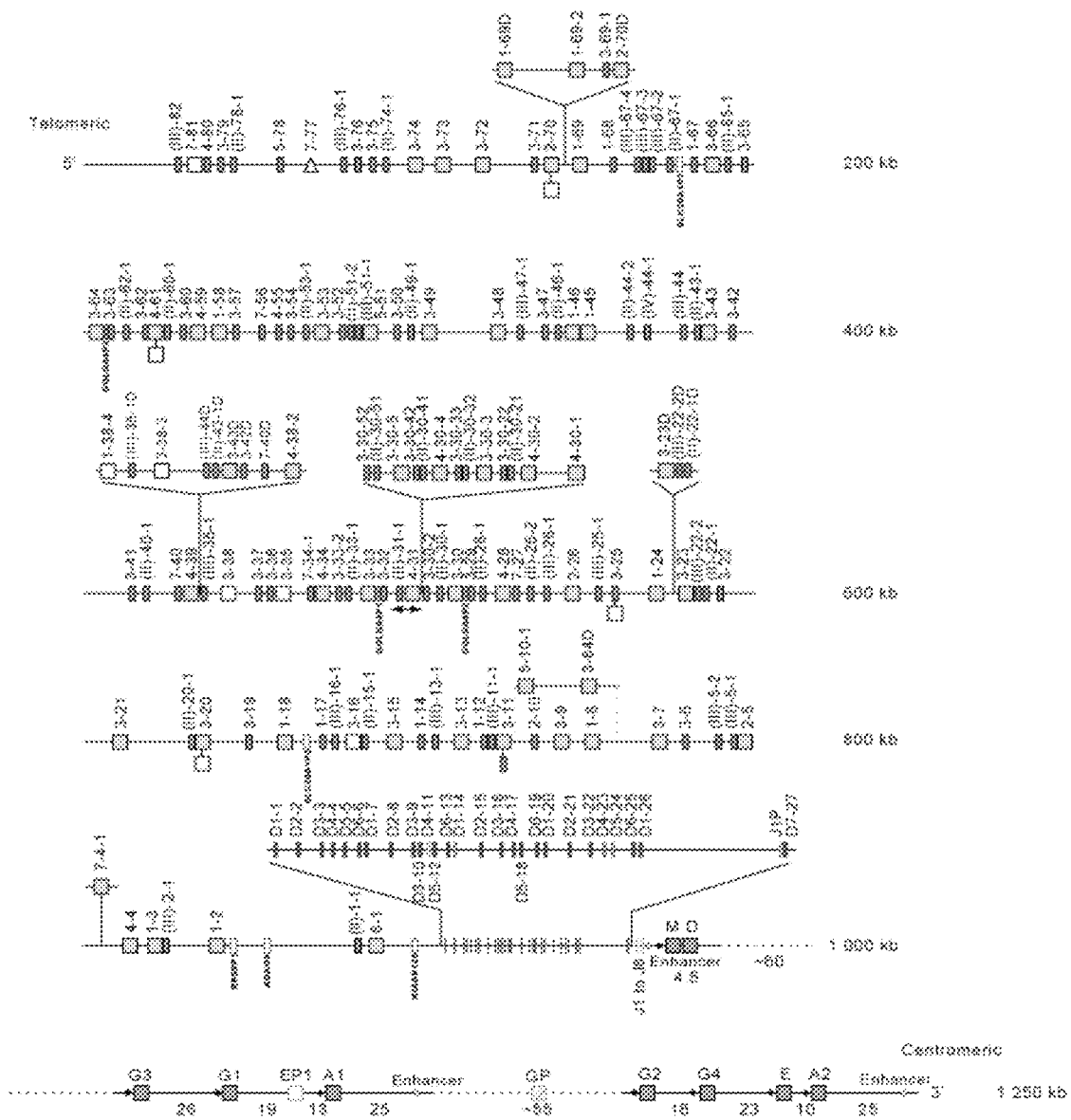
FIG. 37 is a schematic diagram showing human immunoglobulin heavy chain (IGH) locus on chromosome 14 (14q32.33).

RPS8P1, ADAM6, and KIAA0125 are also located in this locus. The relative order of RPS8P1 is 160, the relative order of ADAM6 is 161, and the relative order of KIAA0125 is 164. Table 2 lists all IGHD genes and its relative orders on human chromosome 14. Table 3 lists all IGHJ genes and its relative orders on human chromosome 14. The genes for immunoglobulin constant domains are located after the IGHV, IGHD, and IGHJ genes. These genes include (as shown in the following order): immunoglobulin heavy constant mu (IGHM), immunoglobulin heavy constant delta (IGH δ), immunoglobulin heavy constant gamma 3 (IGHG3), immunoglobulin heavy constant gamma 1 (IGHG1), immunoglobulin heavy constant epsilon P1 (pseudogene) (IGHEP1), immunoglobulin heavy constant alpha 1 (IGHA1), immunoglobulin heavy constant gamma P (non-functional) (IGHGP), immunoglobulin heavy constant gamma 2 (IGHG2), immunoglobulin heavy constant gamma 4 (IGHG4), immunoglobulin heavy constant epsilon (IGHE), and immunoglobulin heavy constant alpha 2 (IGHA2). These genes and the order of these genes are also shown in FIG. 37 and FIG. 41.

TABLE 2

List of IGHD genes on human chromosome 14

| Gene names | Order |
|---|---|
| IGHD1-1 | 165 |
| IGHD2-2 | 166 |
| IGHD3-3 | 167 |
| IGHD4-4 | 168 |
| IGHD5-5 | 169 |
| IGHD6-6 | 170 |
| IGHD1-7 | 171 |
| IGHD2-8 | 172 |
| IGHD3-9 | 173 |
| IGHD3-10 | 174 |
| IGHD4-11 | 175 |
| IGHD5-12 | 176 |
| IGHD6-13 | 177 |
| IGHD1-14 | 178 |
| IGHD2-15 | 179 |
| IGHD3-16 | 180 |
| IGHD4-17 | 181 |

TABLE 2-continued

List of IGHD genes on human chromosome 14

| Gene names | Order |
|---|---|
| IGHD5-18 | 182 |
| IGHD6-19 | 183 |
| IGHD1-20 | 184 |
| IGHD2-21 | 185 |
| IGHD3-22 | 186 |
| IGHD4-23 | 187 |
| IGHD5-24 | 188 |
| IGHD6-25 | 189 |
| IGHD1-26 | 190 |
| * | |
| IGHD7-27 | 192 |

TABLE 3

List of IGHJ genes on human chromosome 14

| Gene names | Order |
|---|---|
| IGHJ1P | 191 |
| IGHJ1 | 193 |
| IGHJ2 | 194 |
| IGHJ2P | 195 |
| IGHJ3 | 196 |
| IGHJ4 | 197 |
| IGHJ5 | 198 |
| IGHJ3P | 199 |
| IGHJ6 | 200 |

The mouse heavy chain immunoglobulin locus is located on mouse chromosome 12. Table 4 lists IGHV genes and its relative orders in this locus.

TABLE 4

List of IGHV genes on mouse chromosome 12

| Gene names | Order |
|---|---|
| IGHV1-86 | 1 |
| IGHV1-85 | 2 |
| IGHV1-84 | 3 |
| IGHV1-83 | 4 |
| IGHV1-82 | 5 |
| IGHV1-81 | 6 |
| IGHV1-80 | 7 |
| IGHV1-79 | 8 |
| IGHV1-78 | 9 |
| IGHV1-77 | 10 |
| IGHV8-16 | 11 |
| IGHV1-76 | 12 |
| IGHV8-15 | 13 |
| IGHV1-75 | 14 |
| IGHV8-14 | 15 |
| IGHV1-74 | 16 |
| IGHV1-73 | 17 |
| IGHV8-13 | 18 |
| IGHV1-72 | 19 |
| IGHV1-71 | 20 |
| IGHV1-70 | 21 |
| IGHV8-12 | 22 |
| IGHV1-69 | 23 |
| IGHV1-68 | 24 |
| IGHV1-67 | 25 |
| IGHV1-66 | 26 |
| IGHV8-11 | 27 |
| IGHV1-65 | 28 |
| IGHV8-10 | 29 |
| IGHV1-64 | 30 |
| IGHV1-63 | 31 |
| IGHV8-9 | 32 |
| IGHV1-62-3 | 33 |
| IGHV1-62-2 | 34 |

TABLE 4-continued

List of IGHV genes on mouse chromosome 12

| Gene names | Order |
| --- | --- |
| IGHV1-62-1 | 35 |
| IGHV1-62 | 36 |
| IGHV1-61 | 37 |
| IGHV1-60 | 38 |
| IGHV1-59 | 39 |
| IGHV1-58 | 40 |
| IGHV8-8 | 41 |
| IGHV1-57 | 42 |
| IGHV8-7 | 43 |
| IGHV1-56 | 44 |
| IGHV1-55 | 45 |
| IGHV1-54 | 46 |
| IGHV8-6 | 47 |
| IGHV1-53 | 48 |
| IGHV1-52 | 49 |
| IGHV1-51 | 50 |
| IGHV1-50 | 51 |
| IGHV8-5 | 52 |
| IGHV1-49 | 53 |
| IGHV1-48 | 54 |
| IGHV8-4 | 55 |
| IGHV8-3 | 56 |
| IGHV1-47 | 57 |
| IGHV1-46 | 58 |
| IGHV1-45 | 59 |
| IGHV1-44 | 60 |
| IGHV1-43 | 61 |
| IGHV1-42 | 62 |
| IGHV1-41 | 63 |
| IGHV1-40 | 64 |
| IGHV1-39 | 65 |
| IGHV1-38 | 66 |
| IGHV1-37 | 67 |
| IGHV1-36 | 68 |
| IGHV1-35 | 69 |
| IGHV1-34 | 70 |
| IGHV1-33 | 71 |
| IGHV1-32 | 72 |
| IGHV1-31 | 73 |
| IGHV1-30 | 74 |
| IGHV1-29 | 75 |
| IGHV1-28 | 76 |
| IGHV1-27 | 77 |
| IGHV1-26 | 78 |
| IGHV1-25 | 79 |
| IGHV1-24 | 80 |
| IGHV1-23 | 81 |
| IGHV1-22 | 82 |
| IGHV1-21 | 83 |
| IGHV1-21-1 | 84 |
| IGHV1-20 | 85 |
| IGHV1-19 | 86 |
| IGHV1-19-1 | 87 |
| IGHV1-18 | 88 |
| IGHV1-17 | 89 |
| IGHV1-17-1 | 90 |
| IGHV1-16 | 91 |
| IGHV1-15 | 92 |
| IGHV1-14 | 93 |
| IGHV1-13 | 94 |
| IGHV1-12 | 95 |
| IGHV1-11 | 96 |
| IGHV1-10 | 97 |
| IGHV1-9 | 98 |
| IGHV15-2 | 99 |
| IGHV1-8 | 100 |
| IGHV10-4 | 101 |
| IGHV1-7 | 102 |
| IGHV1-6 | 103 |
| IGHV10-3 | 104 |
| IGHV1-5 | 105 |
| IGHV10-2 | 106 |
| IGHV1-4 | 107 |
| IGHV1-3 | 108 |
| IGHV10-1 | 109 |
| IGHV1-2 | 110 |
| IGHV8-2 | 111 |
| IGHV6-7 | 112 |
| IGHV6-6 | 113 |
| IGHV6-5 | 114 |
| IGHV6-4 | 115 |
| IGHV6-3 | 116 |
| IGHV12-3 | 117 |
| IGHV13-2 | 118 |
| IGHV1-1 | 119 |
| IGHV8-1 | 120 |
| IGHV3-8 | 121 |
| IGHV5-21 | 122 |
| IGHV3-7 | 123 |
| IGHV9-4 | 124 |
| IGHV3-6 | 125 |
| IGHV13-1 | 126 |
| IGHV3-5 | 127 |
| IGHV3-4 | 128 |
| IGHV7-4 | 129 |
| IGHV3-3 | 130 |
| IGHV14-4 | 131 |
| IGHV15-1 | 132 |
| IGHV7-3 | 133 |
| IGHV9-3 | 134 |
| IGHV12-2 | 135 |
| IGHV9-2 | 136 |
| IGHV12-1 | 137 |
| IGHV9-1 | 138 |
| IGHV6-2 | 139 |
| IGHV16-1 | 140 |
| IGHV14-3 | 141 |
| IGHV11-2 | 142 |
| IGHV3-2 | 143 |
| IGHV4-2 | 144 |
| IGHV14-2 | 145 |
| IGHV11-1 | 146 |
| IGHV3-1 | 147 |
| IGHV4-1 | 148 |
| IGHV14-1 | 149 |
| IGHV7-2 | 150 |
| IGHV7-1 | 151 |
| IGHV5-19 | 152 |
| IGHV2-9 | 153 |
| IGHV2-8 | 154 |
| IGHV5-18 | 155 |
| IGHV5-17 | 156 |
| IGHV5-16 | 157 |
| IGHV5-15 | 158 |
| IGHV2-7 | 159 |
| IGHV2-6-8 | 160 |
| IGHV2-9-1 | 161 |
| IGHV5-12-4 | 162 |
| IGHV5-9-1 | 163 |
| IGHV2-6 | 164 |
| IGHV5-12 | 165 |
| IGHV5-11 | 166 |
| IGHV2-5 | 167 |
| IGHV5-10 | 168 |
| IGHV5-9 | 169 |
| IGHV5-8 | 170 |
| IGHV2-4 | 171 |
| IGHV5-7 | 172 |
| IGHV5-6 | 173 |
| IGHV5-5 | 174 |
| IGHV2-3 | 175 |
| IGHV6-1 | 176 |
| IGHV5-4 | 177 |
| IGHV5-3 | 178 |
| IGHV2-2 | 179 |
| IGHV5-2 | 180 |
| IGHV2-1 | 181 |
| IGHV5-1 | 182 |

Figure 38:
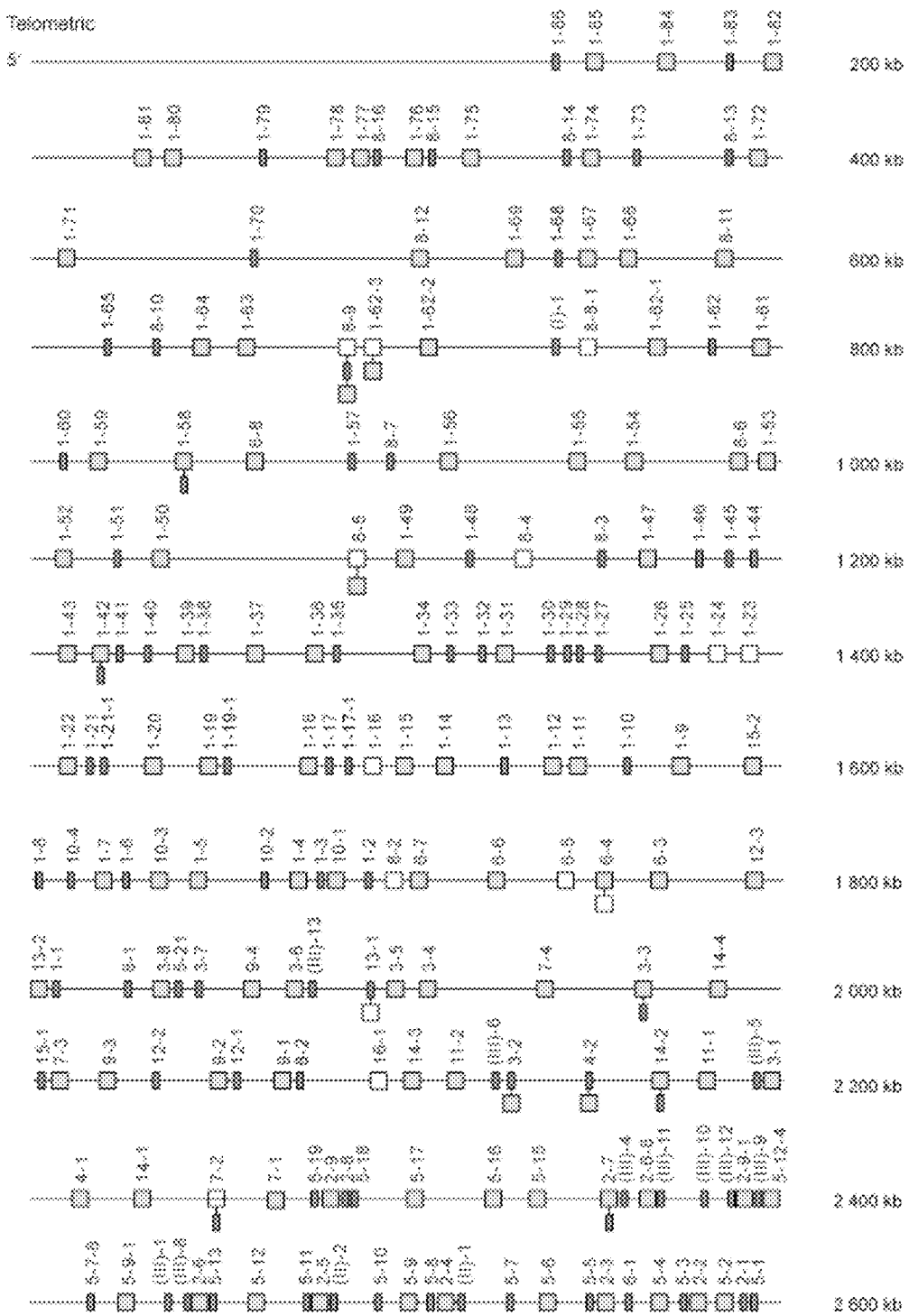
FIG. 38 is a schematic diagram showing mouse (*Mus musculus*) IGH locus on chromosome 12 (12F2) (strain C57BL/6).
Figure 38:
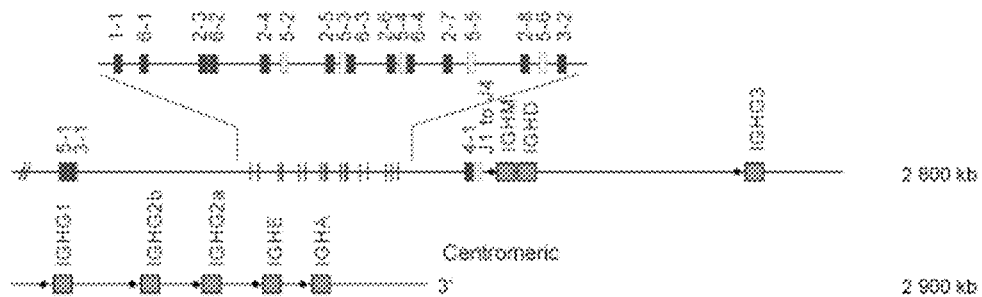

Table 5 lists all IGHD genes and its relative orders on mouse chromosome 12. Table 6 lists all IGHJ genes and its relative orders on mouse chromosome 12. The genes for immunoglobulin constant domains are after the IGHV, IGHD, and IGHJ genes. These genes include (as shown in the following order): immunoglobulin heavy constant mu (IGHM), immunoglobulin heavy constant delta (IGH δ), immunoglobulin heavy constant gamma 3 (IGHG3), immunoglobulin heavy constant gamma 1 (IGHG1), immunoglobulin heavy constant gamma 2b (IGHG2b), immunoglobulin heavy constant gamma 2a (IGHG2a), immunoglobulin heavy constant epsilon (IGHE), and immunoglobulin heavy constant alpha (IGHA) genes. These genes and the order of these genes are also shown in FIG. 38 and FIG. 42.

TABLE 5

List of IGHD genes on mouse chromosome 12

| Gene names | Order |
|---|---|
| IGHD5-1 | 183 |
| IGHD3-1 | 184 |
| IGHD1-1 | 185 |
| IGHD6-1 | 186 |
| IGHD2-3 | 187 |
| IGHD6-2 | 188 |
| IGHD2-4 | 189 |
| IGHD2-5 | 191 |
| IGHD5-3 | 192 |
| IGHD5-7 | 193 |
| IGHD2-6 | 194 |
| IGHD5-4 | 195 |
| IGHD5-8 | 196 |
| IGHD2-7 | 197 |
| IGHD5-5 | 198 |
| IGHD2-8 | 199 |
| IGHD5-6 | 200 |
| IGHD3-2 | 201 |
| IGHD4-1 | 202 |

TABLE 6

List of IGHJ genes on mouse chromosome 12

| Gene names | Order |
|---|---|
| IGHJ1 | 203 |
| IGHJ2 | 204 |
| IGHJ3 | 205 |
| IGHJ4 | 206 |

The present disclosure provides genetically-modified, non-human animal comprising one or more human IGHV genes, one or more human IGHD genes, and/or one or more human IGHJ genes. In some embodiments, the human IGHV genes, the human IGHD genes, and the human IGHJ genes are operably linked together and can undergo VDJ rearrangement. In some embodiments, the human IGHV genes, the human IGHD genes, and the human IGHJ genes are at the endogenous heavy chain immunoglobulin gene locus.

In some embodiments, the animal compromises about or at least 1, 2, 3, 4, 5, 6, 7, 8, 9, 10, 20, 30, 40, 50, 60, 70, 80, 90, 100, 110, 120, 130, 140, 150, 151, 152, 153, 154, 155, 156, 157, 158, 159, 160 or 161 human IGHV genes (e.g., genes as shown in Table 1).

In some embodiments, the animal compromises 1, 2, 3, 4, 5, 6, 7, 8, 9, or 10 genes selected from IGHV(III)-82, IGHV7-81, IGHV4-80, IGHV3-79, IGHV(II)-78-1, IGHV5-78, IGHV7-77, IGHV(III)-76-1, IGHV3-76, and IGHV3-75.

In some embodiments, the animal compromises 1, 2, 3, 4, 5, 6, 7, 8, 9, or 10 genes selected from IGHV(III)-5-2, IGHV(III)-5-1, IGHV2-5, IGHV7-4-1, IGHV4-4, IGHV1-3, IGHV(III)-2-1, IGHV1-2, IGHV(II)-1-1, and IGHV6-1.

In some embodiments, the animal compromises an unmodified human sequence comprising a sequence starting from a gene selected from IGHV(III)-82, IGHV7-81, IGHV4-80, IGHV3-79, IGHV(II)-78-1, IGHV5-78, IGHV7-77, IGHV(III)-76-1, IGHV3-76, and IGHV3-75, and ending at a gene selected from IGHV(III)-5-2, IGHV(III)-5-1, IGHV2-5, IGHV7-4-1, IGHV4-4, IGHV1-3, IGHV(III)-2-1, IGHV1-2, IGHV(II)-1-1, and IGHV6-1. In some embodiments, the unmodified human sequence derived from a human heavy chain immunoglobulin gene locus starting from human IGHV(III)-82 to human IGHV1-2. In some embodiments, the unmodified human sequence derived from a human heavy chain immunoglobulin gene locus starting from human IGHV(III)-82 to human IGHV(II)-1-1. In some embodiments, the unmodified human sequence derived from a human heavy chain immunoglobulin gene locus starting from human IGHV(III)-82 to human IGHV-6-1.

In some embodiments, the animal compromises about or at least 1, 2, 3, 4, 5, 6, 7, 8, 9, 10, 11, 12, 13, 14, 15, 16, 17, 18, 19, 20, 21, 22, 23, 24, 25, 26, or 27 human IGHD genes (e.g., genes as shown in Table 2). In some embodiments, the animal compromises 1, 2, 3, 4, 5, 6, 7, 8, 9, or 10 genes selected from IGHD1-1, IGHD2-2, IGHD3-3, IGHD4-4, IGHD5-5, IGHD4-23, IGHD5-24, IGHD6-25, IGHD1-26, and IGHD7-27.

In some embodiments, the animal compromises about or at least 1, 2, 3, 4, 5, 6, 7, 8, or 9 human IGHJ genes (e.g., genes as shown in Table 3). In some embodiments, the animal compromises 1, 2, 3, 4, 5, 6, 7, 8, or 9 human IGHJ genes selected from IGHJ1P, IGHJ1, IGHJ2, IGHJ2P, IGHJ3, IGHJ4, IGHJ5, IGHJ3P, and IGHJ6.

In some embodiments, the animal compromises an unmodified human sequence comprising a sequence starting from a gene selected from IGHD1-1, IGHD2-2, IGHD3-3, IGHD4-4, IGHD5-5, IGHD4-23, IGHD5-24, IGHD6-25, IGHD1-26, and IGHD7-27, and ending at a gene selected from IGHJ1P, IGHJ1, IGHJ2, IGHJ2P, IGHJ3, IGHJ4, IGHJ5, IGHJ3P, and IGHJ6. In some embodiments, the unmodified human sequence derived from a human heavy chain immunoglobulin gene locus starting from human IGHD1-1 to human IGHJ6.

In some embodiments, the unmodified human sequence derived from a human heavy chain immunoglobulin gene locus starting from human IGHD1-1 to human IGHD7-27.

In some embodiments, the unmodified human sequence derived from a human heavy chain immunoglobulin gene locus starting from human IGHJ1P to human IGHJ6.

In some embodiments, the unmodified human sequence derived from a human heavy chain immunoglobulin gene locus starting from human IGHJ1 to human IGHJ6.

In some embodiments, the unmodified human sequence derived from a human heavy chain immunoglobulin gene locus starting from human IGHV(III)-82 to human IGHJ6.

In some embodiments, the unmodified human sequence derived from a human heavy chain immunoglobulin gene locus starting from human IGHV1-2 to human IGHJ6. In some embodiments, the unmodified human sequence derived from a human heavy chain immunoglobulin gene locus starting from human IGHV(II)-1-1 to human IGHJ6. In some embodiments, the unmodified human sequence derived from a human heavy chain immunoglobulin gene locus starting from human IGHV6-1 to human IGHJ6.

In some embodiments, the animal can have one, two, three, four, five, six, seven, eight, nine, or ten unmodified human sequences. In some embodiments, the unmodified human sequence has a length of about or at least 10, 20, 30, 40, 50, 60, 70, 80, 90, 100, 200, 300, 400, 500, 600, 700, 800, 900, or 1000 kb.

In some embodiments, the animal comprises one or more endogenous genes selected from the group consisting of immunoglobulin heavy constant mu (IGHM), immunoglobulin heavy constant delta (IGHδ), immunoglobulin heavy constant gamma 3 (IGHG3), immunoglobulin heavy constant gamma 1 (IGHG1), immunoglobulin heavy constant gamma 2b (IGHG2b), immunoglobulin heavy constant gamma 2a (IGHG2a), immunoglobulin heavy constant epsilon (IGHE), and immunoglobulin heavy constant alpha (IGHA) genes. In some embodiments, these endogenous genes are operably linked together. In some embodiments, these endogenous genes have the same order as in a wildtype animal. In some embodiments, isotype switching (immunoglobulin class switching) can occur in the animal.

In some embodiments, the IGHV genes, the IGHD genes, and/or the IGHJ genes are operably linked together. The VDJ recombination can occur among these genes and produce functional antibodies. In some embodiments, these genes are arranged in an order that is similar to the order in human heavy chain immunoglobulin locus. This arrangement offers various advantages, e.g., the arrangement of these genes allow the production of heavy chain variable domains with a diversity that is very similar to the diversity of the heavy chain variable domains in human. As some random sequences may be inserted to the sequence during VDJ recombination, in some embodiments, the complete human antibody repertoires with no or minimum modifications can reduce the likelihood that non-human sequence is inserted during the VDJ recombination.

In some embodiments, the IGHV genes, the IGHD genes, and/or the IGHJ genes are operably linked together to one or more genes (e.g., all genes) selected from IGHM, IGHδ, IGHG3, IGHG1, IGHG2b, IGHG2a, IGHE, and IGHA genes.

In some embodiments, the animal comprises a disruption in the animal's endogenous heavy chain immunoglobulin gene locus. In some embodiments, the disruption in the animal's endogenous heavy chain immunoglobulin gene locus comprises a deletion of one or more endogenous IGHV genes, one or more endogenous IGHD genes, and one or more endogenous IGHJ genes.

In some embodiments, the animal is a mouse. The disruption in the animal's endogenous heavy chain immunoglobulin gene locus comprises a deletion of at least or about 1, 2, 3, 4, 5, 6, 7, 8, 9, 10, 20, 30, 40, 50, 60, 70, 80, 90, 100, 110, 120, 130, 140, 150, 160, 170, 171, 172, 173, 174, 175, 176, 177, 178, 179, 180, 181, or 182 mouse IGHV genes (e.g., genes as shown in Table 4). In some embodiments, the disruption compromises a deletion of about or at least 1, 2, 3, 4, 5, 6, 7, 8, 9, or 10 mouse IGHV genes selected from IGHV1-86, IGHV1-85, IGHV1-84, IGHV1-83, IGHV1-82, IGHV1-81, IGHV1-80, IGHV1-79, IGHV1-78, and IGHV1-77. In some embodiments, the mouse still compromises about or at least 1, 2, 3, 4, 5, 6, 7, 8, 9, or 10 mouse IGHV genes selected from IGHV1-86, IGHV1-85, IGHV1-84, IGHV1-83, IGHV1-82, IGHV1-81, IGHV1-80, IGHV1-79, IGHV1-78, and IGHV1-77 (e.g., IGHV1-86).

In some embodiments, the disruption compromises a deletion of about or at least 1, 2, 3, 4, 5, 6, 7, 8, 9, or 10 mouse IGHV genes selected from IGHV5-6, IGHV5-5, IGHV2-3, IGHV6-1, IGHV5-4, IGHV5-3, IGHV2-2, IGHV5-2, IGHV2-1, and IGHV5-1. In some embodiments, the mouse still compromises a deletion of about or at least 1, 2, 3, 4, 5, 6, 7, 8, 9, or 10 mouse IGHV genes selected from IGHV5-6, IGHV5-5, IGHV2-3, IGHV6-1, IGHV5-4, IGHV5-3, IGHV2-2, IGHV5-2, IGHV2-1, and IGHV5-1.

In some embodiments, the disruption in the animal's endogenous heavy chain immunoglobulin gene locus comprises a deletion of at least or about 1, 2, 3, 4, 5, 6, 7, 8, 9, 10, 11, 12, 13, 14, 15, 16, 17, 18, 19, or 20 mouse IGHD genes (e.g., genes as shown in Table 5). In some embodiments, the disruption compromises a deletion of about or at least 1, 2, 3, 4, 5, 6, 7, 8, 9, or 10 mouse IGHD genes selected from IGHD5-1, IGHD3-1, IGHD1-1, IGHD6-1, IGHD2-3, IGHD2-7, IGHD2-8, IGHD5-6, IGHD3-2, and IGHD4-1. In some embodiments, the mouse still compromises about or at least 1, 2, 3, 4, 5, 6, 7, 8, 9, or 10 mouse IGHD genes selected from IGHD5-1, IGHD3-1, IGHD1-1, IGHD6-1, IGHD2-3, IGHD2-7, IGHD2-8, IGHD5-6, IGHD3-2, and IGHD4-1.

In some embodiments, the disruption compromises a deletion of about or at least 1, 2, 3, or 4 mouse IGHJ genes selected from IGHJ1, IGHJ2, IGHJ3, and IGHJ4. In some embodiments, the mouse still compromises about or at least 1, 2, 3, or 4 mouse IGHJ genes selected from IGHJ1, IGHJ2, IGHJ3, and IGHJ4.

In some embodiments, the disruption in the animal's endogenous heavy chain immunoglobulin gene locus comprises a deletion of about or at least 500 kb, 600 kb, 700 kb, 800 kb, 900 kb, 1000 kb, 1500 kb, 2000 kb, 2500 kb, or 3000 kb of an endogenous sequence.

In some embodiments, the deleted sequence starts from IGHV1-86 to IGHJ4, from IGHV1-85 to IGHJ4, from IGHV1-84 to IGHJ4, from IGHV1-83 to IGHJ4, or from IGHV1-82 to IGHJ4 (e.g., from IGHV1-85 to IGHJ4).

In some embodiments, the animal comprises about or at least 1, 2, 3, 4, 5, 6, 7, 8, 9, or 10 sequences that are at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence in the human heavy chain immunoglobulin gene locus. In some embodiments, the sequence has a length of about or at least 10, 20, 30, 40, 50, 60, 70, 80, 90, 100, 200, 300, 400, 500, 600, 700, 800, 900, 1000, 1500, 2000, 2500, 3000 or 3500 kb. In some embodiments, the sequence starts from human IGHV(III)-82 to IGHV1-2. In some embodiments, the sequence starts from human IGHV7-81 to IGHV1-2. In some embodiments, the sequence starts from human IGHV(II)-1-1 to IGHVJ6. In some embodiments, the sequence starts from human IGHV6-1 to IGHVJ6.

The human IGHV genes, the human IGHD genes, and the human IGHJ genes are operably linked together and can undergo VDJ rearrangement. In some embodiments, the modified mouse has complete human IGHV, IGHD, and IGHJ gene repertoires (e.g., including all non-pseudo human IGHV, IGHD, and IGHJ genes). Thus, the modified mouse can produce a complete human antibody repertoire. In some embodiments, after VDJ recombination, one IGHV gene (e.g., IGHV3-21 or IGHV3-74) in Table 15 contributes to the sequence that encodes an antibody heavy chain variable region. One IGHD gene in Table 15 contributes to the sequence that encodes an antibody heavy chain variable region. And one IGHJ gene in Table 15 contributes to the sequence that encodes an antibody heavy chain variable region. In some embodiments, the IGHV gene is IGHV3-21 or IGHV3-74.

Figures 70A, 70B:
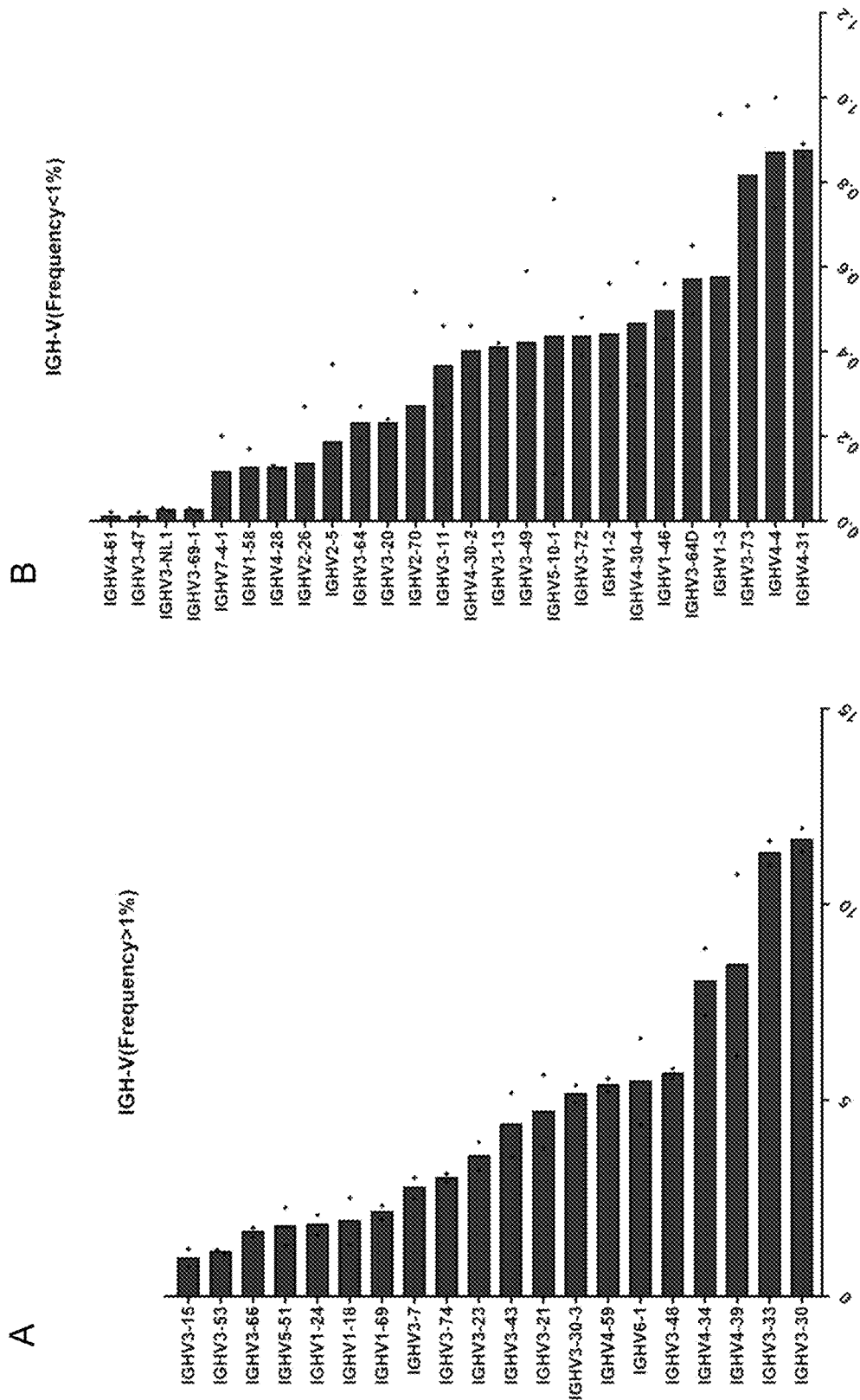
FIG. 70A shows IGHV usage (frequency >1%) in naïve hVH/hVL mice.
FIG. 70B shows IGHV usage (frequency <1%) in naïve hVH/hVL mice.

In some embodiments, one IGHV gene (e.g., IGHV3-30, IGHV3-33, IGHV4-39, or IGHV4-34) in FIG. 70A and FIG. 70B contributes to the sequence that encodes an antibody heavy chain variable region. One IGHD gene (e.g., IGHD6-

Figure 70C:
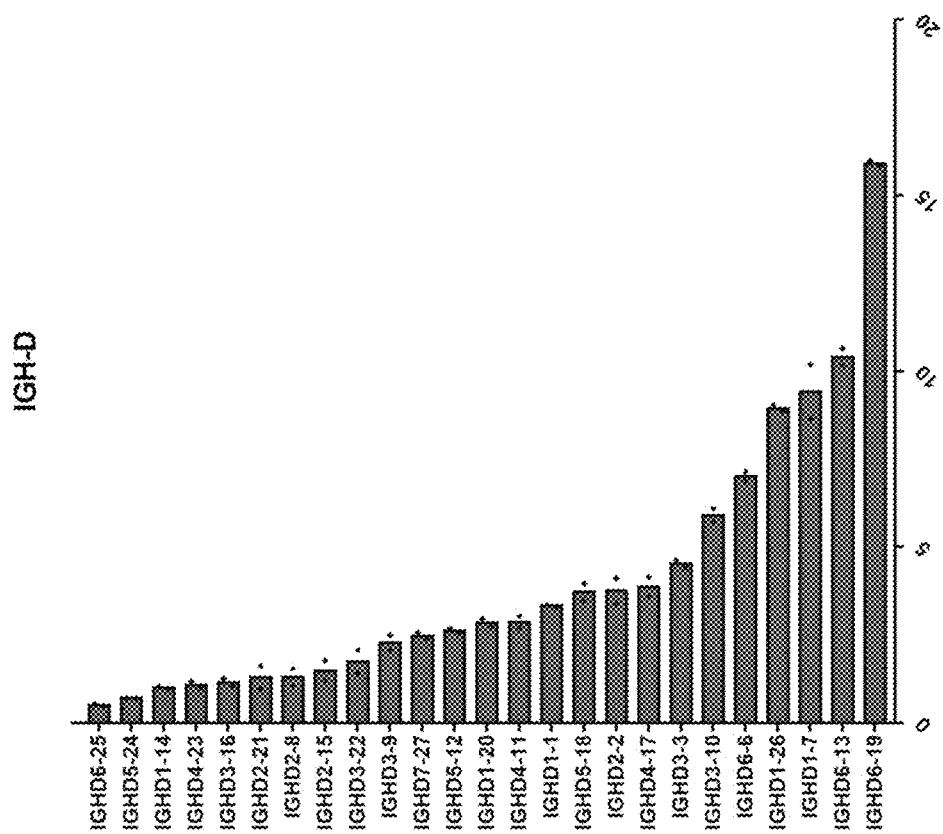
FIG. 70C shows IGHD usage in naïve hVH/hVL mice.
Figure 70D:
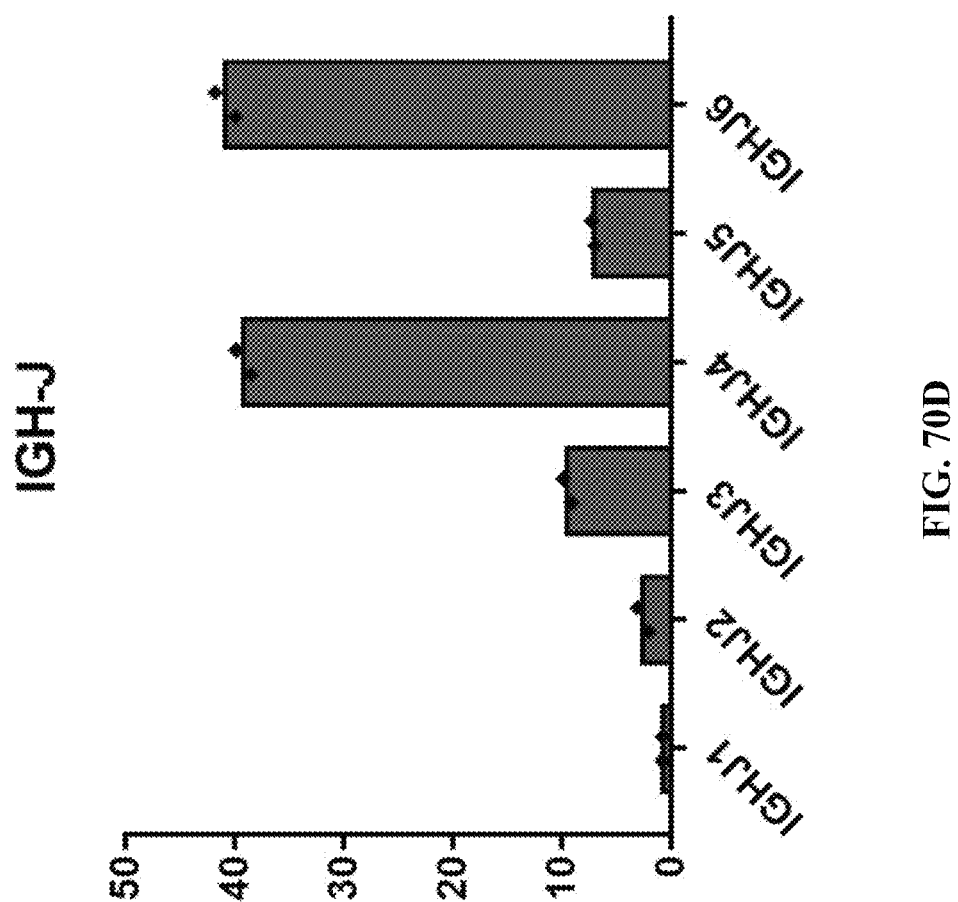
FIG. 70D shows IGHJ usage in naïve hVH/hVL mice.

19) in FIG. 70C contributes to the sequence that encodes an antibody heavy chain variable region. And one IGHJ gene (e.g., IGHJ4 or IGHJ6) in FIG. 70D contributes to the sequence that encodes an antibody heavy chain variable region. In some embodiments, one IGKV gene (e.g., IGKV4-1, IGKV1-33, IGKV2-30) in FIG. 71A and FIG. 71B contributes to the sequence that encodes an antibody light chain variable region. One IGKJ gene (e.g., IGKJ1, IGKJ2, or IGKJ4) in FIG. 71C contributes to the sequence that encodes an antibody light chain variable region.

Furthermore, in some cases, the entire mouse IGHV genes, IGHD genes, and IGHJ genes (e.g., including all none-pseudo genes) are knocked out, and the heavy chain variable region will not have any sequence that is encoded by a sequence derived from the mouse, thereby minimizing immunogenicity in human.

Genetically Modified Kappa Light Chain Immunoglobulin Locus

Kappa chain immunoglobulin locus (also known as IGK or immunoglobulin kappa locus) is a region on the chromosome (e.g., human chromosome 2) that contains genes for the light chains of human antibodies (or immunoglobulins). Similarly, the immunoglobulin light chain genes can also undergo a series rearrangement that lead to the production of a mature immunoglobulin light-chain nucleic acid (e.g., a kappa chain).

The joining of a V segment (also known as an IGKV gene) and a J segment (also known as an IGKJ gene) creates a continuous exon that encodes the whole of the light-chain variable domain. In the unrearranged DNA, the V gene segments (or IGKV gene cluster) are located relatively far away from the C region. The J gene segments (or IGKJ gene cluster) are located close to the C region. Joining of a V segment to a J gene segment also brings the V gene close to a C-region sequence. The J gene segment of the rearranged V region is separated from a C-region sequence only by an intron. To make a complete immunoglobulin light-chain messenger RNA, the V-region exon is joined to the C-region sequence by RNA splicing after transcription.

The human light chain immunoglobulin locus is located on human chromosome 2. Table 7 lists IGKV genes and its relative orders in this locus. There are several different groups for human IGKV genes, including IGKV1 genes (including all IGKV genes starting with IGKV1, also known as VκI), IGKV2 genes (including all IGKV genes starting with IGKV2, also known as VκII), IGKV3 genes (including all IGKV genes starting with IGKV3, also known as VκIII), IGKV4 genes (including all IGKV genes starting with IGKV4, also known as VκIV), IGKV5 genes (including all IGKV genes starting with IGKV5, also known as VκV), IGKV6 genes (including all IGKV genes starting with IGKV6, also known as VκVI), and IGKV7 genes (including all IGKV genes starting with IGKV7, also known as VκVII).

Figures 26, 27, 28:
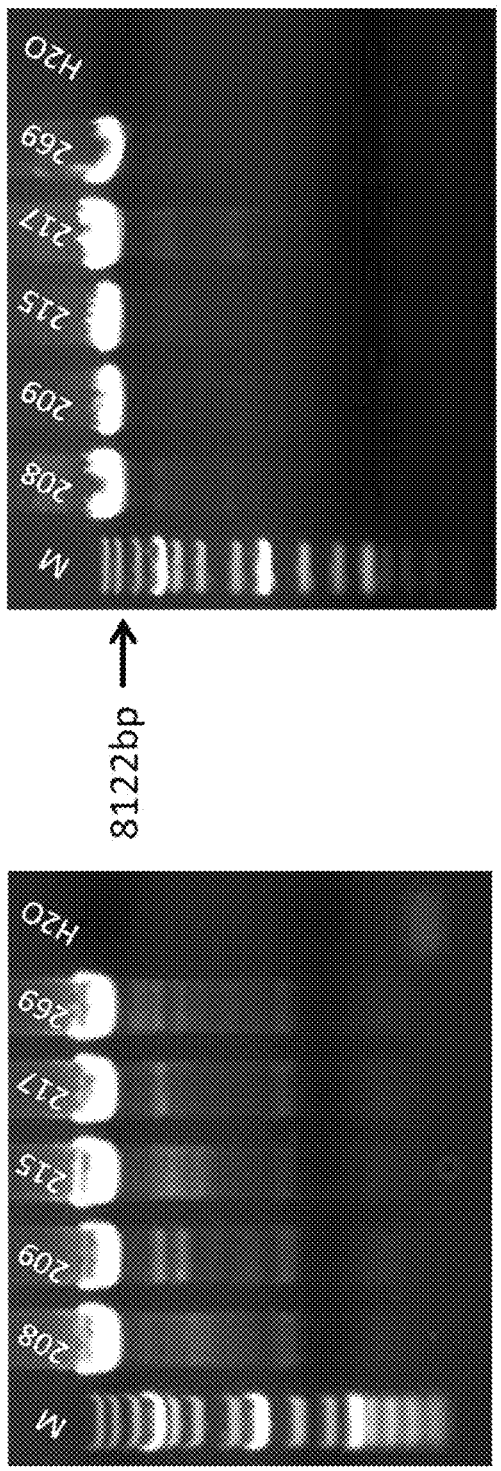
FIG. 26 shows PCR assay results using the IGKV-005-C-5G-L-GT-F/IGKV-005-C-5G-L-GT-R2 primer pair.
FIG. 27 shows PCR assay results using the IGKV-005-C-5G-R-GT-F1/IGKV-005-C-5G-R-GT-R primer pair.
FIG. 28 is a schematic diagram of the human chromosome 2 highlighting the light chain immunoglobulin locus (not drawn to scale). $V_{HK}$ represents the segment for the IGKV gene cluster, $J_{HK}$ represents the segment for the IGKJ gene cluster, and $C_{HK}$ represents the IGKC gene.

These IGKV genes in human chromosome 2 also form two clusters, the proximal Vκ cluster and the distal Vκ cluster (FIG. 28). The sequences in the two clusters are similar but are not identical. This large segmental duplication of the sequence occurred since the divergence of the human lineage from the most recent shared ancestor with other great apes. The relevant IGVκ genes in each cluster is summarized in FIG. 64.

TABLE 7

List of IGKV genes on human chromosome 2

| Gene names | Order |
|---|---|
| IGKV3D-7 | 1 |
| IGKV1D-8 | 2 |
| IGKV1D-43 | 3 |
| IGKV1D-42 | 4 |
| IGKV2D-10 | 5 |
| IGKV3D-11 | 6 |
| IGKV1D-12 | 7 |
| IGKV1D-13 | 8 |
| IGKV2D-14 | 9 |
| IGKV3D-15 | 10 |
| IGKV1D-16 | 11 |
| IGKV1D-17 | 12 |
| IGKV6D-41 | 13 |
| IGKV2D-18 | 14 |
| IGKV2D-19 | 15 |
| IGKV3D-20 | 16 |
| IGKV6D-21 | 17 |
| IGKV1D-22 | 18 |
| IGKV2D-23 | 19 |
| IGKV2D-24 | 20 |
| IGKV3D-25 | 21 |
| IGKV2D-26 | 22 |
| IGKV1D-27 | 23 |
| IGKV2D-28 | 24 |
| IGKV2D-29 | 25 |
| IGKV2D-30 | 26 |
| IGKV3D-31 | 27 |
| IGKV1D-32 | 28 |
| IGKV1D-33 | 29 |
| IGKV3D-34 | 30 |
| IGKV1D-35 | 31 |
| IGKV2D-36 | 32 |
| IGKV1D-37 | 33 |
| IGKV2D-38 | 34 |
| IGKV1D-39 | 35 |
| IGKV2D-40 | 36 |
| IGKV2-40 | 37 |
| IGKV1-39 | 38 |
| IGKV2-38 | 39 |
| IGKV1-37 | 40 |
| IGKV2-36 | 41 |
| IGKV1-35 | 42 |
| IGKV3-34 | 43 |
| IGKV1-33 | 44 |
| IGKV1-32 | 45 |
| IGKV3-31 | 46 |
| IGKV2-30 | 47 |
| IGKV2-29 | 48 |
| IGKV2-28 | 49 |
| IGKV1-27 | 50 |
| IGKV2-26 | 51 |
| IGKV3-25 | 52 |
| IGKV2-24 | 53 |
| IGKV2-23 | 54 |
| IGKV1-22 | 55 |
| IGKV6-21 | 56 |
| IGKV3-20 | 57 |
| IGKV2-19 | 58 |
| IGKV2-18 | 59 |
| IGKV1-17 | 60 |
| IGKV1-16 | 61 |
| IGKV3-15 | 62 |
| IGKV2-14 | 63 |
| IGKV1-13 | 64 |
| IGKV1-12 | 65 |
| IGKV3-11 | 66 |
| IGKV2-10 | 67 |
| IGKV1-9 | 68 |
| IGKV1-8 | 69 |
| IGKV3-7 | 70 |
| IGKV1-6 | 71 |
| IGKV1-5 | 72 |
| IGKV2-4 | 73 |
| IGKV7-3 | 74 |

TABLE 7-continued

List of IGKV genes on human chromosome 2

| Gene names | Order |
|---|---|
| IGKV5-2 | 75 |
| IGKV4-1 | 76 |

Figure 39:
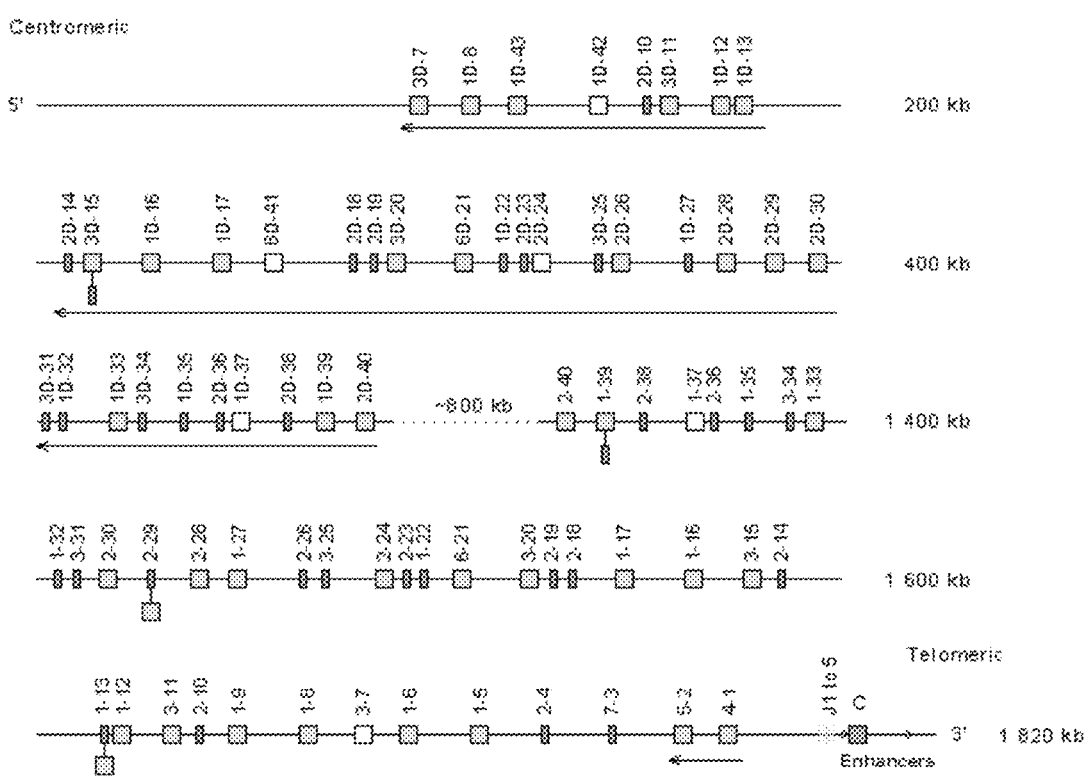
FIG. 39 is a schematic diagram showing human immunoglobulin kappa chain (IGK) locus on chromosome 2 (2p11.2).

Table 8 lists all IGKJ genes and its relative orders on human chromosome 2. The immunoglobulin kappa constant (IGKC) gene, which encodes the light chain immunoglobulin constant domains is located after the IGKV and IGKJ genes. These genes and the order of these genes are also shown in FIG. 39 and FIG. 43.

TABLE 8

List of IGKJ genes on human chromosome 2

| Gene names | Order |
|---|---|
| IGKJ1 | 77 |
| IGKJ2 | 78 |
| IGKJ3 | 79 |
| IGKJ4 | 80 |
| IGKJ5 | 81 |

The mouse light chain immunoglobulin locus is located on mouse chromosome 6. Table 9 lists IGKV genes and its relative orders in this locus.

TABLE 9

List of IGKV genes on mouse chromosome 6

| Gene names | Order |
|---|---|
| IGKV2-137 | 1 |
| IGKV1-136 | 2 |
| IGKV1-135 | 3 |
|  | * |
| IGKV14-134-1 | 5 |
| IGKV17-134 | 6 |
| IGKV1-133 | 7 |
| IGKV1-132 | 8 |
| IGKV1-131 | 9 |
| IGKV14-130 | 10 |
| IGKV9-129 | 11 |
| IGKV9-128 | 12 |
| IGKV17-127 | 13 |
| IGKV14-126-1 | 14 |
| IGKV14-126 | 15 |
| IGKV11-125 | 16 |
| IGKV9-124 | 17 |
| IGKV9-123 | 18 |
| IGKV1-122 | 19 |
| IGKV17-121 | 20 |
| IGKV9-120 | 21 |
| IGKV9-119 | 22 |
| IGKV14-118-2 | 23 |
| IGKV14-118-1 | 24 |
| IGKV11-118 | 25 |
| IGKV1-117 | 26 |
| IGKV2-116 | 27 |
| IGKV1-115 | 28 |
| IGKV11-114 | 29 |
| IGKV2-113 | 30 |
| IGKV2-112 | 31 |
| IGKV14-111 | 32 |
| IGKV1-110 | 33 |
| IGKV2-109 | 34 |
| IGKV1-108 | 35 |
| IGKV2-107 | 36 |
| IGKV11-106 | 37 |
| IGKV2-105 | 38 |
| IGKV16-104 | 39 |

TABLE 9-continued

List of IGKV genes on mouse chromosome 6

| Gene names | Order |
|---|---|
| IGKV15-103 | 40 |
| IGKV15-102 | 41 |
| IGKV20-101-2 | 42 |
| IGKV15-101-1 | 43 |
| IGKV15-101 | 44 |
| IGKV 14-100 | 45 |
| IGKV1-99 | 46 |
| IGKV12-98 | 47 |
| IGKV15-97 | 48 |
| IGKV10-96 | 49 |
| IGKV2-95-2 | 50 |
| IGKV2-95-1 | 51 |
| IGKV10-95 | 52 |
| IGKV10-94 | 53 |
| IGKV2-93-1 | 54 |
| IGKV19-93 | 55 |
| IGKV4-92 | 56 |
| IGKV4-91 | 57 |
| IGKV4-90 | 58 |
| IGKV13-89-1 | 59 |
| IGKV12-89 | 60 |
| IGKV1-88 | 61 |
| IGKV13-87 | 62 |
| IGKV4-86 | 63 |
| IGKV13-85 | 64 |
| IGKV13-84 | 65 |
| IGKV4-83 | 66 |
| IGKV13-82 | 67 |
| IGKV4-81 | 68 |
| IGKV13-80-1 | 69 |
| IGKV4-80 | 70 |
| IGKV4-79 | 71 |
| IGKV13-78-1 | 72 |
| IGKV4-78 | 73 |
| IGKV4-77 | 74 |
| IGKV13-76 | 75 |
| IGKV4-75 | 76 |
| IGKV13-74-1 | 77 |
| IGKV4-74 | 78 |
| IGKV13-73-1 | 79 |
| IGKV4-73 | 80 |
| IGKV4-72 | 81 |
| IGKV13-71-1 | 82 |
| IGKV4-71 | 83 |
| IGKV4-70 | 84 |
| IGKV4-69 | 85 |
| IGKV4-68 | 86 |
| IGKV12-67 | 87 |
| IGKV12-66 | 88 |
| IGKV4-65 | 89 |
| IGKV13-64 | 90 |
| IGKV4-63 | 91 |
| IGKV13-62-1 | 92 |
| IGKV4-62 | 93 |
| IGKV13-61-1 | 94 |
| IGKV4-61 | 95 |
| IGKV4-59 | 96 |
| IGKV4-60 | 97 |
| IGKV4-58 | 98 |
| IGKV13-57-2 | 99 |
| IGKV4-57-1 | 100 |
| IGKV13-57-1 | 101 |
| IGKV4-57 | 102 |
| IGKV13-56-1 | 103 |
| IGKV4-56 | 104 |
| IGKV13-55-1 | 105 |
| IGKV4-55 | 106 |
| IGKV13-54-1 | 107 |
| IGKV4-54 | 108 |
| IGKV4-53 | 109 |
| IGKV4-52 | 110 |
| IGKV4-51 | 111 |
| IGKV4-50 | 112 |
| IGKV12-49 | 113 |
| IGKV5-48 | 114 |
| IGKV12-47 | 115 |

TABLE 9-continued

List of IGKV genes on mouse chromosome 6

| Gene names | Order |
|---|---|
| IGKV12-46 | 116 |
| IGKV5-45 | 117 |
| IGKV12-44 | 118 |
| IGKV5-43 | 119 |
| IGKV12-42 | 120 |
| IGKV12-41 | 121 |
| IGKV5-40-1 | 122 |
| IGKV12-40 | 123 |
| IGKV5-39 | 124 |
| IGKV12-38 | 125 |
| IGKV5-37 | 126 |
| IGKV18-36 | 127 |
| IGKV1-35 | 128 |
| IGKV8-34 | 129 |
| IGKV7-33 | 130 |
| IGKV6-32 | 131 |
| IGKV8-31 | 132 |
| IGKV8-30 | 133 |
| * | |
| IGKV6-29 | 135 |
| IGKV8-28 | 136 |
| IGKV8-27 | 137 |
| IGKV8-26 | 138 |
| IGKV6-25 | 139 |
| IGKV8-24 | 140 |
| IGKV8-23-1 | 141 |
| IGKV6-23 | 142 |
| IGKV8-22 | 143 |
| IGKV8-21 | 144 |
| IGKV6-20 | 145 |
| IGKV8-19 | 146 |
| IGKV8-18 | 147 |
| IGKV6-17 | 148 |
| IGKV8-16 | 149 |
| IGKV6-15 | 150 |
| IGKV6-14 | 151 |
| IGKV6-13 | 152 |
| IGKV3-12-1 | 153 |
| IGKV3-12 | 154 |
| IGKV3-11 | 155 |
| IGKV3-10 | 156 |
| IGKV3-9 | 157 |
| IGKV3-8 | 158 |
| IGKV3-7 | 159 |
| IGKV3-6 | 160 |
| IGKV3-5 | 161 |
| IGKV3-4 | 162 |
| IGKV3-3 | 163 |
| IGKV3-2 | 164 |
| IGKV3-1 | 165 |

Figure 40:
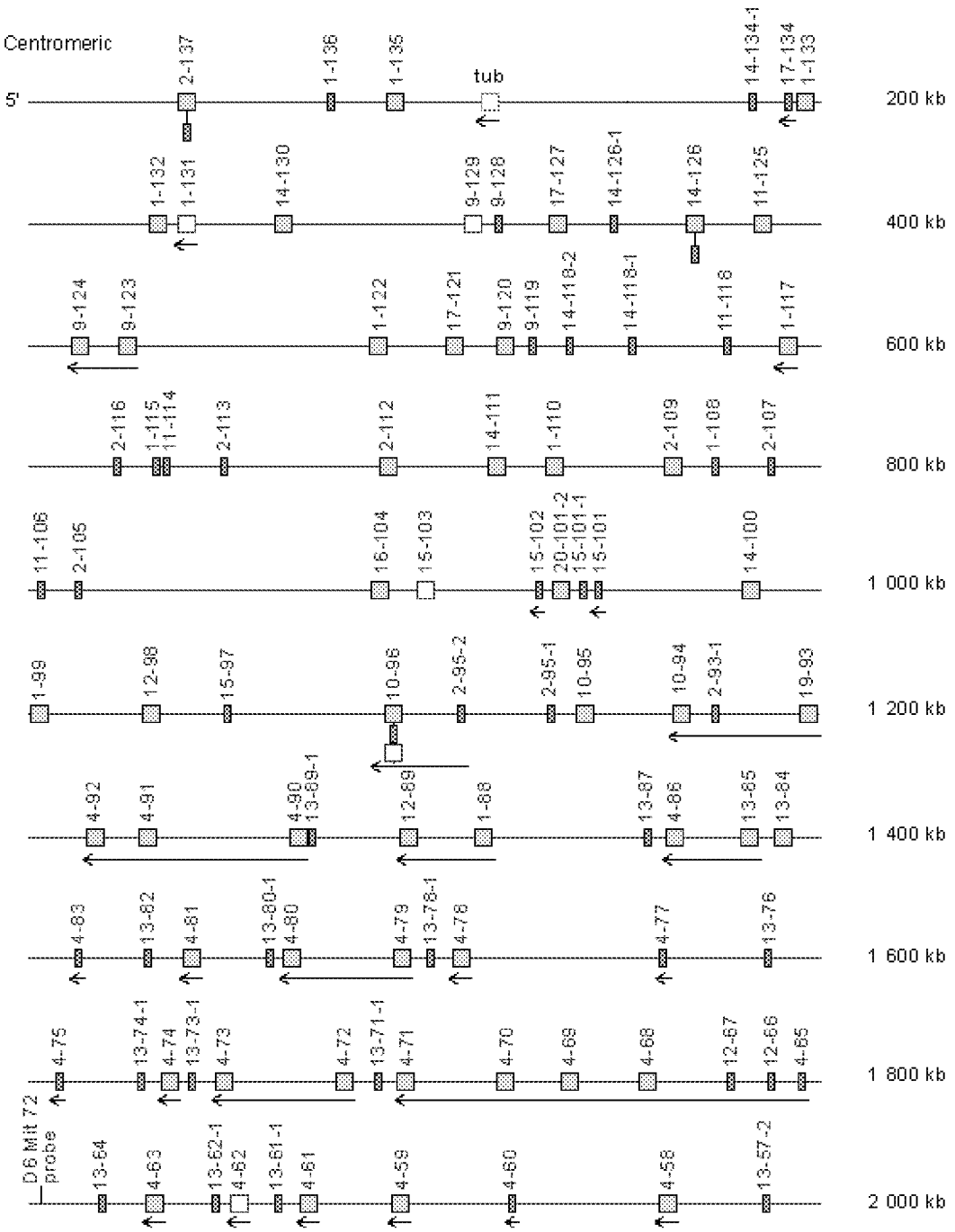
FIG. 40 is a schematic diagram showing mouse (*Mus musculus*) IGK locus on chromosome 6 (6C1).
Figure 40:
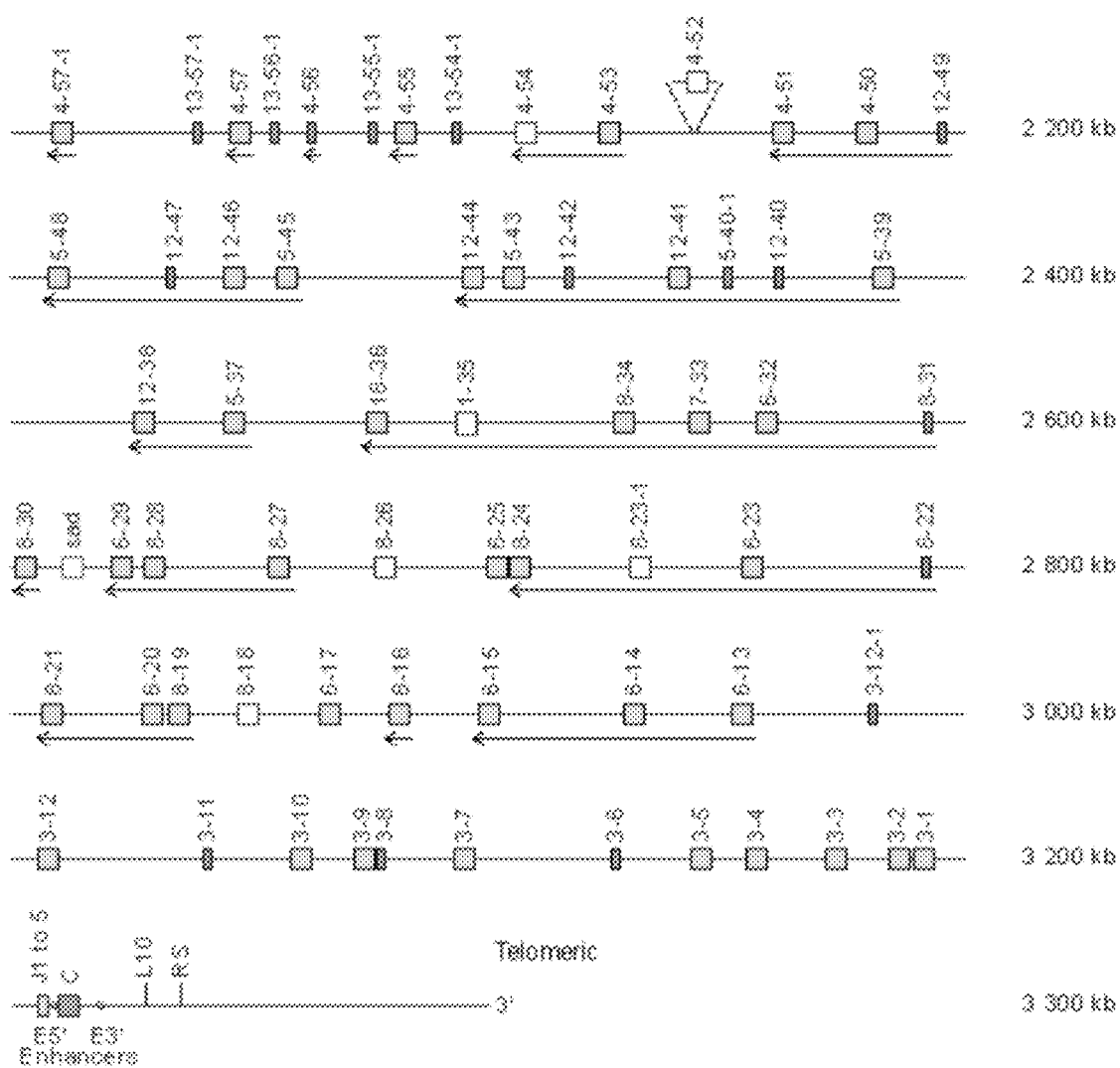

Gm9728 and Amd-ps2 are also located in this locus. The relative order of Gm9728 is 4, and the relative order of Amd-ps2 is 134. Table 10 lists all IGKJ genes and its relative orders on mouse chromosome 6. The IGKC gene, which encodes the light chain immunoglobulin constant domains are after the IGKV and IGKJ genes. These genes and the order of these genes are also shown in FIG. 40 and FIG. 44.

TABLE 10

List of IGKJ genes on mouse chromosome 6

| Gene names | Order |
|---|---|
| IGKJ1 | 166 |
| IGKJ2 | 167 |
| IGKJ3 | 168 |
| IGKJ4 | 169 |
| IGKJ5 | 170 |

The present disclosure provides genetically-modified, non-human animal comprising one or more human IGKV genes and/or one or more human IGKJ genes. In some embodiments, the human IGKV genes and the human IGKJ genes are operably linked together and can undergo VJ rearrangement. In some embodiments, the human IGKV genes and the human IGKJ genes are at endogenous light chain immunoglobulin gene locus.

In some embodiments, the animal compromises about or at least 1, 2, 3, 4, 5, 6, 7, 8, 9, 10, 20, 30, 40, 50, 60, 61, 62, 63, 64, 65, 66, 67, 68, 69, 70, 71, 72, 73, 74, 75, or 76 human IGKV genes (e.g., genes as shown in Table 7).

In some embodiments, the animal compromises 1, 2, 3, 4, 5, 6, 7, 8, 9, or 10 genes selected from IGKV3D-7, IGKV1D-8, IGKV1D-43, IGKV1D-42, IGKV2D-10, IGKV3D-11, IGKV1D-12, IGKV1D-13, IGKV2D-14, and IGKV3D-15.

In some embodiments, the animal compromises 1, 2, 3, 4, 5, 6, 7, 8, 9, or 10 genes selected from IGKV2-10, IGKV1-9, IGKV1-8, IGKV3-7, IGKV1-6, IGKV1-5, IGKV2-4, IGKV7-3, IGKV5-2, and IGKV4-1.

In some embodiments, the animal compromises about or at least 1, 2, 3, 4, or 5 human IGKJ genes (e.g., genes as shown in Table 3). In some embodiments, the animal compromises 1, 2, 3, 4, or 5 human IGKJ genes selected from IGKJ1, IGKJ2, IGKJ3, IGKJ4, and IGKJ5.

In some embodiments, the animal comprises an endogenous IGKC. In some embodiments, the IGKV genes and/or the IGKJ genes are operably linked together. The VJ recombination can occur among these genes and produce functional antibodies. In some embodiments, these genes are arranged in an order that is similar to the order in human light chain immunoglobulin locus. This arrangement offers various advantages, e.g., the arrangement of these genes allow the production of light chain variable domains with a diversity that is very similar to the diversity of the light chain variable domains in human.

In some embodiments, the IGKV genes and/or the IGKJ genes are operably linked together to the IGKC gene (e.g., endogenous IGKC gene).

In some embodiments, the animal comprises a disruption in the animal's endogenous light chain immunoglobulin gene locus. In some embodiments, the disruption in the animal's endogenous light chain immunoglobulin gene locus comprises a deletion of one or more endogenous IGKV genes, and one or more endogenous IGKJ genes.

In some embodiments, the animal is a mouse. The disruption in the animal's endogenous heavy chain immunoglobulin gene locus comprises a deletion of at least or about 1, 2, 3, 4, 5, 6, 7, 8, 9, 10, 20, 30, 40, 50, 60, 70, 80, 90, 100, 110, 120, 130, 140, 150, 151, 152, 153, 154, 155, 156, 157, 158, 159, 160, 161, 162, or 163 mouse IGKV genes (e.g., genes as shown in Table 9). In some embodiments, the disruption compromises a deletion of about or at least 1, 2, 3, 4, 5, 6, 7, 8, 9, or 10 mouse IGKV genes selected from IGKV2-137, IGKV1-136, IGKV1-135, IGKV14-134-1, IGKV17-134, IGKV1-133, IGKV1-132, IGKV1-131, IGKV14-130, and IGKV9-129. In some embodiments, the mouse still compromises about or at least 1, 2, 3, 4, 5, 6, 7, 8, 9, or 10 mouse IGKV genes selected from IGKV2-137, IGKV1-136, IGKV1-135, IGKV14-134-1, IGKV17-134, IGKV1-133, IGKV1-132, IGKV1-131, IGKV14-130, and IGKV9-129.

In some embodiments, the disruption compromises a deletion of about or at least 1, 2, 3, 4, 5, 6, 7, 8, 9, or 10 mouse IGKV genes selected from IGKV3-10, IGKV3-9, IGKV3-8, IGKV3-7, IGKV3-6, IGKV3-5, IGKV3-4, IGKV3-3, IGKV3-2, and IGKV3-1. In some embodiments, the mouse still compromises about or at least 1, 2, 3, 4, 5, 6, 7, 8, 9, or 10 mouse IGKV genes selected from IGKV3-10, IGKV3-9, IGKV3-8, IGKV3-7, IGKV3-6, IGKV3-5, IGKV3-4, IGKV3-3, IGKV3-2, and IGKV3-1.

In some embodiments, the disruption compromises a deletion of about or at least 1, 2, 3, 4, or 5 mouse IGKJ genes selected from IGKJ1, IGKJ2, IGKJ3, IGKJ4, and IGKJ5. In some embodiments, the mouse still compromises about or at least 1, 2, 3, 4, or 5 mouse IGKJ genes selected from IGKJ1, IGKJ2, IGKJ3, IGKJ4, and IGKJ5 (e.g., IGKJ5).

In some embodiments, the disruption in the animal's endogenous kappa light chain immunoglobulin gene locus comprises a deletion of about or at least 500 kb, 600 kb, 700 kb, 800 kb, 900 kb, 1000 kb, 1500 kb, 2000 kb, 2500 kb, 3000 kb or 3500 kb of an endogenous sequence.

In some embodiments, the deleted sequence starts from IGKV2-137 to IGKJ4, from IGKV1-136 to IGKJ4, from IGKV1-135 to IGKJ4, from IGKV2-137 to IGKJ5, from IGKV1-136 to IGKJ5, or from IGKV1-135 to IGKJ5 (e.g., from IGKV2-137 to IGKJ5).

In some embodiments, the animal comprises about or at least 1, 2, 3, 4, 5, 6, 7, 8, 9, or 10 sequences that are at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence in the human light chain immunoglobulin gene locus. In some embodiments, the sequence has a length of about or at least 10, 20, 30, 40, 50, 60, 70, 80, 90, 100, 200, 300, 400, 500, 600, 700, 800, 900, 1000, 1500, 2000, 2500, 3000 or 3500 kb.

In some embodiments, the animal can have one, two, three, four, five, six, seven, eight, nine, or ten unmodified human sequences. In some embodiments, the unmodified human sequence has a length of about or at least 10, 20, 30, 40, 50, 60, 70, 80, 90, 100, 200, 300, 400, 500, 600, 700, 800, 900, 1000, 1500, 2000, 2500, 3000 or 3500 kb.

In some embodiments, the sequence starts from human IGKV3D-7 to IGKJ5. In some embodiments, the sequence starts from human IGKV3D-7 to IGKJ4. In some embodiments, the sequence starts from human IGKV1D-8 to IGKJ5. In some embodiments, the sequence starts from human IGKV1D-8 to IGKJ4.

The human IGKV genes and the human IGKJ genes are operably linked together and can undergo VJ rearrangement. In some embodiments, the modified mouse has complete human IGKV and IGKJ gene repertoires (e.g., including all non-pseudo human IGKV and IGKJ genes). Thus, the modified mouse can produce a complete human antibody repertory. In some embodiments, after VJ recombination, one IGKV gene (e.g., IGKV1D-43, IGKV1D-13, IGKV1D-16, or IGKV1D-12) in Table 16 contributes to the sequence that encodes an antibody light chain variable region. One human IGKJ gene contributes to the sequence that encodes an antibody light chain variable region. In some embodiments, the IGKV gene is IGKV1D-43, IGKV1D-13, IGKV1D-16, or IGKV1D-12. Furthermore, in some cases, the entire mouse IGKV genes, and IGKJ genes (all none-pseudo genes) are knocked out, and the light chain variable region will not have any sequence that is encoded by a sequence derived from the mouse, thereby minimizing immunogenicity in humans.

In some embodiments, the human proximal Vκ cluster IGKV genes are included in the modified chromosome. In some embodiments, the human distal Vκ cluster IGKV genes are included in the modified chromosome. In some embodiments, both the human proximal Vκ cluster IGKV genes and the human distal Vκ cluster IGKV genes are included in the modified chromosome.

Genetically Modified Lambda Light Chain Immunoglobulin Locus

Lambda chain immunoglobulin locus (also known as IGL or immunoglobulin lambda locus) is a region on the chromosome (e.g., human chromosome 22) that contains genes for the light chains of human antibodies (or immunoglobulins). Similarly, the immunoglobulin light chain genes can also undergo a series rearrangement that lead to the production of a mature immunoglobulin light-chain nucleic acid (e.g., a lambda chain). In a healthy human individual, the total kappa to lambda ratio is roughly 2:1 in serum (measuring intact whole antibodies) or 1:1.5 if measuring free light chains. In mice, the total kappa to lambda ratio is roughly 9:1.

In some embodiments, the animal comprises a human lambda chain immunoglobulin locus.

In some embodiments, the animal comprises a disruption in the animal's endogenous lambda light chain immunoglobulin gene locus. In some embodiments, the disruption in the animal's endogenous light chain immunoglobulin gene locus comprises a deletion of one or more endogenous IGLV genes, one or more endogenous IGLJ genes, and/or one or more immunoglobulin lambda constant (IGLC) genes (e.g., IGLC1, IGLC2, IGLC3, and IGLC4).

The mouse lambda light chain immunoglobulin locus (IGL locus) is located on mouse chromosome 16. Table 11 lists IGLV, IGLJ, and IGLC genes and its relative orders in this locus.

TABLE 11

List of genes at mouse IGL locus

| IMGT Gene | Chromosomal localization | Gene orientation on chromosome | NCBI Gene ID | Reference GRCm38.p3 C57BL/6J | Gene positions in sequence |
| --- | --- | --- | --- | --- | --- |
| IGLV2 | 16A3 (11.93 cM) | REV | 110612 | NC_000082.6 | 19260403 . . . 19260844 |
| IGLV3 | 16A3 (11.91 cM) | REV | 404743 | NC_000082.6 | 19241208 . . . 19241679 |
| IGLJ2 | 16A3 (11.89 cM) | REV | 404739 | NC_000082.6 | 19200198 . . . 19200235 |
| IGLC2 | 16A3 (11.89 cM) | REV | 110786 | NC_000082.6 | 19198536 . . . 19198852 |
| IGLJ4 | 16A3 (11.89 cM) | REV | 404742 | NC_000082.6 | 19196495 . . . 19196536 |
| IGLC4 | 16A3 (11.89 cM) | REV | 404736 | NC_000082.6 | 19194999 . . . 19195312 |
| IGLV1 | 16A3 (11.82 cM) | REV | 16142 | NC_000082.6 | 19085017 . . . 19085460 |
| IGLJ3 | 16A3 (11.81 cM) | REV | 404740 | NC_000082.6 | 19067041 . . . 19067078 |
| IGLJ3P | 16A3 (11.81 cM) | REV | 404741 | NC_000082.6 | 19066371 . . . 19066408 |
| IGLC3 | 16A3 (11.81 cM) | REV | 110787 | NC_000082.6 | 19065365 . . . 19065681 |
| IGLJ1 | 16A3 (11.81 cM) | REV | 404737 | NC_000082.6 | 19063225 . . . 19063262 |
| IGLC1 | 16A3 (11.80 cM) | REV | 110785 | NC_000082.6 | 19061752 . . . 19062071 |

The disruption in the animal's endogenous lambda light chain immunoglobulin gene locus comprises a deletion of at least or about 1, 2, 3, 4, 5, 6, 7, 8, 9, 10, 11, or 12 mouse IGLV, IGLJ, and IGLC genes (e.g., genes as shown in Table 11). In some embodiments, the deletion compromises about or at least 1, 2, 3, or 4 mouse IGKC genes selected from IGLC1, IGLC2, IGLC3, and IGLC4. In some embodiments, the disruption compromises a deletion of about or at least 1, 2, or 3 mouse IGLV genes selected from IGLV1, IGLV2, and IGLV3. In some embodiments, the disruption compromises a deletion of about or at least 1, 2, 3, 4, or 5 mouse IGLJ genes selected from IGLJ1, IGLJ2, IGLJ3, IGLJ3P, and IGLJ4.

In some embodiments, the disruption in the animal's endogenous lambda light chain immunoglobulin gene locus comprises a deletion of about or at least 10 kb, 20 kb, 30 kb, 40 kb, 50 kb, 60 kb, 70 kb, 80 kb, 90 kb, 100 kb, 110 kb, 120 kb, 130 kb, 140 kb, 150 kb, 160 kb, 170 kb, 180 kb, 190 kb, 200 kb, 210 kb, 220 kb, 230 kb, 240 kb, 250 kb, 260 kb, 270 kb, 280 kb, 290 kb, 300 kb, 350 kb, 400 kb, 450 kb, 500 kb, or 1000 kb of nucleotides. In some embodiments, there is no disruption in the animal's endogenous lambda light chain immunoglobulin gene.

In some embodiments, the deleted sequence starts from IGLV2 to IGLC1, from IGLV3 to IGLC1, or from IGLJ2 to IGLC1.

Genetically Modified Animals

In one aspect, the present disclosure provides genetically-modified, non-human animal comprising a humanized heavy chain immunoglobulin locus and/or a humanized light chain immunoglobulin locus. In some embodiments, the animal comprises one or more human IGHV genes, one or more human IGHD genes, one or more human IGHJ genes, one or more human IGKV genes and/or one or more human IGKJ genes. In some embodiments, these genes are at the endogenous immunoglobulin gene locus.

In some embodiments, the animal comprises a human lambda chain immunoglobulin locus. In some embodiments, the animal comprises a disruption in the animal's endogenous lambda light chain immunoglobulin gene locus. In some embodiments, the animal does not have a disruption in the animal's endogenous lambda light chain immunoglobulin gene locus.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety. Thus, in various embodiments, human V, D, and/or J segments can be operably linked to non-human animal (e.g., rodent, mouse, rat, hamster) constant region gene sequences. During B cell development, these rearranged human V, D, and/or J segments are linked to the non-human animal immunoglobulin constant region.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57 background (e.g., a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola). In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized animal is made.

Genetically modified non-human animals that comprise a modification of an endogenous non-human immunoglobulin gene locus. In some embodiments, the modification can comprise a human nucleic acid sequence encoding at least a portion of a human protein (e.g., at least 10%, 20%, 30%, 40%, 50%, 60%, 70%, 80%, 90%, 95%, 96%, 97%, 98%, or 99% identical to the human heavy chain variable domain or light chain variable domain sequence). Although genetically modified cells are also provided that can comprise the modifications described herein (e.g., ES cells, somatic cells), in many embodiments, the genetically modified non-human animals comprise the modification of the endogenous locus in the germline of the animal.

Genetically modified animals can express a humanized antibody and/or a chimeric antibody from endogenous mouse loci, wherein one or more endogenous mouse immunoglobulin genes have been replaced with human immunoglobulin genes and/or a nucleotide sequence that is at least 10%, 20%, 30%, 40%, 50%, 60%, 70%, 80%, 90%, 95%, 96%, 97%, 98%, or 99% identical to the human immunoglobulin gene sequences (e.g., IGHV, IGHD, IGHJ, IGKV and/or IGKJ genes). In various embodiments, an endogenous non-human immunoglobulin gene locus is modified in whole or in part to comprise human nucleic acid sequence.

Genetic, molecular and behavioral analyses for the non-human mammals described above can performed. The present disclosure also relates to the progeny produced by the non-human mammal provided by the present disclosure mated with the same or other genotypes. Non-human mammals can be any non-human animal known in the art and which can be used in the methods as described herein. Preferred non-human mammals are mammals, (e.g., rodents). In some embodiments, the non-human mammal is a mouse.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human or humanized immunoglobulins can be detected by a variety of methods.

There are many analytical methods that can be used to detect exogenous DNA or modifications on the genomic DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized proteins.

Antibodies and Antigen Binding Fragments

The present disclosure provides antibodies and antigen-binding fragments thereof (e.g., humanized antibodies or chimeric antibodies) that are produced by the methods described herein.

In general, antibodies (also called immunoglobulins) are made up of two classes of polypeptide chains, light chains and heavy chains. A non-limiting antibody of the present disclosure can be an intact, four immunoglobulin chain antibody comprising two heavy chains and two light chains. The heavy chain of the antibody can be of any isotype including IgM, IgG, IgE, IgA, or IgD or subclasses including IgG1, IgG2, IgG2a, IgG2b, IgG3, IgG4, IgE1, IgE2, etc. The light chain can be a kappa light chain or a lambda light chain. An antibody can comprise two identical copies of a light chain and two identical copies of a heavy chain. The heavy chains, which each contain one variable domain (or variable region, $V_H$) and multiple constant domains (or constant regions), bind to one another via disulfide bonding within their constant domains to form the "stem" of the antibody. The light chains, which each contain one variable domain (or variable region, VL) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR).

These hypervariable regions, known as the complementary determining regions (CDRs), form loops that comprise the principle antigen binding surface of the antibody. The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen-binding region.

Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. These methods and definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-3839; Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (January 1998); Chothia et al., Nature 342(6252):877-83 (December 1989); Ponomarenko and Bourne, BMC Structural Biology 7:64 (2007); each of which is incorporated herein by reference in its entirety.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

In some embodiments, the antibody is an intact immunoglobulin molecule (e.g., IgG1, IgG2a, IgG2b, IgG3, IgG4, IgM, IgD, IgE, IgA). The IgG subclasses (IgG1, IgG2, IgG3, and IgG4) are highly conserved, differ in their constant region, particularly in their hinges and upper CH2 domains. The sequences and differences of the IgG subclasses are known in the art, and are described, e.g., in Vidarsson, et al, "IgG subclasses and allotypes: from structure to effector functions." Frontiers in immunology 5 (2014); Irani, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; each of which is incorporated herein by reference in its entirety.

The antibody can also be an immunoglobulin molecule that is derived from any species (e.g., human, rodent, mouse, rat, camelid). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')2, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

In some embodiments, the antigen binding fragment can form a part of a chimeric antigen receptor (CAR). In some embodiments, the chimeric antigen receptor are fusions of single-chain variable fragments (scFv) as described herein, fused to CD3-zeta transmembrane- and endodomain.

In some embodiments, the scFV has one heavy chain variable domain, and one light chain variable domain. In some embodiments, the scFV has two heavy chain variable domains, and two light chain variable domains. In some embodiments, the scFV has two antigen binding regions, and the two antigen binding regions can bind to the respective target antigens.

The antibodies and antigen-binding fragments thereof (e.g., humanized antibodies or chimeric antibodies) that are produced by the methods described herein have various advantages. In some embodiments, no further optimization is required to obtain desired properties (e.g., binding affinities, thermal stabilities, and/or limited aggregation).

In some implementations, the antibody (or antigen-binding fragments thereof) specifically binds to a target with a dissociation rate (koff) of less than $0.1\ s^{-1}$, less than $0.01\ s^{-1}$, less than $0.001\ s^{-1}$, less than $0.0001\ s^{-1}$, or less than $0.00001\ s^{-1}$. In some embodiments, the dissociation rate (koff) is greater than $0.01\ s^{-1}$, greater than $0.001\ s^{-1}$, greater than $0.0001\ s^{-1}$, greater than $0.00001\ s^{-1}$, or greater than $0.000001\ s^{-1}$.

In some embodiments, kinetic association rates (kon) is greater than $1\times10^2$/Ms, greater than $1\times10^3$/Ms, greater than $1\times10^4$/Ms, greater than $1\times10^5$/Ms, or greater than $1\times10^6$/Ms. In some embodiments, kinetic association rates (kon) is less than $1\times10^5$/Ms, less than $1\times10^6$/Ms, or less than $1\times10^7$/Ms.

Affinities can be deduced from the quotient of the kinetic rate constants (KD=koff/kon). In some embodiments, KD is less than $1\times10^{-6}$M, less than $1\times10^{-7}$M, less than $1\times10^{-8}$M, less than $1\times10^{-9}$M, or less than $1\times10^{-10}$ M. In some embodiments, the KD is less than 50 nM, 40 nM, 30 nM, 20 nM, 15 nM, 10 nM, 9 nM, 8 nM, 7 nM, 6 nM, 5 nM, 4 nM, 3 nM, 2 nM, or 1 nM. In some embodiments, KD is greater than $1\times10^{-7}$ M, greater than $1\times10^{-8}$M, greater than $1\times10^{-9}$M, greater than $1\times10^{-10}$ M, greater than $1\times10^{-11}$M, or greater than $1\times10^{-12}$M. In some embodiments, the antibody binds to a target with KD less than or equal to about 0.9 nM, 0.8 nM, 0.7 nM, 0.6 nM, 0.5 nM, 0.4 nM, 0.3 nM, 0.2 nM, or 0.1 nM.

In some embodiments, thermal stabilities are determined. The antibodies or antigen binding fragments as described herein can have a Tm greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

As IgG can be described as a multi-domain protein, the melting curve sometimes shows two transitions, or three transitions, with a first denaturation temperature, Tm D1, and a second denaturation temperature Tm D2, and optionally a third denaturation temperature Tm D3.

In some embodiments, the antibodies or antigen binding fragments as described herein has a Tm D1 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D2 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D3 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, Tm, Tm D1, Tm D2, Tm D3 are less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the antibodies or antigen binding fragments as described herein do not form aggregation when the temperate is less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

Methods of Making Genetically Modified Animals

The genetically modified animals can be made by introducing human immunoglobulin genes into the genome of non-human animals to produce animals that can express humanized antibodies or chimeric antibodies. FIG. 1A shows the methods of making the humanized animals. In some embodiments, the methods first involve modifying the human immunoglobulin locus on the human chromosome. The modified human chromosomes are then introduced into the mouse recipient cell. The human immunoglobulin variable region is then introduced into the corresponding region of the mouse genome by direct replacement. Then, the recipient cells are screened. In some embodiments, the cells do not contain the human chromosomes. The cells are then injected to blastocysts to prepare chimeric mice. Subsequent breeding can be performed to obtain mice containing intact humanized immunoglobulin locus.

Several other techniques may be used in making genetically modified animals, including, e.g., nonhomologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

The genetic modification process can involve replacing endogenous sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous sequence with human sequence.

In some embodiments, the methods for making a genetically modified, humanized animal, can include the step of replacing at an endogenous locus (or site), a nucleic acid (e.g., V, D, J regions, or V, J regions) with a corresponding region of human sequence. The sequence can include a region (e.g., a part or the entire region) of IGHV, IGHD, IGHJ, IGKV, and/or IGKJ genes. In some embodiments, the replacement is mediated by homologous recombination. In some embodiments, the replacement is mediated by Cre recombinase.

Figure 9:
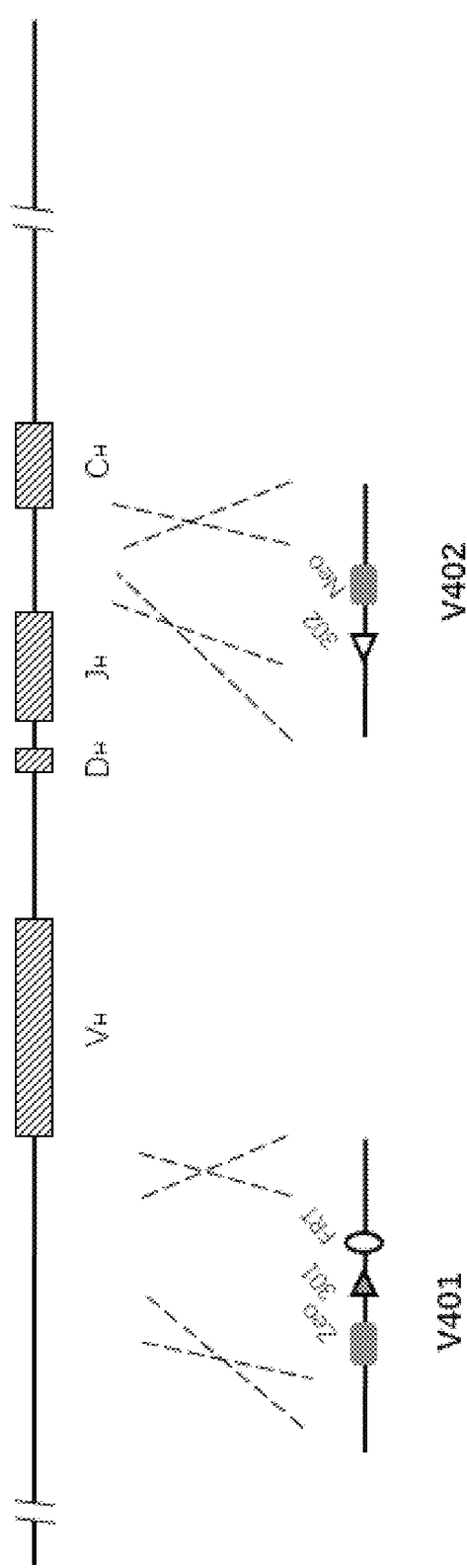
FIG. 9 shows modifications on the human chromosome 14 with two vectors.

FIG. 9 shows a targeting strategy for adding functional genetic elements into the human chromosome. These vectors can be inserted at the upstream of the V region, between the J region and the C region.

In some embodiments, the first vector has from 5' to 3' one or more of the following: DNA homology arm sequence at upstream of the insertion site, PGK promoter, red fluorescent protein reporter gene (tdTomato), FMDV (Foot-And-Mouth Disease Viruses) self-cleaving peptide (2A), zeomycin resistance gene (Zeo), transcription termination/polyadenylation signal sequence (PolyA; "PA"), the LoxP recognition sequence, hygromycin resistance gene (partial sequence of hygromycin phosphotransferase; "3'HygR"), and the Flp recognition target ("FRT"), downstream DNA homology arm sequence, and DTA gene.

The second vector has from 5' to 3' one or more of the following: DNA homology arm sequence at the upstream of the insertion site, the LoxP recognition sequence, PGK promoter, a partial sequence of Puromycin resistance gene (5'PuroR), a mammalian expression promoter (EF-1a) from human elongation factor 1 alpha, piggyBac transposase gene sequence (PBase), an internal Ribosomal Entry Sites (IRES), kanamycin resistance gene sequence (Neo), transcription termination/polyadenylation signal sequence, DNA homology arm sequence at the downstream of insertion site, and DTA.

These vectors can be integrated into the genome of the cells, and the cells can be selected by drug resistance markers or a combination thereof (e.g., Zeocin, G418, and/or Puromycin). In some embodiments, the PB transposase is expressed, and the genetic elements between the transposase target sequence can be deleted.

In some embodiments, these vectors are integrated into a human chromosome that has been modified. The human chromosome can be modified first, before the first and the second vectors are integrated into the genome. In some embodiments, one or more additional vectors can be added at various locations of the chromosome as needed. In some embodiments, the vector is added between the C region and the centromere. The third vector can have from 5' to 3' one or more of the following: DNA homology arm sequence at the upstream of the insertion site, PGK promoter, Puromycin resistance gene sequence (PuroR), thymidine kinase gene sequence (TK), the LoxP recognition sequence, PGK promoter, puromycin resistance gene partial sequence (5'PuroR), a mammalian expression promoter (EF-1a), PBase, IRES, Neo, transcription termination/polyadenylation signal sequence, DNA homology arm sequence at the downstream of insertion site, and DTA. In some embodiments, these vectors can be inserted into the variable gene region or constant region. In some embodiments, a part of endogenous variable gene region or endogenous constant region is deleted. In some embodiments, a large fragment of the chromosome is deleted (e.g., between the constant region and the centromere). The cells can also be treated with Cre enzyme, leading to the recombination of the loxP sites, thereby removing genomic DNA sequences between the J region and the centromere on human chromosome 14 or between the C region and the centromere on human chromosome 14. In some embodiments, spontaneous chromosome breakage can occur. Modified human chromosomes with desired chromosome breakage can be selected for experiments.

The human chromosome can be obtained from human cell lines, cancer cells, primary cell culture, and/or human fibroblasts. In some embodiments, the human cell is introduced with a first vector and is then fused with a recipient cell. The modified chromosome is then separated and introduced into another appropriate recipient cell. Cells with the desired resistance are selected to obtain cells containing only one human chromosome. Then, a second vector is introduced into the cells, and the cells are selected by resistance. Then, if needed, a third vector, and/or a fourth vector can be introduced. The recipient cell can be a mammalian cell, a human cell, or a mouse cell. In some embodiments, the recipient cell is a CHO cell, or preferably an A9 cell. In some embodiments, the modified chromosomes are labeled by fluorescence and separated. And the modified chromosomes are injected into the recipient cells by chromosome microinjection. In some embodiments, the donor cells are induced to multinucleate their chromosomes. These nuclei are then forced through the cell membrane to create microcells, which can be fused to a recipient cell. In some embodiments, microcell-mediated chromosome transfer can also be used. The chromosome manipulation techniques are described e.g., in CN1200014A; CN109837307A; US20120093785A1; and US2009253902; Kuroiwa et al. "Manipulation of human minichromosomes to carry greater than megabase-sized chromosome inserts." Nature Biotechnology 18.10 (2000)): 1086-1090; Chinese patent CN1717483A; Paulis, Marianna. "Chromosome Transfer Via Cell Fusion." Methods in Molecular Biology 738(2011): 57; Genes, Chromosomes & Cancer 14: 126127 (1995); Tomizuka et al. "Functional expression and germline atransmission of a human chromosome fragment in chimaeric mice." Nature Genetics 16.2 (1997): 133-143; Somatic Cell and Molecular Genetics, Vol. 13, No. 3, 1987, pp. 279-284; each of which is incorporated herein by reference in its entirety.

Figure 4:
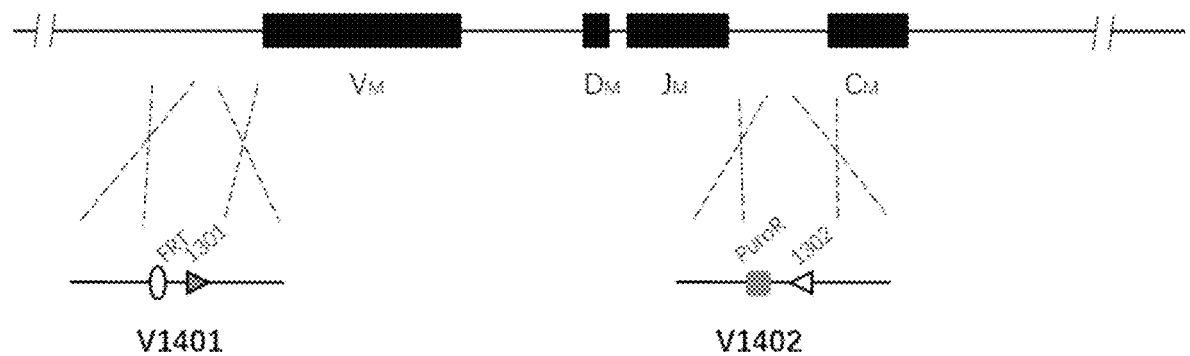
FIG. 4 shows a targeting strategy for modifying the mouse heavy chain immunoglobulin locus.
Figures 5A, 5B:
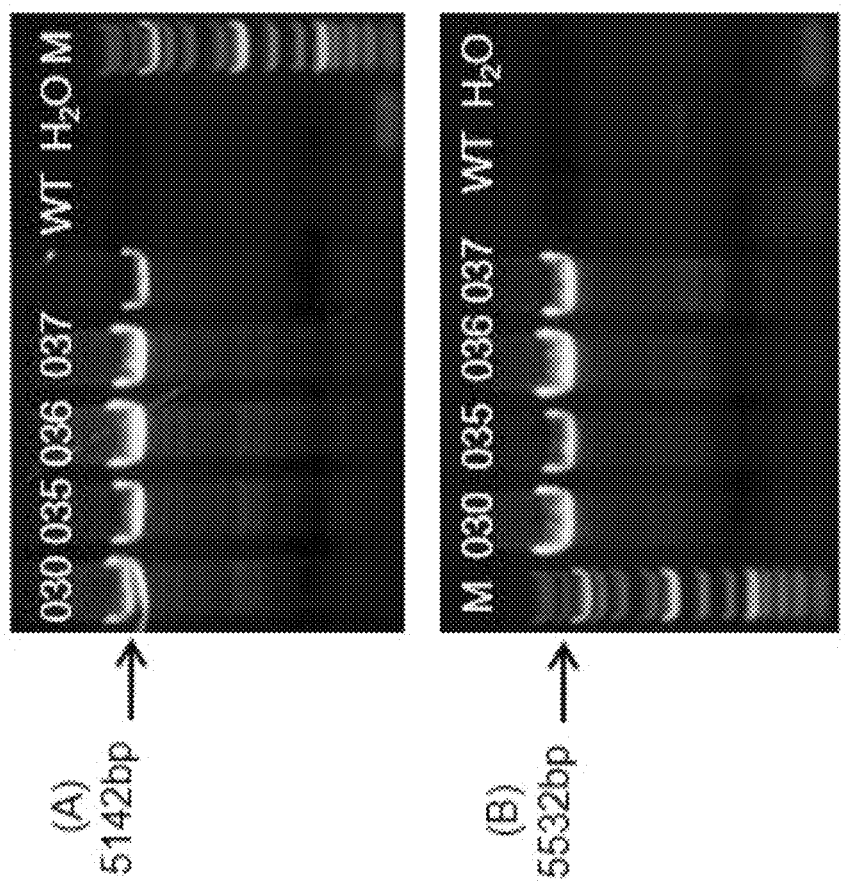
FIG. 5A shows PCR assay results using the mIgHV-5'loxP-L-GT-F/mIGHV-005-L-GT-R2 primer pair.
FIG. 5B shows PCR assay results using the mIGHV-005-5'loxP-R-GT-F2/mIgHV-5'loxP-R-GT-R primer pair.
Figures 6A, 6B:
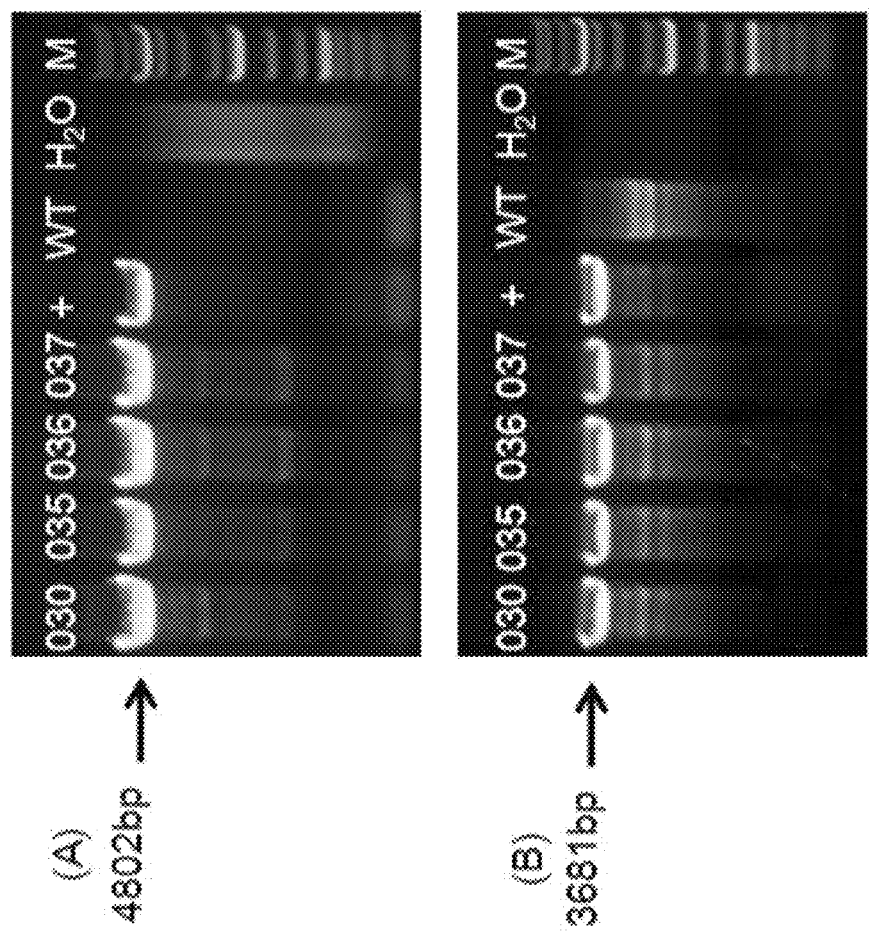
FIG. 6A shows PCR assay results using the mIGHV-3'lox-L-GT-F2/mIGHV-3'lox-L-GT-R2 primer pair.
FIG. 6B shows PCR assay results using the mIGHV3'lox-R-GT-F2/mIGHV-3'lox-R-GT-R1 primer pair.

In some embodiments, the modification can be made to the mouse chromosome. The targeting strategy is shown in FIG. 4. The first vector can have DNA homology arm sequence at upstream and downstream of the insertion site, and a LoxP sequence. In some embodiments, the first vector has from the 5' to 3' one or more of the following: DNA homology arm sequence at upstream of the insertion site, Flp recognition target (FRT), CAG promoter, hygromycin resistance gene (partial sequence of hygromycin phosphotransferase; "5'HygR"), LoxP, FRT, 5' PB transposon sequence (PB5'), PGK promoter, blue fluorescent protein reporter gene (BFP), FMDV self-cleaving peptide (2A), hygromycin resistance gene (hygromycin phosphotransferase; HygR), 3' PB transposon sequence (PB3'), the DNA homology arm sequence at downstream of the insertion site, and DTA.

The second vector can have DNA homology arm sequence at upstream and downstream of the insertion site, and LoxP sequence. In some embodiments, the second vector has from 5' to 3' one or more of the following: DNA homology arm sequence at upstream of the insertion site, 5' PB transposon sequence (PB5'), PGK promoter, green fluorescent protein reporter gene sequence (EGFP), FMDV self-cleaving peptide (2A), Puromycin resistance gene sequence (PuroR), 3' PB transposon sequence (PB3'), Flp recognition target (FRT), puromycin resistance gene partial sequence (3'PuroR), FMDV self-cleaving peptide (2A), DT receptor (DTR), LoxP recognition sequence, DNA homology arm sequence at downstream of insertion site, and DTA.

FIG. 30 show a similar targeting strategy for kappa light chain immunoglobulin locus. Two vectors can first be integrated to human chromosome. The first vector has DNA homology arm sequences at upstream and downstream of the insertion site, and LoxP recognition sequence. In some embodiments, the first vector has from 5' to 3' one or more of the following: DNA homology arm sequence at upstream of the insertion site, PGK promoter, tdTomato, FMDV self-cleaving peptide (2A), Bsr, termination of transcription/polyadenylation signal sequence, LoxP recognition sequence, hygromycin resistance gene (partial sequence of hygromycin phosphotransferase; "3'HygR"), FRT, the DNA homology arm sequence at downstream of the insertion site, and DTA.

The second vector has DNA homology arm sequences at upstream and downstream of the insertion site, and LoxP recognition sequence. In some embodiments, the second vector has from 5' to 3' one or more of the following: the DNA homology arm sequence at upstream of the insertion site, the LoxP recognition sequence, the PGK promoter, a portion of puromycin resistance gene sequence (5'PuroR), EF-1a, PBase, IRES, Neo, transcription termination/polyadenylation signal sequence, DNA homology arm sequence at downstream of insertion site, and DTA.

LoxP recognition sequences can also be added to the human chromosome (e.g., human chromosome 2, 14, 22). The cells can also be treated with Cre enzyme, leading to the recombination of the loxP sites, thereby removing genomic DNA sequences. In some embodiments, spontaneous chromosome breakage can be used to remove genomic DNA sequences as well.

The modification on mouse light chain immunoglobulin locus can be directly performed. In some embodiments, a vector is directly used to replace the entire mouse light chain immunoglobulin variable region. In some embodiments, the vector has from the 5' to 3': DNA homology arm sequence at upstream of the insertion site, Flp recognition target (FRT), mammalian expression promoter (EF-1a) from human elongation factor 1 alpha, hygromycin resistance gene (partial sequence of hygromycin phosphotransferase; "5'HygR"), the LoxP recognition sequence for the Cre recombinase, 5' PB transposon sequence (PB5'), blue fluorescent protein reporter gene (BFP), DT receptor (DTR), FMDV self-cleaving peptide (2A), kanamycin resistance gene sequence (Neo), transcription termination/polyadenylation signal sequence (PolyA; "PA"), 3' PB transposon sequence (PB3'), puromycin resistance gene partial sequence (3'PuroR), FMDV self-cleaving peptide (2A), DT receptor (DTR), the LoxP recognition sequence for the Cre recombinase, DNA homology arm sequence at downstream of insertion site, and DTA.

The mouse immunoglobulin variable region can be replaced by the human immunoglobulin variable region by replacement (e.g., homologous recombination, or Cre mediated recombination). In some embodiments, Cre recombination can be used to mediate the replacement. In some embodiments, the vectors can add LoxP recognition sequence into the human chromosome. Similar modifications can be made to the mouse chromosome, wherein two LoxP recognition sequences can be added to the chromosome. For example, Cre recombinase can then mediate the replacement of V, J regions on mouse chromosome with the V, J regions on human chromosome or the replacement of V, D, J regions on mouse chromosome with the V, D, J regions on human chromosome.

The cells can be further screened for cells that do not have human chromosomes (e.g., by DT). In some cases, cells that are not screened by DT may contain recombinant human chromosome fragments, but these fragments are small and are unstable in mouse cells (e.g., Shinohara et al. (2000) Chromosome Research, 8: 713-725), and will naturally disappear during cell proliferation. In some embodiments, a large fragment of the modified human chromosome is deleted, e.g., by Cre-mediated deletion or by spontaneous chromosomal breakage.

The 5' end homology arm and/or the 3' end homology arm can have a desired length to facilitate homologous recombination. In some embodiments, the homology arm is about or at least 1, 2, 3, 4, 5, 6, 7, 8, 9, 10, 20, 30, 40, or 50 kb (e.g., about 3 kb). In some embodiments, the homology arm is less than 1, 2, 3, 4, 5, 6, 7, 8, 9, 10, 20, 30, 40, or 50 kb.

In some embodiments, the vector may also optionally include a reporter protein, e.g., a luciferase (e.g., Gluc) or a fluorescent protein (e.g., EGFP, BFP, etc.).

These modifications can be performed in various cells. In some embodiments, the cell is a stem cell, an embryonic stem cell, or a fertilized egg cell.

The present disclosure further provides a method for establishing a humanized animal model, involving the following steps:
  (a) providing the cell (e.g. a fertilized egg cell) based on the methods described herein;
  (b) culturing the cell in a liquid culture medium;
  (c) transplanting the cultured cell to the fallopian tube or uterus of the recipient female non-human mammal, allowing the cell to develop in the uterus of the female non-human mammal;
  (d) identifying the germline transmission in the offspring genetically modified humanized non-human mammal of the pregnant female in step (c).

In some embodiments, the non-human mammal in the foregoing method is a mouse (e.g., a C57 mouse, a BALB/c mouse, or a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

Cells, tissues, and animals (e.g., mouse) are also provided that comprise the nucleotide sequences as described herein, as well as cells, tissues, and animals (e.g., mouse) that express humanized or chimeric antibodies from an endogenous non-human locus.

The present disclosure also provides various targeting vectors (e.g., vectors that are useful for making the genetically modified animals). In some embodiments, the vector can comprise: a) a DNA fragment homologous to the 5' end of a region to be altered (5' homology arm); b) a sequence comprising desired genetic elements (e.g., LoxP recognition site, drug resistance genes, and/or reporter genes etc.); and c) a second DNA fragment homologous to the 3' end of the region to be altered (3' homology arm). The disclosure also relates to a cell comprising the targeting vectors as described herein.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

The present disclosure further relates to methods for generating genetically modified animal model with two or more human or chimeric genes. The animal can comprise one or more human or humanized immunoglobulin locus and a sequence encoding an additional human or chimeric protein. In some embodiments, the additional human or chimeric protein can be programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), or TNF Receptor Superfamily Member 4 (TNFRSF4 or OX40).

The methods of generating genetically modified animal model with additional human or chimeric genes (e.g., humanized genes) can include the following steps:
(a) using the methods as described herein to obtain a genetically modified non-human animal;
(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, CD27, CD28, CD47, CD137, CD154, TIGIT, TIM-3, GITR, SIRPa, or OX40. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/120388, PCT/CN2018/081628, PCT/CN2018/081629; each of which is incorporated herein by reference in its entirety.

In some embodiments, the genetically modified animals can have a human ADAM6 gene, an endogenous ADAM6 gene or a modified ADAM6 gene. The ADAM6 protein is a member of the ADAM family of proteins, where ADAM is an acronym for A Disintegrin And Metalloprotease. The human ADAM6 gene, normally found between human IGHV genes IGHV1-2 and IGHV6-1, is a pseudogene (FIG. 37). In mice, there are two ADAM6 genes, ADAM6a and ADAM6b. They are located in an intergenic region between mouse IGHV and IGHD gene clusters. The mouse ADAM6a is located between mouse IGHV5-1 and mouse IGHD5-1. The mouse ADAM6b is located between mouse IGHD3-1 and mouse IGHD1-1. Thus, in some embodiments, the genetically modified animals can have a human ADAM6 gene. In some embodiments, the genetically modified animals do not have an endogenous ADAM6 gene.

In some embodiments, the genetically modified animals are mice. In some embodiments, the mice are modified to include a nucleotide sequence that encodes an ADAM6 protein (e.g., ADAM6a or ADAM6b). In some embodiments, the sequence is placed at any suitable position. It can be placed in the intergenic region, or in any suitable position in the genome. In some embodiments, the nucleic acid encodes a sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a mouse ADAM6a gene (e.g., 113539230-113547024 of NC 000078.6; SEQ ID NO: 53) or a mouse ADAM6b gene (e.g., 113486188-113492125 of NC 000078.6; SEQ ID NO: 54). In some embodiments, the nucleic acid additionally includes the regulatory elements for the ADAM6a gene and ADAM6b gene (e.g., promoters).

In some embodiments, a functional mouse ADAM6 locus can be placed in the midst of human IGHV gene cluster. In some embodiment, the mouse ADAM6 locus is between two human IGVH genes. In some embodiments, the human ADAM6 pseudogene between human VH1-2 and human VH(II)-1-1 is replaced with the mouse ADAM6 locus. In some embodiments, the ADAM6a gene and the ADAM6b gene are located between human IGHV1-2 and human VH(II)-1-1 in the genome of the animal. In some embodiments, the location of the mouse ADAM6 sequence within the human gene sequence can approximate the position of the human ADAM6 pseudogene or can approximate the position of the mouse ADAM6 sequence (e.g., within the V-D intergenic region). In some embodiments, the genetic modified mice has a humanized heavy chain immunoglobulin locus. In some embodiments, the mouse ADAM6a and the mouse ADAM6b are located between human IGHV1-2 and IGHV6-1 genes. Placing the mouse ADAM6a and the mouse ADAM6b between human IGHV1-2 and IGHV6-1 genes can have various advantages. For example, because these genes replaces the human ADAM6 gene at the same locus, it is likely that the replacement of human ADAM6 gene will have limited impact on the VDJ recombination and the mouse ADAM6a and the mouse ADAM6b gene can also function properly (as in a location that is similar to the endogenous locus).

Thus, in one aspect, the disclosure provides a genetically-modified animal comprising at an endogenous heavy chain immunoglobulin gene locus, a first sequence comprising one or more human IGHV genes; a second sequence comprising a ADAM6 gene; and a third sequence comprising one or more human IGHD genes, and one or more human IGHJ genes. In some embodiments, the first sequence, the second sequence, and the third sequence are operably linked.

In some embodiments, the first sequence comprises all human IGHV genes in Table 1 except IGHV2-10, IGHV3-9, IGHV1-8, IGHV(II)-1-1, and IGHV6-1. In some embodiments, the first sequence comprises all human IGHV genes in Table 1 except IGHV5-10-1 and IGHV3-64D, IGHV(II)-1-1, and IGHV6-1. In some embodiments, the first sequence is an unmodified sequence derived from a human heavy chain immunoglobulin gene locus.

In some embodiments, the second sequence comprises either one or both of a mouse ADAM6a gene and a mouse ADAM6b gene. In some embodiments, the animal is a fertile male mouse. In some embodiments, the second sequence does not have a mouse ADAM6a gene or a mouse ADAM6b gene.

In some embodiments, the third sequence comprises all human IGHD genes in Table 2, and all human IGHJ genes in Table 3. In some embodiments, the third sequence comprises human IGHV6-1. In some embodiments, the third sequence comprises human IGHV(II)-1-1. In some embodiments, the third sequence is an unmodified sequence derived from a human heavy chain immunoglobulin gene locus.

In some embodiments, the AMAM6a and/or ADAM6b are endogenous sequences. In some embodiments, the AMAM6a and/or ADAM6b are not replaced, and/or located in its endogenous or native position. In some embodiments, the mouse IGHV genes before mouse IGHV1-2 in the heavy chain variable region locus are replaced with human IGHV genes. In some embodiments, the mouse IGHV, IGHD and IGHJ genes after mouse IGHV6-1 in the heavy chain variable region locus are replaced with one or more human IGHV genes, IGHD and/or IGHJ genes.

Thus, in some embodiments, the mouse IGHV, IGHD and IGHJ genes can be replaced with human IGHV, IGHD and IGHJ by more than one replacements. In the first step, a selected number of mouse IGHV genes on the 5' side of the ADAM6a (e.g., all mouse IGHV genes in Table 4) are replaced with human IGHV genes. In the second step, a selected number of mouse IGHD and IGHJ genes on the 3' side of the ADAM6b (e.g., all mouse IGHD genes in Table 5 except IGHD5-1 and IGHD3-1 and all IGHJ genes in Table 6) are replaced with human IGHD and human IGHJ genes. The replacement can be performed by homologous recombination or Cre-mediated recombination.

In some embodiments, the mice do not have mouse ADAM6a or ADAM6b genes. In some embodiments, the mice have human ADAM6 genes.

Various methods can be used to increase the fertility of the mice. In some embodiments, female mice with superovulation can be used in mating. In some embodiments, in vitro fertilization can be used. Superovulation can be induced by injecting serum gonadotropin and chorionic gonadotropin (e.g., human or mouse CG) into a mature female mouse. A mature male mouse can be sacrificed and its cauda epididymides can be isolated. The duct of cauda epididymis is cut open to release sperm. Next, a superovulating mature female mouse can be sacrificed and the oviducts can be isolated. Cumulus-oocyte-complexes (COCs) can be released from the oviduct. Next, sperm suspension can be added to the COCs and incubated for insemination. Pathenogenic oocytes containing only one pronucleus can be removed. After the incubation, embryos at 2-cell stage can be transferred to recipient females. Methods of increasing mouse fertility are known in the art.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein.

In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, 200, 250, 300, 350, or 400 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include e.g., amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage. Thus, the present disclosure also provides an amino acid sequence that has at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% homology percentage to any amino acid sequence as described herein, or a nucleic acid encoding these amino acid sequences.

Methods of Using Genetic Modified Animals

The genetic modified animals can be used to generate humanized or chimeric antibodies that can bind specifically to a target. In some embodiments, the target (e.g., a protein or a fragment of the protein) can be used as an immunogen to generate antibodies in these animals using standard techniques for polyclonal and monoclonal antibody preparation. In some embodiments, the genetic modified animal is exposed to a selected antigen for a time and under conditions which permit the animal to produce antibody specific for the antigen.

Polyclonal antibodies can be raised in animals by multiple injections (e.g., subcutaneous or intraperitoneal injections)

of an antigenic peptide or protein. In some embodiments, the antigenic peptide or protein is injected with at least one adjuvant. In some embodiments, the antigenic peptide or protein can be conjugated to an agent that is immunogenic in the species to be immunized. Animals can be injected with the antigenic peptide or protein more than one time (e.g., twice, three times, or four times).

The full-length polypeptide or protein can be used or, alternatively, antigenic peptide fragments thereof can be used as immunogens. The antigenic peptide of a protein comprises at least 8 (e.g., at least 10, 15, 20, or 30) amino acid residues of the amino acid sequence and encompasses an epitope of the protein such that an antibody raised against the peptide forms a specific immune complex with the protein.

An immunogen typically is used to prepare antibodies by immunizing a suitable subject (e.g., the genetically modified animal as described herein). An appropriate immunogenic preparation can contain, for example, a recombinantly-expressed or a chemically-synthesized polypeptide (e.g., a fragment of the protein). The preparation can further include an adjuvant, such as Freund's complete or incomplete adjuvant, or a similar immunostimulatory agent.

Polyclonal antibodies can be prepared as described above by immunizing a suitable subject with a polypeptide, or an antigenic peptide thereof (e.g., part of the protein) as an immunogen. The antibody titer in the immunized subject can be monitored over time by standard techniques, such as with an enzyme-linked immunosorbent assay (ELISA) using the immobilized polypeptide or peptide. If desired, the antibody molecules can be isolated from the mammal (e.g., from the blood) and further purified by well-known techniques, such as protein A of protein G chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, NY). Hybridoma cells producing a monoclonal antibody are detected by screening the hybridoma culture supernatants for antibodies that bind the polypeptide or epitope of interest, e.g., using a standard ELISA assay.

In one aspect, the disclosure provides a mouse that comprises a modification of an endogenous immunoglobulin heavy chain locus, wherein the mouse produces a B cell that comprises a rearranged immunoglobulin sequence operably linked to a heavy chain constant region gene sequence. In some embodiment, the rearranged immunoglobulin sequence operably linked to the heavy chain constant region gene sequence comprises a human heavy chain V, D, and/or J sequence. In some embodiments, the heavy chain constant region gene sequence comprises a human or a mouse heavy chain sequence selected from the group consisting of a CH1, a hinge, a CH2, a CH3, and a combination thereof.

In one aspect, the disclosure provides a mouse that comprises a modification of an endogenous immunoglobulin light chain (e.g., kappa or lambda) locus, wherein the mouse produces a B cell that comprises a rearranged immunoglobulin sequence operably linked to a light chain constant region gene sequence. In some embodiments, the rearranged immunoglobulin sequence operably linked to the light chain constant region gene sequence comprises a human light chain V and/or J sequence. In some embodiments, the light chain constant region gene sequence comprises a human or a mouse light chain constant region.

The mouse B cells or spleen cells can comprise a rearranged non-mouse immunoglobulin variable gene sequence, e.g., operably linked to a mouse immunoglobulin constant region gene. The sequences for encoding human heavy chain variable region and human light chain variable region are determined. The sequences can be determined by e.g., sequencing the hybridoma of interest or B cells. In some embodiments, single B cell screening is used. It can screen the natural antibody repertoire without the need for hybridoma fusion and combinatorial display. For example, B cells can be mixed with a panel of DNA-barcoded antigens, such that both the antigen barcode(s) and B-cell receptor (BCR) sequences of individual B cells are recovered via single-cell sequencing protocols.

The antibodies can be further modified to obtain a humanized antibody or a human antibody, e.g., by operably linking the sequence encoding human heavy chain variable region to a sequence encoding a human heavy chain constant region, and/or operably linking the sequence encoding human light chain variable region to a sequence encoding a human light chain constant region.

In some embodiments, if the mouse expresses a protein that is very similar to the antigen of interest, it can be difficult to elicit an immune response in the mouse. This is because during immune cell development, B-cells and T-cells that recognize MHC molecules bound to peptides of self-origin are deleted from the repertoire of immune cells. In those cases, the humanized mouse can be further modified. The corresponding gene in the mouse can be knocked out, and the mouse is then exposed to the antigen of interest. Because the mouse does not go through negative selection for the gene product, the mouse can generate an antibody that can specifically bind to the target easily.

The disclosure also provides methods of making antibodies, nucleic acids, cells, tissues (e.g., spleen tissue). In some embodiments, the methods involve exposing the animal as described herein to the antigen. Antibodies (e.g., hybrid antibodies), nucleic acids encoding the antibodies, cells, and/or tissues (e.g., spleen tissue) can be obtained from the animal. In some embodiments, the nucleic acids encoding human heavy and light chain immunoglobulin variable regions are determined, e.g., by sequencing. In some embodiments, the nucleic acid encoding the human heavy chain immunoglobulin variable region can be operably linked with a nucleic acid encoding a human heavy chain immunoglobulin constant region. In some embodiments, the nucleic acid encoding the human light chain immunoglobulin variable region can be operably linked with a nucleic acid encoding a human light chain immunoglobulin constant region. In some embodiments, the cells containing the nucleic acids as described herein are cultured and the antibodies are collected.

In some embodiments, no mouse immunoglobulin V, D, J genes (e.g., no mouse IGHV, IGHD, IGHJ, IGKV, or IGKJ genes) contributes to the heavy chain and/or light chain variable region sequence. In some embodiments, the heavy chain and/or light chain variable region sequence produced by the animal are fully human, and are completely contributed by human immunoglobulin V, D, J genes (e.g., human IGHV, IGHD, IGHJ, IGKV, and IGKJ genes).

Variants of the antibodies or antigen-binding fragments described herein can be prepared by introducing appropriate nucleotide changes into the DNA encoding a human, humanized, or chimeric antibody, or antigen-binding fragment thereof described herein, or by peptide synthesis. Such variants include, for example, deletions, insertions, or substitutions of residues within the amino acids sequences that make-up the antigen-binding site of the antibody or an antigen-binding domain. In a population of such variants, some antibodies or antigen-binding fragments will have increased affinity for the target protein. Any combination of deletions, insertions, and/or combinations can be made to arrive at an antibody or antigen-binding fragment thereof that has increased binding affinity for the target. The amino acid changes introduced into the antibody or antigen-binding fragment can also alter or introduce new post-translational modifications into the antibody or antigen-binding fragment, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

Antibodies disclosed herein can be derived from any species of animal, including mammals. Non-limiting examples of native antibodies include antibodies derived from humans, primates, e.g., monkeys and apes, cows, pigs, horses, sheep, camelids (e.g., camels and llamas), chicken, goats, and rodents (e.g., rats, mice, hamsters and rabbits), including transgenic rodents genetically engineered to produce human antibodies.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs.

Additional modifications to the antibodies or antigen-binding fragments can be made. For example, a cysteine residue(s) can be introduced into the Fc region, thereby allowing interchain disulfide bond formation in this region. The homodimeric antibody thus generated may have any increased half-life in vitro and/or in vivo. Homodimeric antibodies with increased half-life in vitro and/or in vivo can also be prepared using heterobifunctional cross-linkers as described, for example, in Wolff et al. (*Cancer Res.* 53:2560-2565, 1993). Alternatively, an antibody can be engineered which has dual Fc regions (see, for example, Stevenson et al., *Anti-Cancer Drug Design* 3:219-230, 1989).

In some embodiments, a covalent modification can be made to the antibody or antigen-binding fragment thereof. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

EXAMPLES

The invention is further described in the following examples, which do not limit the scope of the invention described in the claims.

Example 1: Overview

Experiments were performed to introduce human immunoglobulin genes into the mouse genome to produce mice expressing humanized antibodies. FIG. 1A shows the methods of making the humanized mice. The methods first involve modifying the human immunoglobulin region on the human chromosome. The modified human chromosomes were then introduced into the mouse recipient cell.

The mouse immunoglobulin variable region was replaced by the human immunoglobulin variable region by direct replacement (e.g., homologous recombination, or Cre mediated recombination). In some cases, the human immunoglobulin variable region can be introduced into the mouse genome by a stepwise approach. Then, the recipient cells were screened for the correct replacement. The cells were then injected to blastocysts to prepare chimeric mice. Subsequent breeding was performed to obtain mice containing intact human immunoglobulin variable regions.

Figure 1B:
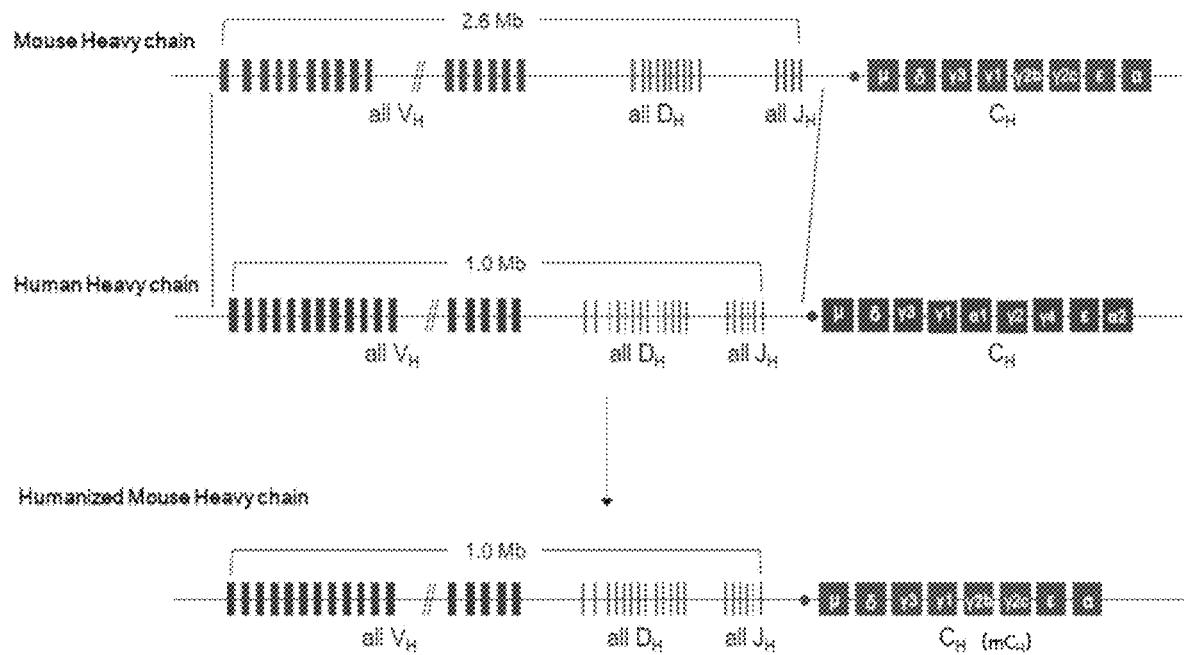
FIG. 1B is an overview of replacing mouse immunoglobulin heavy chain variable region with human immunoglobulin heavy chain variable region.
Figure 1C:
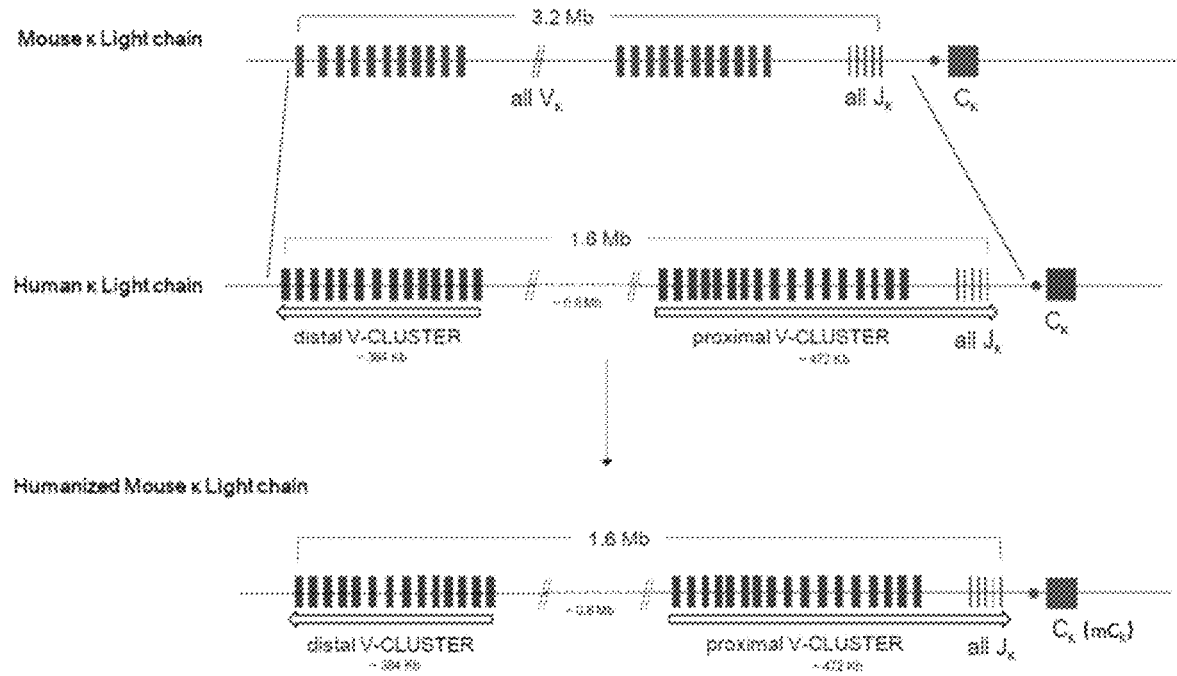
FIG. 1C is an overview of replacing mouse immunoglobulin light chain variable region with human immunoglobulin light chain variable region.

Because the mouse heavy chain gene and the two light chain genes are located on chromosomes 12, 6, and 16, respectively, mice containing the human heavy chain variable region or the human light chain variable region can be prepared separately (FIGS. 1B and 1C). These mice can then be mated with each other to obtain mice that can express both the human heavy chain variable domain and the human light chain variable domain.

Example 2: Modification of the Mouse Heavy Chain Immunoglobulin Locus

Figure 2:
FIG. 2 is a schematic diagram showing the mouse heavy chain immunoglobulin locus.
Figure 3A:
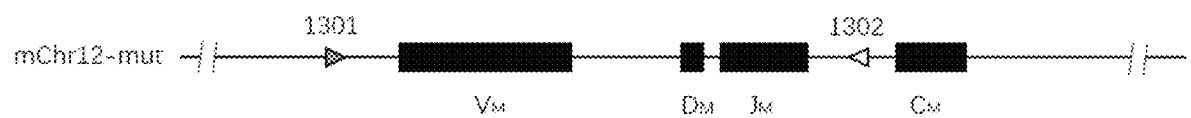
FIG. 3A is a schematic diagram showing the mouse heavy chain immunoglobulin locus after two recombination sites were introduced to the genome.
Figure 3B:
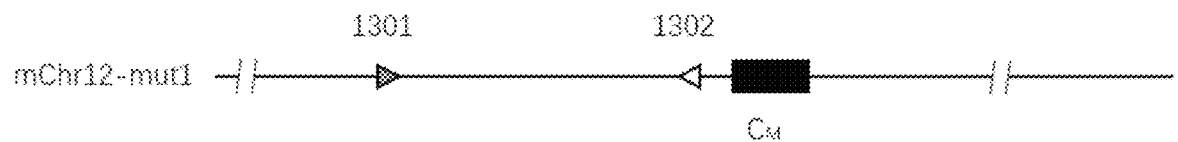
FIG. 3B is a schematic diagram showing the mouse heavy chain immunoglobulin locus after recombination with a targeting vector.

The heavy chain immunoglobulin locus is located on mouse chromosome 12. FIG. 2 is a schematic diagram showing the mouse heavy chain immunoglobulin locus. Two recombination sites (1301, 1302) were introduced on both sides of the variable region of the heavy chain immunoglobulin locus, and the resulting modified chromosome is shown in FIG. 3A-3B. One of them is a wildtype loxP site, the other is a heterospecific mutant lox site (lox2272). The recombination cannot occur between the wildtype loxP site and the heterospecific mutant lox site. The modification was performed in mouse embryonic stem cells. An overview of the targeting strategy is shown in FIG. 4. The vector (V1401) has from the 5' to 3': DNA homology arm sequence at upstream of the insertion site, Flp recognition target (FRT), CAG promoter, hygromycin resistance gene (partial sequence of hygromycin phosphotransferase; "5'HygR"), LoxP (1301), FRT, 5' PB transposon sequence (PB5'), PGK promoter, blue fluorescent protein reporter gene (BFP), FMDV self-cleaving peptide (2A), hygromycin resistance gene (hygromycin phosphotransferase; HygR), 3' PB transposon sequence (PB3'), the DNA homology arm sequence at downstream of the insertion site, and DTA.

The vector (V1402) has from 5' to 3': DNA homology arm sequence at upstream of the insertion site, 5' PB transposon sequence (PB5'), PGK promoter, green fluorescent protein reporter gene sequence (EGFP), FMDV self-cleaving peptide (2A), Puromycin resistance gene sequence (PuroR), 3' PB transposon sequence (PB3'), Flp recognition target (FRT), puromycin resistance gene partial sequence (3'PuroR), FMDV self-cleaving peptide (2A), DT receptor (DTR), LoxP recognition sequence (1302), DNA homology arm sequence at downstream of insertion site, and DTA.

The vectors (V1401 and V1402) were introduced into mouse embryonic stem cells. The cells were then screened by hygromycin B and puromycin. The integration of the exogenous genes into mouse genomes was confirmed by PCR. The results are shown in FIGS. 5A-5B and FIGS. 6A-6B. The clones numbered 030, 035, 036 and 037 were confirmed to be positive.

The PCR assay was performed using the following primers:

```
mIgHV-5'loxP-L-GT-F:
                                       (SEQ ID NO: 1)
5'-gccaaggaatttaaaaggggattgaaagcaa-3', mIGHV-005-L-GT-R2:
                                       (SEQ ID NO: 2)
5'-gccctccatgtacagcttcatgtgc-3';

mIGHV-005-5'loxP-R-GT-F2:
                                       (SEQ ID NO: 3)
5'-actgggcttgtcgagacagagaaag-3', mIgHV-5'loxP-R-GT-R:
                                       (SEQ ID NO: 4)
5'-ccacagcccgatctacttggcttttt-3';

mIGHV-3'lox-L-GT-F2:
                                       (SEQ ID NO: 5)
5'-gcaaggttttgactaagcggagcac-3';

mIGHV-3'lox-L-GT-R2:
                                       (SEQ ID NO: 6)
5'-tgacgcatgtgttttatcggtctgt-3';

mIGHV3'lox-R-GT-F2:
                                       (SEQ ID NO: 7)
5'-gtgcctgacacgtgctacgagattt-3';

mIGHV-3'lox-R-GT-R1:
                                       (SEQ ID NO: 8)
5'-ttcaacaataagcagggccagaggg-3';
```

Among these primers, mIgHV-5'loxP-L-GT-F and mIgHV-5'loxP-R-GT-R are located on the mouse chromosome, mIGHV-005-L-GT-R2 and mIGHV-005-5'loxP-R-GT-F2 are located on the vector 1401, mIGHV-3'lox-L-GT-F2 and mIGHV-3'lox-R-GT-R1 are located on the mouse chromosome, mIGHV-3'lox-L-GT-R2 and mIGHV3'lox-R-GT-F2 are located on the vector 1402.

Example 3: Modifying Human Chromosome 14

The purpose of the experiment is to generate a modified human chromosome with at least two recombination sites. The two recombination sites were introduced on both sides of the variable region of the heavy chain immunoglobulin locus.

Figure 7:
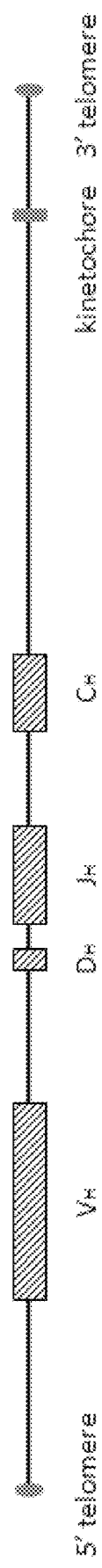
FIG. 7 is a schematic diagram of the human chromosome 14 highlighting the heavy chain immunoglobulin locus (not drawn to scale). The heavy chain immunoglobulin locus has the variable regions ($V_H$, $D_H$, $J_H$) and the constant region ($C_H$). $V_H$ represents the segment for the IGHV gene cluster, $D_H$ represents the segment for the IGHD gene cluster, $J_H$ represents the segment for the IGHJ gene cluster, and $C_H$ represents the gene cluster that express constant domains.

The heavy chain immunoglobulin locus is located on human chromosome 14. FIG. 7 is a schematic diagram of the human chromosome 14 highlighting the heavy chain immunoglobulin locus.

Figure 8:
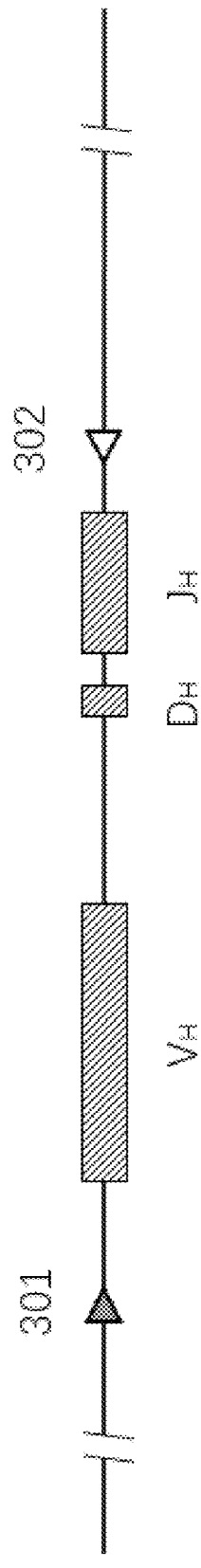
FIG. 8 is a schematic diagram showing the human chromosome 14 after the modification.

The modified human variable region is shown in FIG. 8. An overview of the targeting strategy is shown in FIG. 9. As shown in FIG. 9, the 301 and 302 sites are recombination sites. The recombination site 1301 and the recombination site 301 are identical. The recombination site 1302 and the recombination site 302 are identical.

Experiments were performed to insert vectors into human chromosome 14 at the upstream of the V region, and between the J region and the C region. The first targeting vector (V401) from 5' to 3' has DNA homology arm sequence at upstream of the insertion site, PGK promoter, red fluorescent protein reporter gene (tdTomato), self-cleaving peptide (2A) from FMDV (Foot-And-Mouth Disease Viruses), Zeocin resistance gene sequence (Zeo), transcription termination/polyadenylation signal sequence (PolyA; "PA"), the LoxP recognition sequence (301) for the Cre recombinase, hygromycin resistance gene (partial sequence of hygromycin phosphotransferase; "3'HygR"), and the Flp recognition target ("FRT"), downstream DNA homology arm sequence, and diphtheria toxin subunit A (DTA) gene.

The second vector (V402) from 5' to 3' has the following: DNA homology arm sequence at the upstream of the insertion site, the LoxP recognition sequence (302) for the Cre recombinase, PGK promoter, a partial sequence of Puromycin resistance gene (5'PuroR), a mammalian expression promoter (EF-1a) from human elongation factor 1 alpha, piggyBac transposase gene sequence (PBase), an internal Ribosomal Entry Sites (IRES), kanamycin resistance gene sequence (Neo), transcription termination/polyadenylation signal sequence (PolyA; "PA"), DNA homology arm sequence at the downstream of insertion site, and DTA.

In some experiments, the vectors (V401, V402) were introduced into the cells, and the cells were selected by appropriate drug resistance markers or a combination thereof (Zeocin, G418).

There are many ways to introduce the vectors of interest into the human chromosome. The human chromosome can be obtained from human cell lines, cancer cells, primary cell culture, and/or human fibroblasts. In one experiment, the first vector is introduced into the chromosome. The modified chromosome can be added to the recipient cell, and then the second vector can be inserted to the modified chromosome. In some experiments, V401 was first introduced into human cells, and then the chromosome was labelled by fluoresce and was then separated, and the modified chromosome was then injected into recipient cells by microinjection. V402 was then introduced into the cells. In another experiment, the human fibroblasts were selected and were introduced with vector 402. The human fibroblasts were then fused with recipient cells (A9 cells or CHO cells).

In some experiments, one or more vectors can be inserted into human chromosome 14 at the desired locations by homologous recombination e.g., in the same time. The vectors can contain drug resistance markers (Zeocin, G418) and the cells are then screened. The chromosome is the labelled and is then separated, and the modified chromosome is then injected into recipient cells by chromosome microinjections.

In some experiments, one or more additional vectors are inserted. These additional vectors can be inserted at different locations of human chromosome 14 as needed. In one experiment, a third vector can have from 5' to 3' the following: DNA homology arm sequence at the upstream of the insertion site, PGK promoter, Puromycin resistance gene sequence (PuroR), thymidine kinase gene sequence (TK), the LoxP recognition sequence (302), PGK promoter, puromycin resistance gene partial sequence (5'PuroR), a mammalian expression promoter (EF-1a) from human elongation factor 1 alpha, piggyBac transposase gene sequence (PBase), Internal Ribosomal Entry Sites (IRES), kanamycin resistance gene sequence (Neo), transcription termination/polyadenylation signal sequence (PolyA; "PA"), DNA homology arm sequence at the downstream of insertion site, and DTA. The vector is inserted within the C region.

In one experiment, a third vector (V403) was inserted between the C region and the kinetochore. The vector from 5' to 3' has the following: DNA homology arm sequence at the upstream of the insertion site, PGK promoter, Puromycin resistance gene sequence (PuroR), thymidine kinase gene sequence (TK), the LoxP recognition sequence (302), PGK promoter, puromycin resistance gene partial sequence (5'PuroR), a mammalian expression promoter (EF-1a) from human elongation factor 1 alpha, piggyBac transposase gene sequence (PBase), Internal Ribosomal Entry Sites (IRES), kanamycin resistance gene sequence (Neo), transcription termination/polyadenylation signal sequence (PolyA; "PA"), DNA homology arm sequence at the downstream of insertion site, and DTA.

In one experiment, the human fibroblasts were selected and were introduced with vector 402. The human fibroblasts were then fused with recipient cells (A9 cells or CHO cells). The modified chromosome was separated and introduced into another appropriate recipient cell. Cells were then selected by G418 resistance to obtain cells containing only one human chromosome. Then, vector 401 was introduced into the cells, and the cells were selected by resistance to Zeocin. After that, vector 403 was introduced in the cells, and the cells were selected by resistance to puromycin. The positive clones selected after screening were treated with Cre enzyme. The chromosome techniques were described e.g., in Kuroiwa et al. "Manipulation of human minichromosomes to carry greater than megabase-sized chromosome inserts." Nature Biotechnology 18.10 (2000)): 1086-1090; CN1200014A; CN109837307A; US20120093785A1; US2009253902; CN1717483A; Paulis, Marianna. "Chromosome Transfer Via Cell Fusion." Methods in Molecular Biology 738(2011):57; Genes, Chromosomes & Cancer 14: 126127 (1995); Tomizuka et al. "Functional expression and germline atransmission of a human chromosome fragment in chimaeric mice." Nature Genetics 16.2 (1997): 133-143; and Somatic Cell and Molecular Genetics, Vol. 13, No. 3, 1987, pp. 279-284; each of which is incorporated herein by reference in its entirety.

PCR was performed to confirm the presence of the 5'-end recombination site 301 and the 3'-end recombination site 302 on the chromosome. Cells without random insertion were confirmed by Southern Blot and were analyzed by fluorescence in situ hybridization (FISH).

Figure 10:
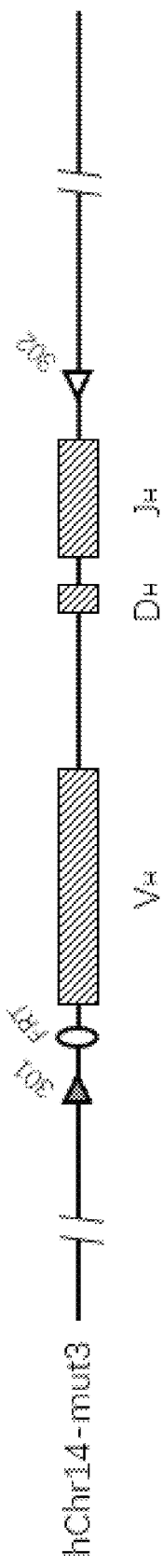
FIG. 10 shows modified human chromosome 14.
Figure 11:
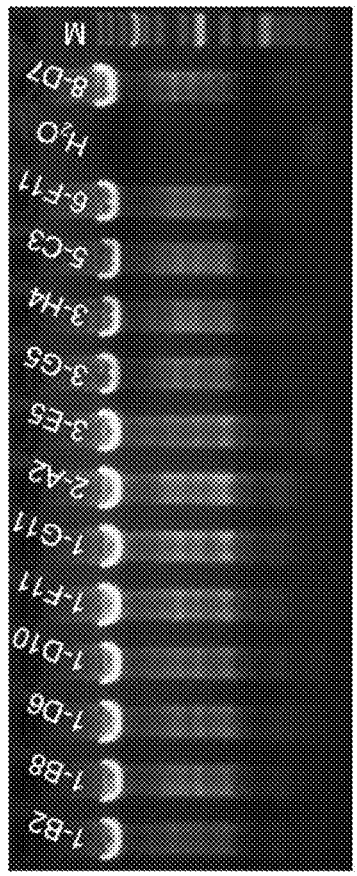
FIG. 11 shows the results of PCR assays for loxP site 301 on chromosome hChr14-mut3 using the hIGHV-5'loxP-L-GT-F1 and hIGHV-5' loxP-R-GT-R primer pair. 8-D7 is a positive control clone.
Figure 12:
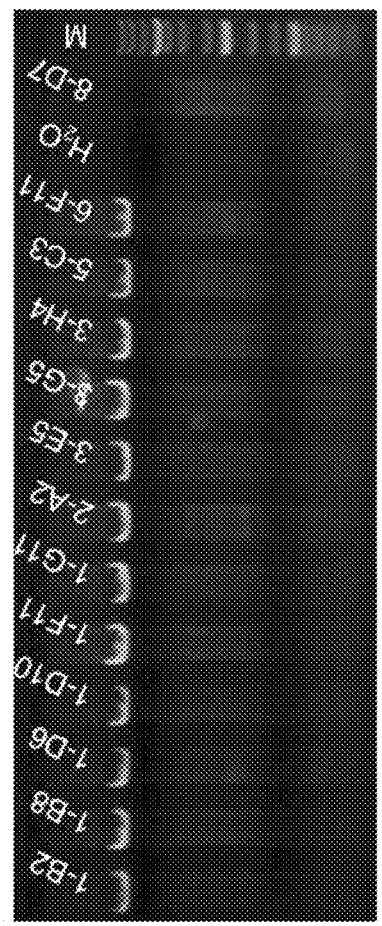
FIG. 12 shows the results of PCR assays for loxP site 302 on chromosome hChr14-mut3. 8-D7 is a negative control clone.

FIG. 10 shows the modified human chromosome 14. FIG. 11 shows the results of PCR identification of loxP site 301 on chromosome hChr14-mut3. FIG. 12 shows the results of PCR identification of loxP site 302 on chromosome hChr14-mut3. As shown in the figures, 12 clones (numbered 1-B2, 1-B8, 1-D6, 1-D10, 1-F11, 1-G11, 2-A2, 3-E5, 3-G5, 3-H4, 5-C3, and 6-F11) were positive clones.

The following PCR primers were used in the experiments:

hIGHV-5'loxP-L-GT-F1:
(SEQ ID NO: 9)
5'-TCAAAGTCAATTTCCTCAGCGAGGCT-3', hIGHV-5'loxP-R-GT-R:
(SEQ ID NO: 10)
5'-AGGGAGGGAATGGAATGAGGGTGAT-3';

hIGHV-3'loxP-L-GT-F1:
(SEQ ID NO: 11)
5'-CCATGTGACCCATTCGAGTGTCCTG-3', hIGHV-3'loxP-R-GT-R:
(SEQ ID NO: 12)
5'-TTGTGAGGGCTCAAGTTCAGTGCAT-3'.

Figure 13:
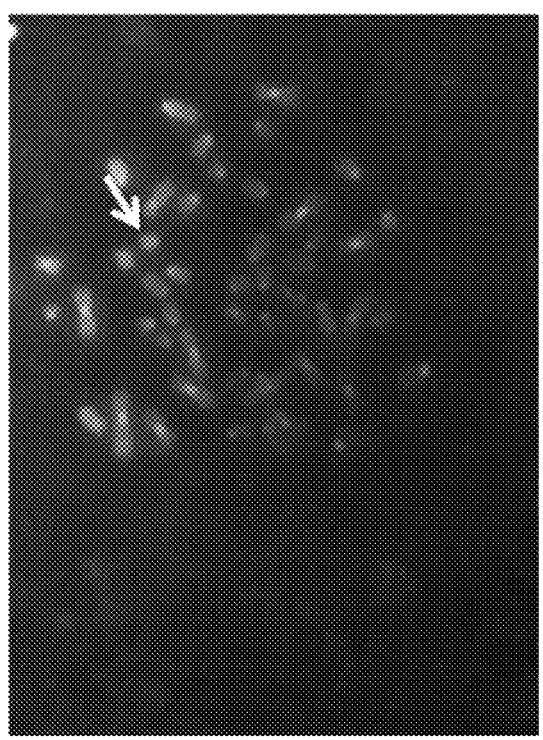
FIG. 13 is a fluorescence in situ hybridization (FISH) image of cells before the human chromosome 14 is modified.
Figure 14:
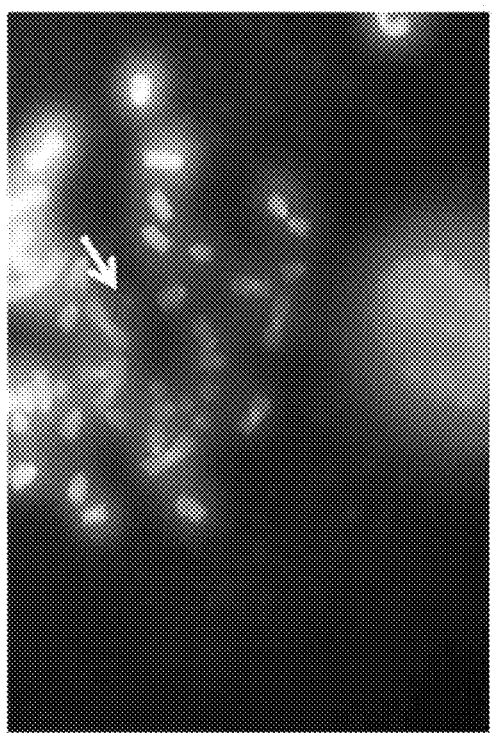
FIG. 14 is a FISH image of cells after the human chromosome 14 is modified.

FISH analysis was performed using the positive clones using CCP14 FISH Probe (CytoTest Inc., Rockville, MD, catalog number CT-CCP014). The representative FISH images for the clone 1-D10 are shown in FIGS. 13 and 14. In FIG. 13, the white arrow indicates the full length of the human chromosome 14 (before the modification). In FIG. 14, the white arrow indicates the modified human chromosome 14 fragment.

Example 4: Introduction of Human Chromosomes or Fragment into Mouse ES Cells

Figure 15:
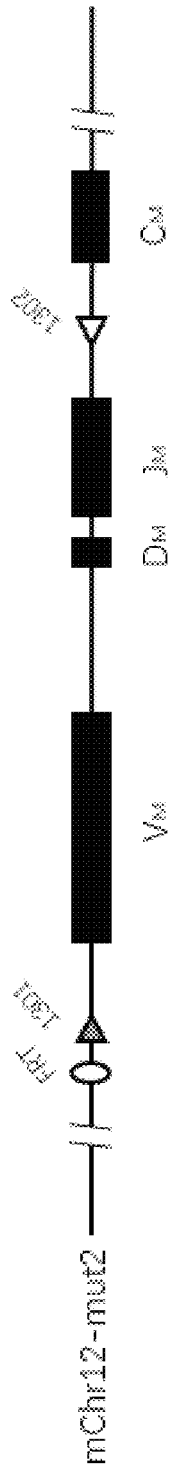
FIG. 15 is a schematic diagram showing the modified mouse chromosome 12.

The modified chromosome obtained in Example 3 was introduced into cell obtained Example 2 by methods described previously. The cells were then screened by G418. Only the cell containing only one human chromosome was selected. FIG. 15 shows the modified mouse chromosome 12.

Figure 16:
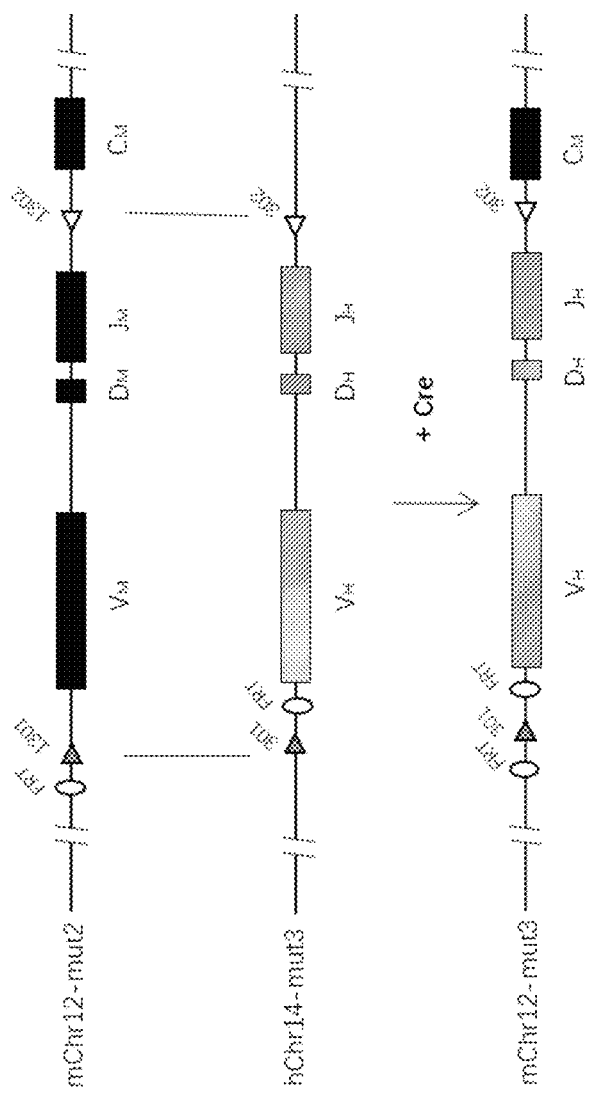
FIG. 16 is a schematic diagram showing Cre mediated recombination, which replaces mouse heavy chain variable region locus with the corresponding human genomic DNA sequence.
Figure 17:
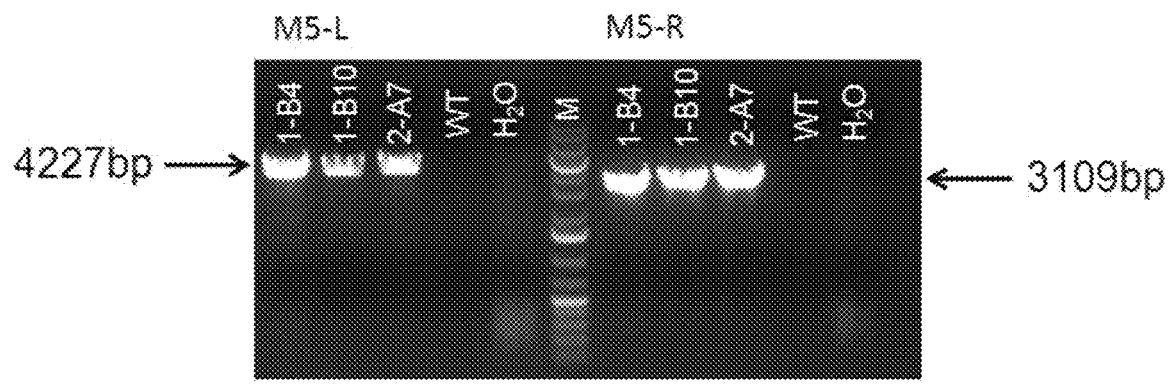
FIG. 17 shows PCR assay results using the M5-L primer pair and the M5-R primer pair.
Figure 18:
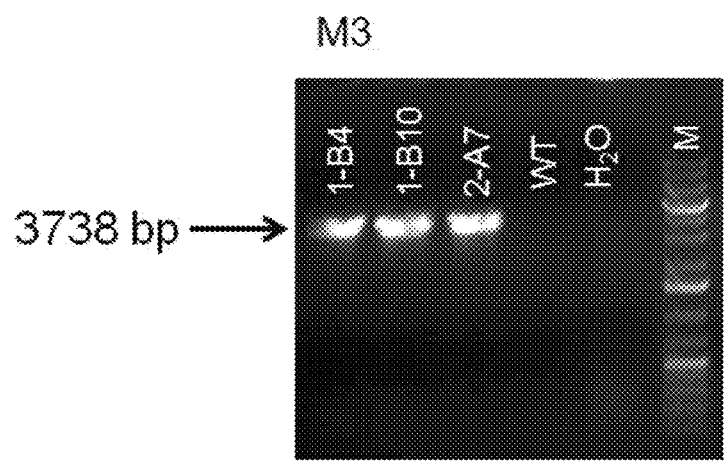
FIG. 18 shows PCR assay results using the M3 primer pair.
Figure 19:
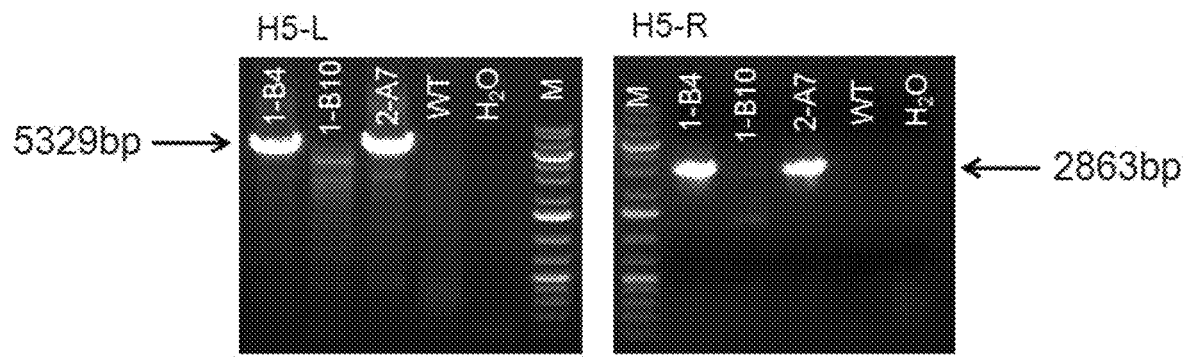
FIG. 19 shows PCR assay results using the H5-L primer pair and the H5-R primer pair.
Figure 20:
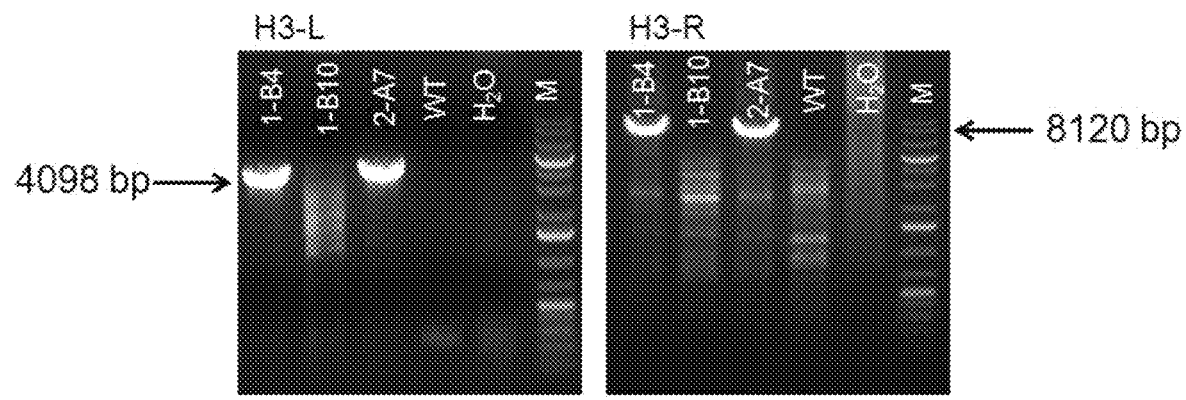
FIG. 20 shows PCR assay results using the H3-L primer pair and the H3-R primer pair.

Cre recombinase then mediated the replacement of V, D, J regions on mouse chromosome mChr12-mut2 with the V, D, J regions on human chromosome hChr14-mut3 (FIG. 16). The human chromosome DNA sequence was replaced by the sequence between the recombination sites 1301 and 1302. Hygromycin and puromycin were used for screening positive cells. The cells were further screened by DT to obtain mouse cells that do not contain human chromosomes before being injected into mouse blastocysts. In some cases, the cells were directly injected into blastocysts without DT screening.

Figure 21:
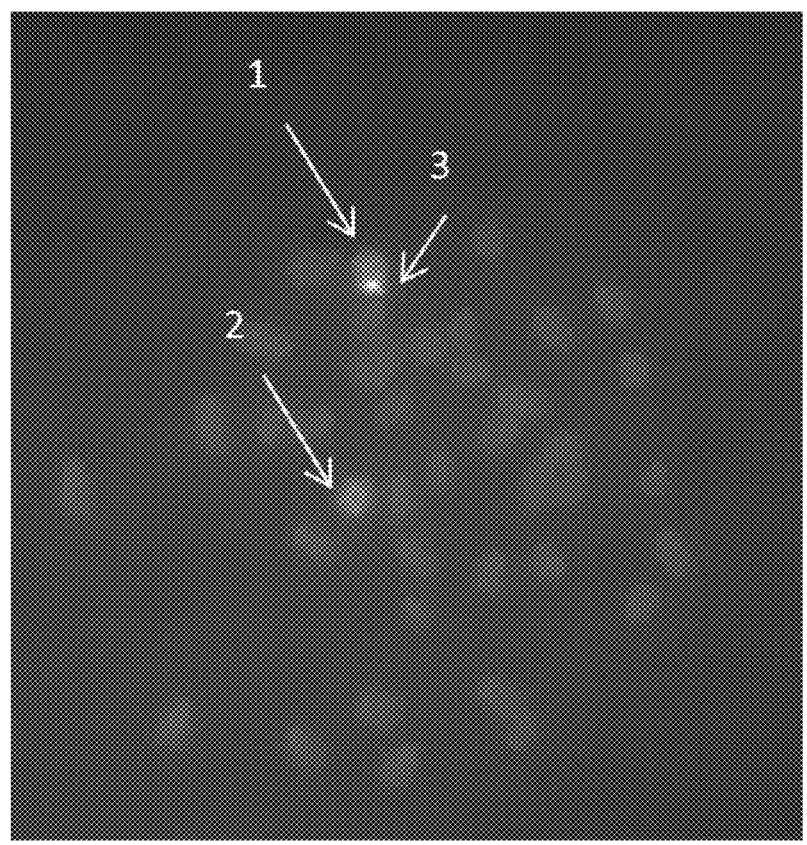
FIG. 21 is a FISH image. The white arrows (1) and (2) indicate mouse chromosome 12. The white arrow (3) indicates human chromosome fragment labeled by human-specific IGH Breakapart probe.

The cells after Cre recombination were tested to confirm that the human gene sequences were integrated into the mouse genome. The PCR results are shown in FIGS. 17, 18, 19, and 20. All PCR results showed that cells numbered 1-B4, 1-B10, and 2-A7 had the correct recombination, and the human chromosomes in 1-B10 cells disappeared. Murine Whole Chromosome Painting Probes (Cytocell Ltd, Cambridge, UK; Cat. No. AMP12R) and human-specific IGH Breakapart Probes (Cytocell Ltd, Cambridge, UK; Cat. No. LPH 014) were used to test 1-B10 cells by FISH. The result is shown in FIG. 21, confirming that human chromosome fragments were present in the mouse chromosome. These primers are shown in the table below.

TABLE 12

| NO. | Primer | | Sequence (5'-3') | Product size (bp) |
|---|---|---|---|---|
| 1 | M5-L | F | gccaaggaatttaaaaggggattgaaagcaa (SEQ ID NO: 13) | 4227 |
|   |      | R | cgagagctgtggagagaaaggcaaa (SEQ ID NO: 14) |   |
| 2 | M5-R | F | tatgtcctgcgggtaaatagctgcg (SEQ ID NO: 15) | 3109 |
|   |      | R | agggagggaatggaatgagggtgat (SEQ ID NO: 16) |   |
| 3 | M3   | F | ccatgtgacccattcgagtgtcctg (SEQ ID NO: 17) | 3738 |
|   |      | R | cttaccatttgcggtgcctggtttc (SEQ ID NO: 18) |   |

TABLE 12-continued

| NO. | Primer | | Sequence (5'-3') | Product size (bp) |
|---|---|---|---|---|
| 4 | H5-L | F | tcaaagtcaatttcctcagcgaggct (SEQ ID NO: 19) | 5329 |
|   |      | R | aggaattgtatcccataggctagcacgt (SEQ ID NO: 20) | |
| 5 | H5-R | F | gacgacgtgaccctgttcatcagc (SEQ ID NO: 21) | 2863 |
|   |      | R | ccacagcccgatctacttggctttt (SEQ ID NO: 22) | |
| 6 | H3-L | F | gcaaggttttgactaagcggagcac (SEQ ID NO: 23) | 4098 |
|   |      | R | cactagtctcgtgcagatggacagc (SEQ ID NO: 24) | |
| 7 | H3-R | F | gttagaagacttcctctgccctcgg (SEQ ID NO: 25) | 8120 |
|   |      | R | ttgtgagggctcaagttcagtgcat (SEQ ID NO: 26) | |

Example 5: Making Mice Containing a Humanized Heavy Chain Immunoglobulin Locus

Figure 22:
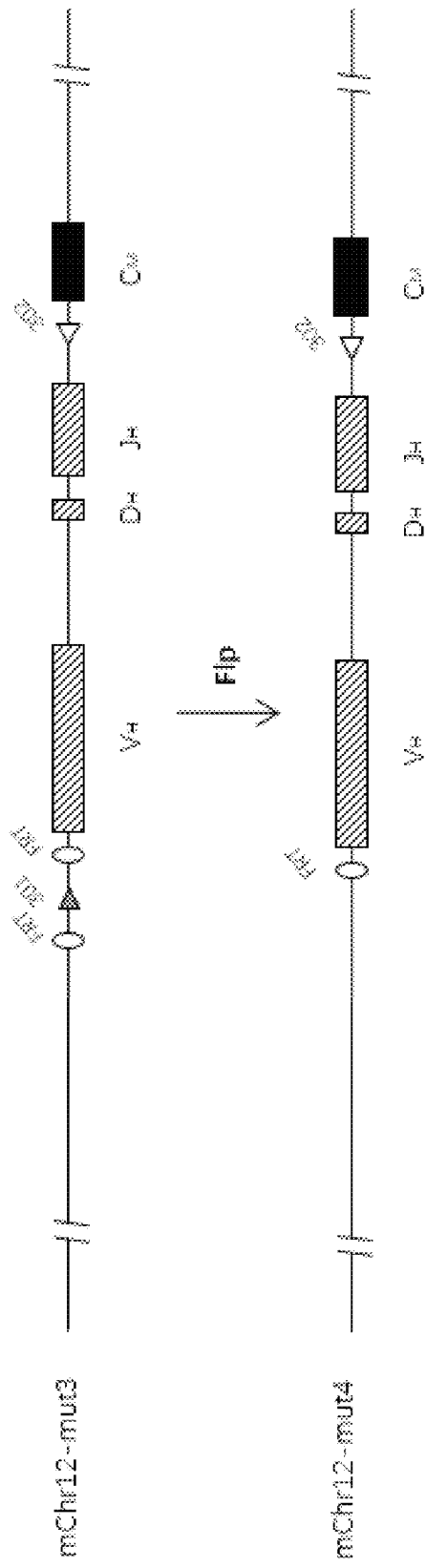
FIG. 22 is a schematic diagram showing the Flp-mediated recombination.

The positive clone cells were injected into the blastocysts of BALB/c mice by microinjection. The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mice were then mated with mice having C57BL/6 background. The black progeny were selected to mate with Flp tool mice (FIG. 22). PCR analysis was performed on the DNA obtained from the tail of the mice. The mice were further crossed with mice with BALB/c background several times (e.g., at least 5 times) to obtain humanized heavy chain immunoglobulin locus heterozygous mice with BALB/c background.

In order to confirm that the mouse expresses the human antibody heavy chain, blood was collected from the mice of the chimeric mouse (F0 generation) and the black mouse (F1 generation). The RNA was extracted and reverse-transcribed to obtain cDNA. The following PCR primer were used to amplify the sequence, and the sequences were further sequenced.

TABLE 13

PCR primers

| NO. | Primer | | Sequence (5'-3') |
|---|---|---|---|
| 1 | VH1 | F | CAGGTSCAGCTGGTRCAGTC (SEQ ID NO: 27) |
|   |     | R | AGGGATCCAGAGTTCCAGGT (SEQ ID NO: 28) |
| 2 | VH2 | F | CAGRTCACCTTGAAGGAGTC (SEQ ID NO: 29) |
|   |     | R | AGGGATCCAGAGTTCCAGGT (SEQ ID NO: 28) |
| 3 | VH3 | F | SAGGTGCAGCTGGTGGAGTC (SEQ ID NO: 30) |
|   |     | R | AGGGATCCAGAGTTCCAGGT (SEQ ID NO: 28) |
| 4 | VH4 | F | CAGGTGCAGCTGCAGGAGTC (SEQ ID NO: 31) |
|   |     | R | AGGGATCCAGAGTTCCAGGT (SEQ ID NO: 28) |
| 5 | VH5 | F | GARGTGCAGCTGGTGCAGTC (SEQ ID NO: 32) |
|   |     | R | AGGGATCCAGAGTTCCAGGT (SEQ ID NO: 28) |
| 6 | VH6 | F | CAGGTACAGCTGCAGCAGTC (SEQ ID NO: 33) |
|   |     | R | AGGGATCCAGAGTTCCAGGT (SEQ ID NO: 28) |

Example 6: Modification of the Mouse Light Chain Immunoglobulin Locus

Figure 23:
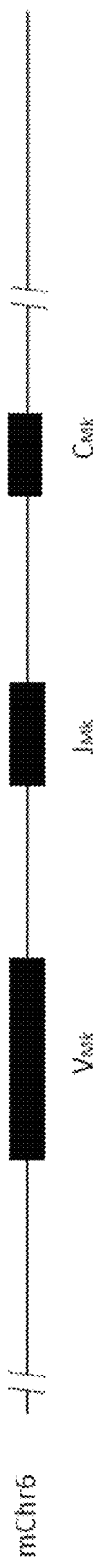
FIG. 23 is a schematic diagram showing the mouse light chain immunoglobulin locus.
Figure 24A:
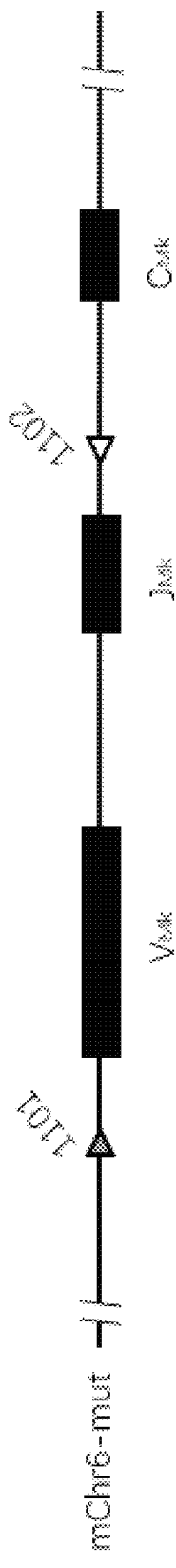
FIG. 24A is a schematic diagram showing the mouse light chain immunoglobulin locus after two recombination sites were introduced to the genome.
Figure 24B:
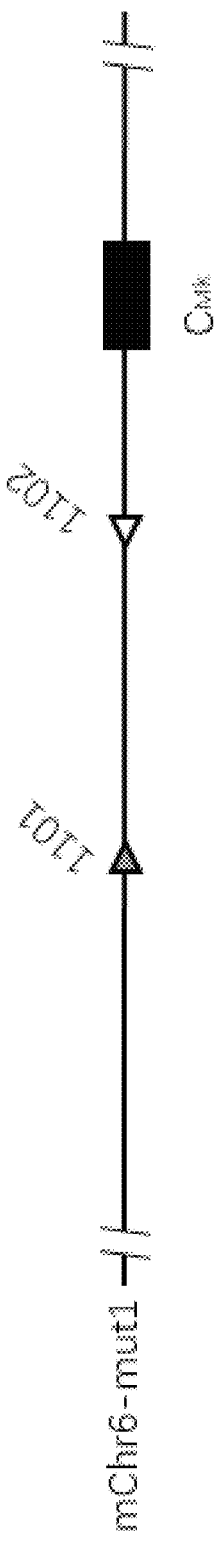
FIG. 24B is a schematic diagram showing the mouse light chain immunoglobulin locus after recombination with a targeting vector.
Figure 25:
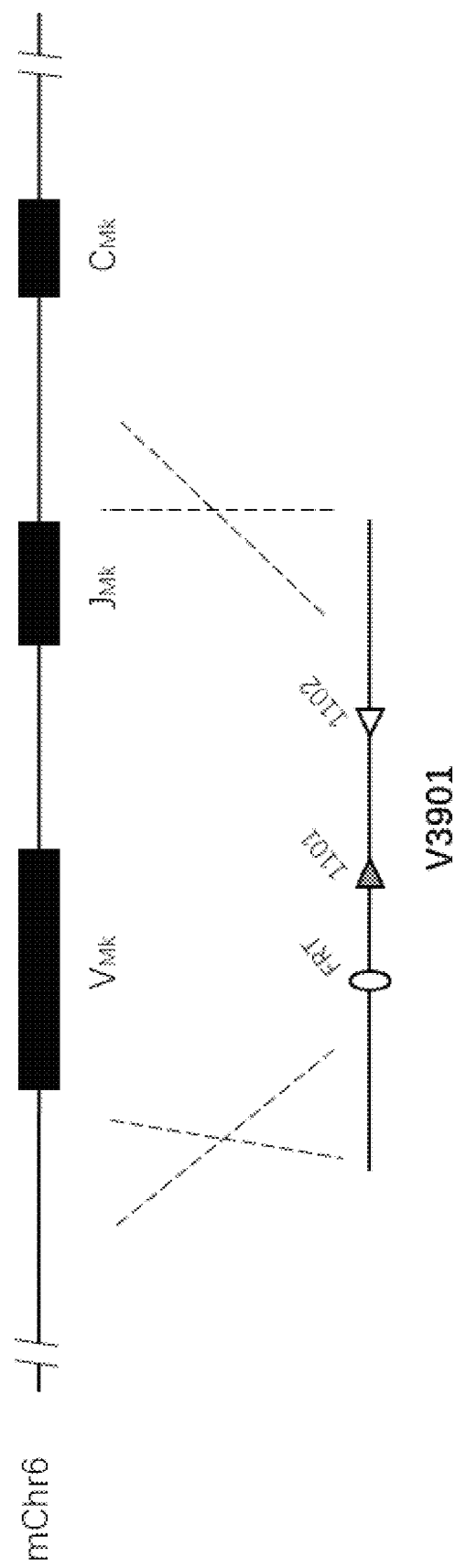
FIG. 25 is a schematic diagram showing a gene targeting strategy for mouse chromosome 6.

The light chain immunoglobulin locus is located on mouse chromosome 6. FIG. 23 was a schematic diagram showing the mouse light chain immunoglobulin locus. Two recombination sites were introduced on both sides of the variable region of the light chain immunoglobulin locus, and the resulting modified chromosome was shown in FIGS. 24A-24B. The detailed targeting strategy were shown in FIG. 25.

The modification was performed in mouse embryonic stem cells. The vector (V3901) had from the 5' to 3': DNA homology arm sequence at upstream of the insertion site, Flp recognition target (FRT), mammalian expression promoter (EF-1a) from human elongation factor 1 alpha, hygromycin resistance gene (partial sequence of hygromycin phosphotransferase; "5'HygR"), the LoxP recognition sequence (1101) for the Cre recombinase, 5' PB transposon sequence (PB5'), blue fluorescent protein reporter gene (BFP), DT receptor (DTR), FMDV self-cleaving peptide (2A), kanamycin resistance gene sequence (Neo), transcription termination/polyadenylation signal sequence (PolyA; "PA"), 3' PB transposon sequence (PB3'), puromycin resistance gene partial sequence (3'PuroR), FMDV self-cleaving peptide (2A), DT receptor (DTR), the LoxP recognition sequence (1102) for the Cre recombinase, DNA homology arm sequence at downstream of insertion site, and DTA.

The vectors (V3901) was introduced into mouse embryonic stem cells. The cells were screened by corresponding antibiotic resistance gene markers, or their combinations. The integration of the vector V3901 into correct locus in mouse genomes was confirmed by PCR. The results were shown in FIGS. 26-27. The two combined PCR results confirmed that the cells numbered 208, 209, 215, 217 and 269 were positive clones.

The PCR assay was performed using the following primers:

```
IGKV-005-C-5G-L-GT-F:
                                       (SEQ ID NO: 34)
5'-TCACACACTACAGCTTCCACCACAA-3';

IGKV-005-C-5G-L-GT-R2:
                                       (SEQ ID NO: 35)
5'-CGGGGAAAAGTCGACTCTAGAACGG-3';

IGKV-005-C-5G-R-GT-F1:
                                       (SEQ ID NO: 36)
5'-ACTGCATTCTAGTTGTGGTTTGTCCA-3';
```

-continued

IGKV-005-C-5G-R-GT-R:
(SEQ ID NO: 37)
5'-GGCCTGGAAAACTCAGCTATCCTTT-3'.

Among these primers, IGKV-005-C-5G-L-GT-F and IGKV-005-C-5G-R-GT-R were located on the mouse chromosome, IGKV-005-C-5G-L-GT-R2 and IGKV-005-C-5G-R-GT-F1 were located on the vector V3901.

Thus, two recombination sites were introduced into mouse chromosome 6 in mouse embryonic stem cells.

Example 7: Modifying Human Chromosome 2

The human light chain immunoglobulin locus is located in human chromosome 2. FIG. 28 is a schematic diagram of the human chromosome 2 highlighting the light chain immunoglobulin locus.

Two recombination sites were introduced on both sides of the variable region of the light chain immunoglobulin locus. The region between $V_{HK}$ and the centromere (kinetochore) was deleted to obtain a shorter artificial chromosome for subsequent experiments. Similar recombination sites were introduced into the variable region of the mouse immunoglobulin locus on chromosome 6. Then the human chromosome was introduced into the mouse recipient cell to obtain a humanized light chain immunoglobulin locus.

The modified human chromosome 2 is shown in FIG. 29. The targeting strategy is shown in FIG. 30. The vector (V2701) has from 5' to 3': DNA homology arm sequence at upstream of the insertion site, PGK promoter, red fluorescent protein reporter gene sequence (tdTomato), FMDV self-cleaving peptide (2A), Blasticidin S deaminase (Bsr) from *Aspergillus terreus*, termination of transcription/polyadenylation signal sequence (PolyA; "PA"), LoxP recognition sequence 2601, hygromycin resistance gene (partial sequence of hygromycin phosphotransferase; "3'HygR"), Flp recognition target (FRT), the DNA homology arm sequence at downstream of the insertion site, and diphtheria toxin subunit A (DTA).

Figure 31:
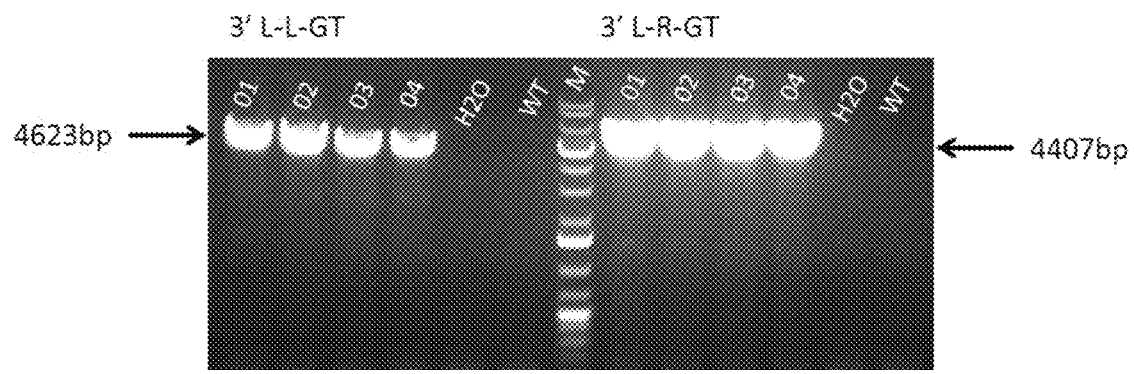
FIG. 31 shows PCR assay results after the first recombination (introducing the vector 2702). WT is the wildtype H9 cells.

Ouabain resistance. The integration of the genes into human genomes was confirmed by PCR. The results are shown in FIG. 31. The clones numbered 01, 02, 03, and 04 were confirmed to be positive clones.

The PCR assay was performed using the following primers:

```
3' L-L-GT-F:
                               (SEQ ID NO: 38)
5'-AAGGTGACTCTGCAATCAGCCTCTG-3',

3' L-L-GT-R1:
                               (SEQ ID NO: 39)
5'-TCATCTACAGCCACAACGTGAGCAG-3';

3' L-R-GT-F1:
                               (SEQ ID NO: 40)
5'-CCCATGTACAGGTTCCGCATGAACT-3',

3' L-R-GT-R:
                               (SEQ ID NO: 41)
5'-CTCCGTCCGCTTTTATTTCCCCTGT-3'.
```

Cells with modified chromosomes that were suitable for further experiments were selected. The modified human chromosome was introduced into recipient cells by chromosome technique. The recipient cells A9 cells were screened for G418 resistance. The cells containing only one human chromosome were selected for further gene editing.

Figure 32:
FIG. 32 is a FISH image result. The white arrow indicates the modified human chromosome 2 with the correct recombination.

During the screening, the clone numbered 03 shown in FIG. 31 had the correct recombination and was labeled by a human chromosome 2 counting probe (CCP2 FISH Probe) (CytoTest Inc., Rockville, MD, catalog number CT-CCP002). The result confirmed that there was a modified human chromosome 2 in the cell (FIG. 32).

Figure 33:
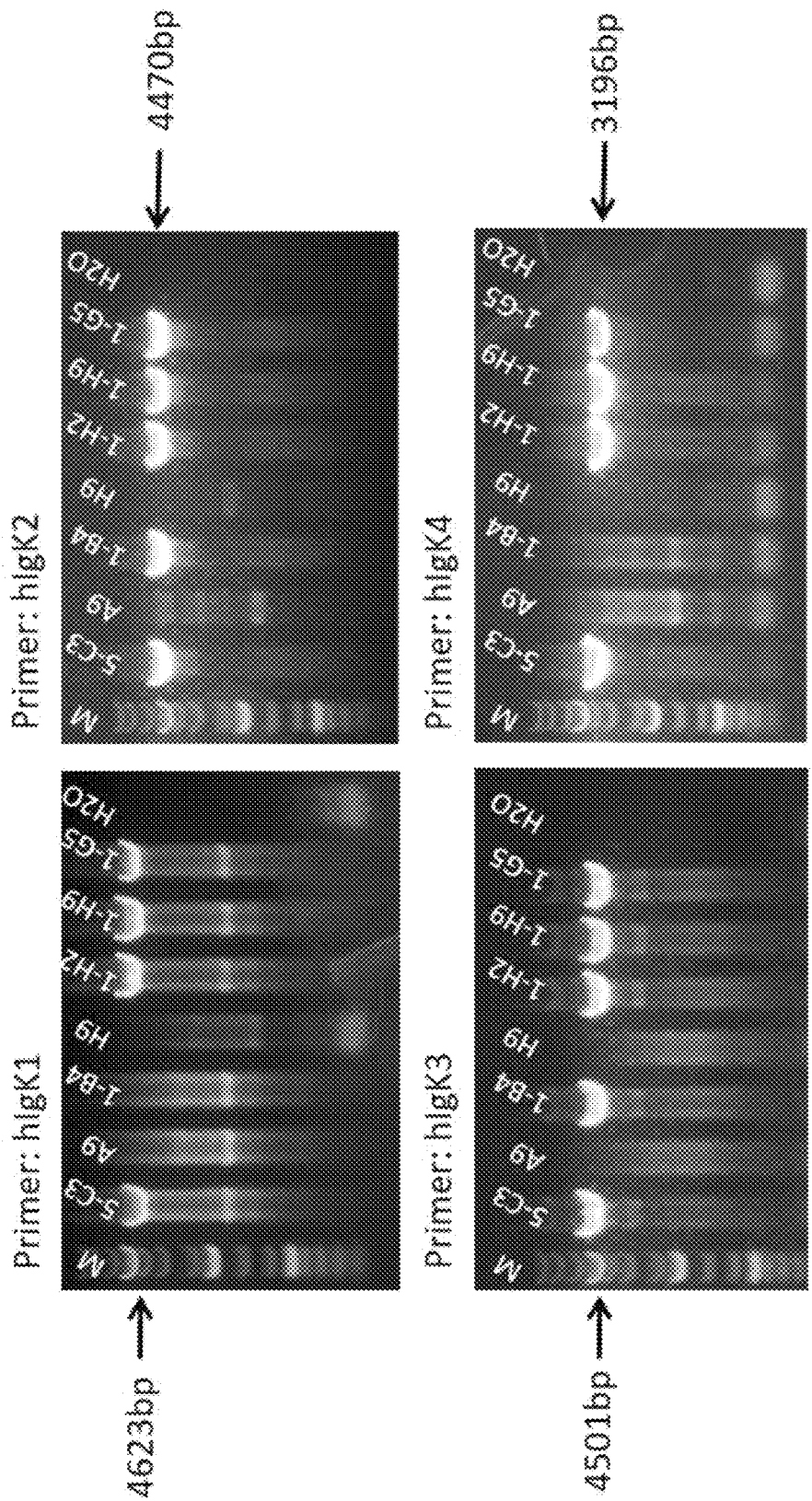
FIG. 33 shows PCR assay results after the second recombination (introducing the vector 2701).

The vector (V2701) was then further introduced into the cells. The cells were screened by G418 and Blasticidin S resistance. The recombination was confirmed by PCR. The primers are shown in the table below. The results showed that 5-C3, 1-H2, 1-H9 and 1-G5 were positive clones (FIG. 33).

TABLE 14

| NO. | Primer | | Sequence (5'-3') | Product size (bp) |
|---|---|---|---|---|
| 1 | hIgK3 | F | GTTATAACACGGGGAGTGCGTGTGC (SEQ ID NO: 42) | 4501 |
|   |       | R | GTTTGGACAAACCACAACTAGAATGCAGTG (SEQ ID NO: 43) | |
| 2 | hIgK4 | F | GCAACGGCTACAATCAACAGCATCC (SEQ ID NO: 44) | 3196 |
|   |       | R | TGGGTCTGGGACAGACTTCACTCTC (SEQ ID NO: 45) | |
| 3 | hIgK1 | F | AAGGTGACTCTGCAATCAGCCTCTG (SEQ ID NO: 46) | 4623 |
|   |       | R | TCATCTACAGCCACAACGTGAGCAG (SEQ ID NO: 47) | |
| 4 | hIgK2 | F | CCCATGTACAGGTTCCGCATGAACT (SEQ ID NO: 48) | 4470 |
|   |       | R | CTCCGTCCGCTTTTATTTCCCCTGT (SEQ ID NO: 49) | |

The vector (V2702) has from 5' to 3': the DNA homology arm sequence at upstream of the insertion site, the LoxP recognition sequence 2602, the PGK promoter, a portion of puromycin resistance gene sequence (5'PuroR), EF-1a, PBase, IRES, kanamycin resistance gene sequence (Neo), transcription termination/polyadenylation signal sequence (PolyA; "PA"), DNA homology arm sequence at downstream of insertion site, and DTA.

Figure 34:
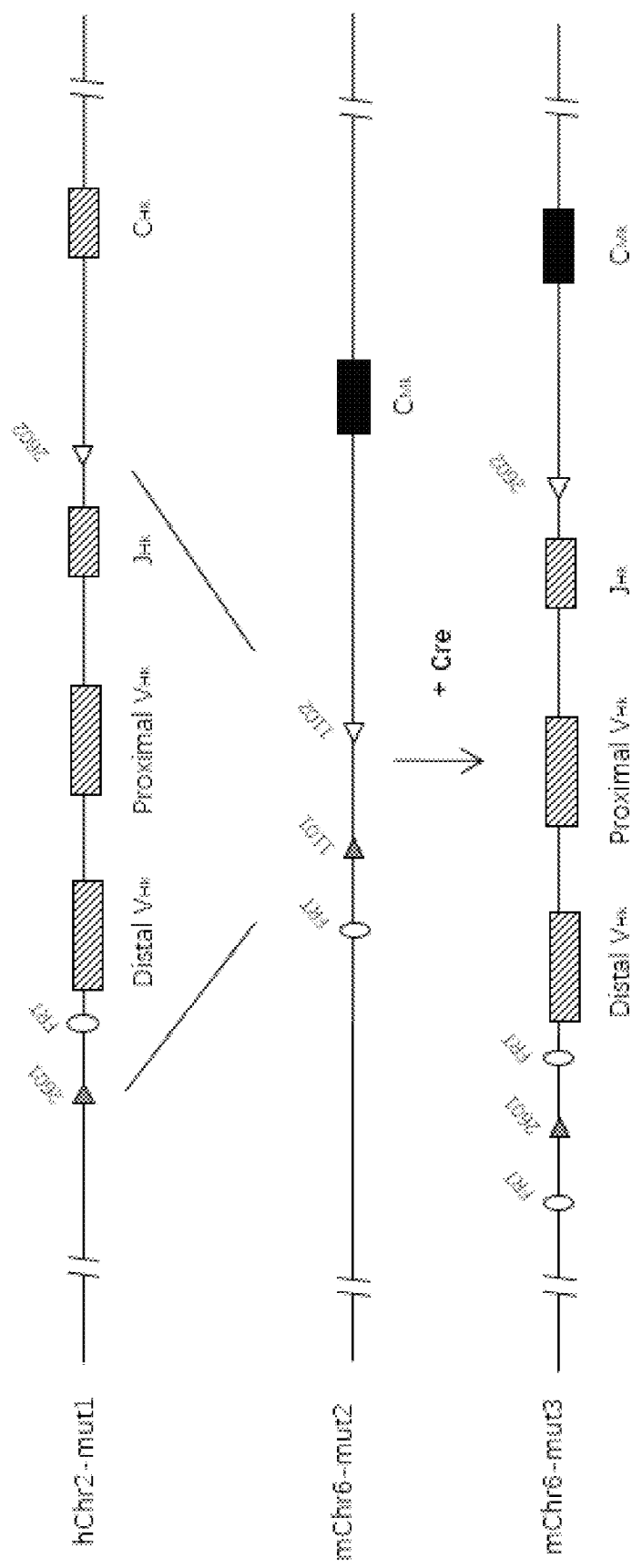
FIG. 34 is a schematic diagram showing Cre mediated recombination, in which human light chain variable region genomic DNA sequence was added to the corresponding mouse locus.
Figure 35:
FIG. 35 is a fluorescence in situ hybridization (FISH) image. The arrows (1) and (3) indicate mouse chromosome 6. The arrow (2) indicates human chromosome fragment labeled by human-specific IGK Breakapart probe.

The sequence of vector (V2702) was verified by sequencing. The vector was introduced into human H9 cells by transfection. The cells were then screened by G418 and Example 8: Making Mice that can Produce Humanized Antibodies The mouse embryonic stem cells and the cells obtained in Example 7 were fused and the modified human chromosome 2 was introduced into mouse embryonic stem cell obtained in Example 6. The mouse ES cells containing only one modified human chromosome 2 was selected, and the cells were screened after Cre-mediated recombination (Cre mediated recombination) was shown in FIG. 34. The cells after Cre recombination were tested to confirm that the human gene sequences were integrated into the mouse genome. Mouse Whole Chromosome Painting Probes (Cytocell Ltd, Cambridge, UK; Cat. No. AMP06G) and human-specific IGK Breakapart Probes (Cytocell Ltd, Cambridge, UK; Cat. No. LPH 034) were used to verify PCR-confirmed positive clones by fluorescence in situ hybridization (FISH). The result was shown in FIG. 35, confirming that human chromosome fragments were present in the mouse chromosome. The cells were injected into the blastocysts. Mice containing the humanized light chain immunoglobulin locus can be obtained.

Figure 36:
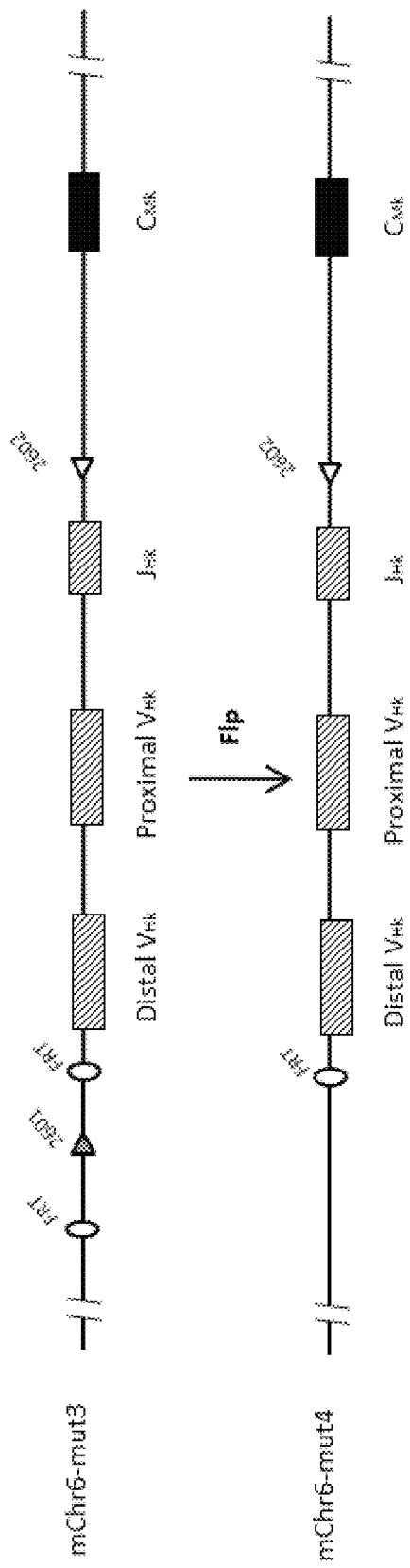
FIG. 36 is a schematic diagram showing the Flp-mediated recombination.

The chimeric mice were selected to mate with C57BL/6 mice, producing gray and black progeny (F1 generation). PCR analysis was performed on the DNA obtained from the tail of the black mice, and positive F1 generation mice were selected to mate with Flp tool mice. FIG. 36 showed a schematic diagram of the Flp-mediated recombination. The mice prepared by the methods contained C57BL/6 background. Mice with different background can have different advantages, and the heterozygous or homozygous mice prepared by the methods herein can be used to generate mice with some other background by backcrossing (for example, BALB/c mice have a humoral immune advantage) for several generations to obtain mice with the desired backgrounds.

A few mice were selected and crossed with BALB/c mice several times to obtain heterozygous mice with BALB/c background. The heterozygous mice then were then crossed with each other to obtain homozygous mice.

The mice with humanized light chain immunoglobulin locus and the mice with humanized heavy chain immunoglobulin locus were crossed with each other to obtain mice with both humanized heavy chain immunoglobulin locus and humanized light chain immunoglobulin locus.

Example 9: B-Cell Development in Transgenic Mice

Experiments were performed to compare the immune systems of the humanized mice and the wild-type mice. Three 9-10 week old wild-type (WT), three mice with heterozygous humanized heavy chain immunoglobulin locus, and three mice with homozygous humanized heavy chain immunoglobulin locus were selected. Among them, the heterozygous mice and the homozygous mice had similar body weight, appearance and vitality as compared to the wild-type mice. Peripheral blood, spleen, lymph nodes and bone marrow tissues of these mice were obtained, and no obvious anatomical changes were discovered (for example, there was no observable difference of spleen size, morphology and weight among the three groups of mice). Flow cytometry was performed to analyze lymphocyte populations and distribution in the peripheral blood, spleen, and lymph nodes (FIGS. 45-47) and B cell populations in the spleen, lymph nodes, and bone marrow (FIGS. 48-50) of the mice. In the results, the leukocytes included: B cells (e.g., characterized by CD45+, CD19+, TCR−), T cells, and natural killer (NK) cells (e.g., characterized by CD45+, TCR−, NK1.1+). T cells were characterized by CD45+, CD19−, TCR+. CD4+ T Cells (CD4) were characterized by CD45+, CD19−, TCR+, CD4+, CD8−. And CD8+ T cells (CD8) were characterized by CD45+, CD19−, TCR+, CD4−, CD8+. Only intact, single, live leukocytes were included in the flow cytometry analysis.

Figure 45:
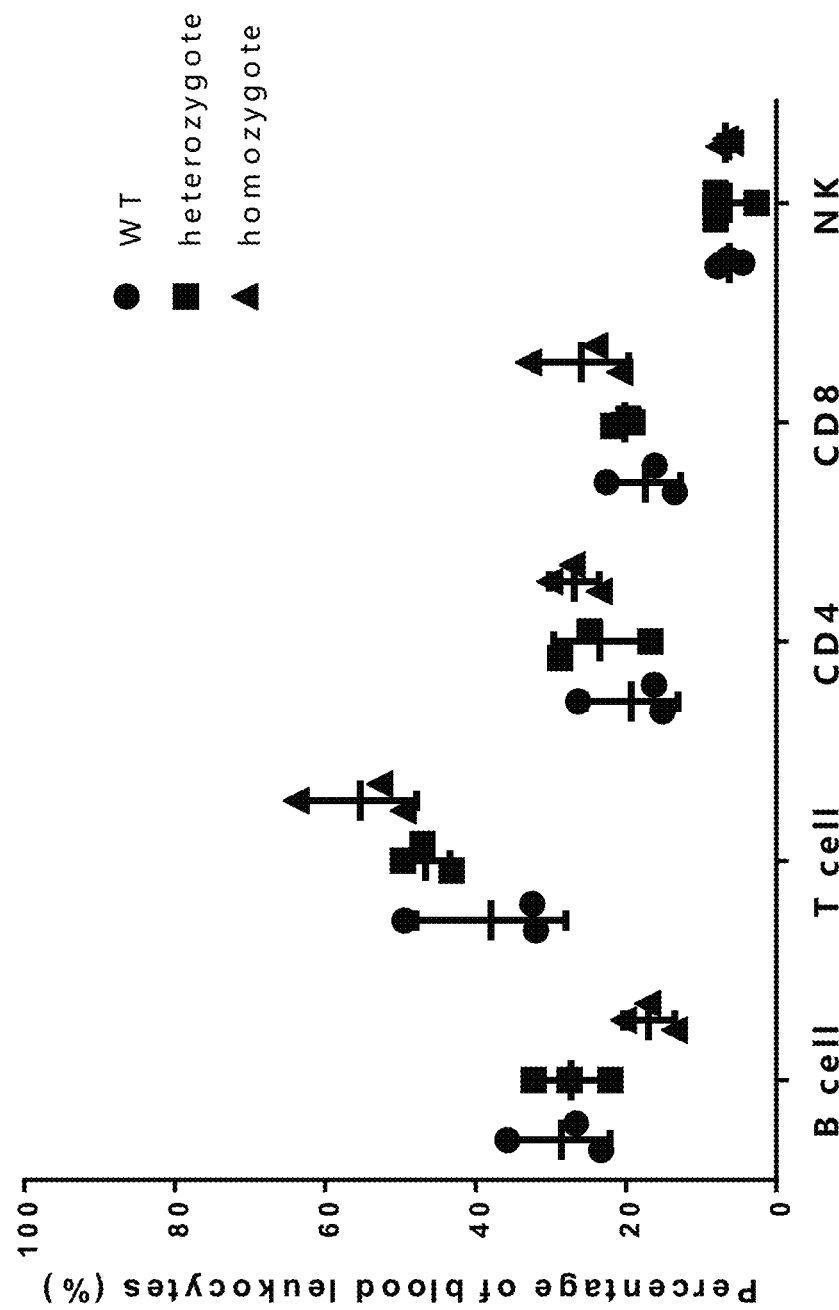
FIG. 45 shows percentages of leukocytes detected in peripheral blood.
Figure 46:
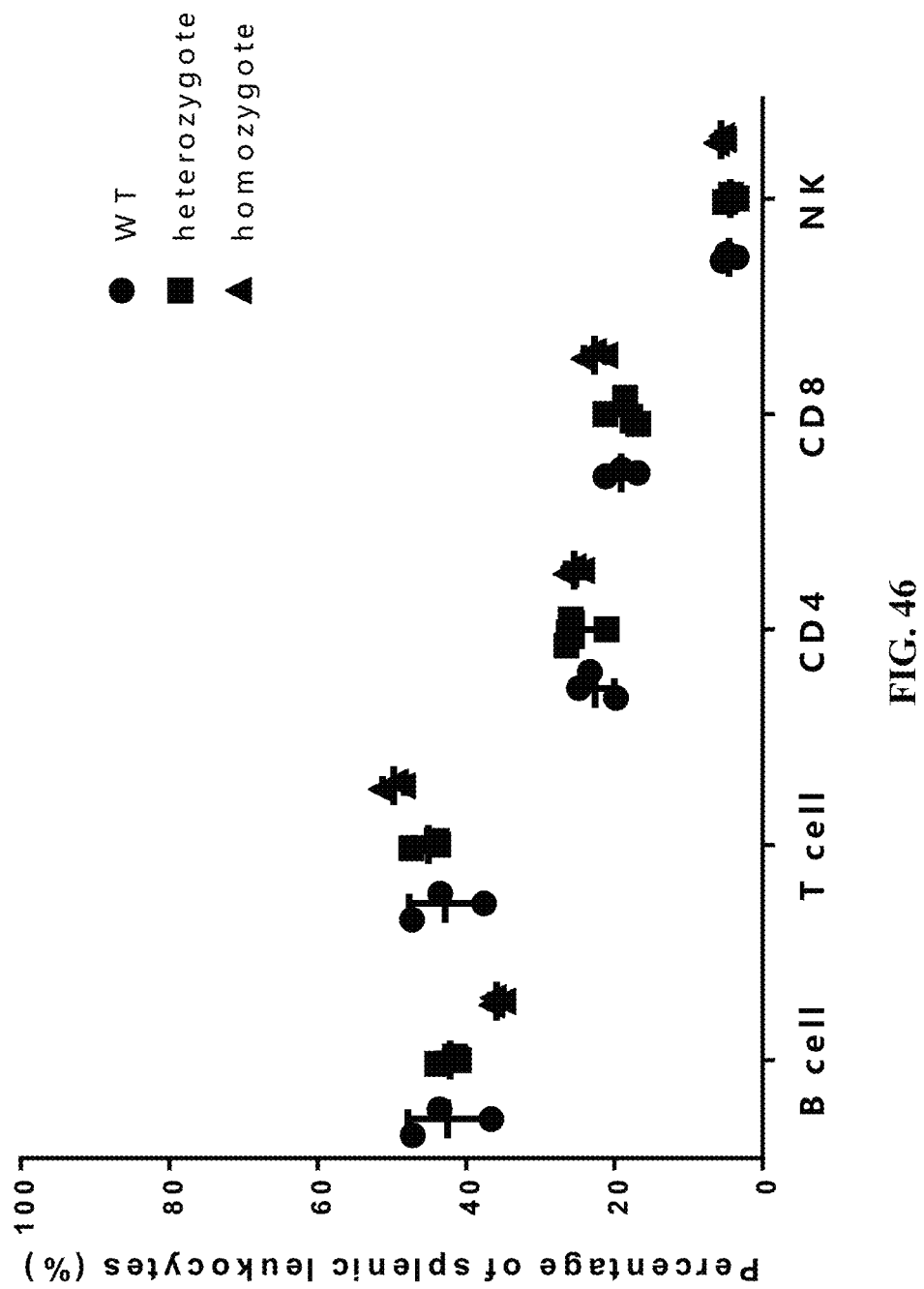
FIG. 46 shows percentages of leukocytes detected in spleen cells.
Figure 47:
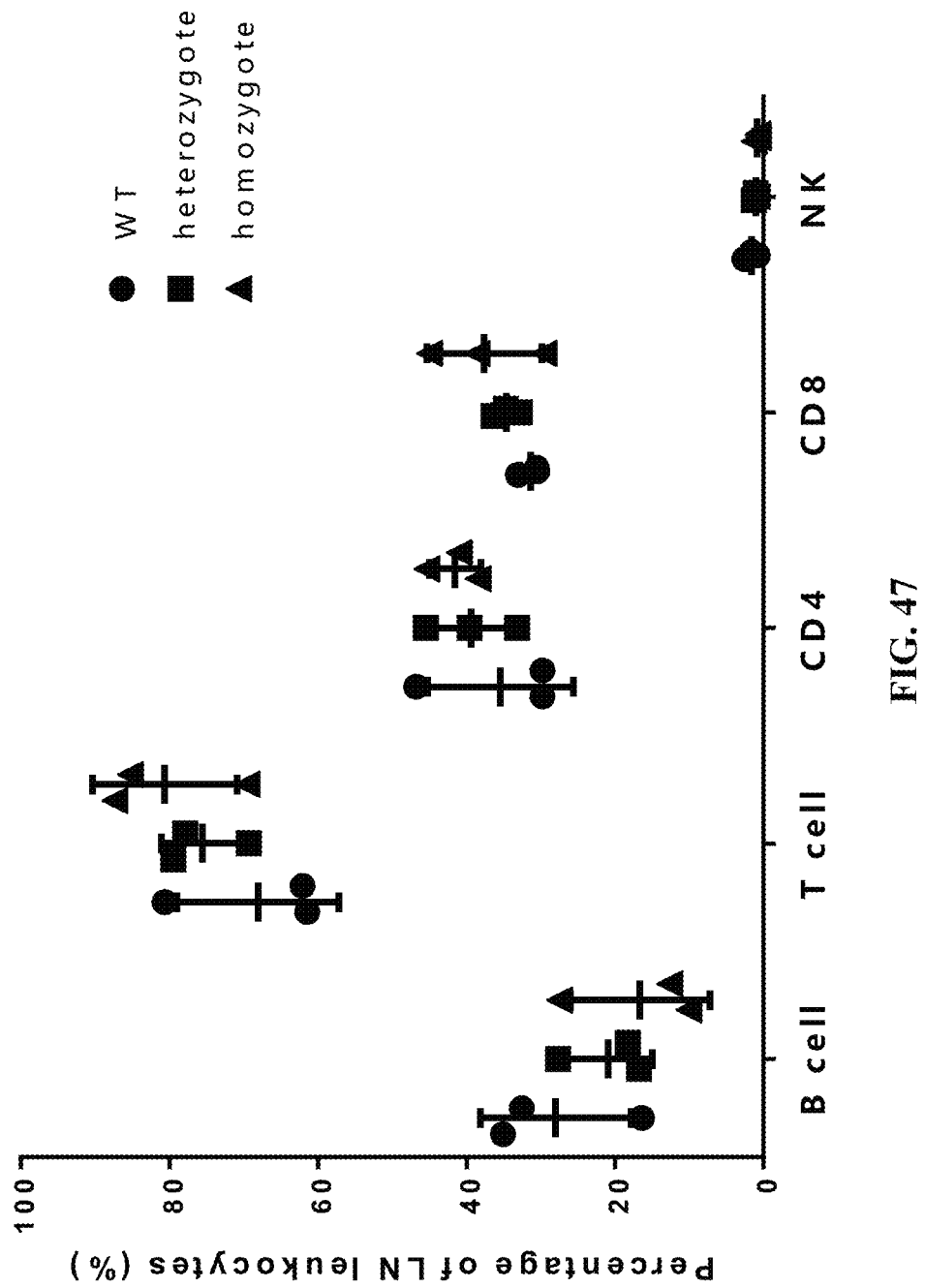
FIG. 47 shows percentages of leukocytes detected in lymph nodes.
Figure 48:
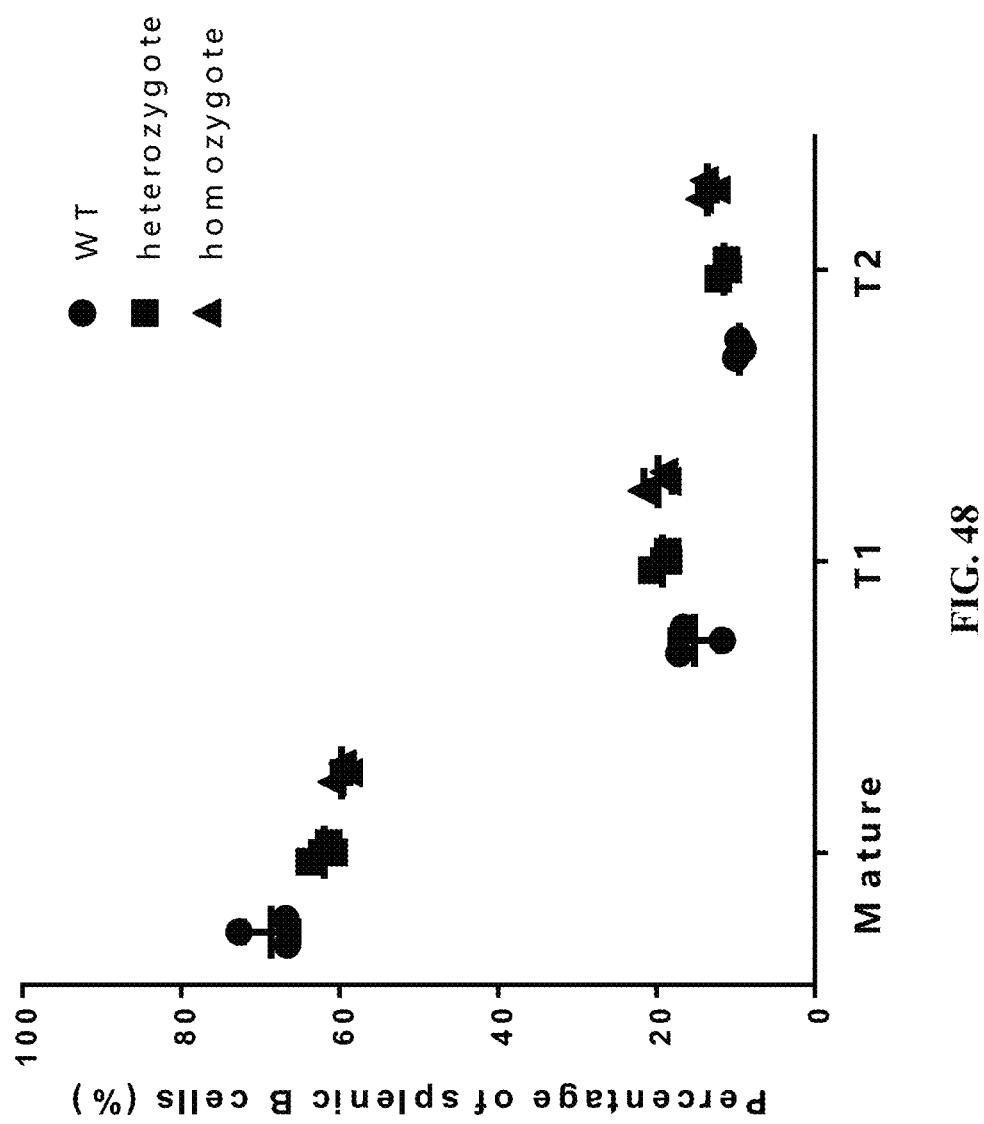
FIG. 48 shows percentages of splenic B cells at different developmental stages.
Figure 49:
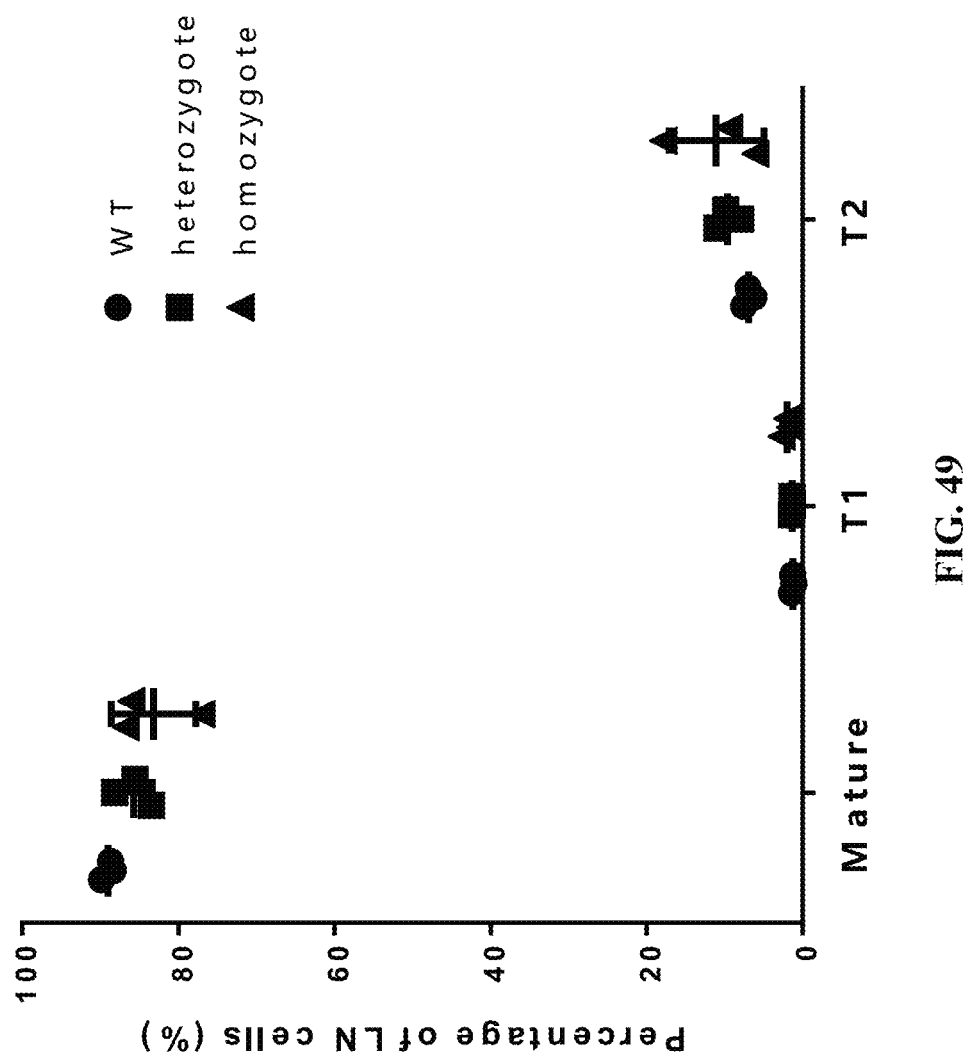
FIG. 49 shows percentages of lymph nodes B cells at different development stages.

The development stages of B cells in lymph nodes and spleen are categorized into T1 (Transitional type 1 B cell, characterized by B220$^+$IgM$^+$IgD$^−$), T2 (Transitional type 2 B cell, characterized by B220$^+$IgM$^+$IgD$^+$) and mature B cells (characterized by B220$^+$IgM$^{low}$IgD$^+$). FIGS. 45-47 show percentages of leukocytes in different tissue samples. FIGS. 48-49 indicated percentages of B cells at different developmental stages.

Figure 50:
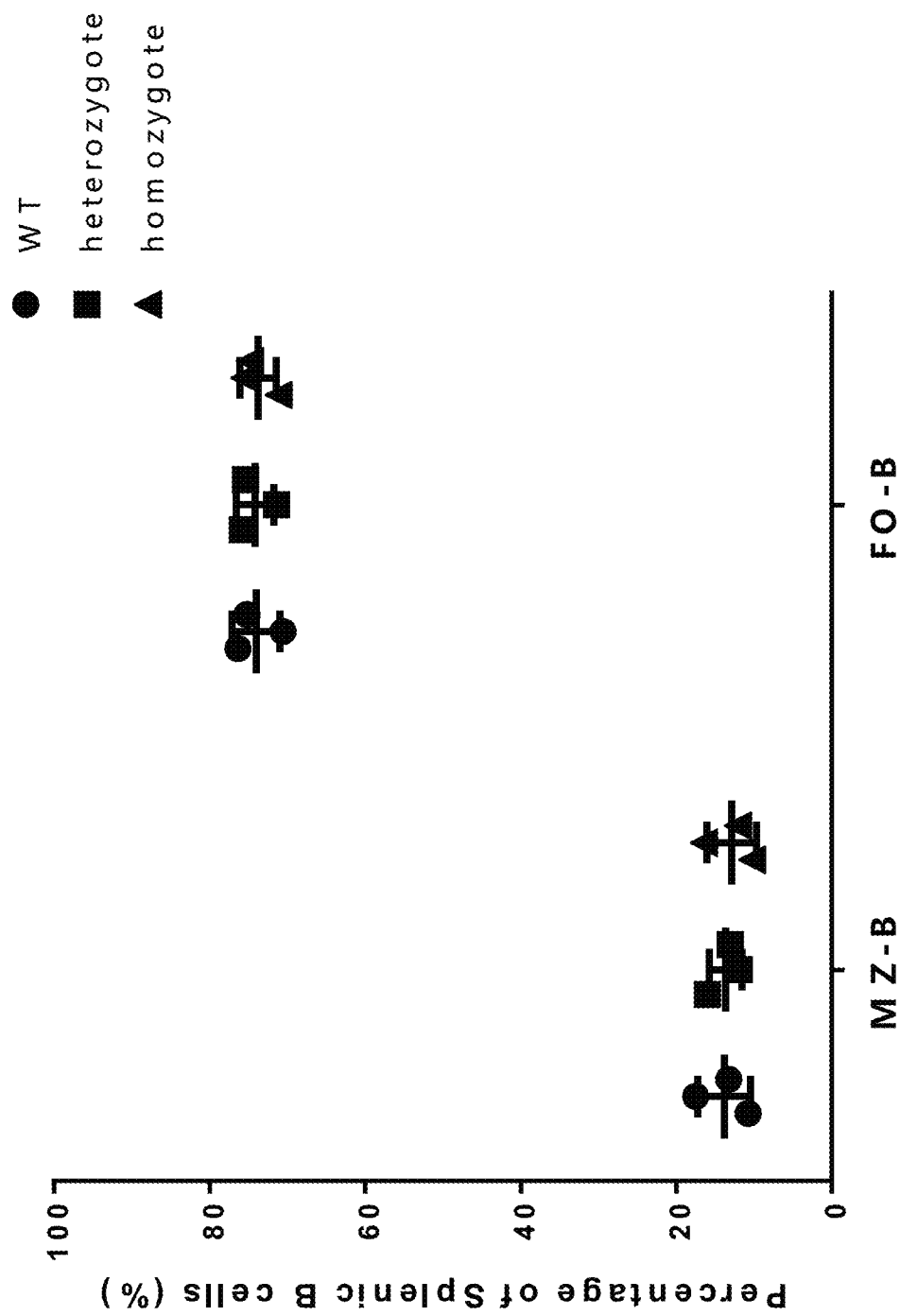
FIG. 50 shows percentages of splenic B cells at spleen marginal zone (MZ-B) and follicular zone (FO-B).

In addition, B cell development were also evaluated at the spleen marginal zone (Marginal-zone B cell, MZ-B, characterized by B220$^+$CD21$^+$CD23$^−$) and follicular zone (Follicular B cell, referred to as FO-B, characterized by B220$^+$CD21$^{low}$CD23$^+$). FIG. 50 shows percentages of splenic B cells at spleen marginal zone (MZ-B) and follicular zone (FO-B).

Figure 51A:
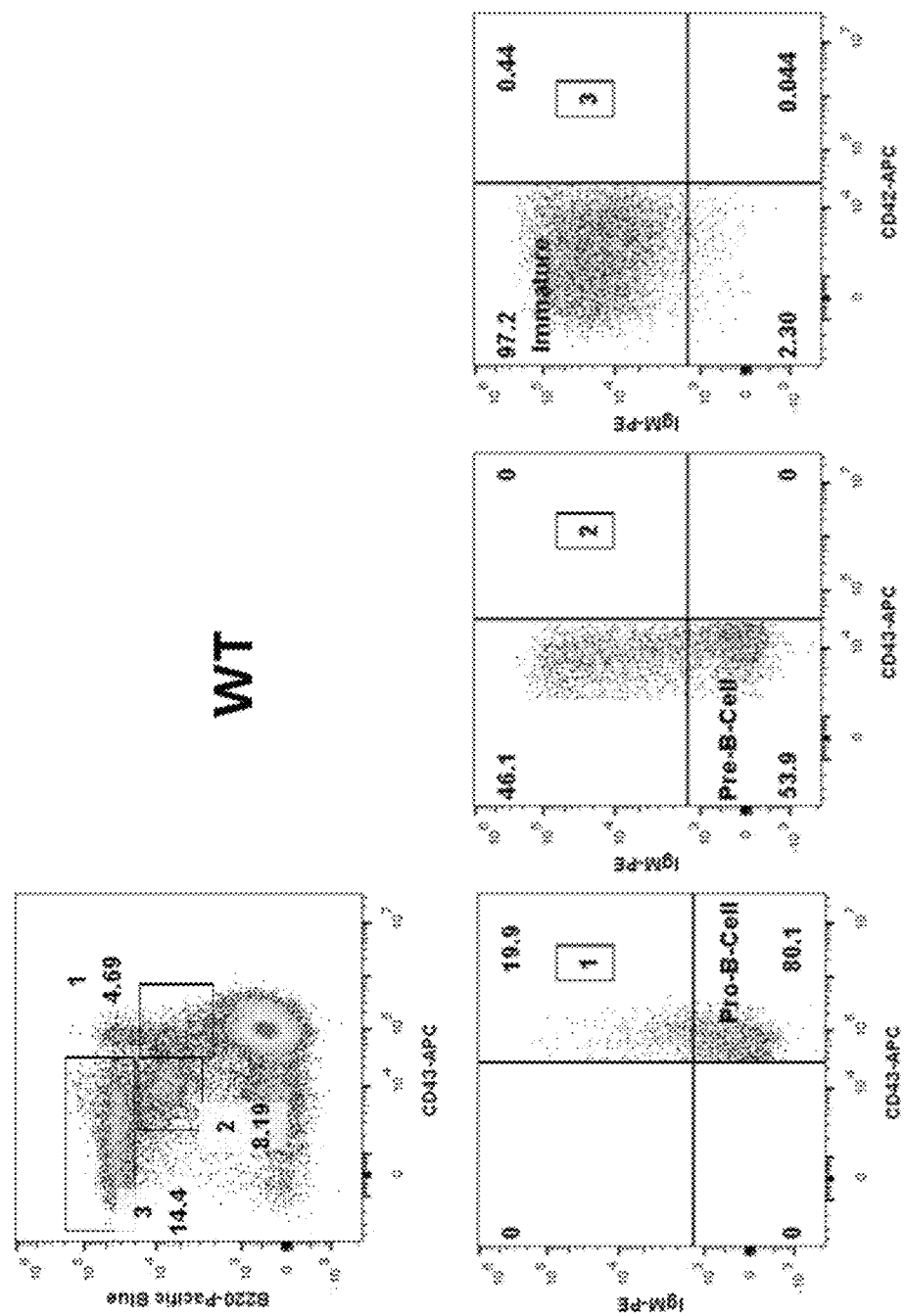
FIG. 51A shows flow cytometry analysis results for B cells at different development stages in the bone marrow obtained from wild-type mice. Area 1 represents pro-B-cells, Area 2 represents pre-B-cells, and Area 3 represents immature B-cells.
Figure 51B:
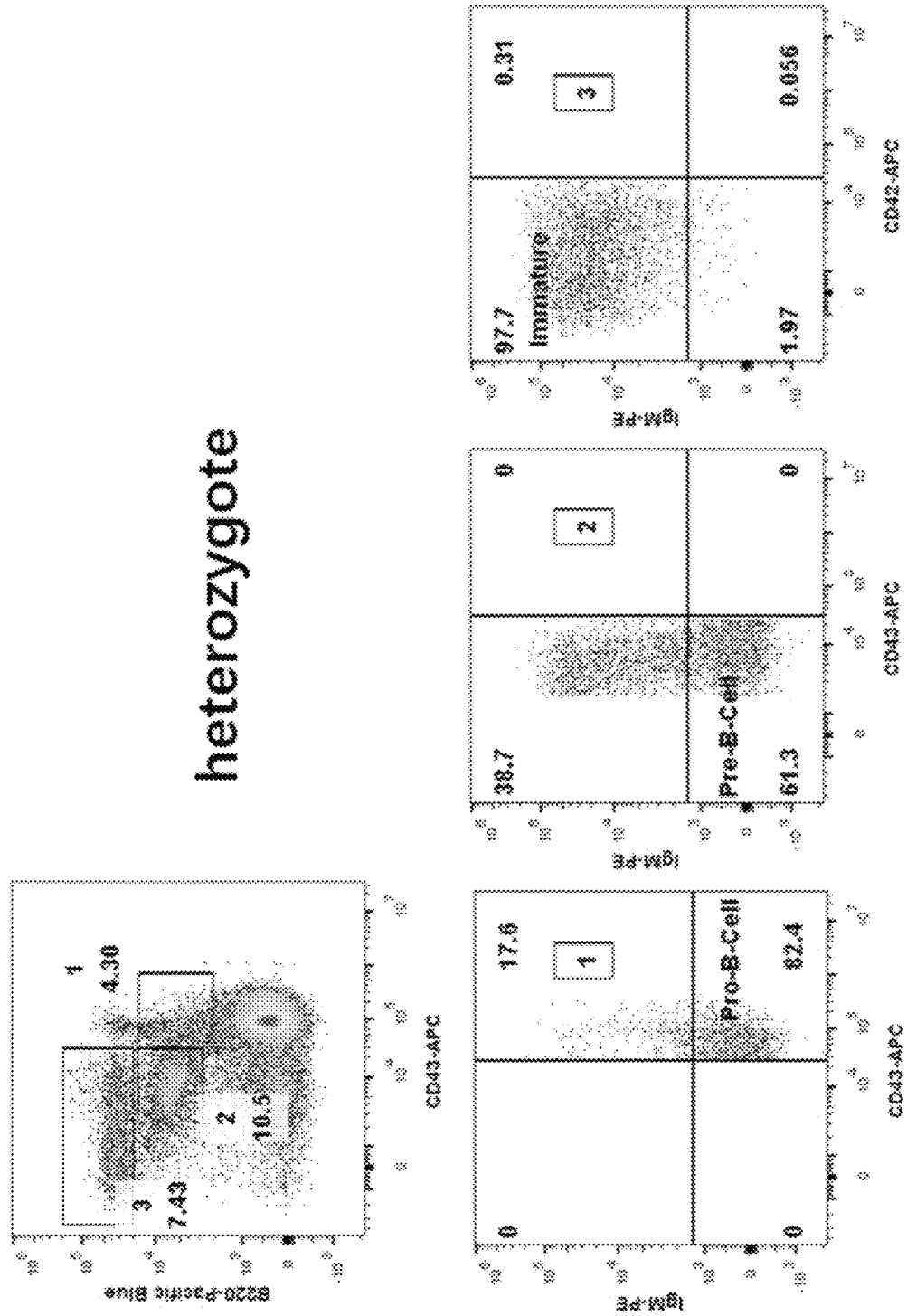
FIG. 51B shows flow cytometry analysis results for B cells at different development stages in the bone marrow obtained from humanized heavy chain heterozygous mice. Area 1 represents pro-B-cells, Area 2 represents pre-B-cells, and Area 3 represents immature B-cells.
Figure 52:
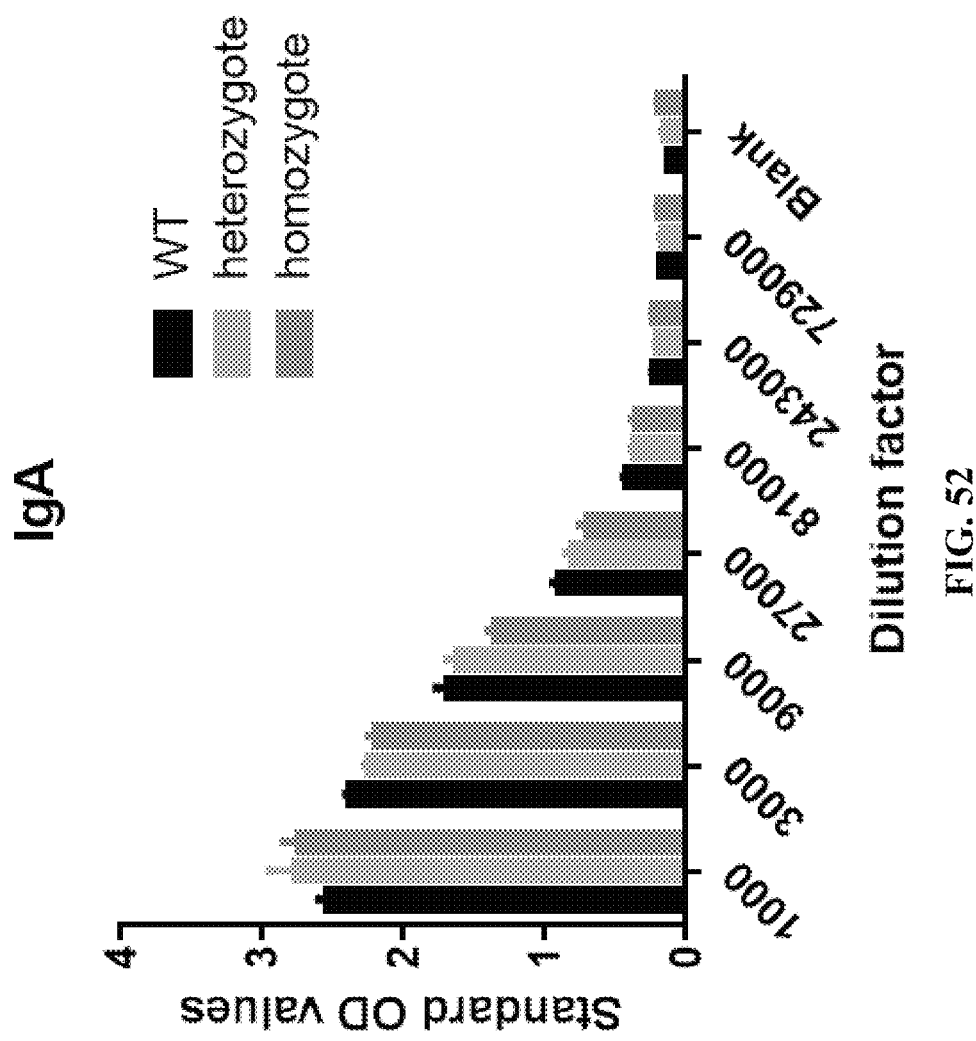
FIG. 52 shows IgA isotype levels in serially diluted mouse serum.
Figure 53:
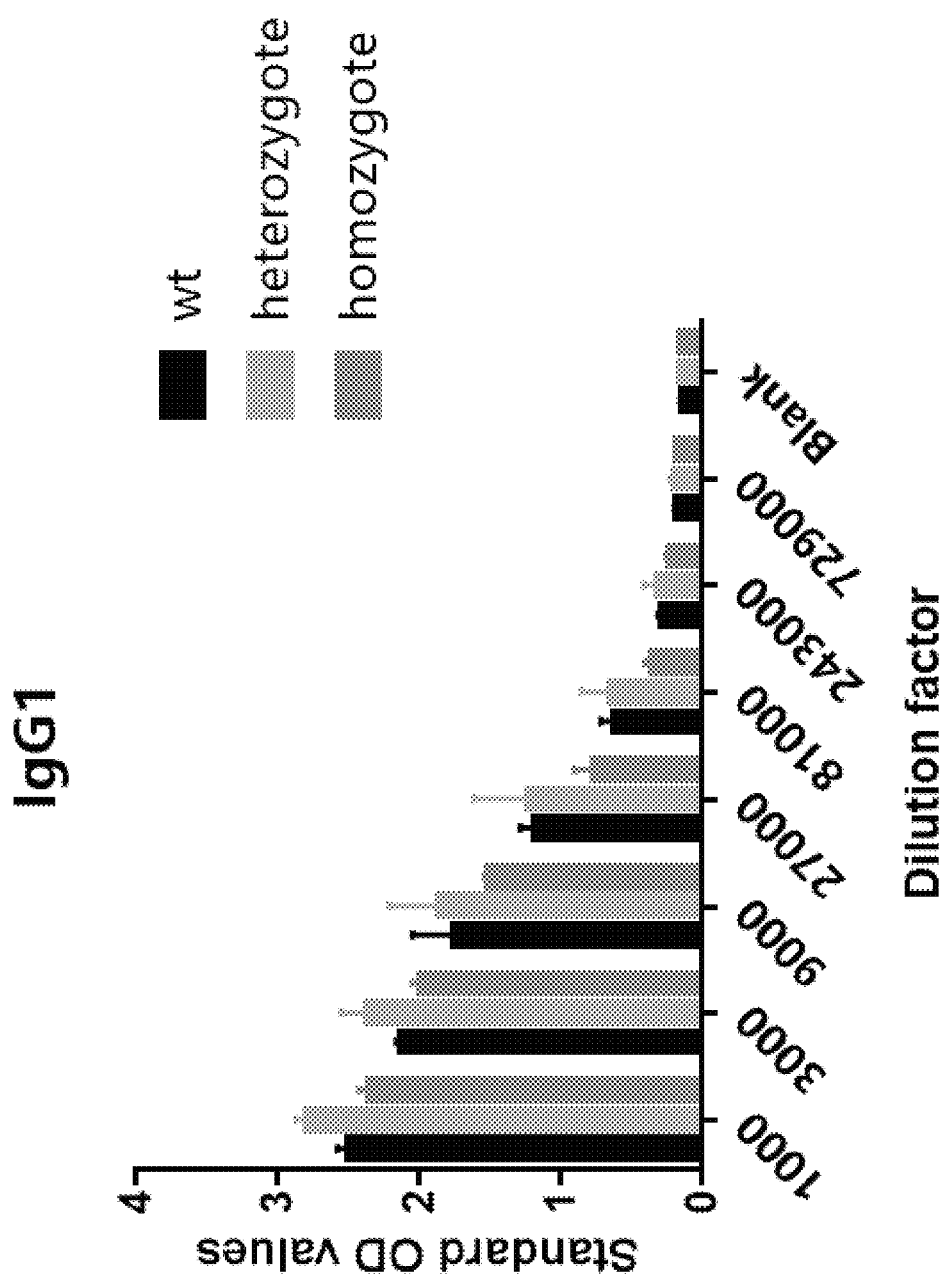
FIG. 53 shows IgG1 isotype levels in serially diluted mouse serum.
Figure 54:
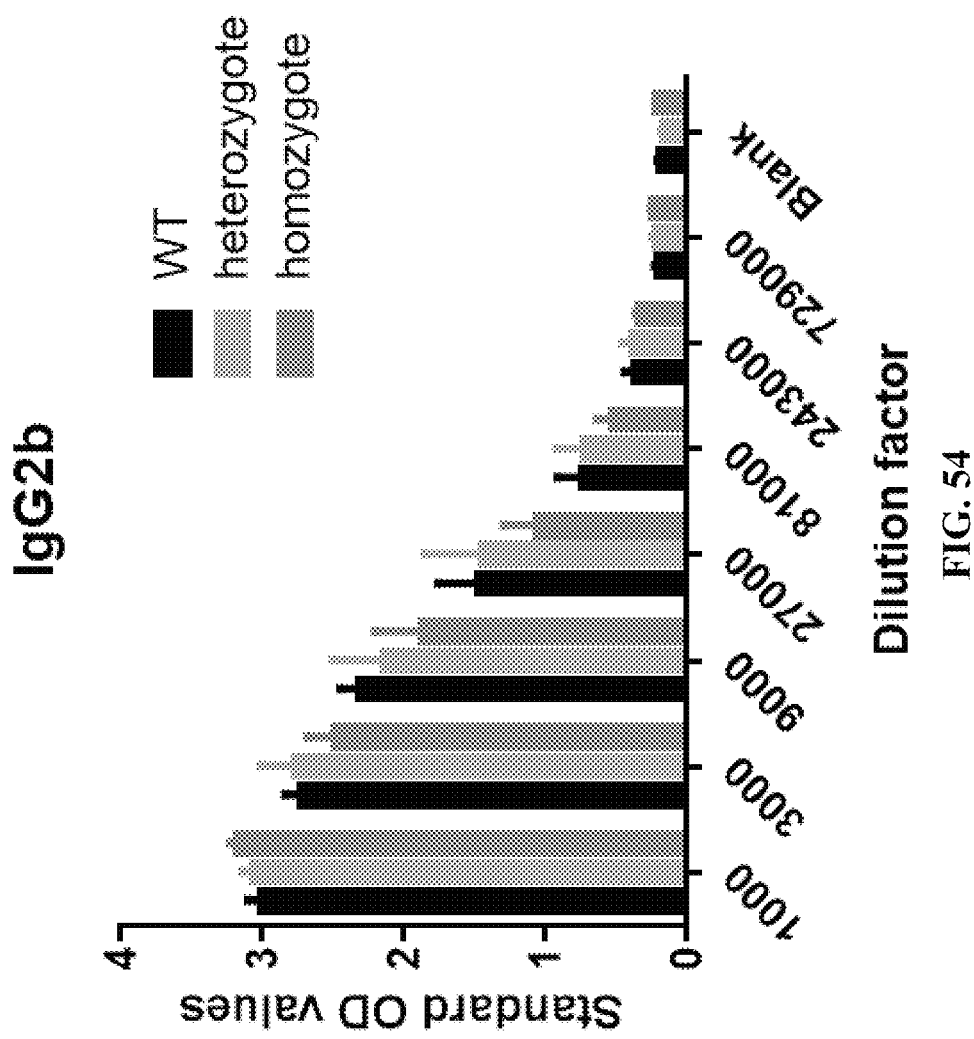
FIG. 54 shows IgG2b isotype levels in serially diluted mouse serum.
Figure 55:
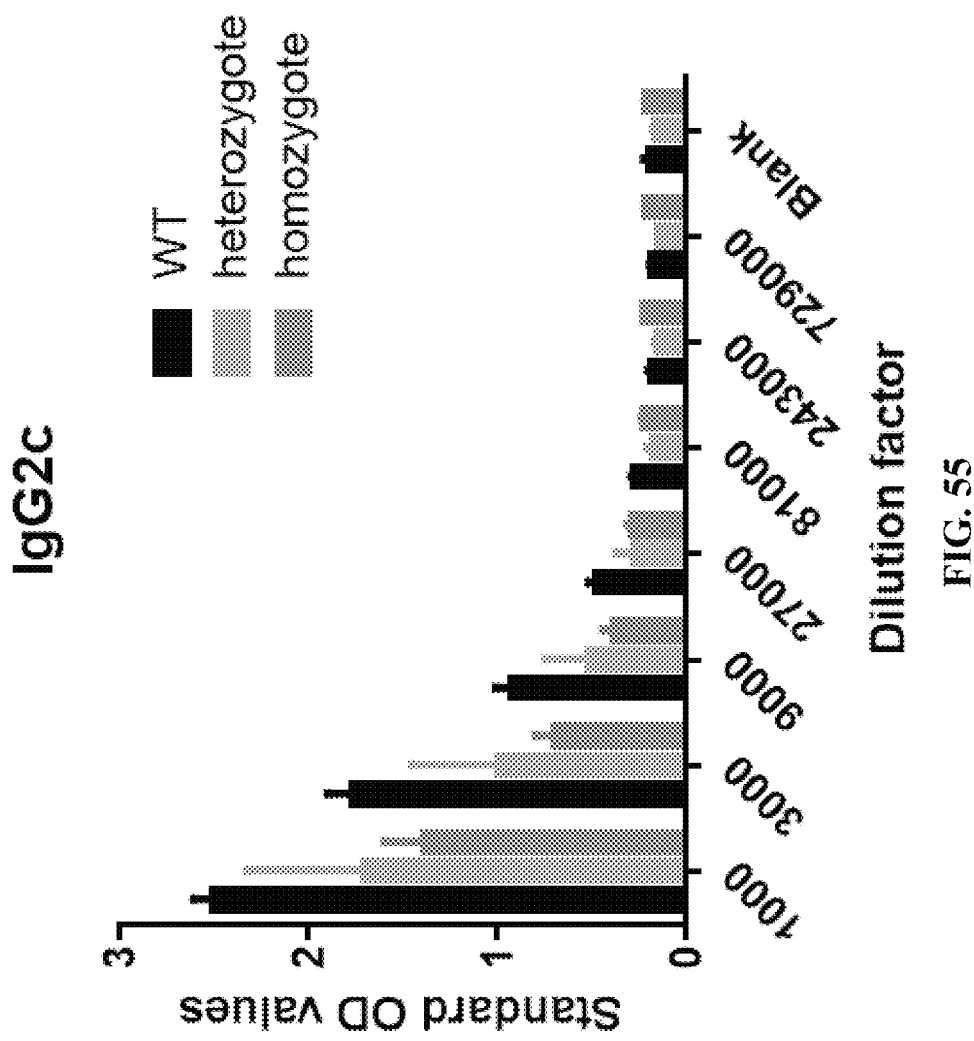
FIG. 55 shows IgG2c isotype levels in serially diluted mouse serum.
Figure 56:
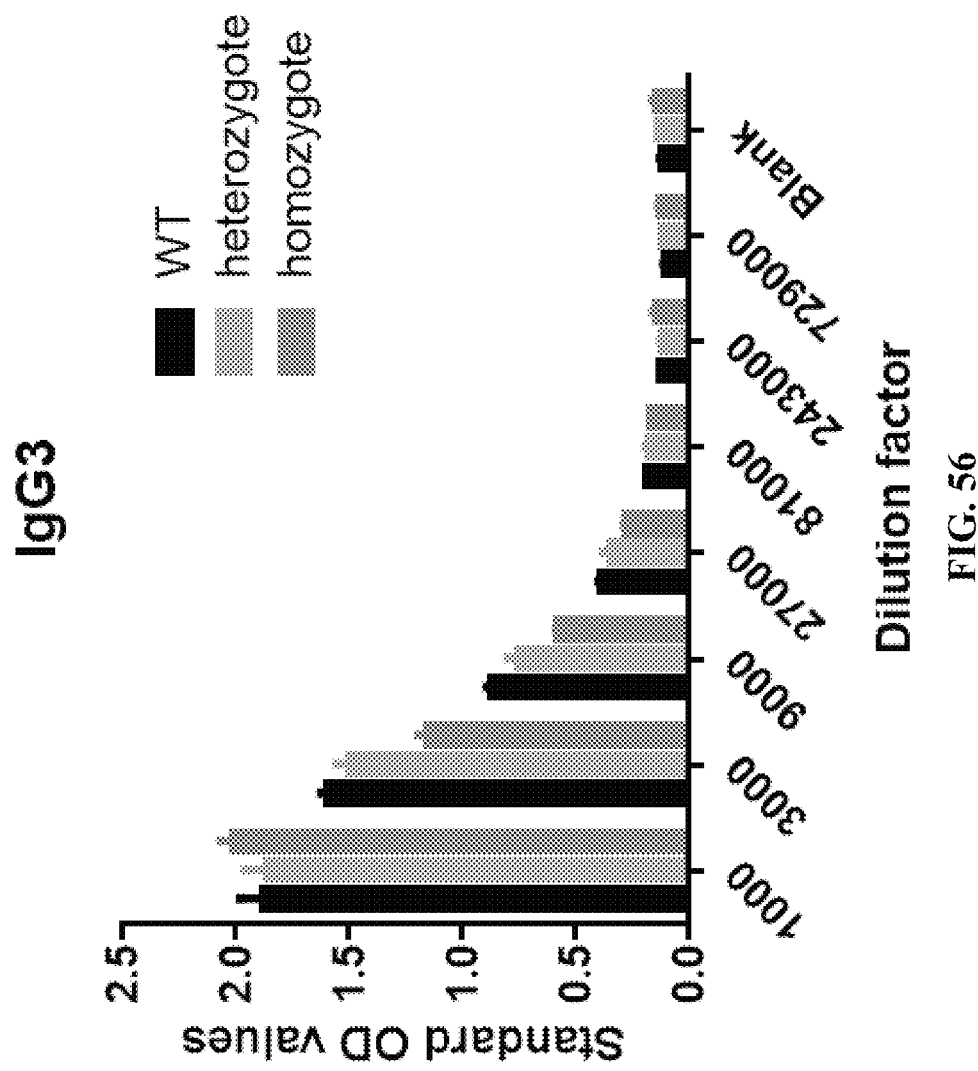
FIG. 56 shows IgG3 isotype levels in serially diluted mouse serum.
Figure 57:
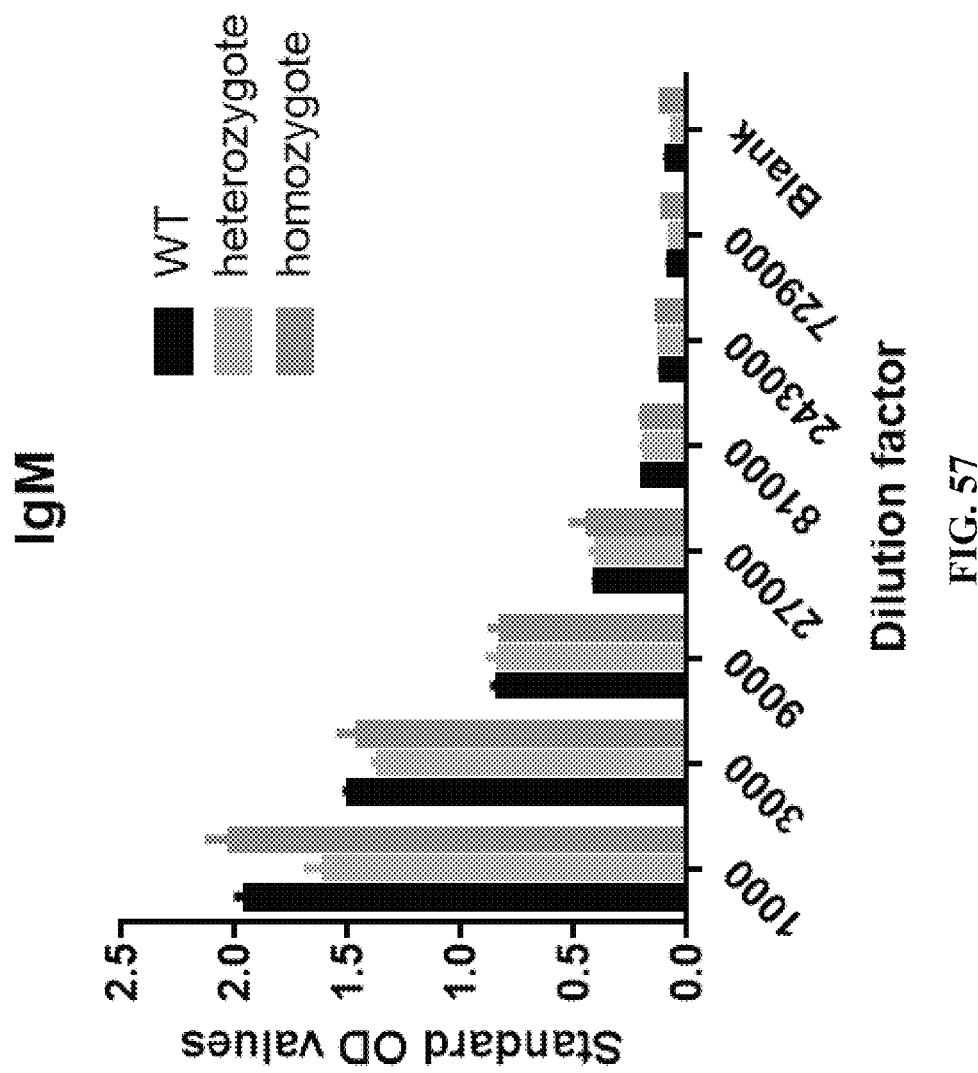
FIG. 57 shows IgM isotype levels in serially diluted mouse serum.

Based on different developmental stages, B cells in the bone marrow were categorized into pro-B-cells (characterized by B220$^{low}$CD43$^{high}$IgM$^{low}$) pre-B-cells (characterized by B220$^{low}$CD43$^{int}$IgM$^{low}$) and immature-B-cells (characterized by B220$^{high}$CD43$^{low}$IgM$^{high}$). FIGS. 51A-51C indicated percentages of B cells at different developmental stages in bone marrows.

Compared with the wild-type mice, percentages of immune cells and B cells in humanized mice were similar and there was no statistical difference among different groups. No significant defects in B cell differentiation were observed in either heavy chain humanized heterozygous mice (heterozygote) or homozygous mice (homozygote).

Example 10: Serum Immunoglobulin Isotype Analysis

Further, the levels of various immunoglobulins in the serum of the unimmunized mice in the Example above were analyzed. The mice included WT mice, mice with heterozygous humanized heavy chain immunoglobulin locus, and mice with homozygous humanized heavy chain immunoglobulin locus.

The experiments were performed using the Clonotyping System-B6/C57J-HRP (Southern Biotech, Cat #5300-05B) kit. First, the capture antibody Goat Anti-Mouse Ig, Human ads-UNLB was diluted to 10 ug/mL with PBS (Solarbio, Cat #P1020). Then, 0.1 mL of the diluted antibody was added to each well of the enzyme-linked immunosorbent assay (ELISA) plate and incubated at 37° C. for 2 hours. Next, the plate was washed and blocked at 4° C. for 12 hours. The serum samples were serially diluted with 1% BSA (Cell Signaling, Cat #9998). 0.1 mL of the diluted samples were added to each well, followed by incubation at 37° C. for 1 hour. 1% BSA was added to a well as a blank control.

Next, the plate was washed with PBS containing 0.05% Tween-20 (Amresco, Cat #M147). HRP-conjugated secondary antibody (Goat Anti-Mouse IgA, IgG (1, 2b, 2c, 3), IgM) (diluted 300-fold by 1% BSA, 0.1 mL per well) was added and incubated with the sample for 1 hour at 37° C. Next, the plate was washed and developed by adding 0.1 mL of TMB chromogen solution (Beyotime Biotechnology, Cat #P0209) to each well. After incubation in the dark at room temperature for 8 minutes, 0.1 mL of reaction solution (Beijing Dingguo Changsheng Biotechnology Co. LTD., Cat #EIA-0032) was added to each well. The optical absorption at 450 nm and 570 nm was measured using a microplate reader (Thermo MULTISKAN GO, Thermo Fisher Scientific), and the standard OD value was calculated.

The results showed that mice with humanized heavy chain immunoglobulin locus were capable of producing IgA, IgG1, IgG2b, IgG2c, IgG3 and IgM antibody isotypes, and the mice had similar expression levels for each isotype compared to wild-type mice (FIGS. 52-57). This indicated that humanization of the heavy chain variable region gene segments did not have a significant adverse effect on antibody class switching, the expression, or the secretion of the various antibody isotypes.

Example 11: V(D)J Recombination of Human Variable Region Gene Segments in Mice The mRNA sequences of the heavy chain variable region and the light chain variable region in mice were analyzed by next generation sequencing.

One unimmunized (not exposed to a particular antigen) humanized heavy chain homozygous mouse was selected. Spleen cells were collected from the mouse for RNA extraction. A 5' RACE kit (SMARTer RACE 5'/3' Kit, Takara Bio USA, Inc., Cat #634858) was used to perform reverse transcription to obtain cDNA. The obtained cDNA was PCR-amplified using the IgM constant region-specific primer and the UPM primer of the 5' RACE kit to obtain the heavy chain variable region sequence fragment, followed by sequencing. The IgM constant region-specific primer sequence was 5'-ccaagcttacgaggggggaagacatttgggaa-3' (SEQ ID NO: 50).

In another experiment, eleven light chain humanized heterozygous mice were selected, and RNA was extracted from retro-orbital blood. After reverse transcription by the method as described above, primers VKF1 and IgKC-tag were used to amplify the VκI family light chain genes, followed by sequencing. The following primer sequences were used:

```
VKF1 sequence:
                            (SEQ ID NO: 51)
5'-cataagatctcgmcatccrgwtgacccagt-3';

IgKC-tag primer sequence:
                            (SEQ ID NO: 52)
5'-ctaacactcattcctgttgaagctcttgac-3'.
```

The sequencing results were compared to the NCBI Ig Blast tool for human immunoglobulin sequences to identify the expression of human $V_H$, $D_H$, $J_H$ and Vκ, Jκ genes after V(D)J recombination. In the 135 analyzed clones, preliminary results detected the expressions of certain $V_H$, $D_H$ gene segments and all $J_H$ gene segments (Table 15). Some of these gene segments were located close to the modification site on the humanized fragment, and some were away from the modification site. This indicated that the human $V_H$, $D_H$ and $J_H$ genes on the human chromosome fragment that were integrated into mice can be recombined to express the human heavy chain, after replacing the endogenous chromosome fragment with the human immunoglobulin heavy chain sequence.

Figure 58:
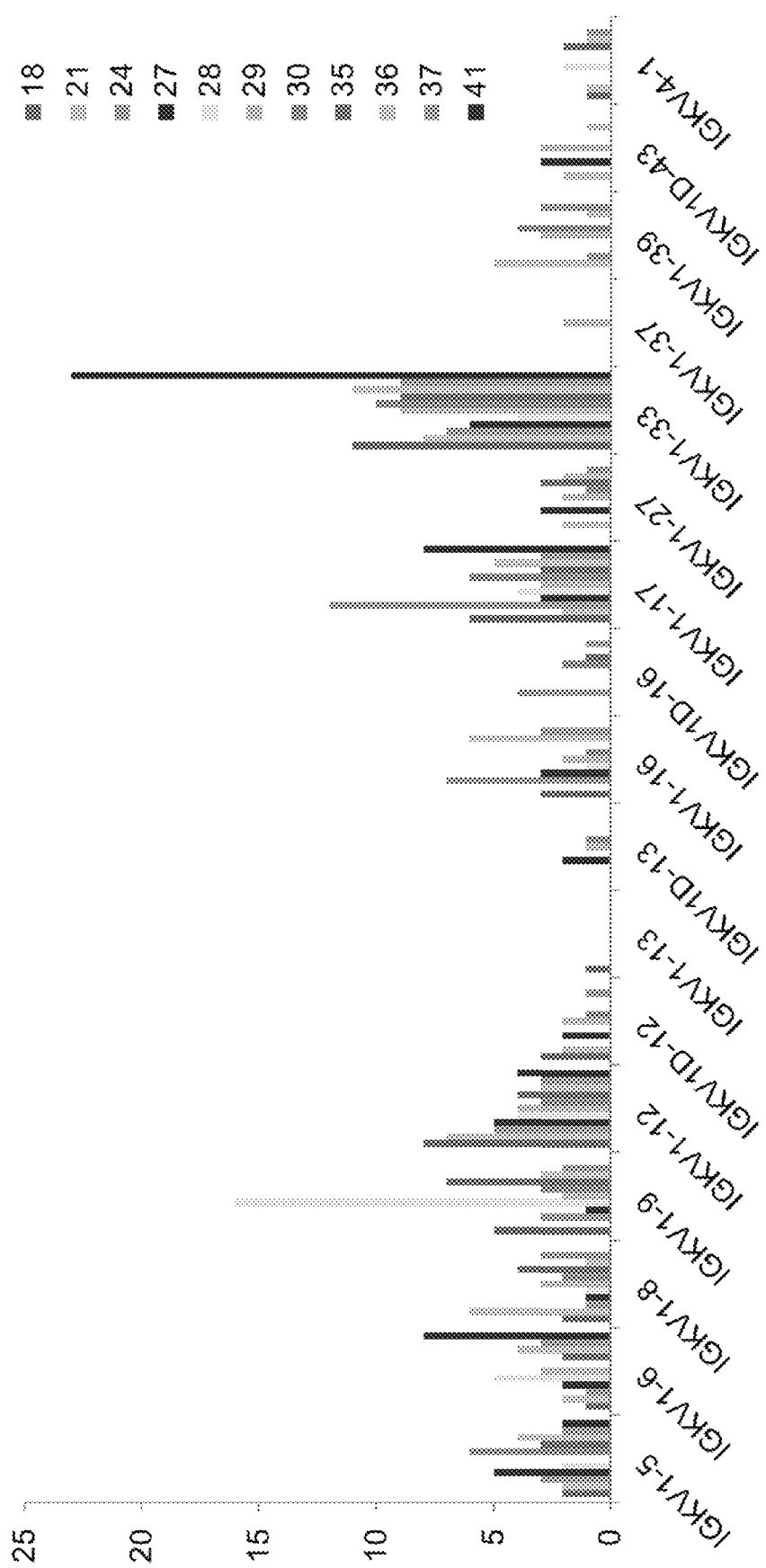
FIG. 58 shows distribution of the detected IGKV gene expression after VJ recombination among individual mice.
Figure 59:
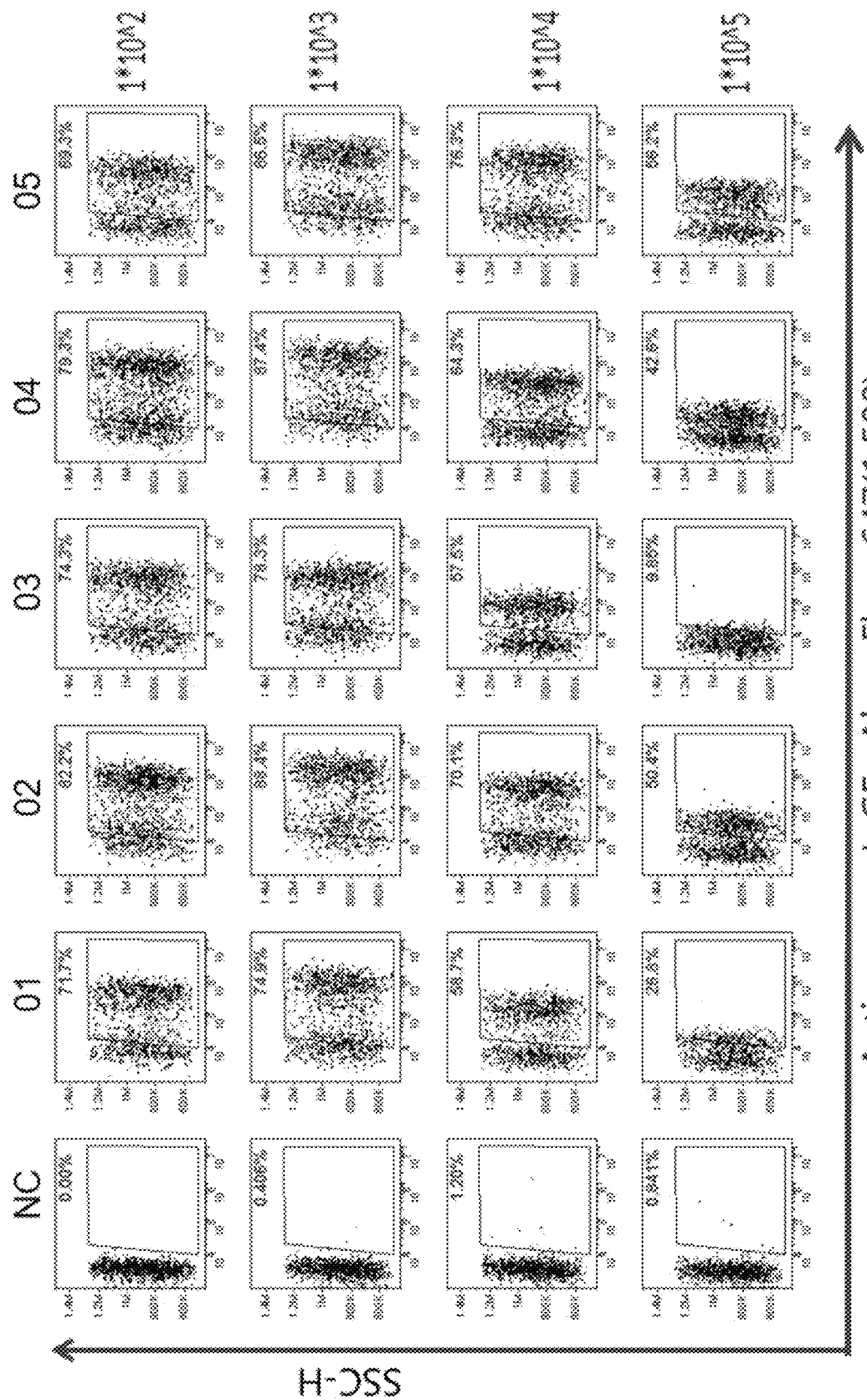
FIG. 59 shows flow cytometry results of wild-type mice after being immunized by human BTLA.
Figure 60:
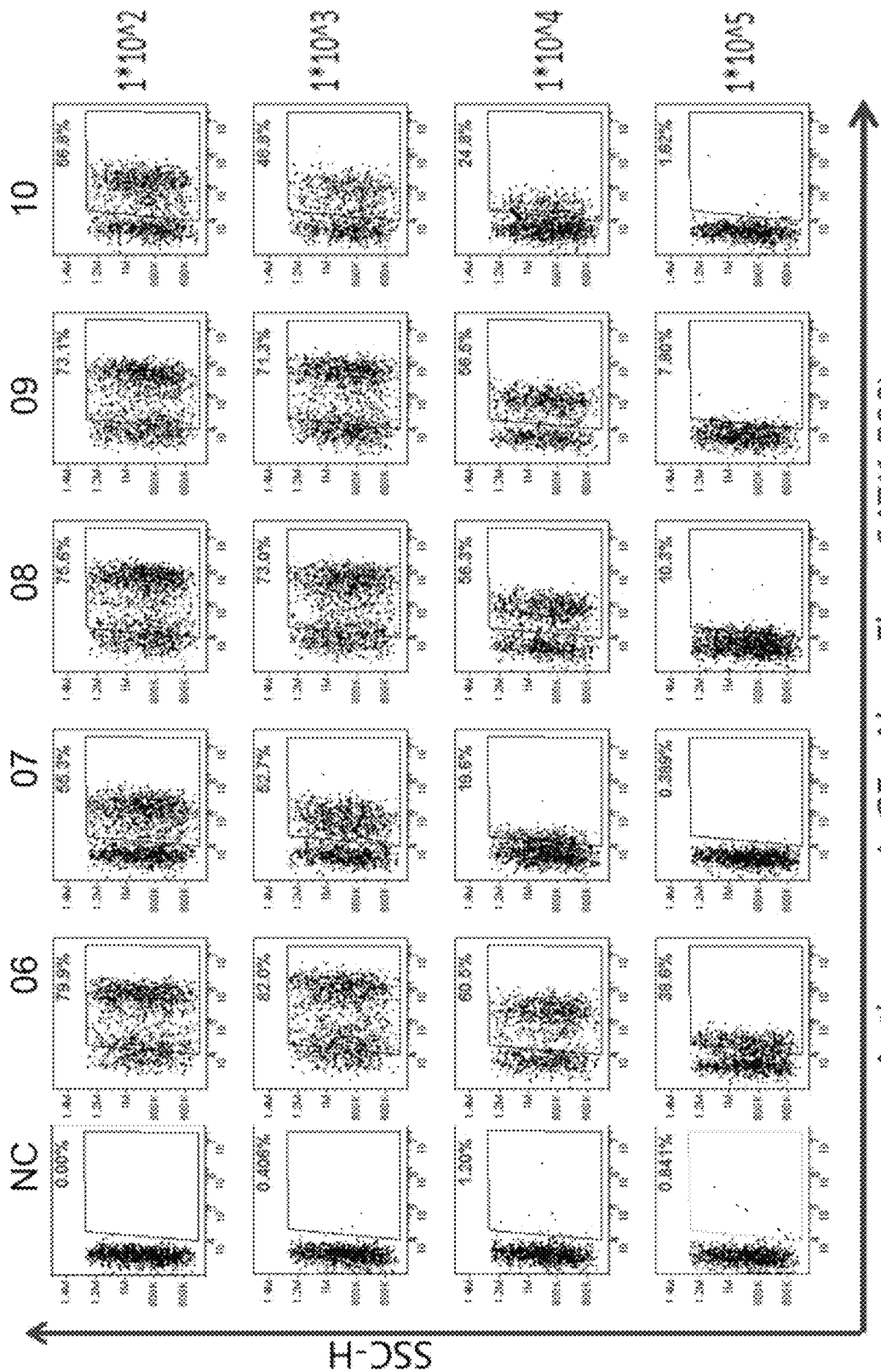
FIG. 60 shows flow cytometry results of humanized heavy chain homozygous mice after being immunized by human BTLA.
Figure 61:
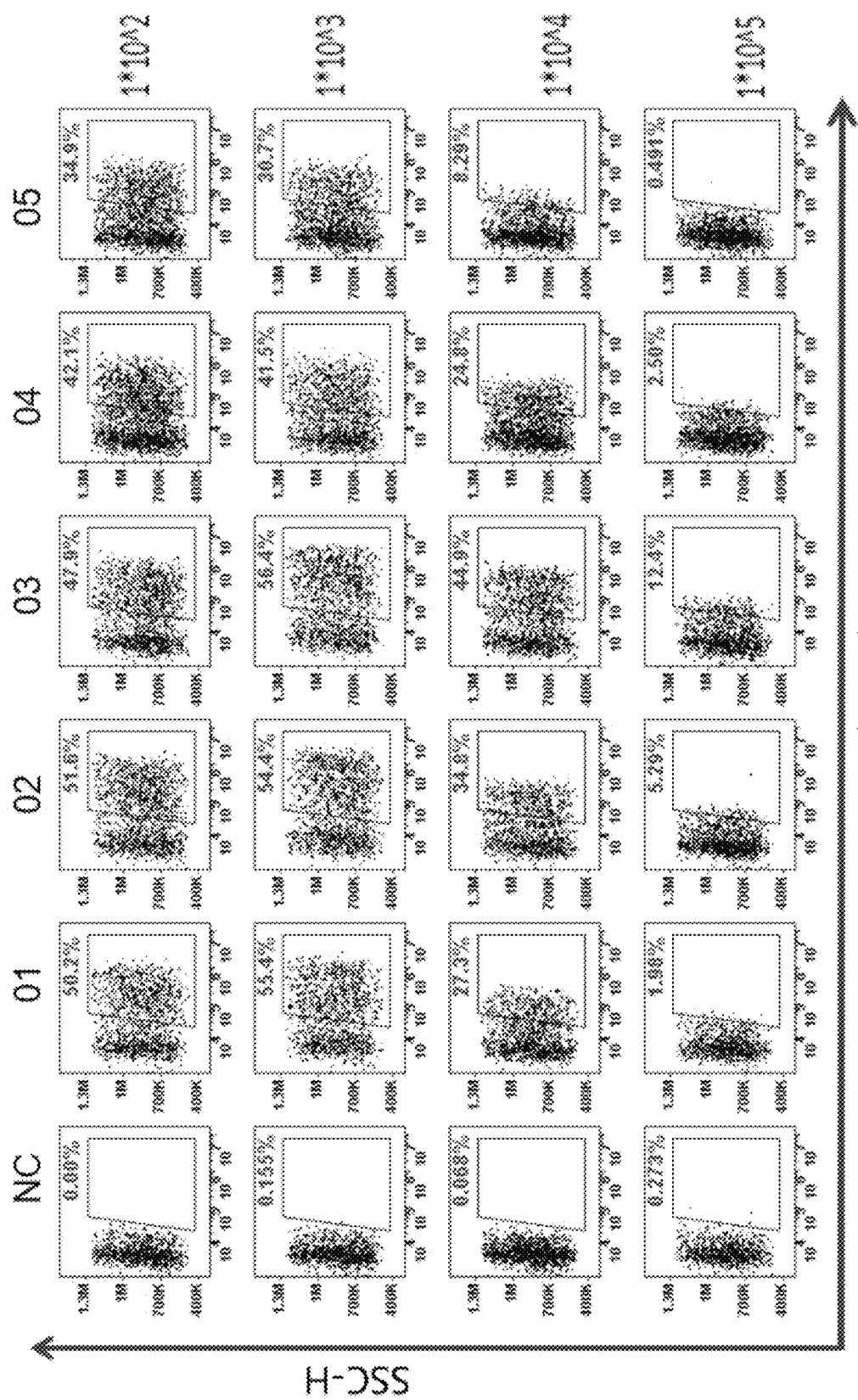
FIG. 61 shows flow cytometry results of wild-type mice after being immunized by canine PD-1 (dPD-1).
Figure 62:
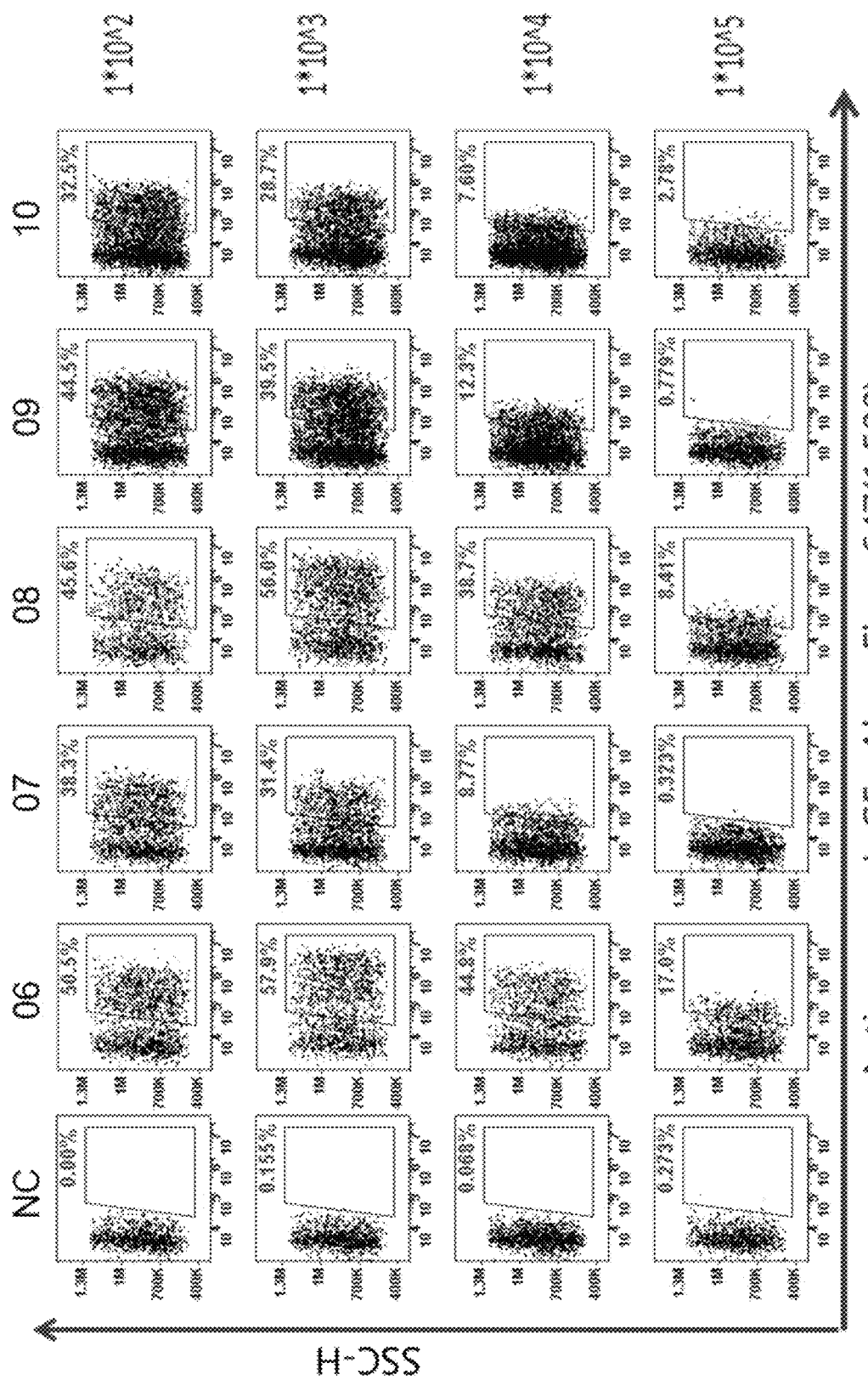
FIG. 62 shows flow cytometry results of humanized heavy chain homozygous mice after being immunized by canine PD-1 (dPD-1).
Figure 63:
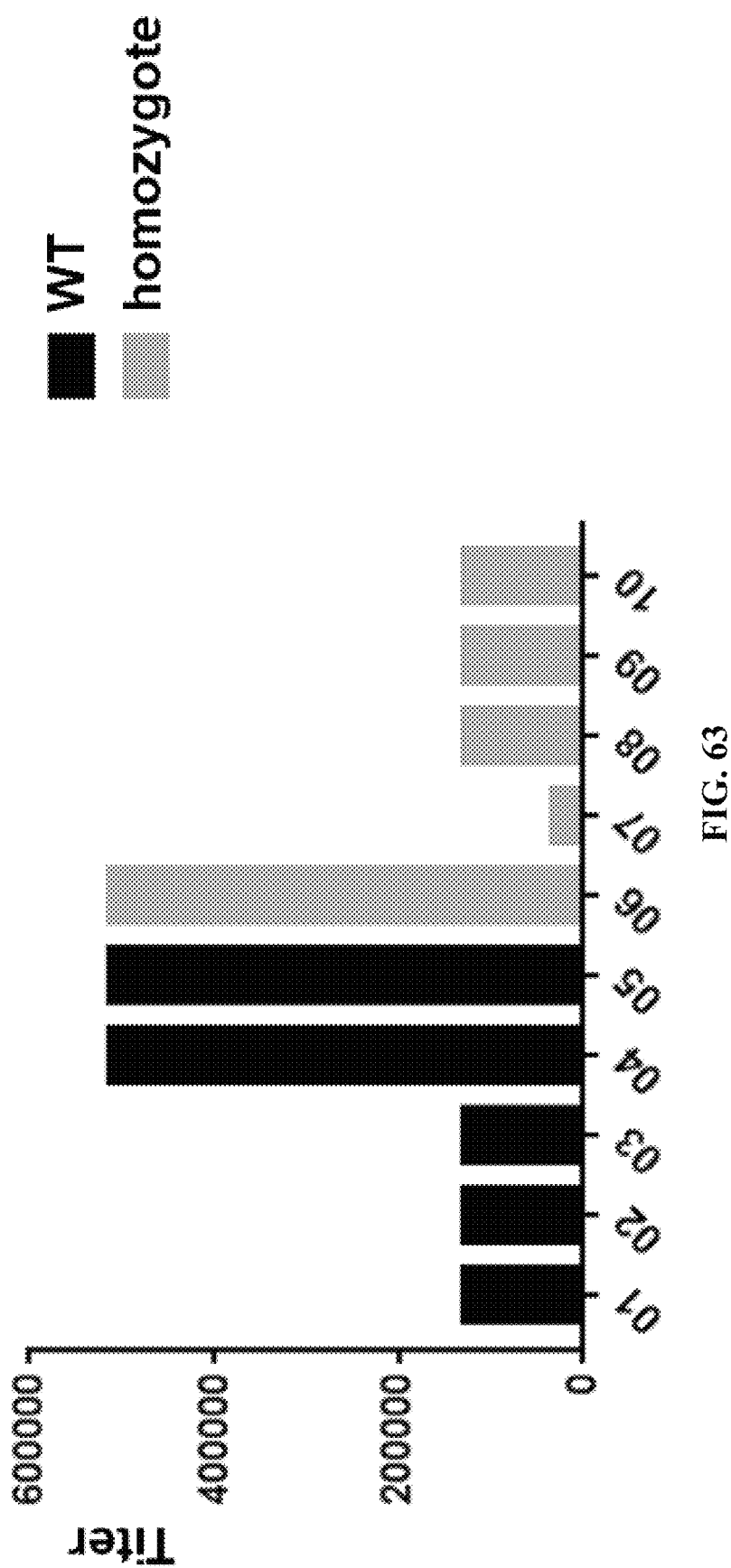
FIG. 63 shows a summary of ELISA results of wildtype mice (black bars; mice were labeled with 1-5) and humanized heavy chain homozygous mice (gray bars; mice were labeled with 6-10) after being immunized by ovalbumin (OVA).

Most of the VκI family light chain genes were detected in the 441 clones derived from humanized light chain heterozygous mice (Table 16). Similar to the heavy chain detection results, some of these genes on humanized fragment were located very close to the modification site, and some were away from the modification site. This indicated that after replacing the endogenous light chain immunoglobulin variable region locus with the human light chain immunoglobulin variable region locus, the human Vκ and Jκ genes that were integrated into the mouse genome can be recombined to express light chain with human light chain variable region. Further analysis of the results in the eleven mice showed that the detected distribution of the IGKV genes was not significantly different among the tested mice (FIG. 58).

TABLE 15

List of detected IGHV genes, IGHD genes, and IGHJ that were expressed after VDJ recombination

| IGHV gene | Observed value (count) | IGHD gene | Observed value (count) | IGHJ gene | Observed value (count) |
|---|---|---|---|---|---|
| IGHV1-18 | 1 | IGHD1-1 | 4 | IGHJ1 | 2 |
| IGHV1-24 | 1 | IGHD1-20 | 2 | IGHJ2 | 16 |
| IGHV1-46 | 2 | IGHD1-26 | 8 | IGHJ3 | 7 |
| IGHV1-69 | 1 | IGHD1-7 | 10 | IGHJ4 | 55 |
| IGHV2-70 | 1 | IGHD2-2 | 2 | IGHJ5 | 12 |
| IGHV3-15 | 1 | IGHD2-21 | 2 | IGHJ6 | 43 |
| IGHV3-21 | 5 | IGHD3-10 | 5 | | |
| IGHV3-23 | 7 | IGHD3-16 | 3 | | |
| IGHV3-30 | 10 | IGHD3-22 | 3 | | |
| IGHV3-30-3 | 2 | IGHD3-3 | 2 | | |
| IGHV3-33 | 6 | IGHD3-9 | 1 | | |
| IGHV3-43 | 7 | IGHD4-11 | 4 | | |
| IGHV3-48 | 5 | IGHD4-17 | 7 | | |
| IGHV3-49 | 1 | IGHD4-23 | 1 | | |
| IGHV3-66 | 1 | IGHD5-12 | 4 | | |
| IGHV3-73 | 1 | IGHD5-18 | 1 | | |
| IGHV3-74 | 3 | IGHD5-24 | 1 | | |
| IGHV4-30-4 | 5 | IGHD6-13 | 17 | | |
| IGHV4-34 | 37 | IGHD6-19 | 22 | | |
| IGHV4-39 | 14 | IGHD6-25 | 1 | | |
| IGHV4-4 | 1 | IGHD6-6 | 5 | | |
| IGHV4-59 | 11 | IGHD7-27 | 14 | | |
| IGHV5-51 | 1 | | | | |
| IGHV6-1 | 11 | | | | |

TABLE 16

List of detected IGKV genes that were expressed after VJ recombination

| Gene names | Observed value (count) |
|---|---|
| IGKV1D-43 | 9 |
| IGKV1D-13 | 4 |
| IGKV1D-16 | 9 |
| IGKV1D-12 | 11 |
| IGKV1-39 | 17 |
| IGKV1-37 | 2 |
| IGKV1-33 | 107 |
| IGKV1-27 | 14 |
| IGKV1-17 | 55 |
| IGKV1-16 | 26 |
| IGKV1-13 | 1 |
| IGKV1-12 | 50 |
| IGKV1-9 | 42 |
| IGKV1-8 | 24 |
| IGKV1-6 | 31 |
| IGKV1-5 | 31 |
| IGKV4-1 | 8 |

Example 12: Immunization and Antibody Production in Humanized Mice

Five wild-type (WT) mice and five humanized heavy chain homozygous mice (9-10 week old) were randomly selected and immunized with exogenous antigens. The mice were repeatedly immunized once every two weeks for a total of three immunizations. Retro-orbital blood was collected after the second immunization and the third immunization. Serum was collected and then the serum titer was measured by ELISA or FACS to determine and analyze the antigen-specific antibody response. Three antigens were used in the study, which were hBTLA, dPD1 and OVA (FIGS. 59-63). The results showed that after the second immunization, most wild-type (WT) and humanized heavy chain homozygous mice produced antigen-specific antibodies. After the third immunization, the antibody titer increased to 1×10$^4$ to 1×10$^5$. The immunopotency test results were essentially the same in humanized mice as compared to the wildtype mice, indicating that the humanized immunoglobulin variable region locus in the mice are functional and can produce antigen-specific antibodies.

Example 13: B-Cell Development in hVH/hVL Mice

The mice with homozygous humanized heavy chain immunoglobulin locus (humanized VH mice or hVH mice) and the mice with humanized light chain immunoglobulin locus (humanized VL mice or hVL mice) were crossed with each other to obtain mice with both homozygous humanized heavy chain immunoglobulin locus and homozygous humanized light chain immunoglobulin locus (humanized VH/VL mice, or hVH/hVL mice). The hVH/hVL mice can be used produce humanized monoclonal antibody in vivo.

Figure 65A:
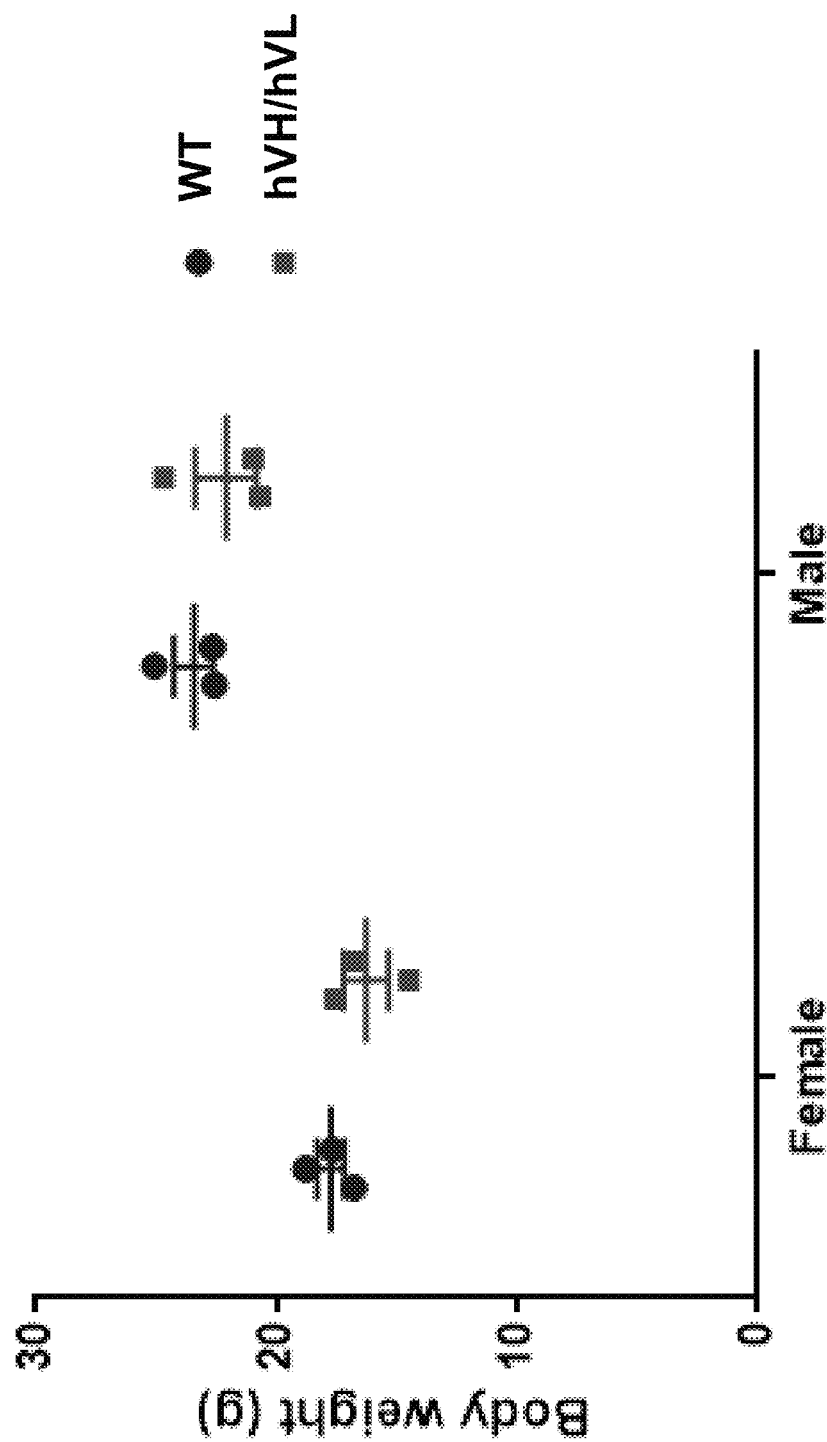
FIG. 65A shows body weight of naïve wild-type mice and hVH/hVL mice.
Figure 65B:
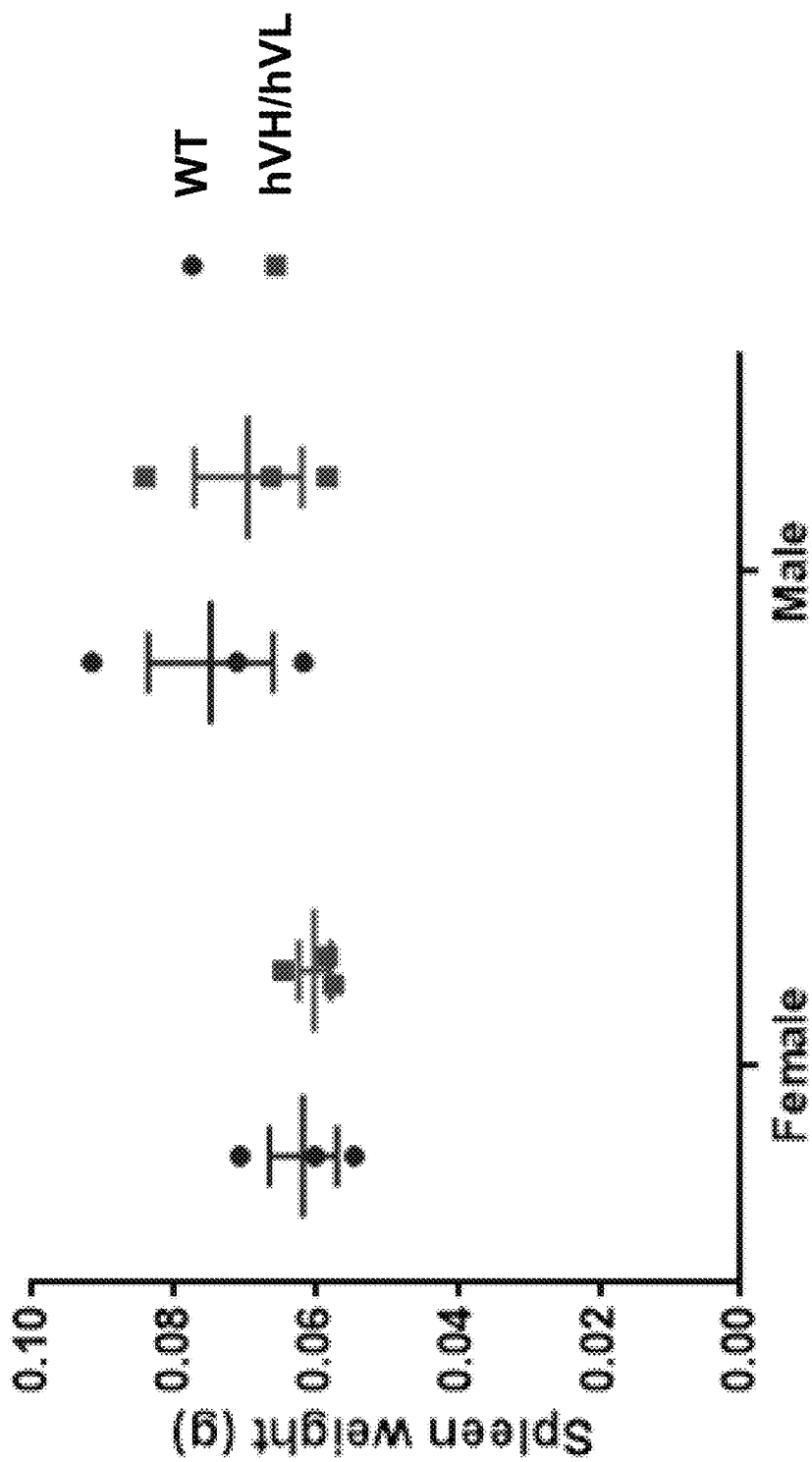
FIG. 65B shows spleen weight of naïve wild-type mice and hVH/hVL.

Experiments were performed to compare the immune systems of the naïve humanized VH/VL mice and the naïve wild-type mice. The body weight and spleen weight were measured in wild-type and hVH/hVL mice (FIGS. 65A-65B). No significant differences in average body weight and spleen weight were detected between wild-type and hVH/hVL mice.

Figure 66:
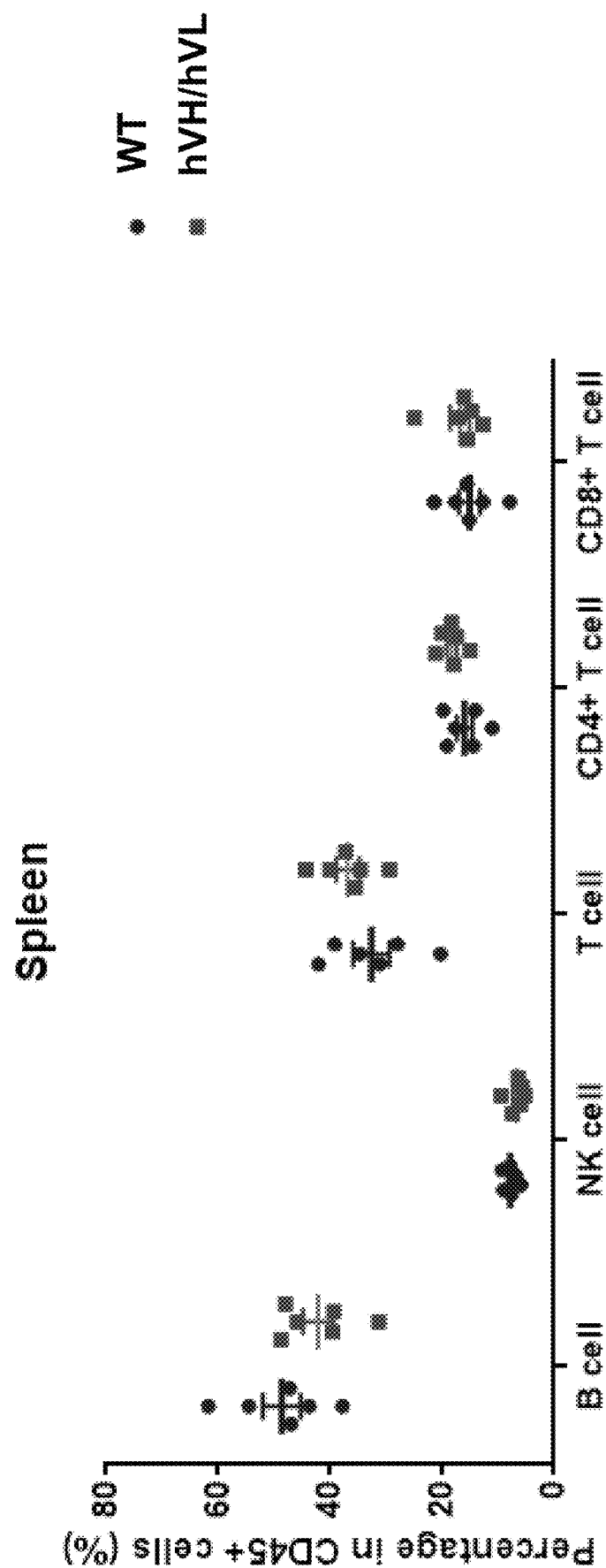
FIG. 66 shows percentage of immune cells in the spleen of naïve wild-type mice and hVH/hVL mice.

Flow cytometry was performed to analyze lymphocyte populations and distribution in the spleen (FIG. 66) and B cell populations in the spleen and bone marrow (FIGS. 67A-67B, 68A-68C) of the mice. The results showed that in hVH/hVL mice, the percentage of B cells, T cells, NK cells, CD4+ T cells and CD8+ T cells in spleen were almost identical to those of wild type mice. In the results, the leukocytes included: B cells (e.g., characterized by CD45+, CD19+, TCR−), T cells, and natural killer (NK) cells (e.g., characterized by CD45+, TCR−, NK1.1+). T cells were characterized by CD45+, CD19−, TCR+. CD4+ T Cells (CD4) were characterized by CD45+, CD19−, TCR+, CD4+, CD8−. And CD8+ T cells (CD8) were characterized by CD45+, CD19−, TCR+, CD4−, CD8+. Only intact, single, live leukocytes were included in the flow cytometry analysis.

Figure 67A:
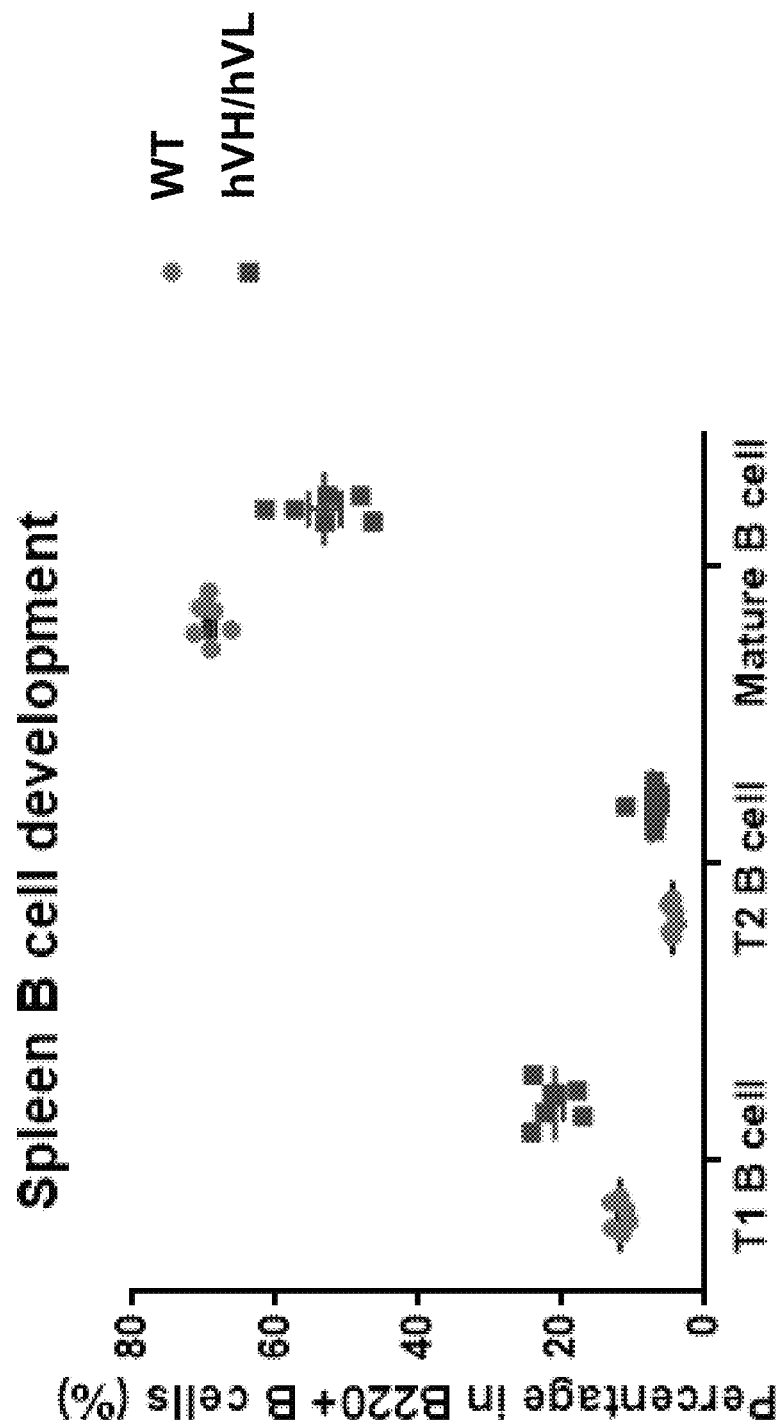
FIG. 67A shows percentage of transitional type 1 (T1, $B220^+IgM^+IgD^-$), transitional type 2 (T2, $B220^+IgM^+IgD^+$) and mature (M, $B220^+IgM^{low}IgD^+$) B cell population in spleen B cells. The spleen B cells are from naïve wild-type or hVH/hVL mice.
Figure 67B:
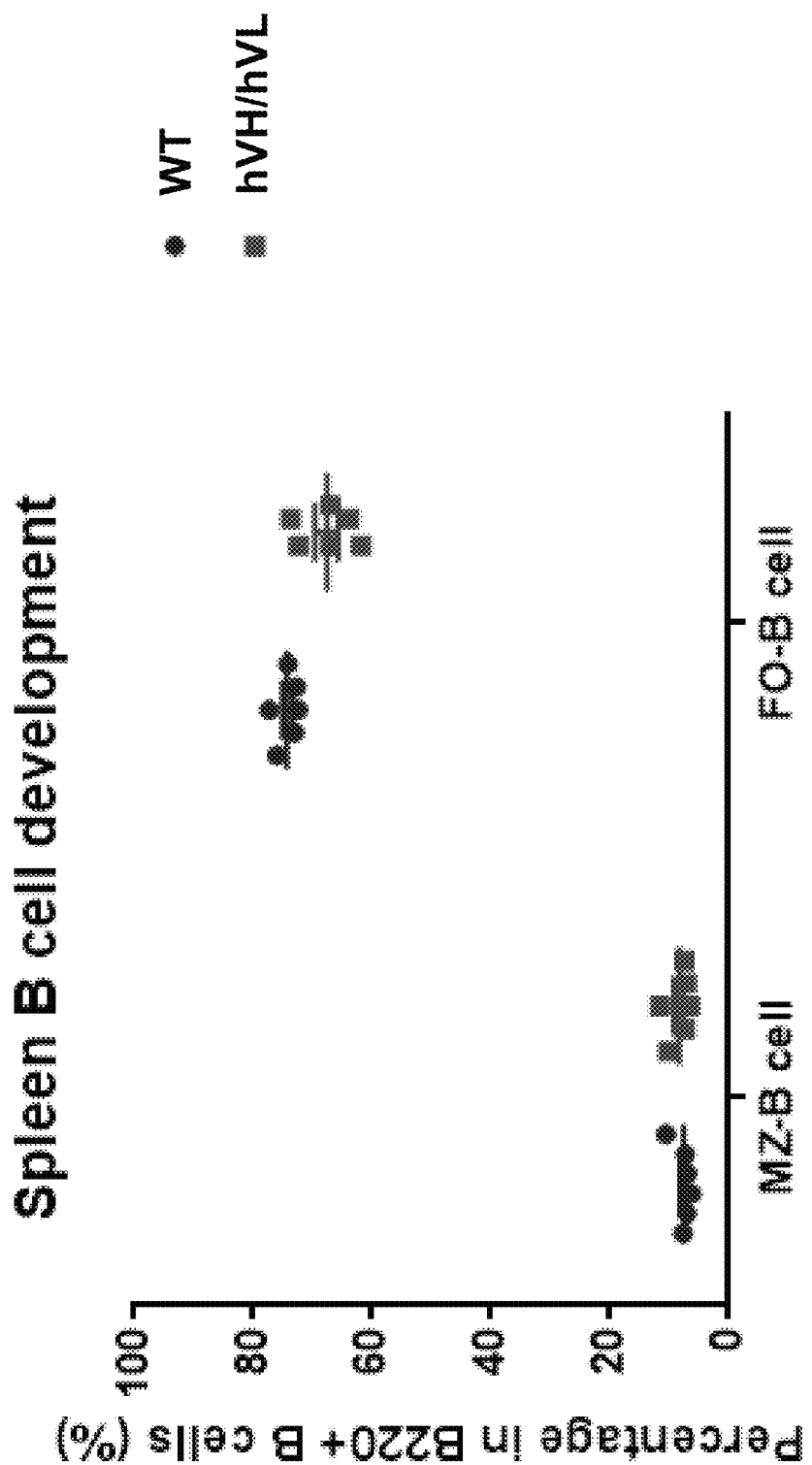
FIG. 67B shows percentage of marginal-zone (MZ) and follicular (FO) B cell population in spleen B cells. The spleen B cells are from naïve wild-type or hVH/hVL mice.

FIG. 67A indicated percentages of B cells at different developmental stages. The development stages of B cells in spleen were categorized into T1 (Transitional type 1 B cell, characterized by B220$^+$IgM$^+$IgD$^-$), T2 (Transitional type 2 B cell, characterized by B220$^+$IgM$^+$IgD$^+$) and mature B cells (characterized by B220$^+$IgM$^{low}$IgD$^+$). In addition, B cell development were also evaluated at the spleen marginal zone (Marginal-zone B cell, MZ-B, characterized by B220$^+$ CD21$^+$CD23$^-$) and follicular zone (Follicular B cell, referred to as FO-B, characterized by B220$^+$ CD21$^{low}$CD23$^+$). FIG. 67B showed percentages of splenic B cells at spleen marginal zone (MZ-B) and follicular zone (FO-B). No significant differences were observed between the wild-type mice and hVH/hVL mice.

Figure 68A:
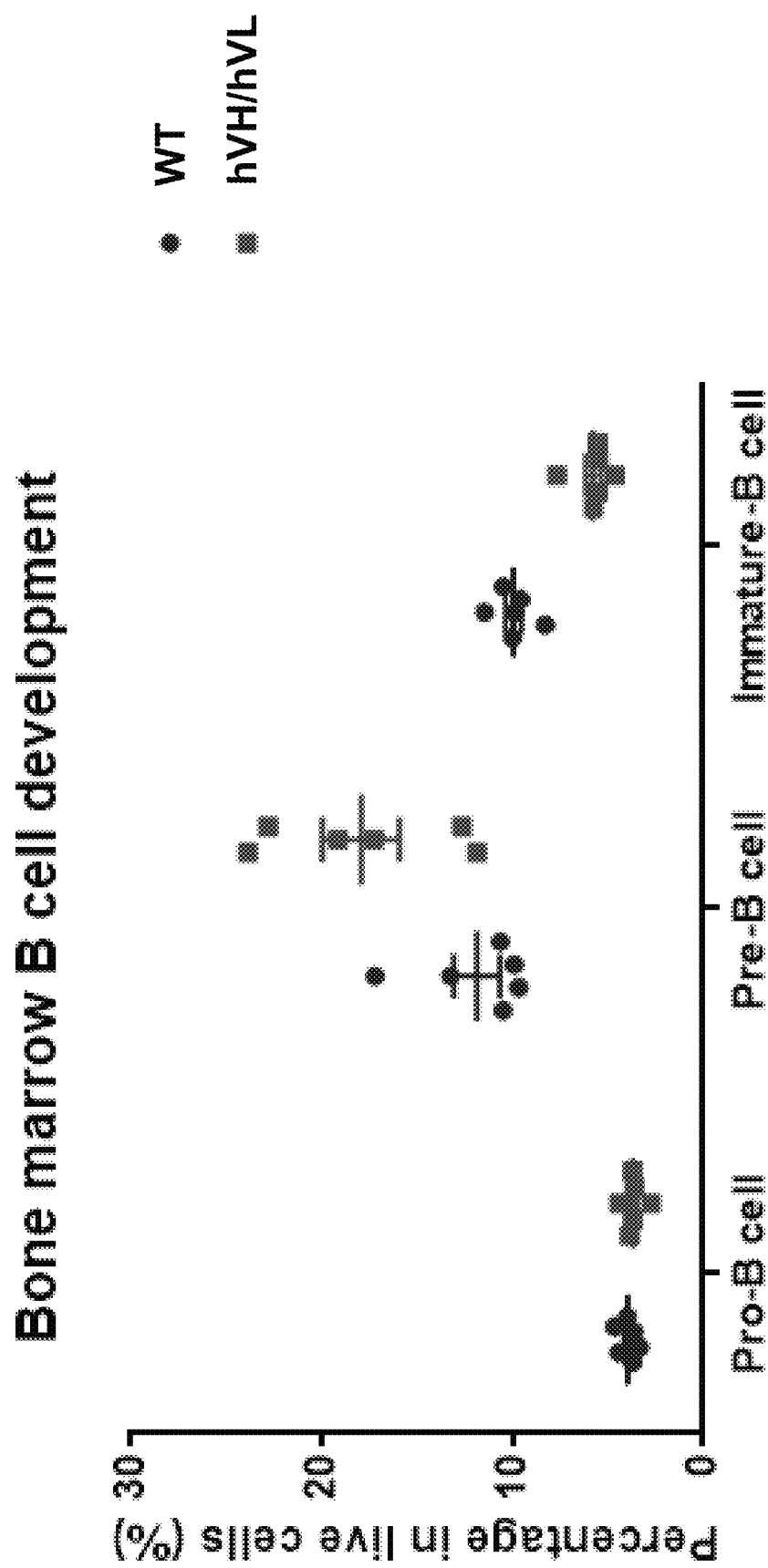
FIG. 68A shows percentage of pro-B-cell ($B220^{low}CD43^{high}IgM^{low}$), pre-B-cell ($B220^{low}CD43^{int}IgM^{low}$) and immature-B-cell ($B220^{high}CD43^{low}IgM^{high}$) population in bone marrow B cells. The bone marrow B cells are from naïve wild-type or hVH/hVL mice.

FIG. 68A indicated percentages of B cells at different developmental stages in bone marrows. B cell progenitor cells in bone marrow were analyzed by flow cytometry. Based on expression levels of B220 and CD43, B cell progenitor cells in bone marrow can be divided into 3 cell populations pro-B-cells (characterized by B220$^{low}$CD43$^{high}$IgM$^{low}$) pre-B-cells (characterized by B220$^{low}$ CD43$^{int}$IgM$^{low}$) and immature-B-cells (characterized by B220$^{high}$CD43$^{low}$IgM$^{high}$). No significant differences were observed between the wild-type mice and hVH/hVL mice.

Figure 68B:
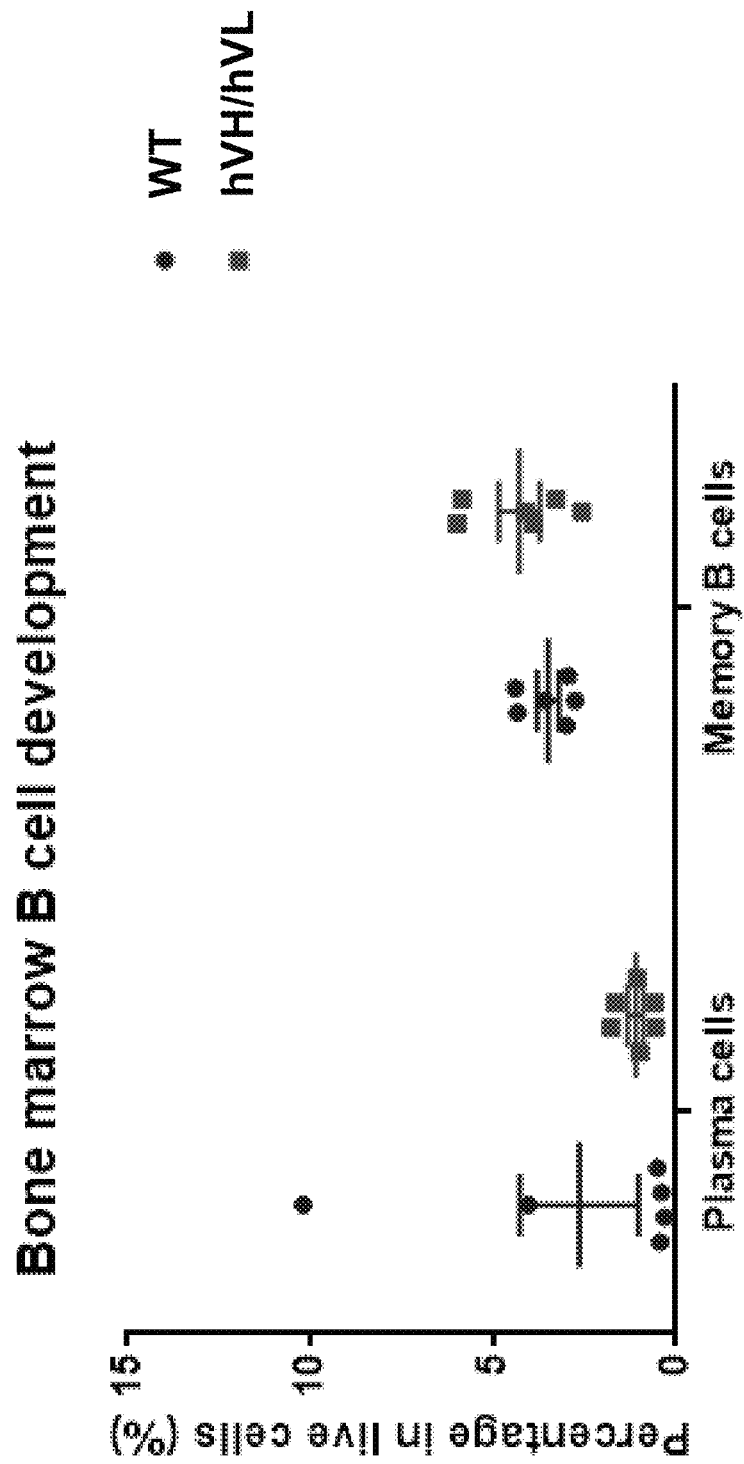
FIG. 68B shows percentage of plasma cell ($B220^{low}IgM^-IgD^-CD138^-$) and memory B cell ($B220^+IgM^+IgD^-CD38^+$) population in bone marrow B cells. The bone marrow B cells are from naïve wild-type or hVH/hVL mice.
Figure 68C:
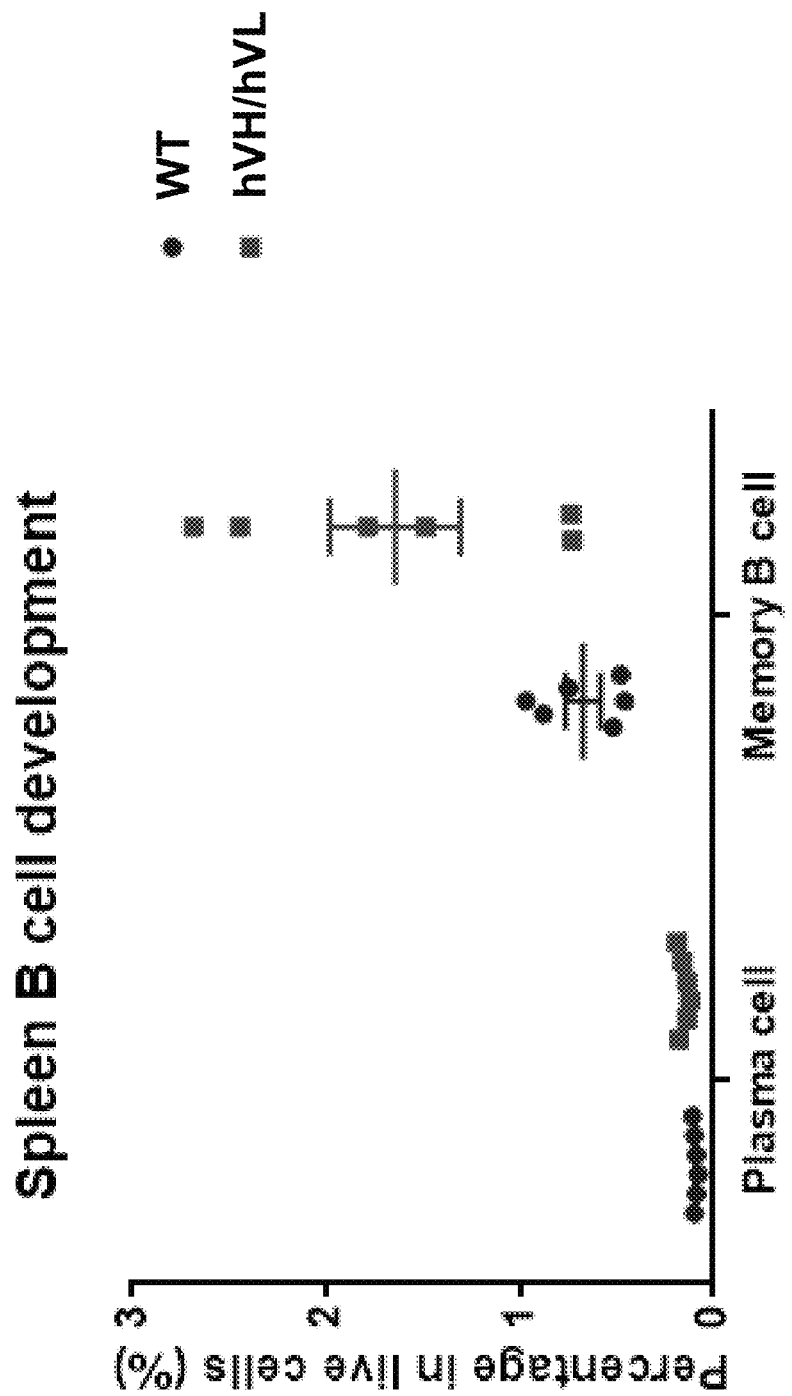
FIG. 68C shows percentage of plasma cell ($B220^{low}IgM^-IgD^-CD138^-$) and memory B cell ($B220^+IgM^+IgD^-CD38^+$) population in spleen B cells. The spleen B cells are from naïve wild-type or hVH/hVL mice.

In addition, B cell development were also evaluated in bone marrow or spleen by flow cytometry to selectively stain plasma cells (B220$^{low}$IgM$^-$IgD$^-$CD138$^-$) and memory B cells (B220$^+$IgM$^+$IgD$^-$CD38$^+$) (FIGS. 68B-68C). No significant difference was observed between the wild-type mice and hVH/hVL mice.

Figure 69:
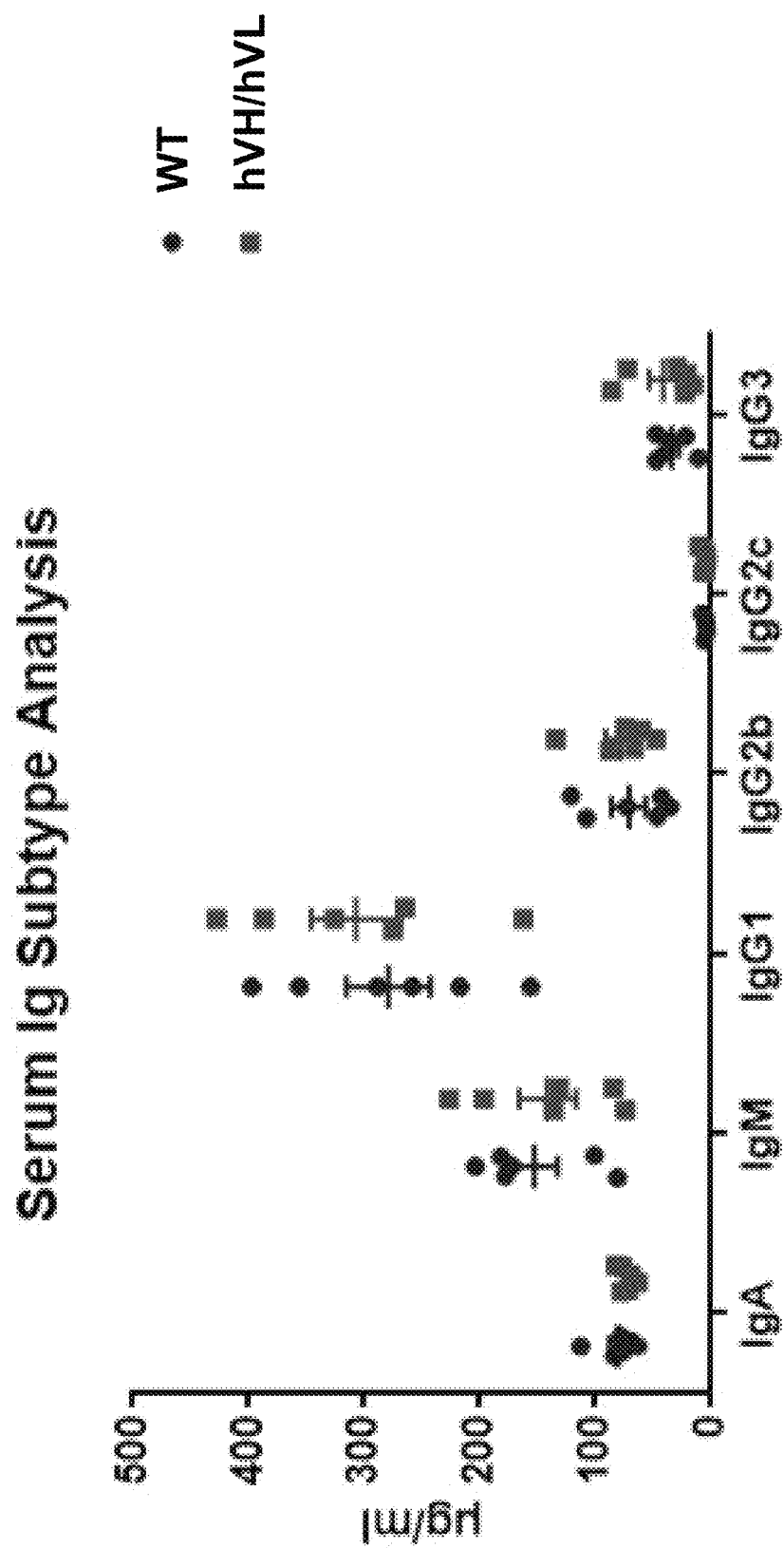
FIG. 69 shows concentration of serum immunoglobulin (Ig) subtypes in naïve wild-type or hVH/hVL mice. The Ig subtype concentrations were quantitatively measured by ELISA.

Different immunoglobulin (Ig) subtypes in the serum of hVH/hVL and wild-type mice were quantitatively measured by ELISA. A total of six mice were selected for each group. No significant differences in IgA, IgG1, IgG2b, IgG2c, IgG3 and IgM levels were observed (FIG. 69).

These experiments showed that the immune system in the hVH/hVL mice is functional and the humanized immunoglobulin locus in hVH/hVL mice can properly interact with the mouse immunoglobulin constant regions.

Example 14: Analysis of Germline Usage in hVH/hVL Mice

Figures 71A, 71B:
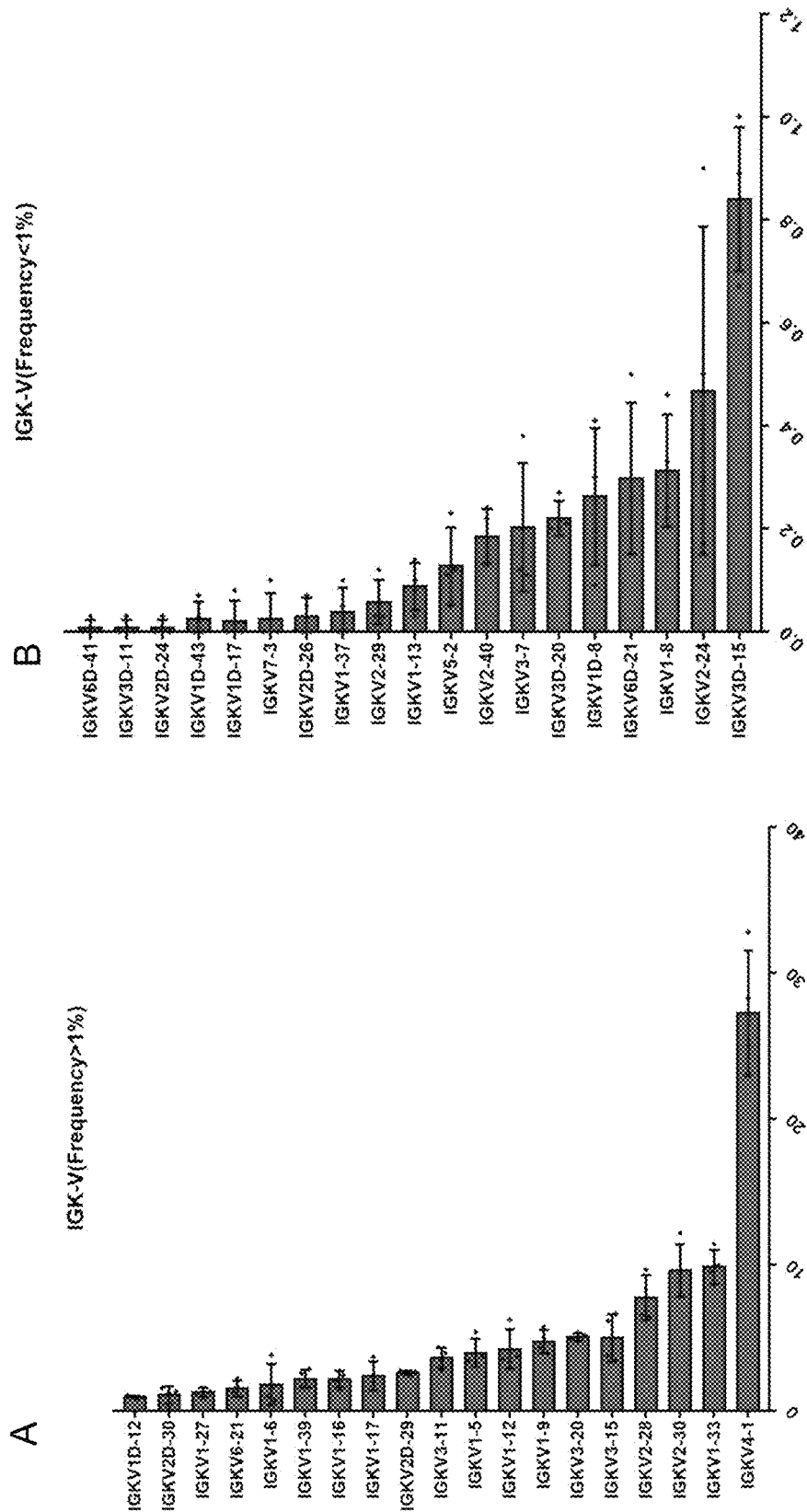
FIG. 71A shows IGKV usage (frequency >1%) in naïve hVH/hVL mice.
FIG. 71B shows IGKV usage (frequency <1%) in naïve hVH/hVL mice.
Figure 71C:
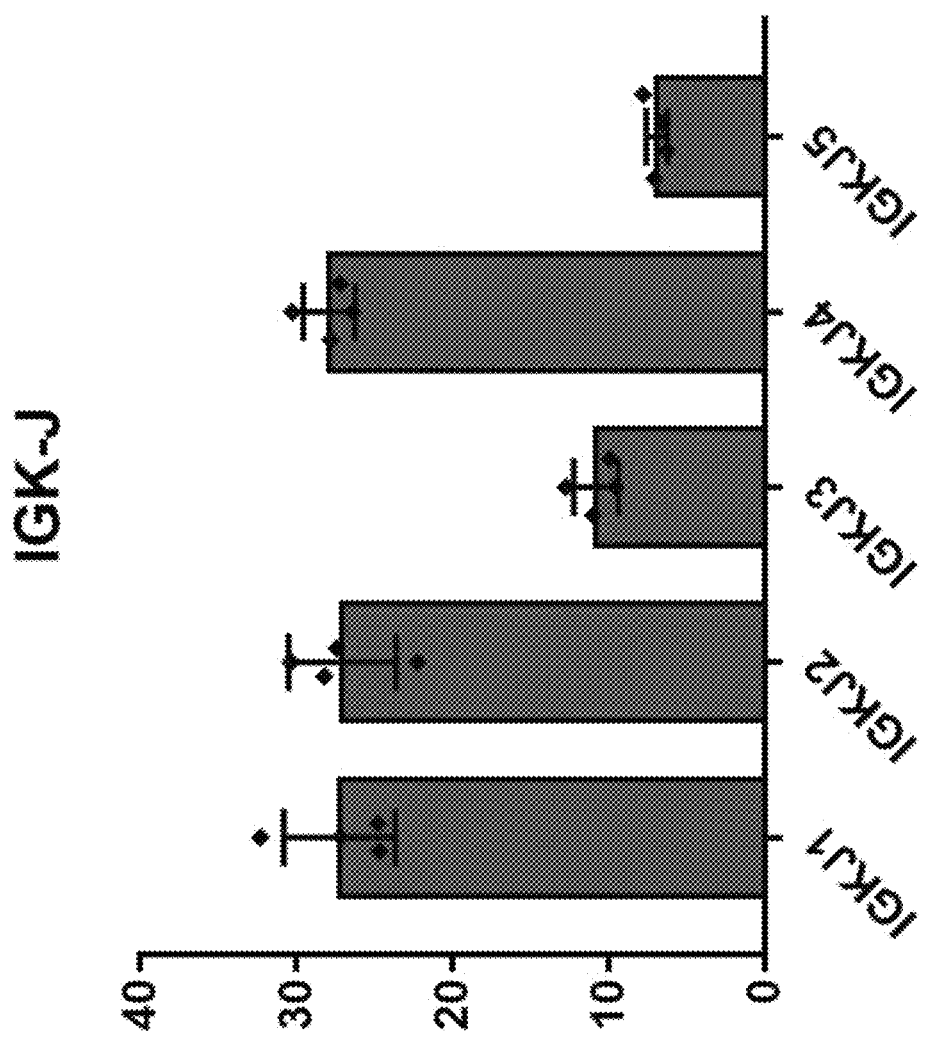
FIG. 71C shows IGKJ usage in naïve hVH/hVL mice.

The heavy chain IGHV, IGHD and IGHJ usage in the hVH/hVL naïve mice (without antigen stimulation) was analyzed. The results are shown in FIGS. 70A-70D. In addition, the kappa chain IGKV and IGKJ usage was also analyzed. The results are shown in FIGS. 71A-71C.

Germline usage in naïve hVH/hVL mice was determined by next generation sequencing (NGS). For example, as shown in FIG. 71C, IGKJ1, IGKJ2 and IGKJ4 were frequently used in naïve hVH/hVL mice, while IGKJ3 and IGKJ5 were less frequently observed. Such an IGKJ germline usage pattern is consistent with literature reports of human IGKJ germline usage.

Figure 72:
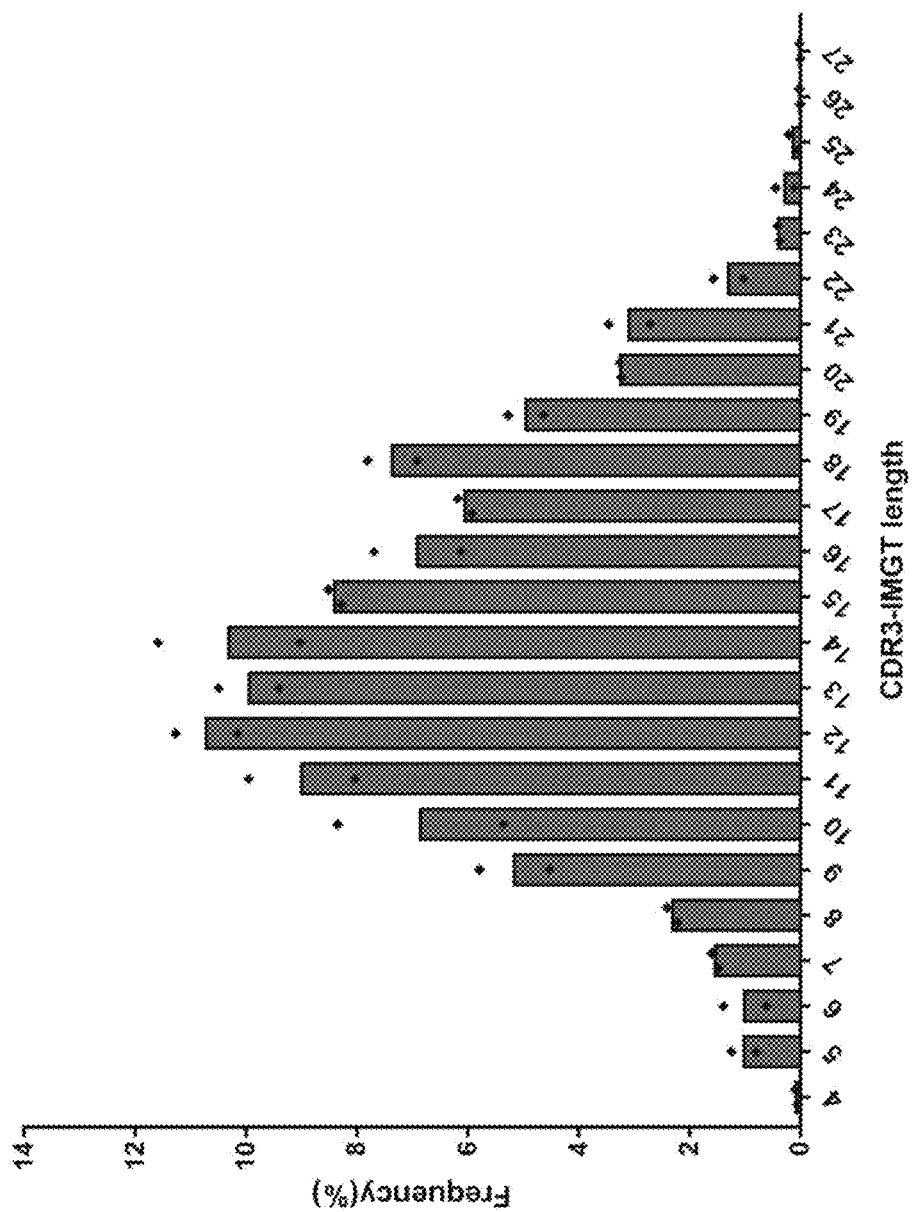
FIG. 72 is a histogram showing heavy chain CDR3 amino acid length distribution from naïve hVH/hVL mice.

The heavy chain CDR3 length distribution was determined by NGS sequencing of immune repertoire from the splenocytes of naïve hVH/hVL mice (n=2). As shown in FIG. 72, the median length of CDR3 was 14 amino acids. The results were consistent with the median length of human heavy chain CDR3 in the human immune system.

Figure 73:
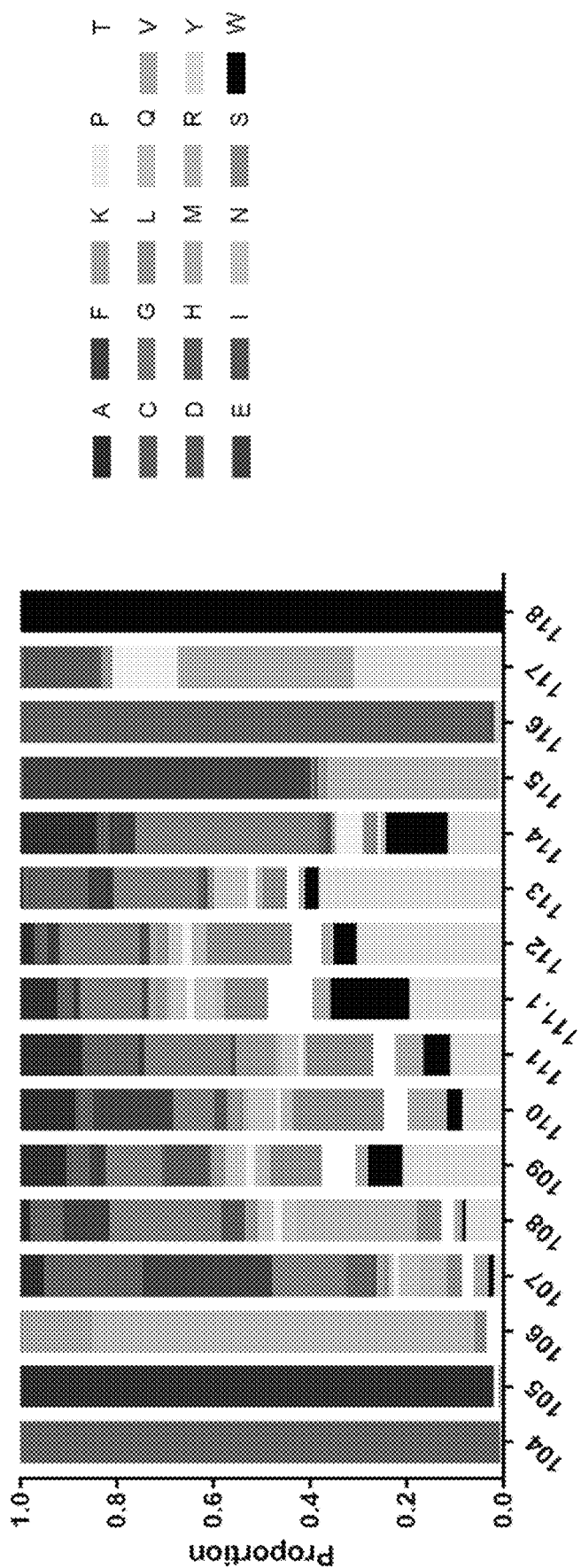
FIG. 73 shows amino acid frequency at heavy chain CDR3 in naïve hVH/hVL mice.

The type of amino acids at each position of heavy chain CDR3 (HCDR3) was analyzed (FIG. 73). Multiple patterns, including the increasing frequency of tyrosine usage and the increasing usage of DH2 (IGHD2) germline family, were observed. These patterns are similar to the amino acid composition in human HCDR3.

Figure 74:
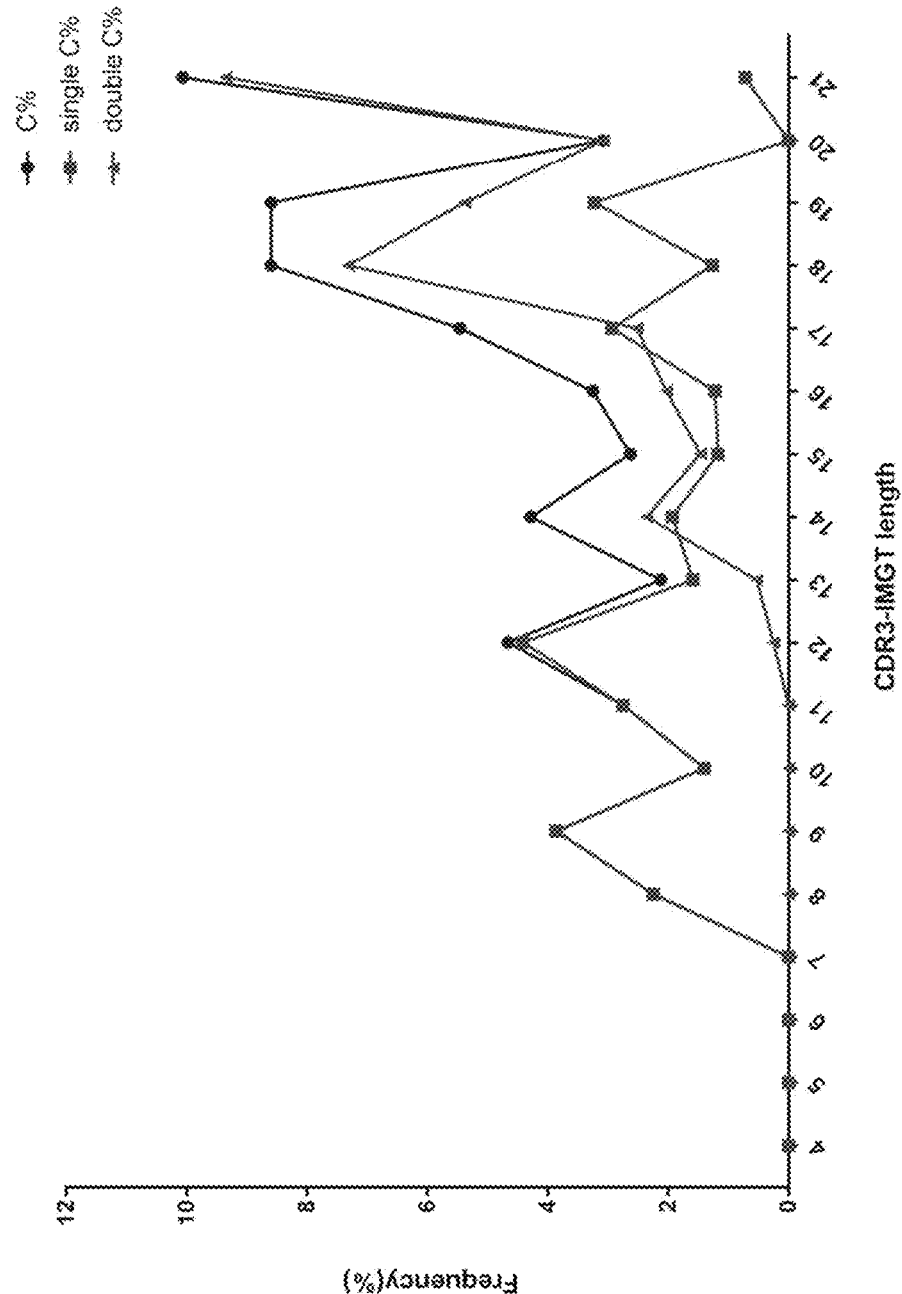
FIG. 74 shows the frequency of HCDR3 that contains cysteine residues in the hVH/hVL mice.
Figures 75A, 75B, 75C, 75D, 75E, 75F:
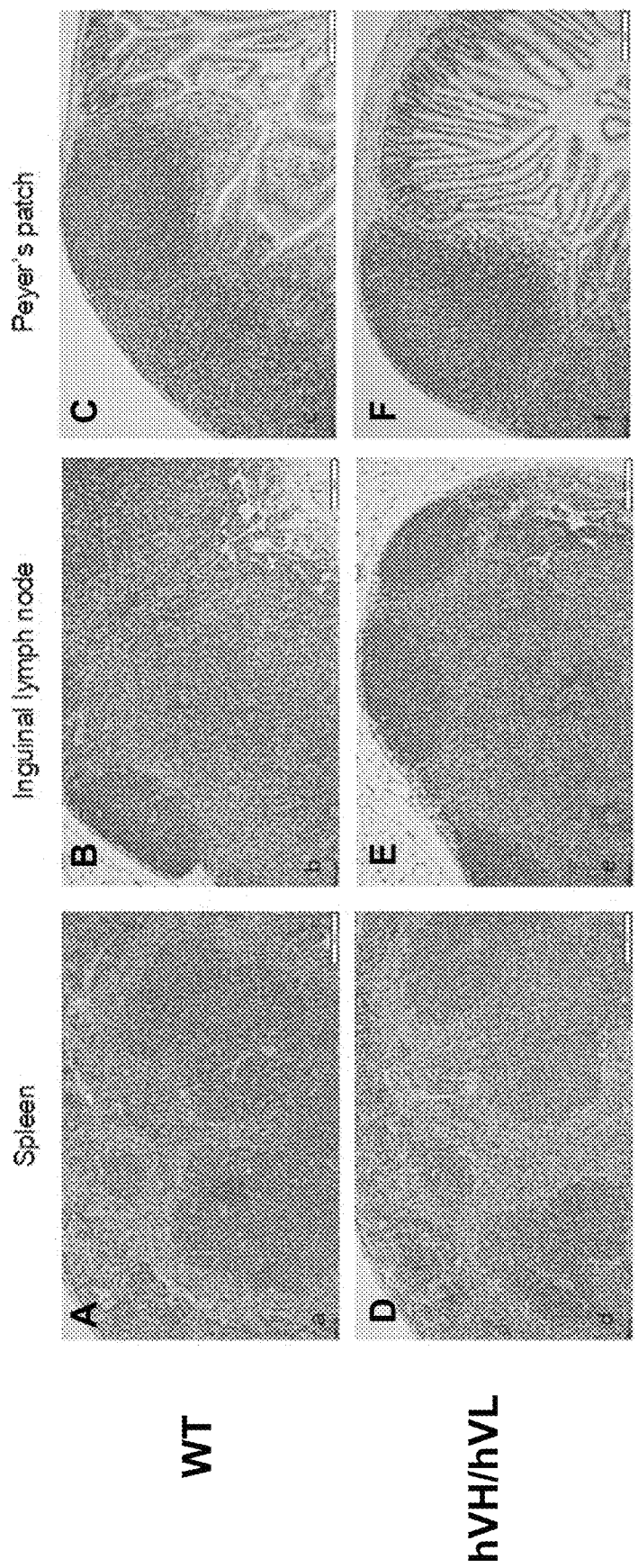
FIG. 75A is a histology image of spleen from naïve wild-type mice.
FIG. 75B is a histology image of inguinal lymph node from naïve wild-type mice.
FIG. 75C is a histology image of Peyer's patch from naïve wild-type mice.
FIG. 75D is a histology image of spleen from naïve hVH/hVL mice.
FIG. 75E is a histology image of inguinal lymph node from naïve hVH/hVL mice.
FIG. 75F is a histology image of Peyer's patch from naïve hVH/hVL mice.
Figure 76A:
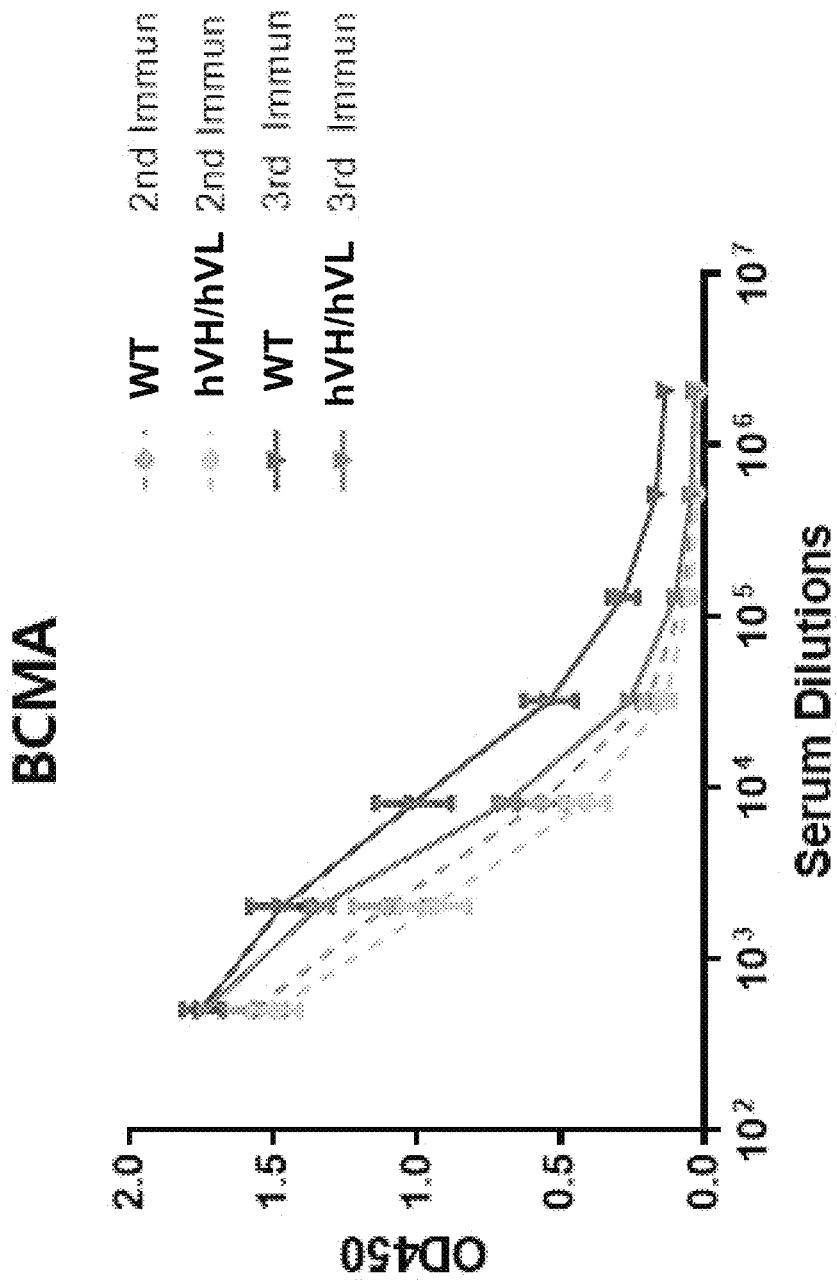
FIG. 76A shows BCMA-specific antibody titer post second and third immunization using human BCMA (B-cell maturation antigen) as antigens in wild-type and hVH/hVL mice.
Figure 76B:
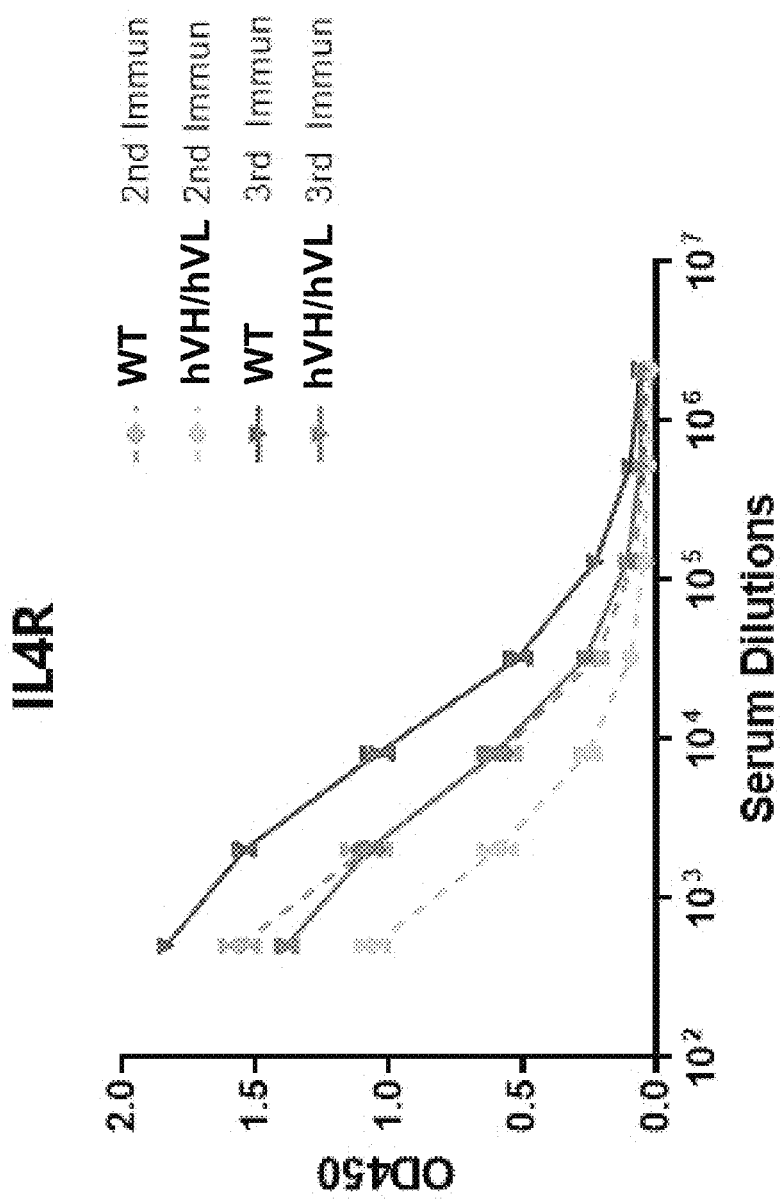
FIG. 76B shows IL4R-specific antibody titer post second and third immunization using human IL4R (interleukin-4 receptor) as antigens in wild-type and hVH/hVL mice.
Figure 76C:
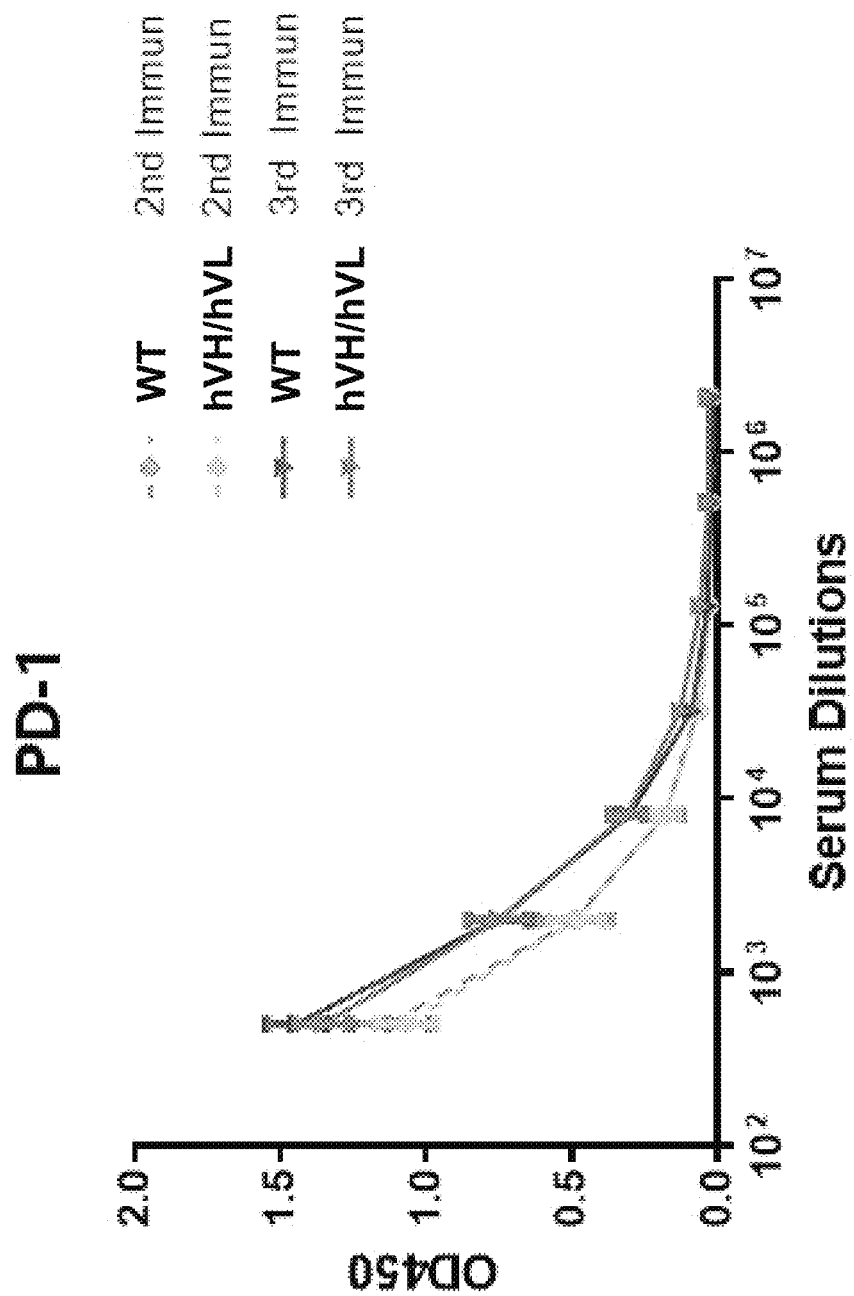
FIG. 76C shows PD-1-specific antibody titer post second and third immunization using human PD-1 (Programmed cell death protein 1) as antigens in wild-type and hVH/hVL mice.
Figure 76D:
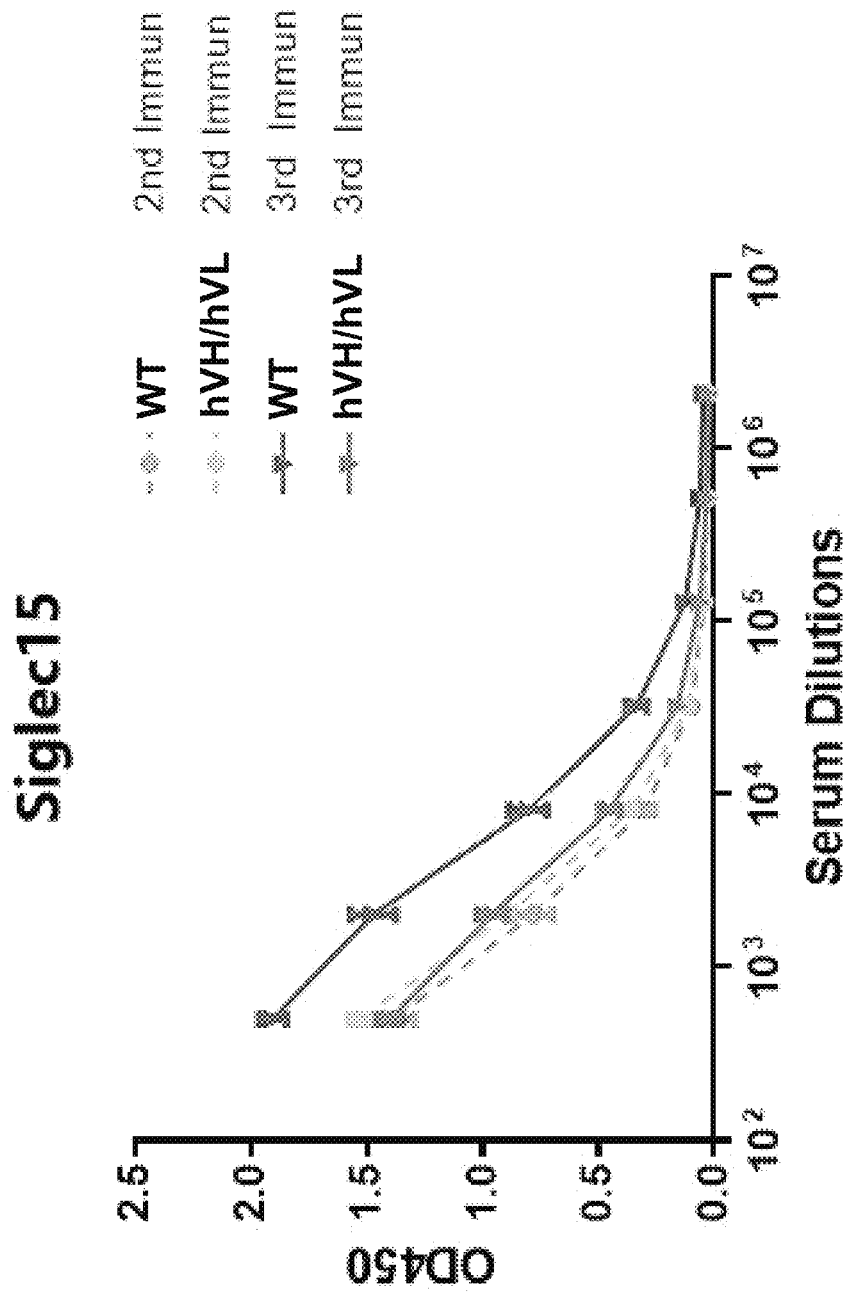
FIG. 76D shows Siglec15-specific antibody titer post second and third immunization using human Siglec15 (sialic acid binding ig-like lectin 15) as antigens in wild-type and hVH/hVL mice.
Figure 76E:
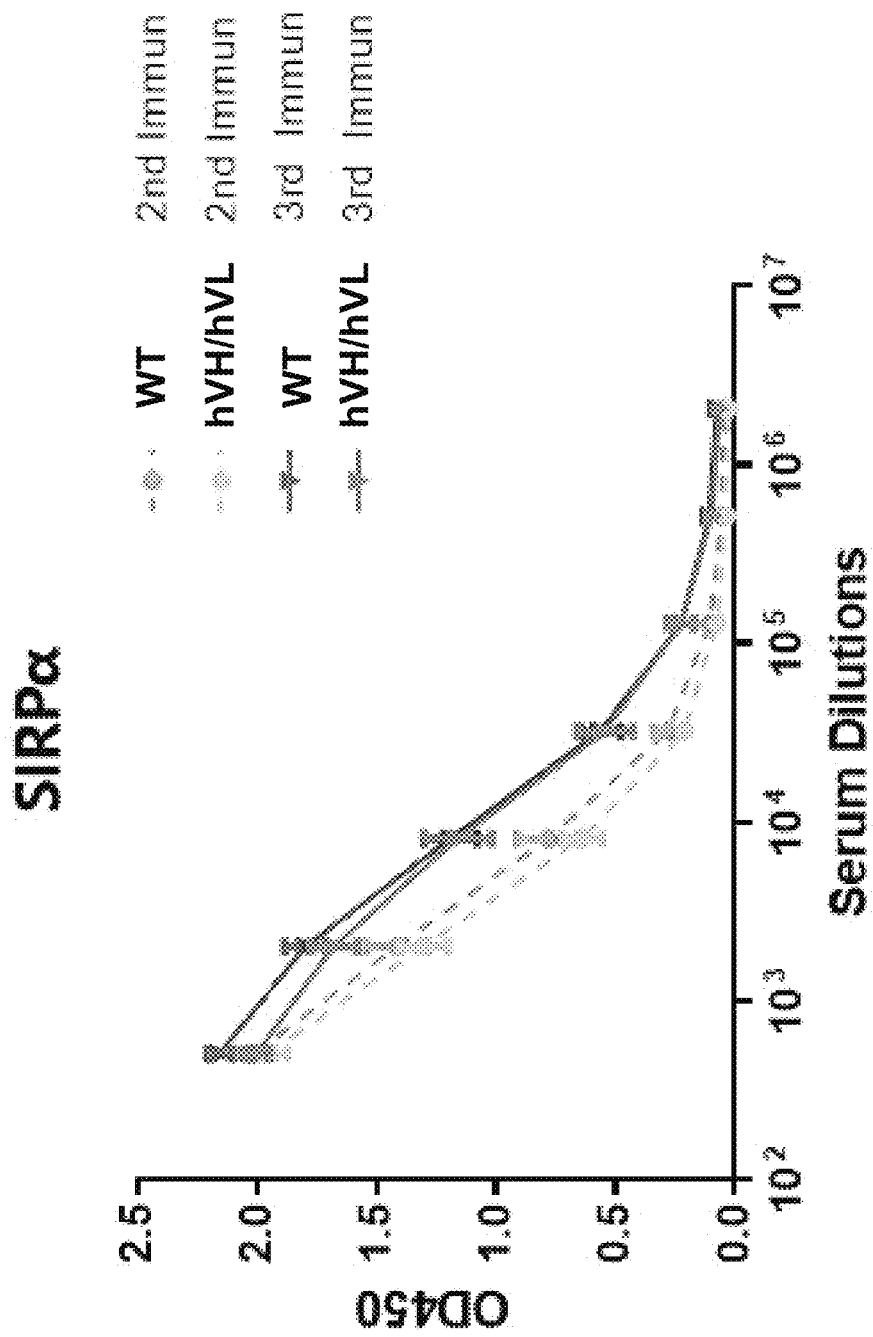
FIG. 76E shows SIRPα-specific antibody titer post second and third immunization using human SIRPα (signal regulatory protein a) as antigens in wild-type and hVH/hVL mice.

Cysteine residue can form disulfide bond. Human HCDR3 may contain one cysteine residue or two cysteine residues, while mouse HCDR3 typically contains no cysteine. Results in FIG. 74 shows that the frequency of HCDR3 of the hVH/hVL mice that contains cysteine residues and the frequency increases as the length of HCDR3 increases. This result is consistent with the HCDR3 diversity in human peripheral blood mononuclear cells (PBMCs).

Example 15: Lymphoid Organ Histology Analysis

Spleen, inguinal lymph node, and Peyer's patch from naïve wild-type or naïve hVH/hVL mice were stained with H&E. Representative sections are shown in FIGS. 75A-75F. Wild-type (C57BL/6) mice and hVH/hVL mice exhibited normal structure with well-defined follicles and no significant differences in histological morphology were observed.

Example 16: Antibody Generation in hVH/hVL Mice

After the second and the third immunization with BCMA, IL4R, PD-1, Siglec15, and SIRPa antigens, blood was collected and the antigen-specific antibody titers of wildtype (C57BL/6) mice and hVH/hVL mice were analyzed by ELISA (FIGS. 76A-76E). The results showed that hVH/hVL mice can produce antibodies that specifically binds to the antigen and the immune response of the wild-type and hVH/hVL mice were similar.

Example 17: B-Cell Development in hVH/hVL Mice

Figure 77A:
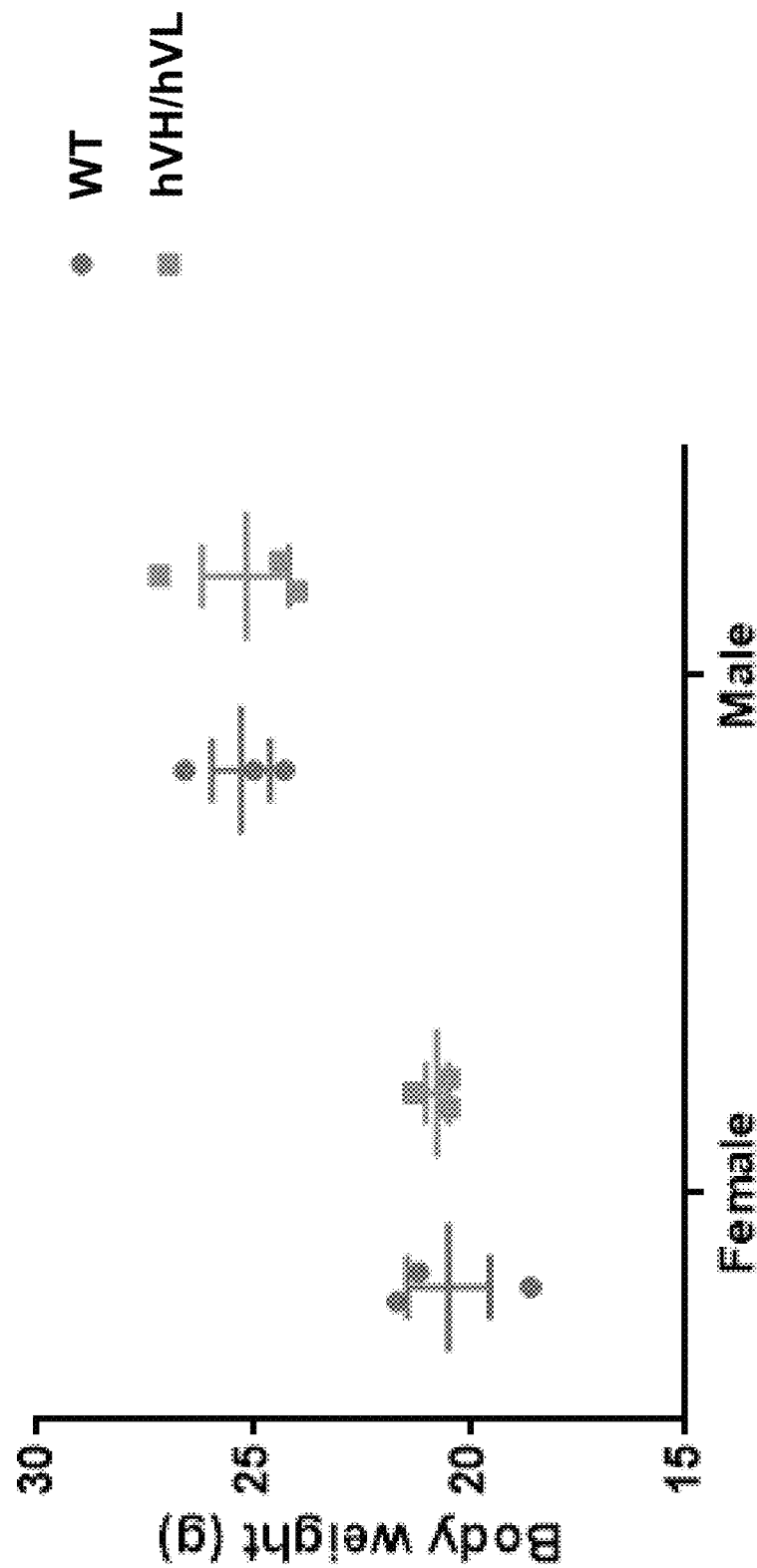
FIG. 77A shows body weight of wild-type mice and hVH/hVL mice after immunization.
Figure 77B:
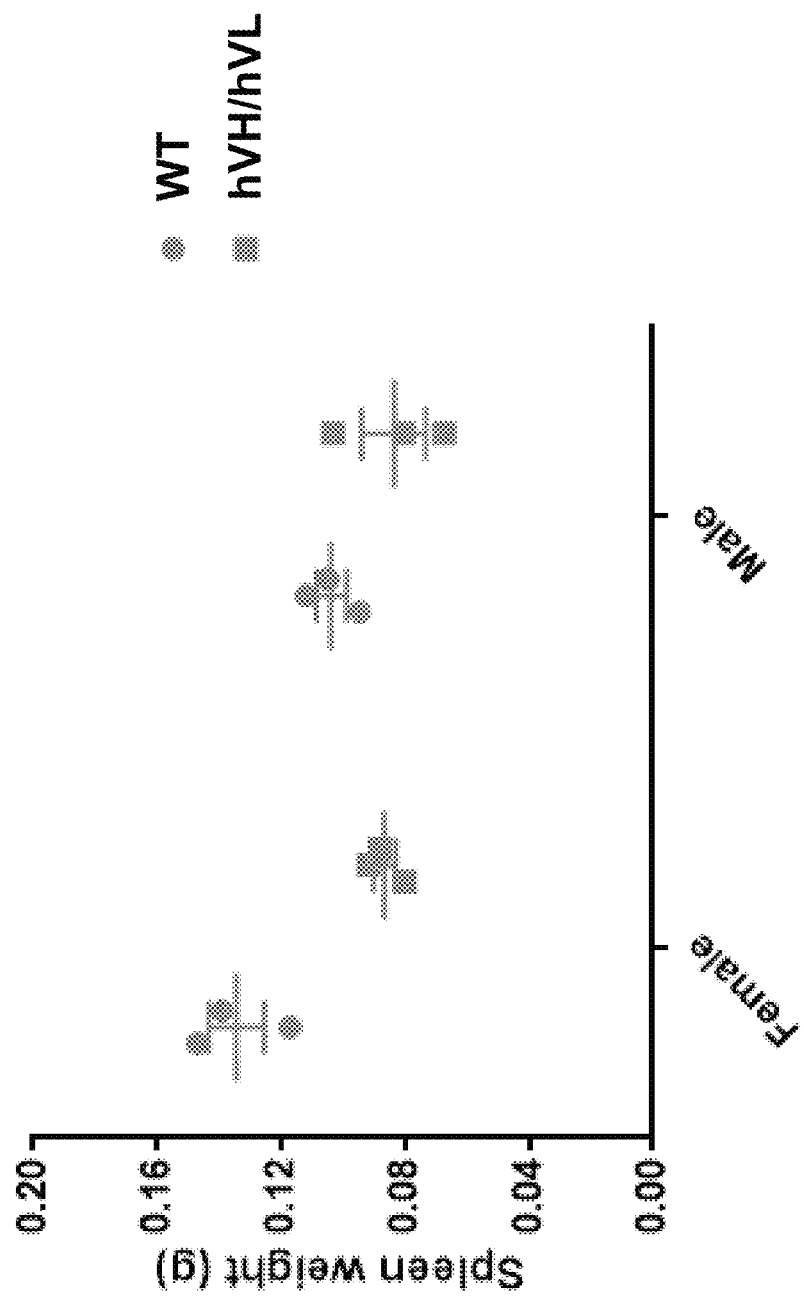
FIG. 77B shows spleen weight of wild-type mice and hVH/hVL mice after immunization.

Experiments were performed to compare the immune systems of the humanized VH/VL mice and the wild-type mice after immunization. The body weight and spleen weight were measured in wild-type and hVH/hVL mice (FIGS. 77A-77B). No significant differences in average body weight and spleen weight were detected between wild-type and hVH/hVL mice.

Figure 78:
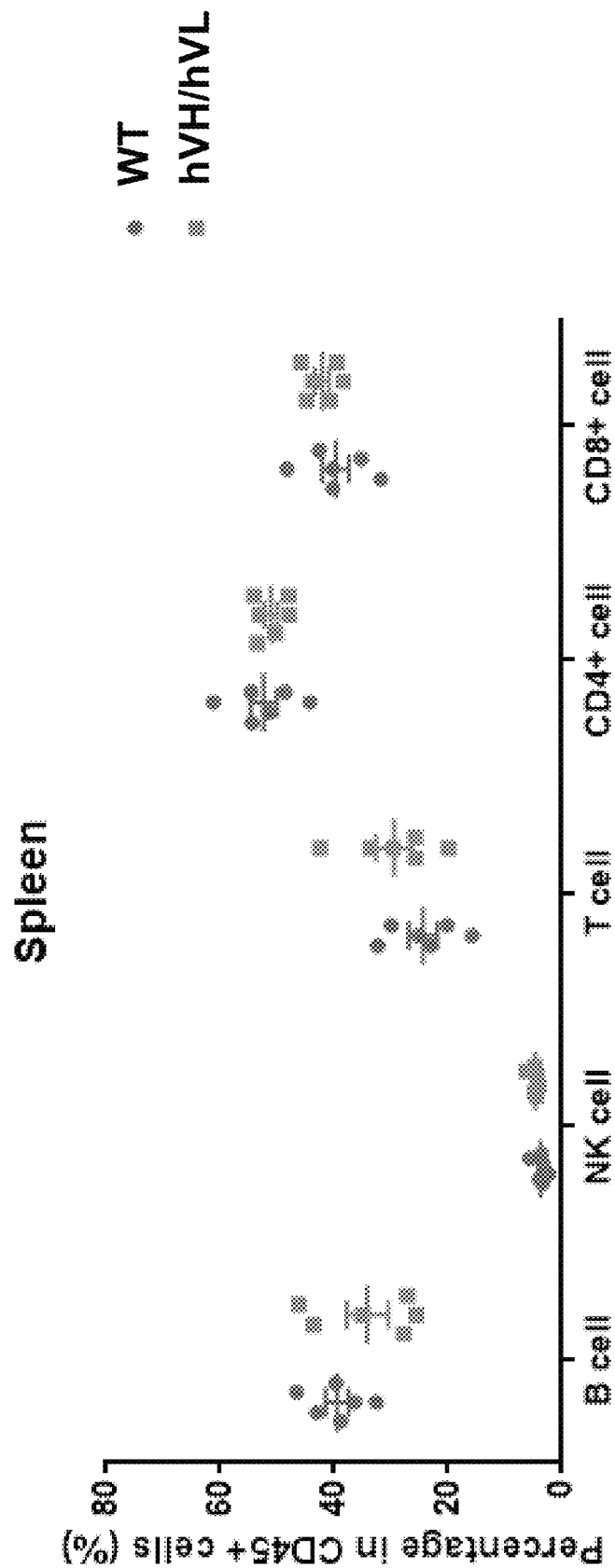
FIG. 78 shows percentage of immune cells in the spleen of wild-type mice and hVH/hVL mice after immunization.

Flow cytometry was performed to analyze lymphocyte populations and distribution in the spleen (FIG. 78) and B cell populations in the spleen and bone marrow (FIGS. 79A-79B, 80A-80C) of the mice.

Figure 79A:
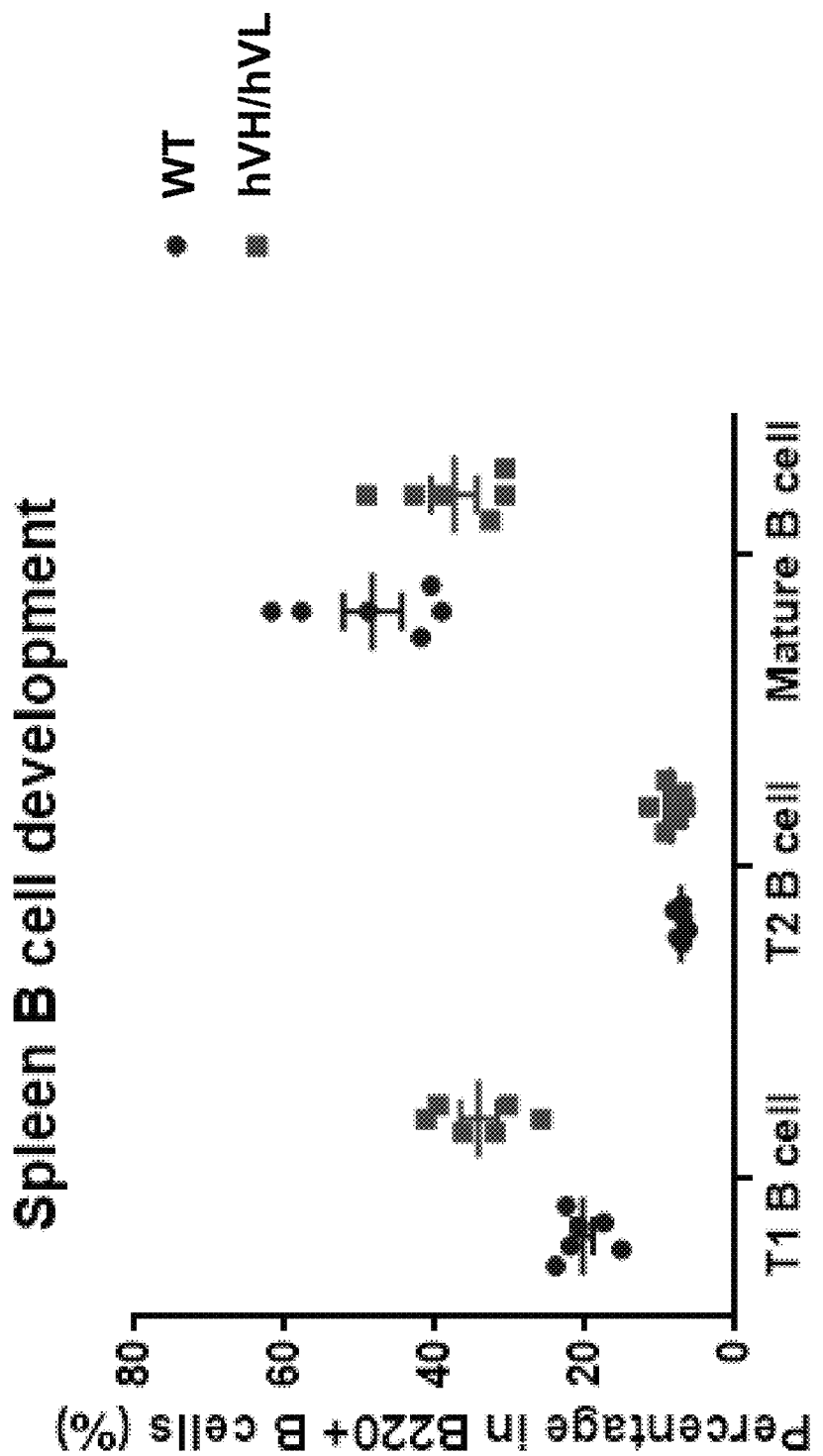
FIG. 79A shows percentage of transitional type 1 (T1, $B220^+IgM^+IgD^-$), transitional type 2 (T2, $B220^+IgM^+IgD^+$) and mature (M, $B220^+IgM^{low}IgD^+$) B cell population in spleen B cells. The spleen B cells are from wild-type or hVH/hVL mice after immunization.
Figure 79B:
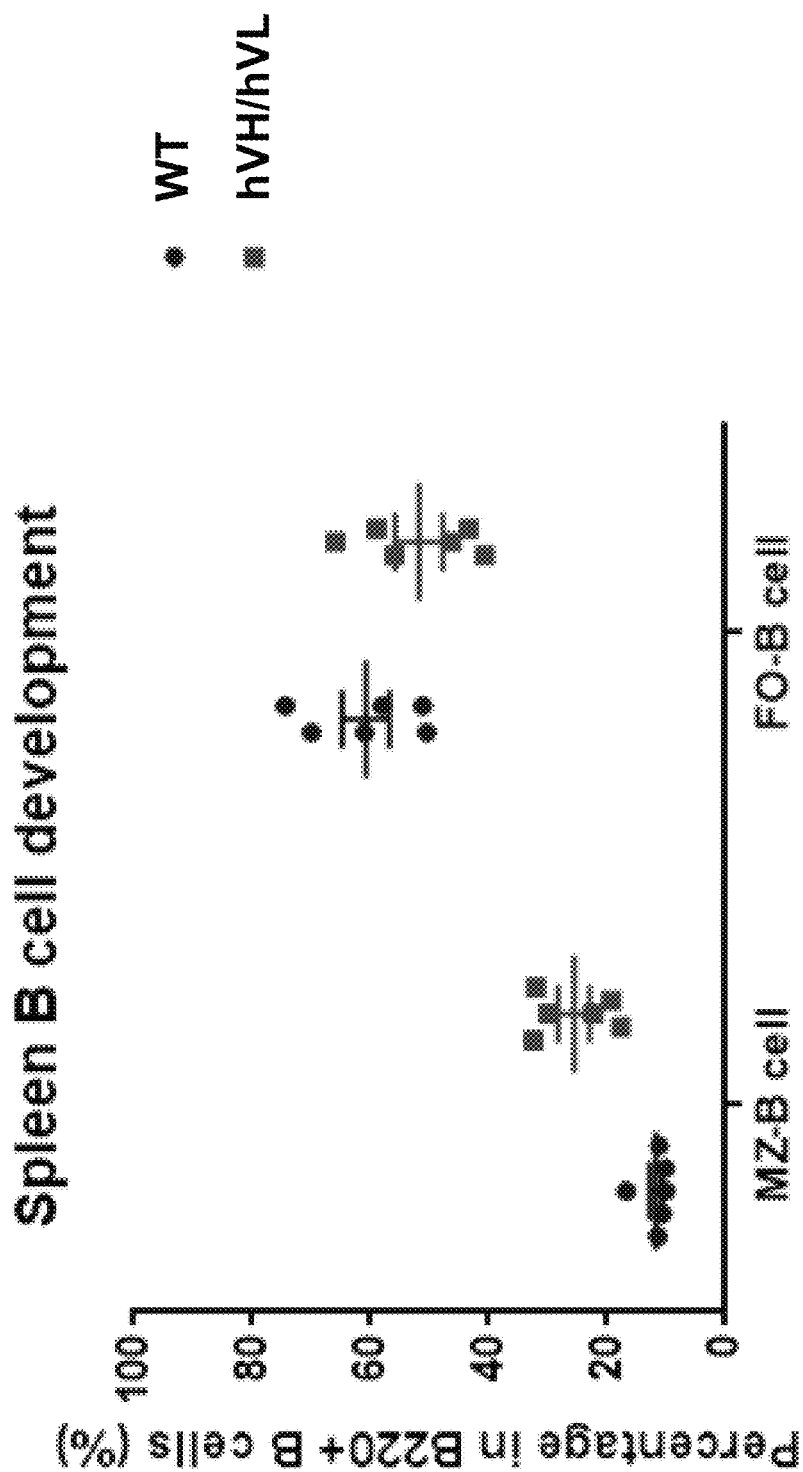
FIG. 79B shows percentage of marginal-zone (MZ) and follicular (FO) B cell population in spleen B cells. The spleen B cells are from wild-type or hVH/hVL mice after immunization.

FIG. 79A indicated percentages of B cells at different developmental stages in spleen. In addition, B cell development were also evaluated at the spleen marginal zone and follicular zone. FIG. 79B showed percentages of splenic B cells at spleen marginal zone (MZ-B) and follicular zone (FO-B). No significant differences were observed between the wild-type mice and the hVH/hVL mice.

Figure 80A:
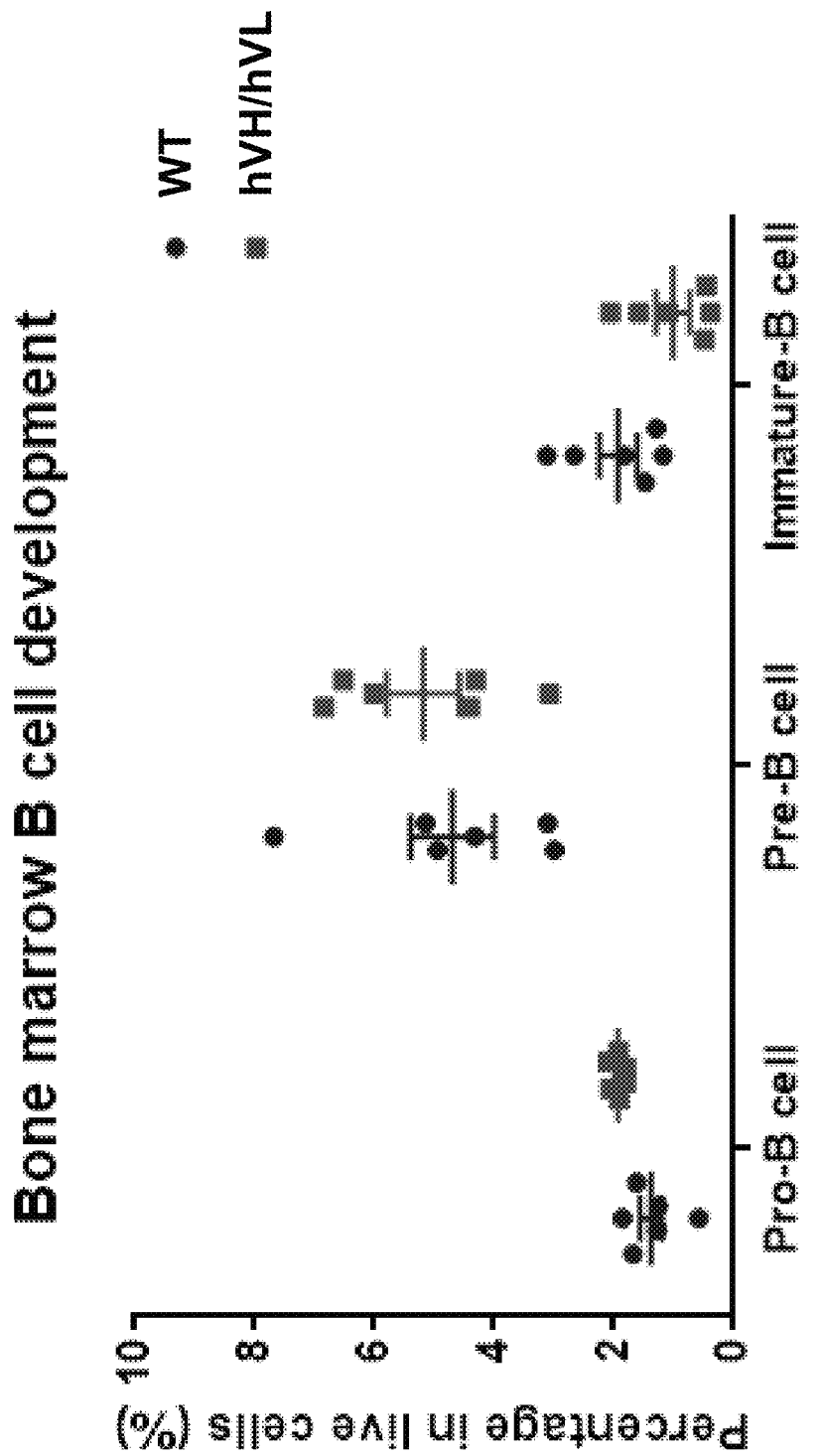
FIG. 80A shows percentage of Pro-B-cell ($B220^{low}CD43^{high}IgM^{low}$), Pre-B-cell ($B220^{low}CD43^{int}IgM^{low}$) and immature-B-cell ($B220^{high}CD43^{low}IgM^{high}$) population in bone marrow B cells. The bone marrow B cells are from wild-type or hVH/hVL mice after immunization.

FIG. 80A indicated percentages of B cells at different developmental stages in bone marrows. B cell progenitor cells in bone marrow were analyzed by flow cytometry. No significant differences were observed between the wild-type mice and the hVH/hVL mice.

Figure 80B:
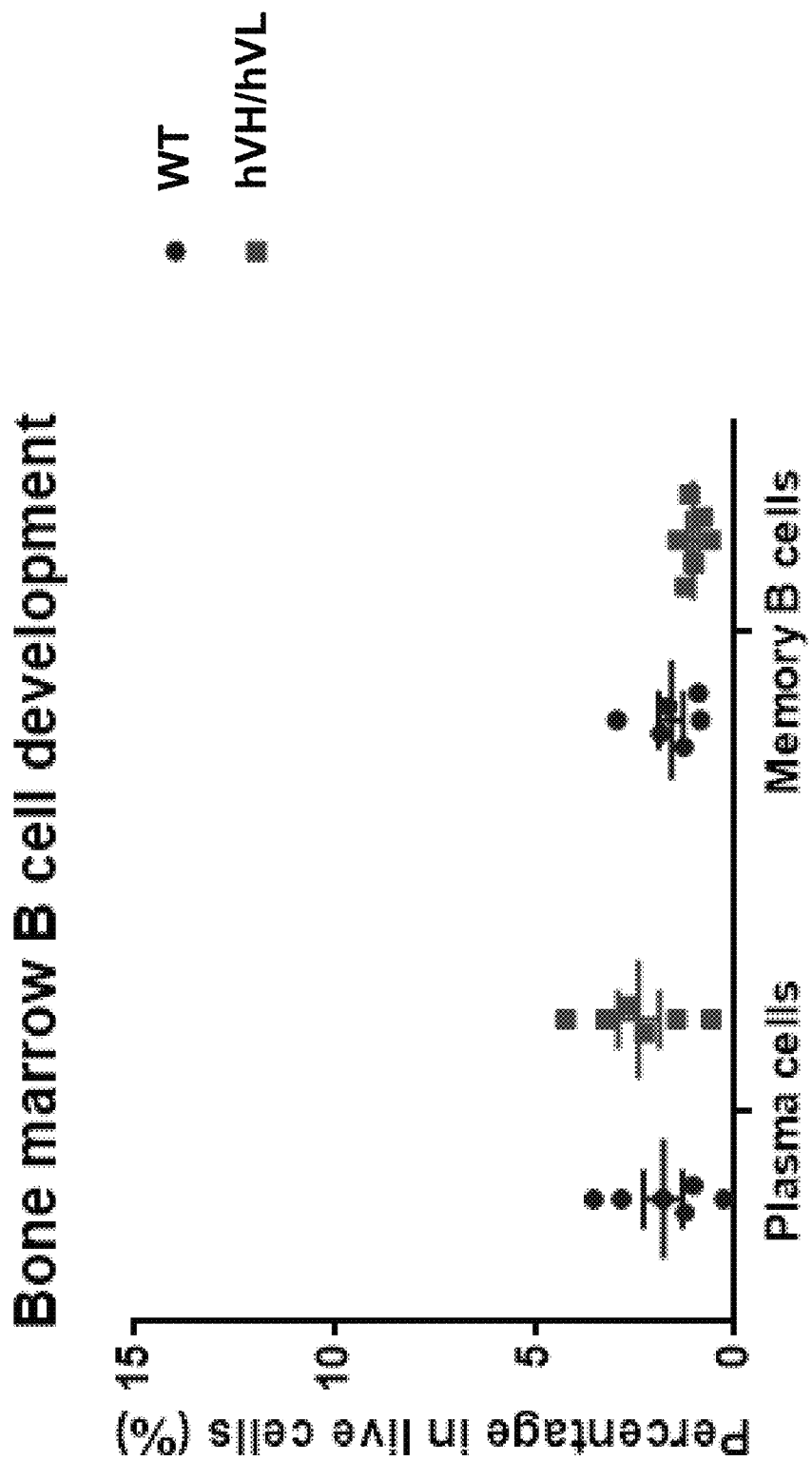
FIG. 80B shows percentage of plasma cell ($B220^{low}IgM^-IgD^-CD138^-$) and memory B cell ($B220^+IgM^+IgD^-CD38^+$) population in bone marrow B cells. The bone marrow B cells are from wild-type or hVH/hVL mice after immunization.
Figure 80C:
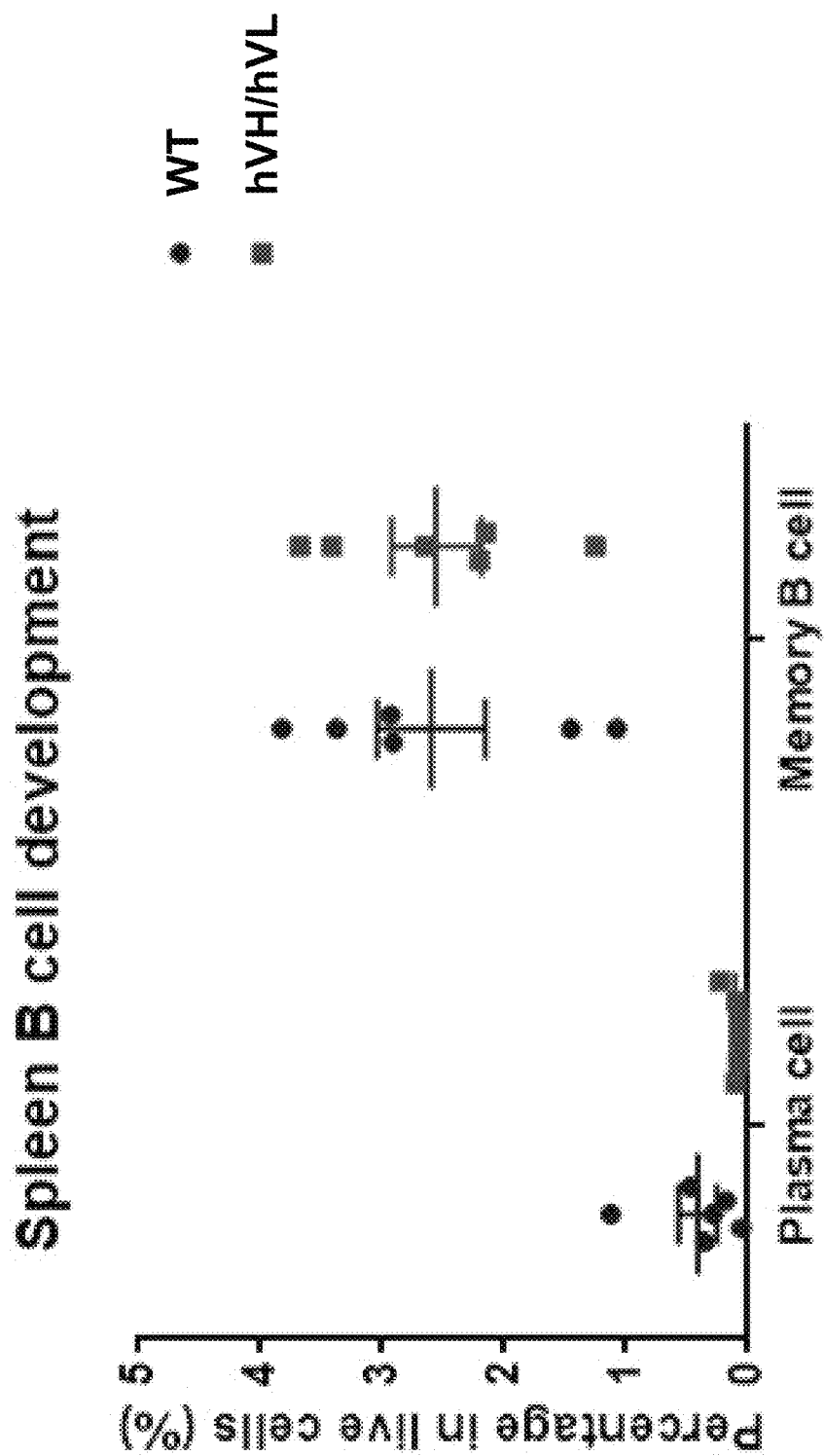
FIG. 80C shows percentage of plasma cell ($B220^{low}IgM^-IgD^-CD138^-$) and memory B cell ($B220^+IgM^+IgD^-CD38^+$) population in spleen B cells. The spleen B cells are from wild-type or hVH/hVL mice after immunization.

In addition, B cell development were also evaluated in bone marrow or spleen by flow cytometry to selectively stain plasma cells (B220$^{low}$IgM$^-$IgD$^-$CD138$^-$) and memory B cells (B220$^+$IgM$^-$IgD$^-$CD38$^+$) (FIGS. 80B-80C). No significant differences were observed between the wild-type mice and the hVH/hVL mice.

Figure 81:
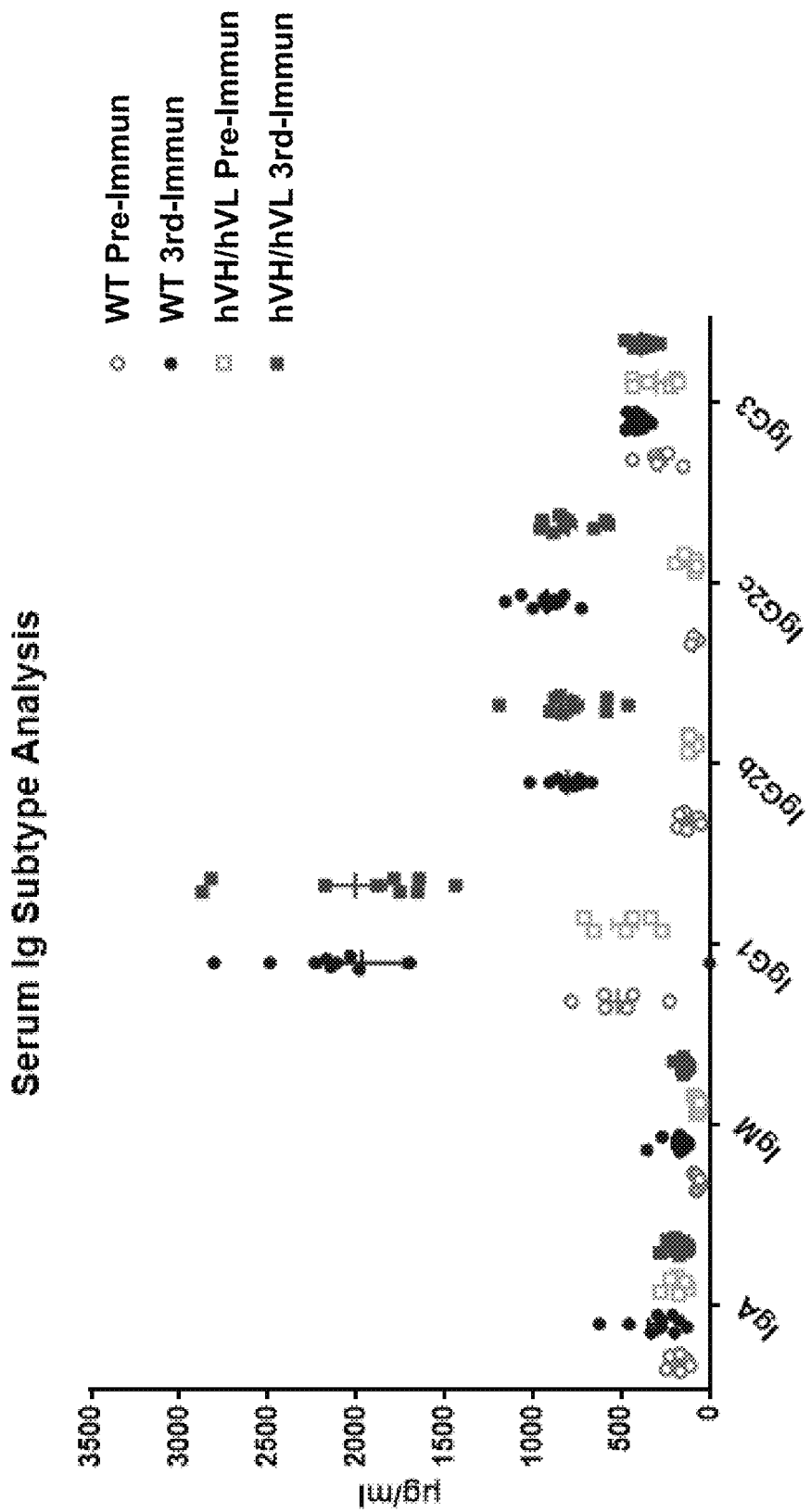
FIG. 81 shows concentration of serum immunoglobulin (Ig) subtypes in naïve wild-type or hVH/hVL mice or after the third immunization. The Ig subtype concentrations were determined by ELISA.
Figure 82:
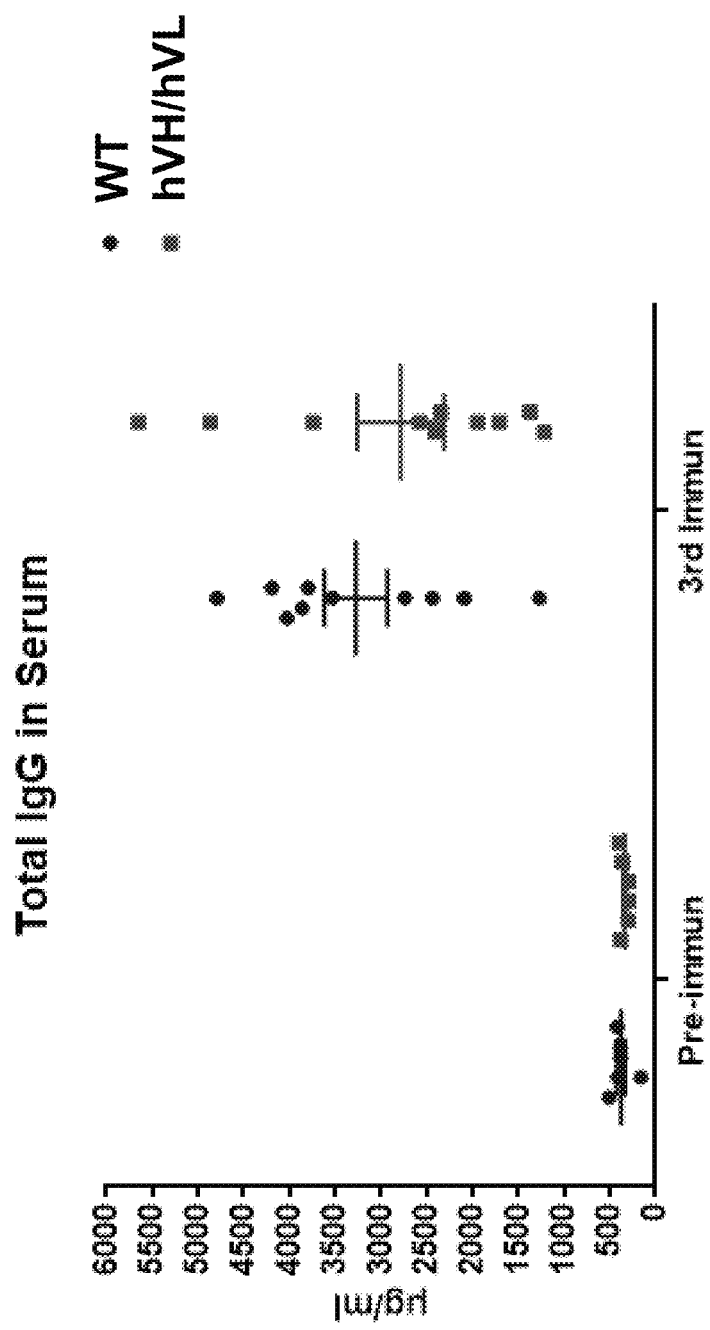
FIG. 82 shows serum total IgG concentration in naïve wild-type or hVH/hVL mice or after immunization. The IgG concentrations were determined by ELISA.

Different immunoglobulin (Ig) subtypes in the serum of hVH/hVL and wild-type mice were quantitatively measured by ELISA. A total of six mice were selected for each group. No significant differences in IgA, IgG1, IgG2b, IgG2c, IgG3 and IgM levels were observed (FIG. 81). In addition, the total amount of IgG in the serum of hVH/hVL and wild-type mice were quantitatively measured by ELISA. No significant differences were observed (FIG. 82).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified rodent comprising at an endogenous heavy chain immunoglobulin gene locus human Immunoglobulin Heavy Variable (IGHV) genes, human Immunoglobulin Heavy Diversity (IGHD) genes, and human Immunoglobulin Heavy Joining (IGHJ) genes at the heavy chain immunoglobulin gene locus of human chromosome 14 from a human cell, wherein the human IGHV genes, the human IGHD genes, and the human IGHJ genes are operably linked and can undergo VDJ rearrangement, wherein a contiguous human sequence is integrated into the endogenous chromosome by recombination, and the human sequence is at least 500 kb, wherein the modification can be detected by PCR using one or more primer pairs selected from the group consisting of:
(a) SEQ ID NO: 13 and SEQ ID NO: 14;
(b) SEQ ID NO: 15 and SEQ ID NO: 16;
(c) SEQ ID NO: 17 and SEQ ID NO: 18;
(d) SEQ ID NO: 19 and SEQ ID NO: 20;
(e) SEQ ID NO: 21 and SEQ ID NO: 22;
(f) SEQ ID NO: 23 and SEQ ID NO: 24; and
(g) SEQ ID NO: 25 and SEQ ID NO: 26.

2. The rodent of claim 1, wherein the rodent comprises a disruption in the rodent's endogenous heavy chain immunoglobulin gene locus.

3. The rodent of claim 2, wherein the rodent is a mouse and the disruption in the endogenous heavy chain immunoglobulin gene locus comprises a deletion of a contiguous sequence starting from mouse IGHV1-85 gene to mouse IGHJ4 gene.

4. The rodent of claim 1, wherein the rodent is homozygous with respect to the integrated human sequence at the endogenous heavy chain immunoglobulin gene locus.

5. The rodent of claim 1, wherein the rodent comprises a disruption in the rodent's endogenous light chain immunoglobulin gene locus.

6. The rodent of claim 1, wherein the rodent further comprises at an endogenous light chain immunoglobulin gene locus, one or more human Immunoglobulin Kappa Variable (IGKV) genes, and one or more human Immunoglobulin Kappa Joining (IGKJ) genes.

7. The rodent of claim 6, wherein the rodent further comprises all human IGKV genes and all human IGKJ genes at the endogenous light chain immunoglobulin gene locus.

8. The rodent of claim 7, wherein the rodent can detectably express IGKV1D-12, IGKV2D-30, IGKV1-27, IGKV6-21, IGKV1-6, IGKV1-39, IGKV1-16, IGKV1-17, IGKV2D-29, IGKV3-11, IGKV1-5, IGKV1-12, IGKV1-9, IGKV3-20, IGKV3-15, IGKV2-28, IGKV2-30, IGKV1-33, IGKV4-1, IGKV6D-41, IGKV3D-11, IGKV2D-24, IGKV1D-43, IGKV1D-17, IGKV7-3, IGKV2D-26, IGKV1-37, IGKV2-29, IGKV1-13, IGKV5-2, IGKV2-40, IGKV3-7, IGKV3D-20, IGKV1D-8, IGKV6D-21, IGKV1-8, IGKV2-24, and IGKV3D-15.

9. The rodent of claim 1, wherein the rodent can produce a humanized antibody.

10. A cell obtained from the rodent of claim 1.

11. The rodent of claim 1, wherein the rodent is a mouse.

12. The rodent of claim 1, wherein the rodent comprises human IGHV3-64D and IGHV5-10-1 at the endogenous heavy chain immunoglobulin gene locus.

13. The rodent of claim 1, wherein the rodent comprises human IGHV(III)-82, IGHV7-81, IGHV4-80, IGHV3-79, IGHV(II)-78-1, IGHV5-78, IGHV7-77, IGHV(III)-76-1, IGHV3-76, IGHV3-75, and IGHV(II)-74-1 at the endogenous heavy chain immunoglobulin gene locus.

14. The rodent of claim 1, wherein the rodent can detectably express IGHV3-15, IGHV3-53, IGHV3-66, IGHV5-51, IGHV1-24, IGHV1-18, IGHV1-69, IGHV3-7, IGHV3-74, IGHV3-23, IGHV3-43, IGHV3-21, IGHV3-30-3, IGHV4-59, IGHV6-1, IGHV3-48, IGHV4-34, IGHV4-39, IGHV3-33, IGHV3-30, IGHV4-61, IGHV3-47, IGHV3-NL1, IGHV3-69-1, IGHV7-4-1, IGHV1-58, IGHV4-28, IGHV2-26, IGHV2-5, IGHV3-64, IGHV3-20, IGHV2-70, IGHV3-11, IGHV4-30-2, IGHV3-13, IGHV3-49, IGHV5-10-1, IGHV3-72, IGHV1-2, IGHV4-30-4, IGHV1-46, IGHV3-64D, IGHV1-3, IGHV3-73, IGHV4-4, and IGHV4-31.

15. The rodent of claim 1, wherein the rodent comprises at the endogenous heavy chain immunoglobulin gene locus one short flippase recognition target (FRT) site and one loxP recognition sequence, wherein the integrated human sequence is between the FRT site and the loxP recognition sequence.

16. The rodent of claim 1, wherein the modification can be detected by PCR using the primer pair of SEQ ID NO: 13 and SEQ ID NO: 14.

17. The rodent of claim 1, wherein the modification can be detected by PCR using the primer pair of SEQ ID NO: 15 and SEQ ID NO: 16.

18. The rodent of claim 1, wherein the modification can be detected by PCR using the primer pair of SEQ ID NO: 17 and SEQ ID NO: 18.

19. The rodent of claim 1, wherein the modification can be detected by PCR using the primer pair of SEQ ID NO: 19 and SEQ ID NO: 20.

20. The rodent of claim 1, wherein the modification can be detected by PCR using the primer pair of SEQ ID NO: 21 and SEQ ID NO: 22.

21. The rodent of claim 1, wherein the modification can be detected by PCR using the primer pair of SEQ ID NO: 23 and SEQ ID NO: 24.

22. The rodent of claim 1, wherein the modification can be detected by PCR using the primer pair of SEQ ID NO: 25 and SEQ ID NO: 26.

\* \* \* \* \*

UNITED STATES PATENT AND TRADEMARK OFFICE
CERTIFICATE OF CORRECTION

PATENT NO. : 12,004,495 B2
APPLICATION NO. : 17/010587
DATED : June 11, 2024
INVENTOR(S) : Yuelei Shen et al.

Page 1 of 1

It is certified that error appears in the above-identified patent and that said Letters Patent is hereby corrected as shown below:

In the Claims

In Column 94, Line 35, in Claim 8, delete "IGKVID-12," and insert -- IGKV1D-12, --;

In Column 94, Line 40, in Claim 8, delete "IGKVID-43, IGKVID-17," and insert -- IGKV1D-43, IGKV1D-17, --.

Signed and Sealed this
Twenty-fourth Day of December, 2024

Derrick Brent
*Acting Director of the United States Patent and Trademark Office*

SEQUENCE LISTING

```
<160> NUMBER OF SEQ ID NOS: 54

<210> SEQ ID NO 1
<211> LENGTH: 31
<212> TYPE: DNA
<213> ORGANISM: Artificial Sequence
<220> FEATURE:
<223> OTHER INFORMATION: Synthetic primer

<400> SEQUENCE: 1
gccaaggaat ttaaaagggg attgaaagca a                              31

<210> SEQ ID NO 2
<211> LENGTH: 25
<212> TYPE: DNA
<213> ORGANISM: Artificial Sequence
<220> FEATURE:
<223> OTHER INFORMATION: Synthetic primer

<400> SEQUENCE: 2
gccctccatg tacagcttca tgtgc                                     25

<210> SEQ ID NO 3
<211> LENGTH: 25
<212> TYPE: DNA
<213> ORGANISM: Artificial Sequence
<220> FEATURE:
<223> OTHER INFORMATION: Synthetic primer

<400> SEQUENCE: 3
actgggcttg tcgagacaga gaaag                                     25

<210> SEQ ID NO 4
<211> LENGTH: 25
<212> TYPE: DNA
<213> ORGANISM: Artificial Sequence
```

```
<220> FEATURE:
<223> OTHER INFORMATION: Synthetic primer

<400> SEQUENCE: 4
ccacagcccg atctacttgg ctttt                                    25

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
gcaaggtttt gactaagcgg agcac                                    25

<210> SEQ ID NO 6
<211> LENGTH: 25
<212> TYPE: DNA
<213> ORGANISM: Artificial Sequence
<220> FEATURE:
<223> OTHER INFORMATION: Synthetic primer

<400> SEQUENCE: 6
tgacgcatgt gttttatcgg tctgt                                    25

<210> SEQ ID NO 7
<211> LENGTH: 25
<212> TYPE: DNA
<213> ORGANISM: Artificial Sequence
<220> FEATURE:
<223> OTHER INFORMATION: Synthetic primer

<400> SEQUENCE: 7
gtgcctgaca cgtgctacga gattt                                    25

<210> SEQ ID NO 8
<211> LENGTH: 25
<212> TYPE: DNA
<213> ORGANISM: Artificial Sequence
<220> FEATURE:
<223> OTHER INFORMATION: Synthetic primer

<400> SEQUENCE: 8
ttcaacaata agcagggcca gaggg                                    25

<210> SEQ ID NO 9
<211> LENGTH: 26
<212> TYPE: DNA
<213> ORGANISM: Artificial Sequence
<220> FEATURE:
<223> OTHER INFORMATION: Synthetic primer

<400> SEQUENCE: 9
tcaaagtcaa tttcctcagc gaggct                                   26

<210> SEQ ID NO 10
<211> LENGTH: 25
<212> TYPE: DNA
<213> ORGANISM: Artificial Sequence
<220> FEATURE:
<223> OTHER INFORMATION: Synthetic primer

<400> SEQUENCE: 10
agggagggaa tggaatgagg gtgat                                    25
```

```
<210> SEQ ID NO 11
<211> LENGTH: 25
<212> TYPE: DNA
<213> ORGANISM: Artificial Sequence
<220> FEATURE:
<223> OTHER INFORMATION: Synthetic primer

<400> SEQUENCE: 11
ccatgtgacc cattcgagtg tcctg                                         25

<210> SEQ ID NO 12
<211> LENGTH: 25
<212> TYPE: DNA
<213> ORGANISM: Artificial Sequence
<220> FEATURE:
<223> OTHER INFORMATION: Synthetic primer

<400> SEQUENCE: 12
ttgtgagggc tcaagttcag tgcat                                         25

<210> SEQ ID NO 13
<211> LENGTH: 31
<212> TYPE: DNA
<213> ORGANISM: Artificial Sequence
<220> FEATURE:
<223> OTHER INFORMATION: Synthetic primer

<400> SEQUENCE: 13
gccaaggaat ttaaaagggg attgaaagca a                                  31

<210> SEQ ID NO 14
<211> LENGTH: 25
<212> TYPE: DNA
<213> ORGANISM: Artificial Sequence
<220> FEATURE:
<223> OTHER INFORMATION: Synthetic primer

<400> SEQUENCE: 14
cgagagctgt ggagagaaag gcaaa                                         25

<210> SEQ ID NO 15
<211> LENGTH: 25
<212> TYPE: DNA
<213> ORGANISM: Artificial Sequence
<220> FEATURE:
<223> OTHER INFORMATION: Synthetic primer

<400> SEQUENCE: 15
tatgtcctgc gggtaaatag ctgcg                                         25

<210> SEQ ID NO 16
<211> LENGTH: 25
<212> TYPE: DNA
<213> ORGANISM: Artificial Sequence
<220> FEATURE:
<223> OTHER INFORMATION: Synthetic primer

<400> SEQUENCE: 16
agggagggaa tggaatgagg gtgat                                         25

<210> SEQ ID NO 17
<211> LENGTH: 25
<212> TYPE: DNA
<213> ORGANISM: Artificial Sequence
<220> FEATURE:
<223> OTHER INFORMATION: Synthetic primer
```

<400> SEQUENCE: 17
ccatgtgacc cattcgagtg tcctg                                           25

<210> SEQ ID NO 18
<211> LENGTH: 25
<212> TYPE: DNA
<213> ORGANISM: Artificial Sequence
<220> FEATURE:
<223> OTHER INFORMATION: Synthetic primer

<400> SEQUENCE: 18
cttaccattt gcggtgcctg gtttc                                           25

<210> SEQ ID NO 19
<211> LENGTH: 26
<212> TYPE: DNA
<213> ORGANISM: Artificial Sequence
<220> FEATURE:
<223> OTHER INFORMATION: Synthetic primer

<400> SEQUENCE: 19
tcaaagtcaa tttcctcagc gaggct                                          26

<210> SEQ ID NO 20
<211> LENGTH: 28
<212> TYPE: DNA
<213> ORGANISM: Artificial Sequence
<220> FEATURE:
<223> OTHER INFORMATION: Synthetic primer

<400> SEQUENCE: 20
aggaattgta tcccataggc tagcacgt                                        28

<210> SEQ ID NO 21
<211> LENGTH: 24
<212> TYPE: DNA
<213> ORGANISM: Artificial Sequence
<220> FEATURE:
<223> OTHER INFORMATION: Synthetic primer

<400> SEQUENCE: 21
gacgacgtga ccctgttcat cagc                                            24

<210> SEQ ID NO 22
<211> LENGTH: 25
<212> TYPE: DNA
<213> ORGANISM: Artificial Sequence
<220> FEATURE:
<223> OTHER INFORMATION: Synthetic primer

<400> SEQUENCE: 22
ccacagcccg atctacttgg cttttt                                          25

<210> SEQ ID NO 23
<211> LENGTH: 25
<212> TYPE: DNA
<213> ORGANISM: Artificial Sequence
<220> FEATURE:
<223> OTHER INFORMATION: Synthetic primer

<400> SEQUENCE: 23
gcaaggtttt gactaagcgg agcac                                           25

<210> SEQ ID NO 24

```
<211> LENGTH: 25
<212> TYPE: DNA
<213> ORGANISM: Artificial Sequence
<220> FEATURE:
<223> OTHER INFORMATION: Synthetic primer

<400> SEQUENCE: 24
cactagtctc gtgcagatgg acagc                                          25

<210> SEQ ID NO 25
<211> LENGTH: 25
<212> TYPE: DNA
<213> ORGANISM: Artificial Sequence
<220> FEATURE:
<223> OTHER INFORMATION: Synthetic primer

<400> SEQUENCE: 25
gttagaagac ttcctctgcc ctcgg                                          25

<210> SEQ ID NO 26
<211> LENGTH: 25
<212> TYPE: DNA
<213> ORGANISM: Artificial Sequence
<220> FEATURE:
<223> OTHER INFORMATION: Synthetic primer

<400> SEQUENCE: 26
ttgtgagggc tcaagttcag tgcat                                          25

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
caggtscagc tggtrcagtc                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
agggatccag agttccaggt                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
cagrtcacct tgaaggagtc                                                20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
```
saggtgcagc tggtggagtc                                          20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
caggtgcagc tgcaggagtc                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
gargtgcagc tggtgcagtc                                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
caggtacagc tgcagcagtc                                          20

<210> SEQ ID NO 34
<211> LENGTH: 25
<212> TYPE: DNA
<213> ORGANISM: Artificial Sequence
<220> FEATURE:
<223> OTHER INFORMATION: Synthetic primer

<400> SEQUENCE: 34
tcacacacta cagcttccac cacaa                                    25

<210> SEQ ID NO 35
<211> LENGTH: 25
<212> TYPE: DNA
<213> ORGANISM: Artificial Sequence
<220> FEATURE:
<223> OTHER INFORMATION: Synthetic primer

<400> SEQUENCE: 35
cggggaaaag tcgactctag aacgg                                    25

<210> SEQ ID NO 36
<211> LENGTH: 26
<212> TYPE: DNA
<213> ORGANISM: Artificial Sequence
<220> FEATURE:
<223> OTHER INFORMATION: Synthetic primer

<400> SEQUENCE: 36
actgcattct agttgtggtt tgtcca                                   26

<210> SEQ ID NO 37
<211> LENGTH: 25
<212> TYPE: DNA

```
<213> ORGANISM: Artificial Sequence
<220> FEATURE:
<223> OTHER INFORMATION: Synthetic primer

<400> SEQUENCE: 37
ggcctggaaa actcagctat ccttt                                      25

<210> SEQ ID NO 38
<211> LENGTH: 25
<212> TYPE: DNA
<213> ORGANISM: Artificial Sequence
<220> FEATURE:
<223> OTHER INFORMATION: Synthetic primer

<400> SEQUENCE: 38
aaggtgactc tgcaatcagc ctctg                                      25

<210> SEQ ID NO 39
<211> LENGTH: 25
<212> TYPE: DNA
<213> ORGANISM: Artificial Sequence
<220> FEATURE:
<223> OTHER INFORMATION: Synthetic primer

<400> SEQUENCE: 39
tcatctacag ccacaacgtg agcag                                      25

<210> SEQ ID NO 40
<211> LENGTH: 25
<212> TYPE: DNA
<213> ORGANISM: Artificial Sequence
<220> FEATURE:
<223> OTHER INFORMATION: Synthetic primer

<400> SEQUENCE: 40
cccatgtaca ggttccgcat gaact                                      25

<210> SEQ ID NO 41
<211> LENGTH: 25
<212> TYPE: DNA
<213> ORGANISM: Artificial Sequence
<220> FEATURE:
<223> OTHER INFORMATION: Synthetic primer

<400> SEQUENCE: 41
ctccgtccgc ttttatttcc cctgt                                      25

<210> SEQ ID NO 42
<211> LENGTH: 25
<212> TYPE: DNA
<213> ORGANISM: Artificial Sequence
<220> FEATURE:
<223> OTHER INFORMATION: Synthetic primer

<400> SEQUENCE: 42
gttataacac ggggagtgcg tgtgc                                      25

<210> SEQ ID NO 43
<211> LENGTH: 30
<212> TYPE: DNA
<213> ORGANISM: Artificial Sequence
<220> FEATURE:
<223> OTHER INFORMATION: Synthetic primer

<400> SEQUENCE: 43
gtttggacaa accacaacta gaatgcagtg                                 30
```

<210> SEQ ID NO 44
<211> LENGTH: 25
<212> TYPE: DNA
<213> ORGANISM: Artificial Sequence
<220> FEATURE:
<223> OTHER INFORMATION: Synthetic primer

<400> SEQUENCE: 44
gcaacggcta caatcaacag catcc                                              25

<210> SEQ ID NO 45
<211> LENGTH: 25
<212> TYPE: DNA
<213> ORGANISM: Artificial Sequence
<220> FEATURE:
<223> OTHER INFORMATION: Synthetic primer

<400> SEQUENCE: 45
tgggtctggg acagacttca ctctc                                              25

<210> SEQ ID NO 46
<211> LENGTH: 25
<212> TYPE: DNA
<213> ORGANISM: Artificial Sequence
<220> FEATURE:
<223> OTHER INFORMATION: Synthetic primer

<400> SEQUENCE: 46
aaggtgactc tgcaatcagc ctctg                                              25

<210> SEQ ID NO 47
<211> LENGTH: 25
<212> TYPE: DNA
<213> ORGANISM: Artificial Sequence
<220> FEATURE:
<223> OTHER INFORMATION: Synthetic primer

<400> SEQUENCE: 47
tcatctacag ccacaacgtg agcag                                              25

<210> SEQ ID NO 48
<211> LENGTH: 25
<212> TYPE: DNA
<213> ORGANISM: Artificial Sequence
<220> FEATURE:
<223> OTHER INFORMATION: Synthetic primer

<400> SEQUENCE: 48
cccatgtaca ggttccgcat gaact                                              25

<210> SEQ ID NO 49
<211> LENGTH: 25
<212> TYPE: DNA
<213> ORGANISM: Artificial Sequence
<220> FEATURE:
<223> OTHER INFORMATION: Synthetic primer

<400> SEQUENCE: 49
ctccgtccgc ttttatttcc cctgt                                              25

<210> SEQ ID NO 50
<211> LENGTH: 31
<212> TYPE: DNA
<213> ORGANISM: Artificial Sequence
<220> FEATURE:

<223> OTHER INFORMATION: IgM constant region-specific primer

<400> SEQUENCE: 50
ccaagcttac gagggggaag acatttggga a                                31

<210> SEQ ID NO 51
<211> LENGTH: 30
<212> TYPE: DNA
<213> ORGANISM: Artificial Sequence
<220> FEATURE:
<223> OTHER INFORMATION: VKF1 primer

<400> SEQUENCE: 51
cataagatct cgmcatccrg wtgacccagt                                  30

<210> SEQ ID NO 52
<211> LENGTH: 30
<212> TYPE: DNA
<213> ORGANISM: Artificial Sequence
<220> FEATURE:
<223> OTHER INFORMATION: IgKC-tag primer

<400> SEQUENCE: 52
ctaacactca ttcctgttga agctcttgac                                  30

<210> SEQ ID NO 53
<211> LENGTH: 7795
<212> TYPE: DNA
<213> ORGANISM: Mus musculus

<400> SEQUENCE: 53
gggatgacag attctctgtt cagtgcactc agggtctgcc tccacgagaa tcaccatgtc    60
ctttctcaag actgtgttct gtgcagtgcc ctgtcagtgg aaatctggag agcatgcttc   120
catgagcttg tgagtagtat atctagtaag ccatggcttt gtgttaatgg tgatgttcta   180
catatcagtt ctctggctta ataatgaggt gatgattcta tgttcctgta acgcttcctc   240
aactgggtcc taagtctttc ttcactccat ctattcctct aaggaatgat cctgaaaatc   300
ccatcacaaa ctataggaga tgggaaccat caaaaaacac agtgacaaag aggtgggaac   360
gcatcagggt tcaggaacca tattttaaaa agatatcgta ataacttct taaaagagat    420 atagacaaat ctccattaat acggagacca gaggcctaag gctaagaacc aatggtggct   480
caaggtctcc tgctacccga ggagcaaacg tagagcagtt tctaatgatt tatttaaaat   540
atagaatcaa aagtaccagt ttgcaattt gaaagattta tttcagcaat gcaacaacat   600
caggtggtgc cgagtccaac acgtcttatg tcccatgata taaacaaagg ccatccagaa   660
ctgtggactg gagttctacc ttgtccccta atgacattca gattttttt ccattctctt    720 tatcttagag gagacagggg gctaactcat tttacttgtc ctttgcttgt tcttgccaag   780
aacgtaaagc agcttgcaag tcttcaaacc taaatatctt agtaactcct acacgagtgg   840
caatgccaaa gagcagtgca acaaagagga agtaaatacg accaaagagt attcttaaat   900
acactactgg ctctaggttc tgttttatta tgcgcctttg aaccggaggg gacccactgt   960
ctatgctccc actgtgtccc tcttctttgc actttggagg gctccaacca aaatggcaat  1020
ggcaattccg acgattgtta cacactcctc tgaaattgca ttttctggg gtgcagtcat   1080 aacccaaacg agataaactt ccattgcaag ctcctcgatc acagaactta ccccttgaac  1140
acggggtacc atgtctcacc aatccagcat ctgctgtttc tgtcccacga tgttcatcaa  1200
gcccaaagca ggtaaccca gagataaccg attgatggaa tgaaacatgt tcttgcaaaa   1260

-continued

```
atggaagatt ggtgacattg gtacactgca accttccaca cagcttgtcc tgatcagcac    1320
aagcattgaa tgtgaggctt tcttctgctc tagtacaatg cccaaatcga aaccgttgtt    1380
tgttgatgtc atagcactta atattagcat tcttagcact tacaccaaag atttccatgc    1440
attgtatgtt gcgatcagtg cagttacctt tatagcagta accctcttct gagcatggtg    1500
tcccatcttg cagataagtg tcatctgggc aaatgaactt agagccacta cagtactctg    1560
gaagatcaca tatgttctgg ataggtctgc agagtgtccc agaaggactg taagtgcaat    1620
ttgcacagca taattcttta tcacaaatgc taccaggtgt taacctgcaa tcatttccac    1680
agcagggatc tgaataacat gccttttggg agccacagtc acactgctca ttgttatcta    1740
ctttgaagtt tccacaaaac ttataagtca atgatgtatt ataataaaca tgacggtcat    1800
agaaaagaca tggcatcaga tcaggagtat taagtatgtt gcttatctct gcaagggaac    1860
aattgctgaa agcatctgtt aattgaggat ttttgaacat gatgcaggtg ttccttctct    1920
ggcagataca gtaccctca tcatgtttta ggcctaaact ccttccaaca cgattggtta    1980
ttataataga taaaaataaa ggatttcgac catgttgacc aagacaaatt agggctgagg    2040
gagaacatat actcctctca gctggattaa cagcatcatc tcctggcgaa ttcttgttaa    2100
ttatagctcc tgcatcaggc ctaaaatgag cataaaatac tctctcatag aaagtatgag    2160
cctgccctcc tggaactcga aaatcttgtg aaaatggatc agcctcggta tacacagtca    2220
tgagaaagac atagtaccgc atatgaagat tggtcagata ggtgtccatt aaactaatga    2280
ctttaaacaa atactcaaca gtagatgaaa gtttgtcacc tccagaagca ctatatacag    2340
aatgggttgc ttgaaagtgg cctttatag cagctggatg tgtagcgtaa ttcttactag    2400
atagtctggg agctccatct gcatattcca atctggagga gggagaacct gtattatggc    2460
tccagtgctt ccatgcattc ataggccctg tgtcatcaga ctcagatact atctgagaaa    2520
caaggtgttc aaagctctgt gaatcattga ggggtttgat ttcataggta aggttatcca    2580
actttatgac ccctgacagg cccccataac aagtatccac agtgaccatg gattgcagga    2640
tcccctccag gtagccaata tagtaacaat ctacaggaaa aaaggggtac tccatctgta    2700
aggctccttg gtcatcttga gttgtcagca acaagtgtct gggccaaatg agtgtctttc    2760
tccgcaggtg gatgatatgt ctctggcccc gaaaacgcaa gctatacgag agcagtcttt    2820
gtgcttgaag tccttggta tggtagatct ccttccgagg aataaccacc tccgatgaga    2880
tgtaacgcca gtgggatgg ccttgagaac accagactgg aaccaggagg agcagccaga    2940
gtgcaaatag caagaggagg accctgggga ccacaggtct ttccactagc tcatgcccc    3000 aggtcagaga taacatcctg ggtggagcta actccctctg ctgtggccac tgcctggtct    3060
agaaaatact gacagaggac taaaaacctc tcaggctcc caacctaagt ggttacccag    3120
acaactggag ttaggtaaca gtcactgggt gtggcaggaa ttgagtctga atgtgttagc    3180
tgaggttgag gttaaatatt gtcaaaaggg atgtctataa atgtgcctgg acaagaaaag    3240
tcagaagcag caaggagtgt ctctgacagg ctcaatcctt tcttttcttt ttttgaagtt    3300
caaaatatca tttccacgtg aatgtatttg gttcccagtg tgactctggg tctctttcta    3360
ggagtcaata tttctttata tcttggctca tgtttttcac agttgttcta acttcttgtt    3420
ttgttttgtt tgtttgtttg tttgaaagtt agaagtaaat actgtctata ttagcctttt    3480
agctataaat gattgttttt atttcttcta atcatgtttt gtttgagttt tggttaaact    3540
atttacaaat gagttttttt tttcctttg ggtgttgctc gaaagtttgg agctttctgt    3600
```

```
taatattgtg ttgttgtttc tccaatatta ttagacctga gaattctacc tgggtacctg    3660
tgaactccag aattttaaa aattccatct cttgggaaca ttatctctga ccccgtctga    3720
ggccgaagtg gctgtccccc tccaacccttt agtatctttc tttcctgact attgggattt    3780
cttcaagcaa tcaggctgat gggttctcag cagtgagacc agtagactgt cggtatgaac    3840
gtcgaagagt ctgccacaca ctccgggttc atcaacagtg ctttcgcgtc tcttactttt    3900
gtagaaggaa atgcagcctc tgagttttct ccaagaaatc attgatgaaa gggtgaaaag    3960
atgggtatca cccggagttc atgacaagcc ctggctcaga cacgtgagca aggtctacag    4020
ccccaaagat aggctgccct gcaacatgta tttataagat aggagaaaaa atgggtagt    4080 tggagggttg atcaacttac ttcctctcaa acatatatat ctcatctaag tgtgcagggg    4140
aaaactctgt agaactactg ggatacctgc tcaccccag gagcctcatg aataagtctc    4200
tgcttctgcc ttgtagccat gagcattact gcacctgata cccctgcagc ttcctaggga    4260
agagggagga agtgacttgg cccctgtctg gttaaggtaa gaggagataa atcccttctc    4320
attgattagg gtgagagggg tcatgtgctc tatcattggt gacccagttg ggacatgggt    4380
ttataccaaa gtcatcactc tgaggttctg tgtaccacca ggctgaactc ccatatccta    4440 catgacata ggacaacacc aagcagaagg aggttttagg actaaactga aggacagaga    4500
tgcggtttct aaacaactag ggagtgccag ggccagcctc tctaaccact ataggacact    4560
gtggagtctg gttacaaaga gagattactc aaggtcctta gcactgatta cagagcatat    4620
ctcagatgcc ttctgctgac cagatgtatc tttgcataat ctgcctatcc agattcagaa    4680
aattgatgcc acatagccaa gtggactttc aggaacagac gatttaaaaa caggcagaga    4740
gatgtgagag aaaggagaag gagagagaga agggagaggg agagaagaga gagggagacg    4800
gagaaggaaa gagggagaag gagaaggaga gaagggggcat ggacagaggg agggacagaa    4860
ggagagagga gatagagagg gggataagga agaagggagg gagggagaga gagagaaggc    4920
taagtctttc catacctggg tcccaatacc tcttataacc caagcacatg gtttcacata    4980
tcacaatgcg gttgggatat agataactgt aaatacttgt gaaaataatg gggctgagat    5040
ctggggtttt catgatagtt tcaaagtcac cgtactgact aaaaccttcc actggcccat    5100
ctccagcttc ctaatctgag ggtatcaaat ttcccactaa gtgtgtttag aaagatctcc    5160 accttttgc ccttgtcttc cagtgcccca cctacgttct ggtctcccac atctgatgtc    5220
ttctcagtga ttctggccct gcctgctcca cagctacaaa ccccttccta taatgagctc    5280
tgtgctgagc catcatcctg aatcaatcca ccttaagcag atgttttgct tattttcct    5340 gtgtccatac tacagaggaa aggtaggcat gtagaagctg aagcatctca cctcattcca    5400
agcaccctca gtctctaaat gtgccccctt gtttccagaa gtgcaacctc aagcatcttt    5460
tattcattca tcttagaggg ccacatgtgc tgtagtgtta taagatgaaa tttaaagcat    5520
taattattcc taacaagcca attaaacaag ccaaaaacat tcatcagtca ttcccatgga    5580
acctctgaag catcttcctg ctctaacctt gggttttcca gggctgctct gggatcacag    5640
gagctgtcct gtctaccagc catataaagg cagacctatc agaattacac cagacttctc    5700
accatagact ataaaagcca gaatatcctg gacagatgtt atacagaaac taagagaaca    5760
caaatgccag cccaggctac tatacccagc aaaactctca attaccatcg atgaagaaac    5820
caagatattc cattacaagt ccaaatttac acaatatctt tccataaatc cagccctaca    5880
aaggatagca gatggaaaac tccaacacag gtaggaaaac tacaccctag aaagagcact    5940
aaagtaatca tctttcaaca cactcaaaag aagataacca cacaaacata attccacctc    6000
```

| | | | |
|---|---|---|---|
| taacaacaaa | aataaagtag gcaacaatca ctattcctta atatctcttt taacatcaat | 6060 |
| ggactcaatt | ctccaataaa aagcatagac taacagagct gaatacataa acaggacaca | 6120 |
| gcattttgct | gcataaagca aacacagcgt tactttttt tttctaaatg acattttta | 6180 |
| ttagatattg | tctttattga catttcaaat gttatcccct ttcctggttt accctctgaa | 6240 |
| atcccctatc | tcctccccct cccctgctc accaatccac ccactcccac ttccaggccc | 6300 |
| tggcaatccc | ctatatttgg gcatagagcc ttcacaggac caaggtactc tccttgcatt | 6360 |
| gatgaccaac | tagtccattc tctgctacaa atgcagctag atctatgagt cccaccatgt | 6420 |
| tttcttttgt | tggtggtttc atgccaggga gctcttggag tactgattgg ttcatattgt | 6480 |
| tgttctccct | atggggttac aaaacccttc aacttcttgg gtcctttctc tggctgcctc | 6540 |
| attggggacc | ttgtgcgaag tccaatggat gactgtgagc atccacttct gtatttgcca | 6600 |
| ggcactggca | gagcctctca aagacagct atatcaagat cctggcagca agctcttgtt | 6660 |
| ggtatccaca | aaagtgtctg gtggttgtct atgggatgga tccccaaagg ggcagtctct | 6720 |
| ggatggtcat | tccttcagtc tctgttccac actttgtctc tttaactcct tccatgacta | 6780 |
| ttttattcct | ccctctaaga aggaccgaag tattcatact ttggtcttcc ttcttgaaat | 6840 |
| tcatgtgttt | tgtgaattgt atctttgata ttccgaactt ctgggctaat atccacttat | 6900 |
| cagtgagtga | atatcatgtg tgttcttatg tgattgagtt acctcactca ggatgatatc | 6960 |
| ctccagaacc | atccatttgt ctaagaattt aatgaattca ttgttttaa tagctgagga | 7020 |
| gtactccatt | gtgtaaatgt accacatttt ctgtacccat tgttctcttg agggacatct | 7080 |
| gggttcttta | aagcttctgg acattaaata taaggctgct atggaaatag tggagaatgt | 7140 |
| gtccttatta | catgttggag catcttctgg gtatatgccc aggagtgcta ttgctggatc | 7200 |
| ctctgatagt | actatgtcca attttctgag gaactgccaa actgatttac agagtggttg | 7260 |
| taccagcttg | caattccacc agcaatggag aaatgttccc cttcctccac atcctcacca | 7320 |
| acatctgctg | tcacctcaat ttgttcttag tgattcagac aggtgtgagg tggaatatca | 7380 |
| gggttgtttg | gcatttccct gatgactagt gatattgaaa aaaattttaa gtgtttctca | 7440 |
| gccattcagt | attcttcagt tgagaattca ctgtttagct ctgtactcag gttttttaa | 7500 |
| tagggttatt | tggttttctg gagtctaacg tcttgaattc tttctatata ttggatatta | 7560 |
| gccctctgtc | atatttagga ttggtaaaga tctttcccaa tatgttggct gccttttgt | 7620 |
| gtcctttgcc | ttacagaacc ttttaattt tatgaggtcc catttgctaa ttcttcattt | 7680 |
| tacagcacaca | gccattggtg ttctgttcaa aaatctttcc ccctgaaccc tatcttcgag | 7740 |
| gatcttcccc | actttctcct ctataagttt cagtgtctct attattgtgc tgagg | 7795 |

<210> SEQ ID NO 54
<211> LENGTH: 5938
<212> TYPE: DNA
<213> ORGANISM: Mus musculus

<400> SEQUENCE: 54

| | | | |
|---|---|---|---|
| tgatgtggga | acgcttcagt gttcaggaac catatgattt atttaaaata tagaatcaaa | 60 |
| agtaccaatt | tgcagttttg aaagatttat tccagtgtaa gcattagcaa tgcaccaaca | 120 |
| tcaggtgatt | tctgaatcca acacgtctta tgtcctcatg atattaaaaa aaaaaaaagg | 180 |
| ccatccagaa | ctgtgaactt gagttctacc ttgttcccta ctgacattca gatttcttt | 240 |
| tttgcattct | ctttatctta caggagacag gaggggaggg ctaactcatt ttactttggc | 300 |

```
ttgtcccttg ctggtccttg cccagaacgt aaagtagctt gcaagtcttc aaatctaaaa    360
atcttagtaa ctcctacacg agtggcaatg ccaaagagca gtgcaacaaa gaggaagtaa    420
atacgaccaa agagtattct taaatacacc actggctctt gttttttgttt tattgtgtgc    480
ctttgaactg gaggggaccc actgtctatg ctcccactta gtccctcttc tttgcactct    540
ggaggcttcc aaccaaaatg acaatggcaa ttccgatgat tgttacacac tcctctaaaa    600
ctgcattttt ctggggtgca gtcataaccc aaatgagata aacttccact gcaagctcct    660
tgatcacaga acttactttt ggagcagggg gtaccatgtc tcaccattcc agcatctgtt    720
gtttctgtcc cacgatgttc atcaagccca aagcaggtaa acccagagat aatcgattga    780
tggaatgaaa catgttcttg caaatatgga agattggtga cattggtaca ctgcaacctt    840
ccacacagct tgtcctgatc agcacaagca ttgaatgtga ggctttcttc tgctctagta    900
caatgcccaa atcgaaaccg ttgtttgttg atgtcatagc acttaatatt agcattctta    960
gcacttacac caaagatttc catgcattgt atgttgcgat cagtgcagtt acctttatag    1020
cagtaaccat cttctgagca tggtgtccca tcttgcagat aagtgtcatc tgggcaaatg    1080
tatttagtcc cattacagta ctctggaaga tcacatatgt tctggatagg tctgcagagt    1140
gtcccagaag gactgtaagt gcaatttgca cagcataatt ctttatcaca aatgctacca    1200
ggtgttaacc tgcaatcatt tccacagcag ggatctgaat aacatgcctt tgggagcca    1260
cagtcacact gctcatcgtt atctactttg aagtttccac aaaacttata agtcaatgat    1320
gtattataat aaacatgacg gtcatagaaa agacatggca tcagaccagg agtattaagt    1380
atgttgctta tctctgcaag ggaacaattg ctgaaagcat ctgttaattg aggatgtctg    1440
aacataatgc aggtgttcct tctctggcag acacagtacc cctcatcata ttttaagcct    1500
aaactccttc caacacgatt ggttattata ggagataaaa ataaaggatt tcgatcatat    1560
ttaccaatac aaattagggc taaggaagaa catatactcc tctcagctgg attaacctgg    1620
ttatcttgtg gcccatactt attaagtaaa actcctgcat caggcttaaa tttattataa    1680
aagactgaca catagtaatt ataagccgac cctcctggaa ctgcaaactc aagtcgaaat    1740
ggatcagaat tggtgtacac agtcatgaga aagacatagt accgcatatg aagattggtc    1800
agataggtgt ccattaaact aatgacttga aacaaatacc aacagtaga tgaaagtttg    1860
tcacctgcag cagaattata tacagaattg gttgcttgaa agtggccttt tatagcagct    1920
ggatgtgtag cgtagttctt actagatatt ctgggagctc catctgcata ttccaatctg    1980
gaggagggag aacctgtatt atggctccag tgcttccatg cattcatagg ccctgtgtca    2040
tcagactcag atactatctg agaaacaagg tgttcaaagc tctgtgaatc attgaggggt    2100
ttgatttcat aggtaaggtc atctaacttc atgaccctg acaggccccc ataacaagta    2160
tccacagtga ccatggattg tgggatcccc tccaggtagc aatatagta acaatctaca    2220
ggaaaaaagg ggtaatccat ctgtaaggct ccttggtcat cttgagttgt cagcaacaag    2280
tgtctgggcc aaatgagtgt cttctccgc aggtggatga tatgtctctg gccccgaaaa    2340
tgcaagctat atgagagcag tctttgtgct tgaagtcctt tggtatggta gatctccttc    2400
cgaggaataa ccacctccga tgagatgtaa cgccaagtag gatggccttg agaacaccag    2460
actggaacca ggaggagcag ccagagtgca aatagcaaga ggaggaccct ggggaccaca    2520
ggtcttttcca ctagcctcat gccccaggtc agagataaca tcctgggtgg agctaaatcc    2580
ctctgctgtg gccactgcct ggtctagaaa atactgacag aggactaaaa acctcctcag    2640
gctcccaacc taagtggtta cccagacaac tggagttagg taacagtcac tgggtgtggc    2700
```

```
aggaattgag tctgaatgtg ttagctgagg ttgaggttaa atattgtcaa aagggatgtc    2760
tataaatgtg cctggacaag aaaagtcaga agcagcaagg agtgtctctg acaggctcaa    2820
tcctttcttt tctttttttg aagttcaaaa tatcatttcc acgtgaatgt atttggttcc    2880
cagtgtgact ctgggtctct ttctaggagt caatatttct ttatatcttg gctcatgttt    2940
ctcacagttg ttctaatttc ttgttttgtt ttgtttgttt gtttgaacgt tagtagtaaa    3000
tactgtctat attagccttt tagctataaa tgattgtttt tatttcttct aatcatattt    3060
tgtttgagtt ttggttaaac tatttacaaa tgagtttttt ttttttcctt ttgggtgttg    3120
ctcgaaagtt tggagctttc tgttaatatt gtgttgttat ttttccaata ttattagacc    3180
tgagaattct atctgggtac ctgtgaactc tagaattttt aaaaattcca tctcttggga    3240
acattacctc tgaccccgtc tgaggccgaa gtggctgtcc ccctccaacc tttagtatct    3300
ttctttcctg actattggga tttcttcaag caatcaggct gatgggttct cagcagtgag    3360
accagtagac tgccggtatg aacgtcgaag agactgccac acactccagg ttcatcaaca    3420
gtgctttcgc gtctcttact tttgtagaag gaaaagcagc ctctgagtta tctccaagaa    3480
atcattaatg aaagagttaa aagatgggta tcacccggag ttcatgacaa gccctggctc    3540
agacacgtga gcaaggtcta cagccccaaa gataggctgc cctgcaacat gtatttataa    3600
gatagaagaa aaaatgggt ggttggaggg ttgatcaact tacttcctct caaacatata    3660
tatctcatct aagtgtgcag gggaaaactc tgtaggacta ctgggattgt tattatcatt    3720
attattatta ttattattat tattattatt attattatta ttaacttaag gcattttatt    3780
agatattttc ttcatttagt tttcaaatgt tatccccgga acctcctata ctctctccct    3840
gccctgctcc ccaacccacc cactcctaca tcctggccct ggcattcccc tatactgtgg    3900
cagatgatct tcgtaagacc aagagccttt cctcccattg atggcctact aggctatcct    3960
cttttacata tgcaactaga gtcacagctc tggggaggta ttgcttagtt catattgttt    4020
ttcctcctat aggggttgcag atcccttag ctccttgggt actttctcta gctcctccat    4080
tgggggccct gtgttccatc caatagatga ctgtgagcat ccacttctgt atttgccagg    4140
tattggcatg gatcttactg caccttctga actctctaag cagctttcct ggtcacctcc    4200
aggagcctca tgaataagtc tctgcttccc ccttgtggct atgagcatta ctgcacctga    4260
tacaccctgc agcttcctag ggaagaggga ggaagtggcc tggcccctgt ctggttaagg    4320
taagaggaga taaatccctt ctcatgaatt agggtgagaa gggtcatgtg ctctatcatt    4380
ggtgaccaac ttggggacat gggcttatac agtcatcact ctgaggctct gtgtaccacc    4440
agactgaact cccatatcct acatgcacat aggacaacac caagtagaag gaggttttag    4500
gactaaactg aaggacagag atgggggttc taaacaacta gggagtgcca gggccagcct    4560
ctctaaccac tataggacac tatggagtct ggttacaaag agagattact caaggtcctt    4620
agcactgatt acagagcata tctcagatgc cttctgctga ccagatgtat ctttgcataa    4680
tctgcctatc cagattcaga aaattgatgc cacatagcca agtggacttt caggaacaga    4740
cgatttaaaa acaggcagag agatgtgaga gaaggagaa ggagagagag aagggagagg    4800
gagagaagag agggagac ggagaaggaa agagggagaa ggagaaggag agaagggca    4860 tggacagagg gagggacaga aggagagagg agatagagag ggggataagg aagaaaggag    4920
ggagggagag agagagaagg ctaagtcttt ccatacctgg gtcccaatac ctcttataac    4980
ccaagcacat ggtttcagat atcacaatgc ggttgggata tagataactg taaatacttg    5040
```

-continued

```
tgaaaataat ggggctgaga tctggggttt tcatgatagt ttcaaagtca ctgtactgac    5100
taaaaccttc cactggccca tctccagctt gttaatctga gggtatcaaa tttcccacta    5160
agtgtgttta gaaagatctc caccttttg ccctagtctt ccagtgcccc acctacgttc     5220
tggtctccca catctgatgt cttctcagtg attctggccc tgcctgctcc acagctacaa    5280
accccttcct ataatgagct ctgtgctgag ccatcatcct gaatcaatcc accttaagca    5340
gatgttttgc ttatttttcc tgtgtccata ctacagagga agggtaggca tgtagaagct    5400
gaggcatctc atctcactct aagcaccctc agtctctaaa tgtgcccctt tgtttccagc    5460
agttcagcct caagcatctt ttattcactc gtcttagagg gacacatgtg ctgtagtgtt    5520
ataagatgaa atttaaagca ttagttattc ccaacaagcc aattaaacaa gccaaaaaca    5580
ttcatcagtc attcccatgg aacctctgaa gcatcttcct gctctaacct tgagtttcct    5640
agggctgctg tgggatcaca ggagctgtcc tgtttaccag cctatcctgt cccacgggat    5700
tcagttatta gtgggtgcga gggggaccgc aaacctggaa gaaaatggga ttggaagaga    5760
aaagagaaac gaagaccaag tagatctttt cctatcaagg tcttcgttta ttaggctgag    5820
gtgcctggtg taaagcatgc atcgcgggga ataggaaggg gtcgaggggg aattttacaa    5880
agaacaaaga agcgggcatc tgctgacatg agggccgaag tcaggctcca ggcagcgg     5938
```